US006867305B2

(12) United States Patent
Danishefsky et al.

(10) Patent No.: US 6,867,305 B2
(45) Date of Patent: Mar. 15, 2005

(54) SYNTHESIS OF EPOTHILONES, INTERMEDIATES THERETO AND ANALOGUES THEREOF

(75) Inventors: Samuel J. Danishefsky, Englewood, NJ (US); Shawn J. Stachel, Perkasie, NJ (US); Chul Bom Lee, Princeton, NJ (US); Mark D. Chappell, Noblesville, IN (US); Zhical Wu, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/796,959

(22) Filed: Mar. 1, 2001

(65) Prior Publication Data

US 2002/0058817 A1 May 16, 2002

Related U.S. Application Data

(63) Continuation-in-part of application No. 09/257,072, filed on Feb. 24, 1999, now Pat. No. 6,204,388, which is a continuation-in-part of application No. 08/986,025, filed on Dec. 3, 1997, now Pat. No. 6,242,469.

(60) Provisional application No. 60/185,968, filed on Mar. 1, 2000, provisional application No. 60/250,447, filed on Nov. 30, 2000, provisional application No. 60/075,947, filed on Feb. 25, 1998, provisional application No. 60/092,319, filed on Jul. 9, 1998, provisional application No. 60/097,733, filed on Aug. 24, 1998, provisional application No. 60/032,282, filed on Dec. 3, 1996, provisional application No. 60/033,767, filed on Jan. 14, 1997, provisional application No. 60/047,566, filed on May 22, 1997, provisional application No. 60/047,941, filed on May 29, 1997, and provisional application No. 60/055,533, filed on Aug. 13, 1997.

(51) Int. Cl.$^7$ ................ C07D 263/32; C07D 277/30
(52) U.S. Cl. ................ 548/204; 548/110; 548/236; 548/311.1
(58) Field of Search .............. 548/204, 236, 548/311.1, 110

(56) References Cited

U.S. PATENT DOCUMENTS

| 5,021,430 | A | 6/1991 | Ksander ............... 514/332 |
| 5,917,084 | A | 6/1999 | Jiang ............... 560/174 |
| 5,969,145 | A | 10/1999 | Schinzer et al. ........ 548/110 |
| 6,043,372 | A | 3/2000 | Schinzer et al. ........ 548/110 |
| 6,156,905 | A | 12/2000 | Schinzer et al. ........ 548/204 |
| 6,204,388 | B1 | 3/2001 | Danishefsky et al. ..... 546/340 |
| 6,242,469 | B1 | 6/2001 | Danishefsky et al. ..... 514/365 |
| 6,262,094 | B1 | 7/2001 | Höefle et al. .......... 514/365 |
| 6,284,781 | B1 | 9/2001 | Danishefsky et al. ..... 514/365 |
| 6,288,237 | B1 | 9/2001 | Hoefle et al. ......... 548/203 |
| 6,291,684 | B1 | 9/2001 | Borzilleri et al. ..... 548/961 |
| 6,300,355 | B1 | 10/2001 | Danishefsky et al. ..... 514/374 |
| 6,302,838 | B1 | 10/2001 | O'Reilly et al. ........ 574/365 |
| 6,316,630 | B1 | 11/2001 | Danishefsky et al. .... 546/281.7 |
| 6,320,045 | B1 | 11/2001 | Kim et al. ............ 540/463 |
| 6,350,878 | B1 | 2/2002 | Altmann et al. ........ 548/110 |
| 6,359,140 | B1 | 3/2002 | Höfle et al. .......... 548/204 |
| 6,365,749 | B1 | 4/2002 | Kim et al. ............ 548/204 |
| 6,369,234 | B1 | 4/2002 | Danishefsky et al. ..... 548/204 |
| 6,515,017 | B1 | 2/2003 | Li et al. ............. 514/449 |
| 6,518,421 | B1 | 2/2003 | Li et al. ............. 540/462 |
| 6,525,197 | B1 | 2/2003 | Fürstner et al. ....... 544/310 |
| 6,531,497 | B1 | 3/2003 | Nicolaou et al. ....... 514/370 |
| 6,537,988 | B2 | 3/2003 | Lee .................. 514/221 |
| 6,538,038 | B1 | 3/2003 | Pero et al. ........... 514/731 |
| 6,544,544 | B2 | 4/2003 | Hunter et al. ......... 424/424 |
| 2001/0031880 | A1 | 10/2001 | Borzilleri et al. ..... 548/961 |
| 2001/0034452 | A1 | 10/2001 | Hofle et al. .......... 548/159 |
| 2002/0002194 | A1 | 1/2002 | Danishefsky et al. ..... 514/365 |
| 2002/0028839 | A1 | 3/2002 | O'Reilly et al. ....... 514/365 |
| 2002/0086812 | A1 | 7/2002 | Schweinfest et al. |
| 2002/0094991 | A1 | 7/2002 | Gallaher |
| 2002/0119202 | A1 | 8/2002 | Hunter et al. |
| 2002/0143038 | A1 | 10/2002 | Bandyopadhyay et al. |
| 2002/0169125 | A1 | 11/2002 | Leung et al. |
| 2002/0169135 | A1 | 11/2002 | Pardee et al. |
| 2002/0169190 | A1 | 11/2002 | Bandyopadhyay et al. |
| 2002/0177615 | A1 | 11/2002 | Bandyopadhyay et al. |
| 2002/0192778 | A1 | 12/2002 | Schupp et al. |
| 2002/0193361 | A1 | 12/2002 | Ashley et al. |
| 2002/0197261 | A1 | 12/2002 | Li et al. |
| 2002/0198141 | A1 | 12/2002 | McChesney et al. |
| 2003/0003094 | A1 | 1/2003 | Hunter et al. |
| 2003/0004209 | A1 | 1/2003 | Hunter et al. |
| 2003/0004338 | A1 | 1/2003 | Li et al. |
| 2003/0023082 | A1 | 1/2003 | Ashley et al. |
| 2003/0036177 | A1 | 2/2003 | Strohhacker |
| 2003/0036515 | A1 | 2/2003 | Pardee et al. |
| 2003/0045711 | A1 | 3/2003 | Ashley et al. |
| 2003/0049841 | A1 | 3/2003 | Short et al. |
| 2003/0054977 | A1 | 3/2003 | Kumar et al. |
| 2003/0060623 | A1 | 3/2003 | Vite et al. |
| 2003/0069277 | A1 | 4/2003 | Danishefsky et al. |
| 2003/0073205 | A1 | 4/2003 | Arslanian et al. |
| 2003/0073615 | A1 | 4/2003 | Li et al. |

(List continued on next page.)

FOREIGN PATENT DOCUMENTS

| DE | 19542986.9 | 11/1995 |
| DE | 19639456.2 | 9/1996 |
| DE | 19636343 | 10/1997 |

(List continued on next page.)

OTHER PUBLICATIONS

U.S. patent application Ser. No. 60/032,864, Nicolaou et al., filed Dec. 13, 1996.

(List continued on next page.)

*Primary Examiner*—Kamal Saeed
(74) *Attorney, Agent, or Firm*—Brenda Herschbach Jarrell; C. Hunter Baker; Choate, Hall & Stewart

(57) ABSTRACT

The present invention provides convergent processes for preparing epothilones, desoxyepothilones, and analogues thereof. The present invention further provides novel compositions and methods for the treatment of cancer and additionally provides methods for the treatment of cancer which has developed a multi-drug phenotype.

14 Claims, 47 Drawing Sheets

U.S. PATENT DOCUMENTS

| | | |
|---|---|---|
| 2003/0073617 A1 | 4/2003 | Li et al. |
| 2003/0073677 A1 | 4/2003 | Lee |
| 2003/0087888 A1 | 5/2003 | Regueiro-Ren et al. |
| 2003/0096381 A1 | 5/2003 | Julien et al. |
| 2003/0105330 A1 | 6/2003 | Danishefsky et al. |

FOREIGN PATENT DOCUMENTS

| | | |
|---|---|---|
| DE | 19639456 | 3/1998 |
| DE | 19645361 | 4/1998 |
| DE | 19645362 | 4/1998 |
| WO | WO97/19086 | 5/1997 |
| WO | WO98/08849 | 3/1998 |
| WO | WO98/22461 | 5/1998 |
| WO | WO 98/25929 | 6/1998 |
| WO | WO 99/02514 | 1/1999 |
| WO | WO 02/42432 | 5/2002 |
| WO | WO 02/46196 | 6/2002 |
| WO | WO 02/058700 | 8/2002 |
| WO | WO 02/058701 | 8/2002 |
| WO | WO 02/062338 | 8/2002 |
| WO | WO 03/007924 | 1/2003 |
| WO | WO 03/014063 | 2/2003 |
| WO | WO 03/014068 | 2/2003 |
| WO | WO 03/018002 | 3/2003 |
| WO | WO 03/026744 | 4/2003 |
| WO | WO 03/029195 | 4/2003 |
| WO | WO 03/029260 | 4/2003 |
| WO | WO 03/042217 | 5/2003 |
| WO | WO 03/045324 | 6/2003 |

OTHER PUBLICATIONS

U.S. patent application Ser. No. 08/856,533, Nicolaou et al., filed May 14, 1997.

U.S. patent application Ser. No. 08/923,869, Nicolaou et al., filed Sep. 4, 1997.

Balog et al., "Stereoselective Syntheses and Evaluation of Compounds in the 8–Desmethylepothilone A Series: Some Surprising Observations . . . " *Tetrahedron Letters* 38:26 4529–4532 (1997).

Bijoy, P. et al., "Synthetic Studies Directed Towards Epothilone A: . . . ", *Tetrahedron Letters* 39:209–212 (1998).

Bollag, Daniel M., "Epothilones, a New Class of MT–stabilizing Agents . . . ", *Cancer Research* 55:2325–2333 (1995).

Chakraborty, T.K. et al., "Radical–induced Opening of Trisubstituted Epothilones", *Tetrahedron Letters* 39:101–104 (1998).

Claus, E. et al., "Synthesis of the C1–C9 Segment of Epothilones", *Tetrahedron Letters* 38:1359–1362 (1997).

Gabriel, T., "The Chromium–Reformatsky Reaction: . . . ", *Tetrahedron Letters* 38:8 1363–1366 (1997).

Giannakakou, P. et al., "Paclitaxel–resistant Human Ovarian Cancer Cells Have Mutant β–Tubulins . . . ", *J. Biol. Chem.* 272:27 17118–17125 (1997).

Höfle, G. et al., "Epothilone A and B–Novel 16–Membered Macrolides with Cytotoxic . . . ", *Chem Int. Ed. Engl.* 35:13, 14, 1567–1569 (1996).

Hofle, G. et al., "N–Oxidation of Epothilone A–C and O–Acyl Rearrangement of C–19 and C–21 Substituted Epothilones" *Angew. Chem. Int. Ed.* 38 (13/14) 1971–1974 (1999).

Höfle, G. et al. "Epothilone A–D and their Thiazole Modified Analogs as Novel Anticancer Agents" *Pure Appl. Chem.* 71:11, 2019–2024 (1999).

Kowalski, R.J. et al., "Activities of the Microtubule–stabilizing Agents Epothilones A and B". . . , *J. Biol. Chem.* 272:4 2534–2541 (1997).

Liu, Z.Y. et al., "Chiral Synthesis of the $C_{3-13}$ Segment of Epothilone A" *Synlett Letters* 1383–84 (1997).

Meng, et al., "Total Syntheses of Epothilones A and B", *J. Am. Chem.* Sci. 110:10073–10092, 1997.

Meng et al. "Studies toward a Synthesis of Epothilone A: Use of Hydropyran Templates for the Management of Acyclic Stereochemical Relationships" *J. Org. Chem.* 61:23 7998–8001 (1996).

Moasser et al., "Farnesyl transferase inhibitors cause enhanced mitotic sensitivity to taxol . . . " *Proc. Natl. Acad. Sci. USA*, 95:1369–1374 (1998).

Muhlradt et al., "Epothilone B Stabilizes Microtubuli of Macrophage Like Taxol . . . ", *Cancer Res.* 57, 3344–46 (1997).

Mulzer, J. et al., "Synthesis of the C(1)–C(9) Segment of the Cytotoxic Macrolides Epothilon A and B", *Tetrahedron Letters* 37:51, 9179–9182 (1996).

Nicolaou, K.C. et al., "Total Synthesis of 26–hydroxyepothilone B and related analogues", *Chem. Commun.* 2343–2344 (1997).

Nicolaou, K.C. et al., "Total Synthesis of Epothilone A: The Macrolactonization Approach", *Angew Chem. Int. Ed. Engl.*, 36: 525–527 (1997).

Nicolaou, K.C. et al. "Total Synthesis of Epothilone A and B via a Macrolactonization–Based Strategy", *J. Am. Chem. .Soc.* 119: 7974–7991 (1997).

Nicolaou, K.C. et al., "Total Synthesis of Oxazole–and Cyclopropane–Containing Epothilone A Analogues . . . ", *Chem. Eur. J.* 3:12 1957–1970 (1997).

Nicolaou, K.C. et al., "Designed Epothilones: Combinatorial Synthesis, Tubulin Assembly . . . " *Agnew Chem. Int. Ed. Engl.* 36:19 2097–2103 (1997).

Nicolaou, K.C. et al., "Synthesis of Epothilones A and B in solid and solution phase", *Nature* 387:15 268–272, 238–239 (1997).

Nicolaou, K.C. et al., "Variation der Ringgrösse von Epothilonen–Totalsyntheses von [14]–, [15]–,[17]–, . . . " *Angew. Chem.* 110:1/2 85–92 (1998).

Nicolaou, K.C. et al., "An Approach to Epothilones Based on Olefin Metathesis" *Angew. Chem. Int. Ed.* 35:20 2399–2401 (1996).

Nicolaou, et al., "The Olefin Metathesis Approach to Epothilone A and Its Analogues", *J. Am. Chem. Soc.* 119: 7960–7973, 1997.

Nicolaou, et al., "Total Synthesis of Oxazole– and Cyclopropane–Containing Epothilone B Analogues by the Macrolactonization Approach", *Chem. Eur. J.* 3(12): 1971–1986, 1997.

Nicolaou, et al., "Probing the Ring Size of Epothilones: Total Synthesis of [14]–, [15]–, [17]–, and [18] Epothilones A", *Angew Chem. Int. Ed.* 37(1/2): 81–83, 1998.

Schinzer, D. et al., "Studies Toward the Total Synthesis of Epothilones: . . . ", *Chem. Eur. J.* 2:11 1477–1488 (1996).

Schinzer, D. et al., "Total Synthesis of ()–Epothilone A", *Angew Chem. Int. Ed.* 36:5 523–524 (1997).

Taylor, R.E., et al., "Towards the Synthesis of Epothilone A: Enantioselective Preparation . . . " *Tetrahedron Letters* 38:12 2061–2064 (1997).

Wessjohann, L., "Epothilones: Promising Natural products with Taxol–Like Activity", *Angew. Chem. Int. Ed. Engl.* 36:7 715–718 (1997).

Victory et al., "Relative Stereochemistry and Solution Conformation of the Novel Paclitaxel–Like Antimitotic Agent Apothilone A" *Bioorganic & Medicinal Chemistry Letters* 6:7 893–898 (1996).

Epothilone B (EpoB)
1

Aza-epothilone B (Aza-EpoB)
2

3a: R = H; 12,13-Desoxyepothilone B (dEpoB)
3b: R = OH; 12,13-Desoxyepothilone F (dEpoF)

4a: 12,13,15-Desoxy-15(S)-aza-epothilone B
4b: 12,13,15-Desoxy-15(R)-aza-epothilone B

SYNTHESIS OF EPOTHILONES, INTERMEDIATES THERETO AND ANALOGUES THEREOF

PRIORITY INFORMATION

The present invention claims priority under 35 U.S.C. §119(e) to co-pending provisional applications No. 60/185,968, filed Mar. 1, 2000, entitled "Synthesis of Epothilones, Intermediates Thereto and Analogues Thereof", and 60/250,447, filed Nov. 30, 2000, entitled "Synthesis of Epothilones, Intermediates Thereto and Analogues Thereof", the entire contents of which are hereby incorporated by reference.

GOVERNMENT SUPPORT

This research was supported by Grants CA-28824, 25848, CA-08748, CA-39821, CA-GM-72231, GM-18248, CA-62948, F32CA81704, and AI0-9355 from the National Institutes of Health, and Grant CHE-9504805 from the National Science Foundation. Furthermore, this research was supported by Postdoctoral Fellowships for Chul Bom Lee (U.S. Army, Grant DAMD 17-98-1-8155), Shawn J. Stachel (NIH, Grant F32CA81704), and Mark D. Chappell. (NIH, Grant, F32GM199721). Accordingly, the government may have certain rights in this invention.

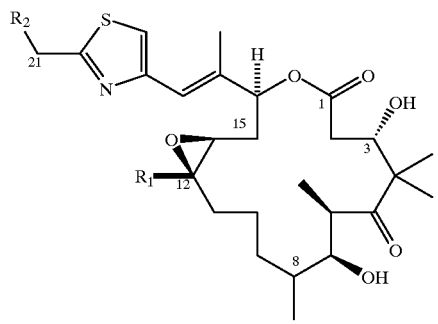

1a $R_1$ = H, $R_2$ = H, Epothilone A
1b $R_1$ = $CH_3$, $R_2$ = H, Epothilone B
1c $R_1$ = H, $R_2$ = OH, Epothilone E
1d $R_1$ = $CH_3$, $R_2$ = OH, Epothilone F

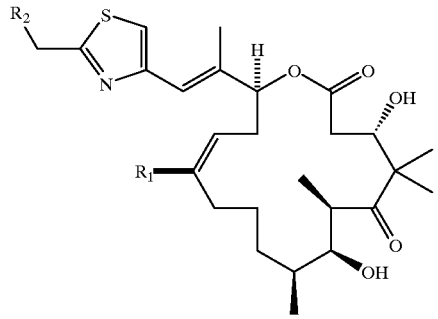

2a $R_1$ = H, $R_2$ = H, Epothilone C
2b $R_1$ = $CH_3$, $R_2$ = H, Epothilone D
2c $R_1$ = H, $R_2$ = OH, Desoxyepothilone E
2d $R_1$ = $CH_3$, $R_2$ = OH, Desoxyepothilone F

BACKGROUND OF THE INVENTION

The epothilones are a family of naturally occurring cytotoxic macrolides that were isolated from the mycobacterium *Sorangium cellulosum*. Though possessing a vastly different structure than that of taxoids, the epothilones, similarly to paclitaxel (Taxol®), apparently function through a similar mechanism involving inhibition of cellular division by stabilization of microtubule assemblies, thereby leading to cell death (Bollag et al. *Cancer Res*. 1995, 55, 2325). Paclitaxel is currently employed as a first-line chemotherapeutic agent; however, concerns for its therapeutic index and formulation difficulties, due to its insolubility in water, are a liability.

By comparison, the epothilones enjoy a greater therapeutic profile as well as increased water solubility, making them attractive therapeutic agents. Specifically, it has been demonstrated that the epothilones retain remarkable potency against multiple-drug-resistant tumor cells. Additionally, the increased water solubility in comparison to paclitaxel is useful for the formulability of epothilones. While the naturally occurring compound, epothilone B (1b, EpoB, in Scheme 1 below), has been found to be most potent member of this family, it unfortunately possesses, at least in xenograft mice, a worrisomely narrow therapeutic index (Su et al. *Angew. Chem. Int. Ed. Engl*. 1997, 36, 1093; Harris et al. *J. Org. Chem*. 1999, 64, 8434).

Despite the narrow therapeutic index of epothilone B, the significant clinical potential of the epothilones has led to several synthetic and therapeutic studies by the present inventors to investigate the cytotoxicity and in vivo antitumor potential of the epothilones. (see, for example, Balog et al. *Angew. Chem. Int. Ed*. 1996, 35, 2801; Su et al. *Angew Chem. Int. Ed*. 1997, 36, 757; Meng et al. *J. Am. Chem. Soc*. 1997, 119, 10073). It has recently been demonstrated during the course of these and other studies that 12,13-desoxyepothilone B (2b, dEpoB), manifests a more promising therapeutic profile than does epothilone B (1b, EpoB). Specifically, it has been found that dEpoB exhibits an enhanced therapeutic range relative to epothilone B due to a reduction in toxic dose levels (Danishefsky et al. *Proc. Natl. Acad. Sci. U.S.A*. 1998, 95, 9642). In vivo experiments based on various mouse models have consistently demonstrated that dEpoB possesses remarkable therapeutic potential and is essentially curative against various sensitive and resistant tumors in xenografts. Due to its impressive in vivo profile, dEpoB has been advanced through toxicology evaluations in dogs, in expectation of human trials anticipating its deployment as an anticancer drug.

Based upon the therapeutic potential of the epothilones, there has been continuing interest in the discovery and isolation of other structural variants of epothilones. Recently, epothilones E and F have been isolated from fermentation and possess a 21-hydroxyl group (Nicolaou et al. *Angew. Chem. Int. Ed. Engl*. 1998, 37, 84; Hofle In GBF Annual Report; Walsdorff, J.-H., Ed.; GBF: Braunschweig, 1997, p. 91). The SAR studies of these compounds suggest that the presence of the hydroxyl function at C21 does not significantly diminish the biological activity (Hofle et al. *Angew. Chem. Int. Ed.* 1999, 38, 1971). Considering the substantial risk of paclitaxel chemotherapy derived from formulation, this feature is particularly useful in that the additional hydroxy would provide a chemotherapeutic having enhanced aqueous solubility, which could result in a major improvement in formulation capabilities. Furthermore, since the 21-hydroxyl group represents a readily accessible primary alcohol, it could be utilized as a molecular handle for further elaboration.

Clearly, in view of the potential benefits of having a functional handle at C21, and based upon the recognition by the present inventors of the superior therapeutic profile of 12,13-desoxyepothilones, it would be desirable to develop novel synthetic methods to enable facile access to 12,13 deoxy, 21-hydroxy analogues of epothilones. It would also desirable to develop efficient methodology that, in addition to enabling access to the desirable 21-hydroxy analogues, would also enable access to other useful analogues, preferably analogues of desoxyepothilones, including analogues functionalized at the 20- or 21-position, or aza-analogues, and derivatives thereof.

SUMMARY OF THE INVENTION

Significantly, the present invention provides novel analogues of epothilones and methods for the synthesis thereof. In one aspect, the present invention provides compounds having the structure:

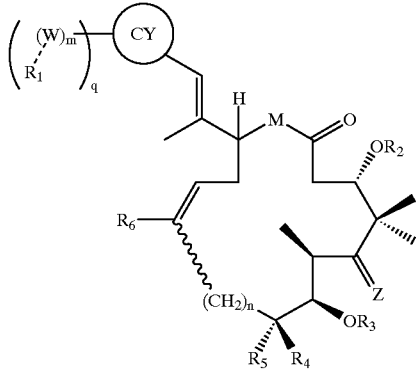

wherein M is NH or O;

wherein CY is an aryl or heteroaryl moiety;

wherein q is 1–5;

wherein each occurrence of W is independently absent; —NH—; C=O; C=S; —O—; —S—; or C(V)$_2$;

wherein each occurrence of V is independently hydrogen; halogen; —OH; —SH; amino; or substituted or unsubstituted alkyl, heteroalkyl, aryl or heteroaryl;

wherein each occurrence of m is independently 1–5;

wherein the bond W—R$_1$ represents a single bond or a double bond;

wherein each occurrence of R$_1$ is independently hydrogen; OR$_A$; SR$_A$; NR$_A$R$_A$; C(O)OR$_A$; C(O)R$_A$; CONHR$_A$; N$_3$; N$_2$; N$_2$R$_A$; halogen; substituted or unsubstituted, cyclic or acyclic, linear or branched aliphatic, heteroaliphatic, aryl, or heteroaryl; polymer; carbohydrate; photoaffinity label; or radiolabel; wherein each occurrence of R$_A$ is independently hydrogen; linear or branched, substituted or unsubstituted, cyclic or acyclic, aliphatic, heteroaliphatic, aryl or heteroaryl; nitrogen protecting group; carbon protecting group; oxygen protecting group; sulfur protecting group; polymer; carbohydrate; photoaffinity label; or radiolabel;

wherein R$_2$ and R$_3$ are each independently hydrogen; substituted or unsubstituted aliphatic, heteroaliphatic, aryl, or heteroaryl; acyl; aroyl; benzoyl; or Si(R$_B$)$_3$, wherein each occurrence of R$_B$ is independently substituted or unsubstituted, cyclic or acyclic, linear or branched aliphatic, heteroaliphatic, aryl or heteroaryl;

wherein R$_4$ and R$_5$ are each independently hydrogen; or substituted or unsubstituted, linear or branched, cyclic or acyclic aliphatic, heteroaliphatic, aryl, or heteroaryl, optionally substituted by one or more of hydroxy, alkoxy, carboxy, carboxaldehyde, linear or branched alkyl or cyclic acetal, fluorine, NR$_C$R$_D$, N-hydroximino, or N-alkoxyimino, wherein R$_C$ and R$_D$ are each independently hydrogen, phenyl, benzyl, linear or branched chain alkyl;

wherein R$_6$ is independently hydrogen; OR$_A$; SR$_A$; NR$_A$R$_A$; C(O)OR$_A$; C(O)R$_A$; CONHR$_A$; N$_3$; N$_2$R$_A$; halogen; cyclic acetal; substituted or unsubstituted, cyclic or acyclic, linear or branched aliphatic, heteroaliphatic, aryl, or heteroaryl; wherein each occurrence of R$_A$ is independently hydrogen; nitrogen protecting group; carbon protecting group; oxygen protecting group; sulfur protecting group; linear or branched, substituted or unsubstituted, cyclic or acyclic, aliphatic, heteroaliphatic, aryl or heteroaryl; polymer; carbohydrate; photoaffinity label; or radiolabel;

wherein Z is O, N(OR$_E$) or N—NR$_F$R$_G$; wherein R$_E$, R$_F$, and R$_G$ are each independently a substituted or unsubstituted, linear or branched, cyclic or acyclic aliphatic moiety; and wherein n is 0, 1, 2, or 3.

In certain embodiments, for each of the compounds as described above and herein, CY is phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl. In still other embodiments, CY is a 4-thiazolyl or 4-oxazolyl moiety substituted with one or two methyl groups, and in certain embodiments the methyl groups are substituted at the 2- or 5-position. In certain other embodiments, CY is 4-thiazolyl; m is 1; and n is 3. In still other embodiments of the invention, R$_2$ and R$_3$ are each hydrogen; R$_4$ is methyl and R$_5$ is hydrogen; and Z is O.

It will also be appreciated that for certain compounds as described above and herein M is O, and in certain other embodiments, M is NH. In still other embodiments of the invention, R$_6$ is H, methyl, ethyl, n-propyl, n-butyl, n-hexyl,

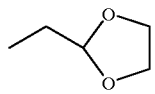

or (CH$_2$)$_p$—OH, wherein p is 1–6. In a certain subset of compounds of the invention, R$_6$ is methyl or ethyl. In yet another subset of compounds of the invention CY is 4-thiazolyl or 4-oxazolyl and R$_6$ is methyl or ethyl. In certain other embodiments, R$_6$ is ethyl.

In yet other embodiments of the invention, compounds having substitution at the 12-position with two or more carbon atoms is contemplated and thus R$_6$ is a substituted or unsubstituted, cyclic or acyclic, branched or unbranched aliphatic or heteroaliphatic moiety, having 2 or more carbon atoms. Furthermore, another subset includes those compounds in which $R_6$ is ethyl, n-propyl, n-butyl, n-hexyl,

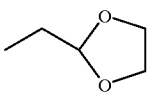

or $(CH_2)_p$—OH, wherein p is 1–6.

In certain embodiments of the invention, as described above, thiazolinyl and oxazolinyl compounds are of interest. Thus, in certain embodiments of the invention, compounds are provided having the general structure:

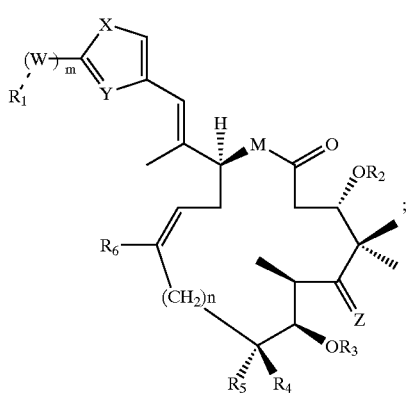

are provided, and the present invention additionally includes all possible stereoisomers and double bond isomers. For example, certain isomers of interest include compounds, as defined above and herein, having the following structures:

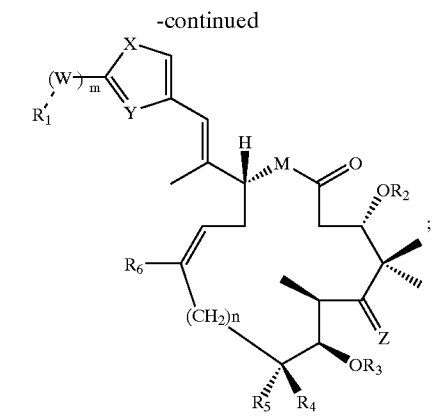

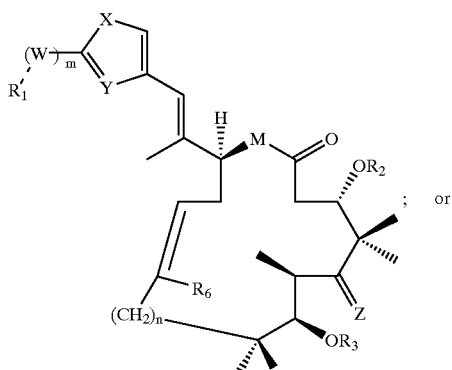

; or

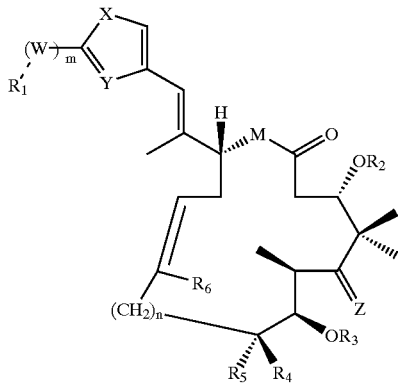

In certain other embodiments for each of the compounds as described above and herein, $R_1$ is $OR_A$ and $R_A$ is hydrogen, linear or branched, substituted or unsubstituted, cyclic or acyclic aliphatic or heteroaliphatic, or substituted or unsubstituted aryl or heteroaryl; W is —$CH_2$—; and m is 1. In yet other embodiments for each of the compounds as described above and herein, $R_1$ is $NR_AR_A$, and $R_A$ is hydrogen, a nitrogen protecting group, or lower alkyl; m is 1; and W is —$CH_2$—. In still other embodiments, W is (C=O), m is 1, and $R_1$ is hydrogen.

In yet other embodiments, $R_1$ is a photoaffinity label. In certain embodiments, the photoaffinity label is a photoactivatable group and is o-, m- or p-azidobenzoyl substituted by one or more halogen moieties. In certain embodiments, the photoactivatable group is 4-azido-2,3,5,6-tetrafluorophenylacyl.

One subset of compounds of the present invention of interest include those compounds having the structure:

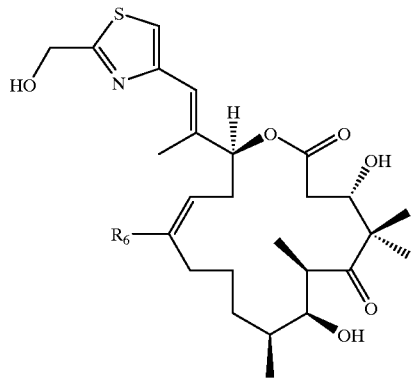

wherein $R_6$ is independently hydrogen; $OR_A$; $SR_A$; $NR_AR_A$; $C(O)OR_A$; $C(O)R_A$; $CONHR_A$; $N_2$; $NR_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel. In certain embodiments of this subset, $R_6$ is a substituted or unsubstituted, cyclic or acyclic, branched or unbranched aliphatic or heteroaliphatic moiety, having 2 or more carbon atoms. In still other embodiments of this subset $R_6$ is H, methyl, ethyl, n-propyl, n-butyl, n-hexyl,

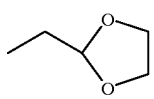

or $(CH_2)_p$—OH, wherein p is 1–6. In certain other embodiments of this subset $R_6$ is ethyl, n-propyl, n-butyl, n-hexyl,

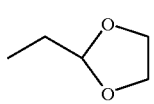

or $(CH_2)_p$—OH, wherein p is 1–6. In yet other embodiments, $R_6$ is methyl and the compound has the structure:

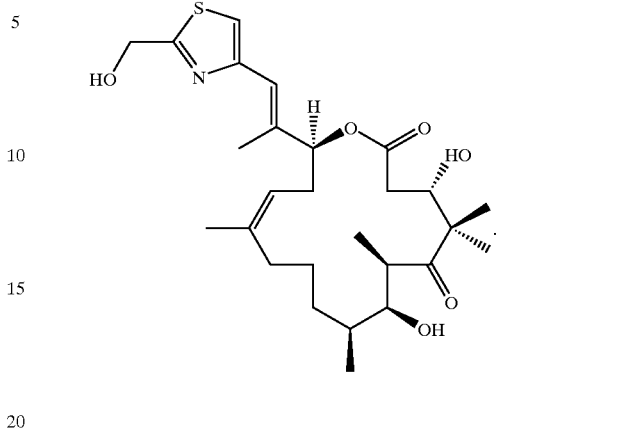

In still other embodiments of the invention, compounds are provided wherein the inventive compounds, as described herein, are linked to polymers, carbohydrates, photoaffinity labels, or radiolabels. In certain embodiments, these inventive compounds have the general structure:

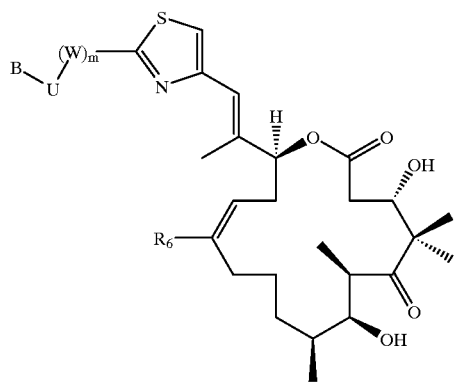

$R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel; wherein W and U are each independently absent; —NH—; C=O; C=S; —O—; —S—; or $C(V)_2$; wherein each occurrence of V is independently hydrogen; halogen; —OH; —SH; amino; or substituted or unsubstituted alkyl, heteroalkyl, aryl or heteroaryl; and wherein B is a peptide or a carbohydrate. In certain embodiments, the peptide is made from 5 to about 25 amino acids. In yet other embodiments, $R_6$ is a substituted or unsubstituted, cyclic or acyclic, branched or unbranched aliphatic or heteroaliphatic moiety, having 2 or more carbon atoms.

In another aspect of the invention, compositions are provided wherein epothilone compounds, as described in detail herein, are multiply presented. For example, inventive compositions comprise a polymeric backbone, wherein the polymeric backbone is a biopolymer or a synthetic polymer; and two or more compounds as described above and herein, wherein the two or more compounds are the same or different, whereby said two or more compounds are linked to the polymeric backbone directly or through a linker, and wherein the two or more compounds are linked through the 12-position, the 20-position or the 21-position of the compound. In certain embodiments, the polymeric backbone is a dendrimer, a peptide, or a biodegradable polymer.

In certain embodiments, a dimeric desoxyepothilone having the structure:

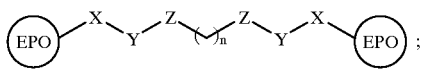

is provided, wherein EPO comprises an inventive compound as described above and herein, linked through functionality present in the 12- 20- or 21-position; wherein X is methylene, (C=O), or is absent; wherein Y is (C=O), O, NH or is absent; wherein Z is (C=O), NH, O, or is absent; and n is 0–5. In certain embodiments, EPO has the structure:

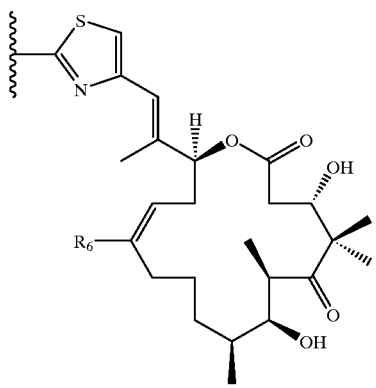

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel. In yet other embodiments, $R_6$ is a substituted or unsubstituted, cyclic or acyclic, branched or unbranched aliphatic or heteroaliphatic moiety, having 2 or more carbon atoms. In still other embodiments, X is methylene, Y is O, and Z is (C=O). In yet other embodiments, X is methylene, Y is NH, and Z is absent. In certain other embodiments, X is (C=O), Y is O or NH, and Z is absent.

In yet another aspect of the present invention, pharmaceutical compositions are provided comprising any one of the inventive compounds as described above and herein, and a pharmaceutically acceptable carrier.

Additionally, the present invention provides a method of treating cancer in a subject suffering therefrom comprising administering to the subject a therapeutically effective amount of any one of the compounds as described above and herein. In certain embodiments, the method is used to treat cancer wherein the cancer is a solid tumor. In certain other embodiments, the method is used to treat cancer wherein the cancer is breast cancer.

The present invention additionally provides a composition comprising an amount of any one of the compounds as described above and herein, effective to inhibit the growth of multidrug resistant cells. The present invention further provides methods of inhibiting the growth of multidrug resistant cells comprising contacting the multidrug resistant cells with an amount of any one of the compounds as described above and herein, effective to inhibit the growth of multidrug resistant cells. It will be appreciated that in certain embodiments, the composition further comprises a pharmaceutically acceptable carrier or diluent. In still other embodiments, the composition further comprises an amount of a cytotoxic agent, including, but not limited to, an anticancer agent. In certain embodiments, the anticancer agent is adriamycin, vinblastin or paclitaxel, or any combination thereof. In still other embodiments, the effective amount of the compound is between about 0.01 mg/kg to about 50 mg/kg of body weight. In certain other embodiments, the effective amount of the compound is between about 0.01 mg/kg to about 25 mg/kg of body weight.

In yet another aspect, the present invention provides a method of preparing a compound having the structure:

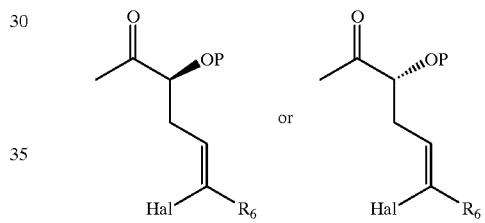

wherein P is an oxygen protecting group; wherein Hal is a halogen; and wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; polymer; nitrogen protecting group; carbon protecting group; sulfur protecting group; or oxygen protecting group; which method comprises the steps of:

a) providing a haloketone having the structure:

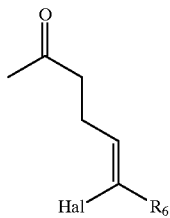

b) subjecting said haloketone to conditions to generate enol ethers and subsequently hydroxylating under suitable conditions to prepare a hydroxyketone having the structure:

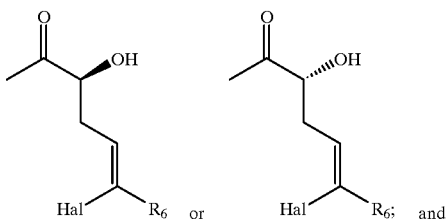

c) protecting the hydroxyketone under suitable conditions to form the compound:

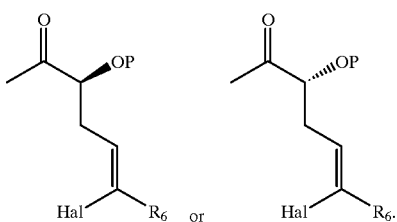

In certain embodiments, the step of hydroxylating comprises reacting the haloketone using asymmetric catalyst to effect asymmetric dihydroxylation, to generate a compound having the structure:

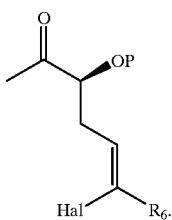

In certain embodiments, the step of hydroxylating is conducted in the presence of $OsO_4$ and AD-mix-α.

In still other embodiments, the step of hydroxylating comprises reacting the haloketone using asymmetric catalyst to effect asymmetric dihydroxylation, to generate a compound having the structure:

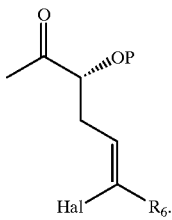

and in certain embodiments the step of hydroxylating is conducted in the presence of $OsO_4$ and AD-mix-β.

For the methods as described above, in certain embodiments P is —$SiR_HR_JR_K$, wherein $R_H$, $R_J$, and $R_K$ are each ethyl. In certain other embodiments $R_6$ linear or branched, cyclic or acyclic, substituted or unsubstituted aliphatic or heteroaliphatic. In still other embodiments, $R_6$ is methyl, ethyl, n- or iso-propyl, phenyl or benzyl. In yet other embodiments, Hal is iodo.

In another aspect, the present invention provides a method of preparing a compound having the structure:

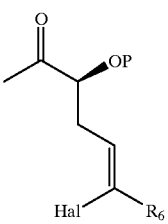

wherein P is an oxygen protecting group; wherein Hal is a halogen; and wherein $R_6$ is independently hydrogen; $OR_A$; $SR_A$; $NR_AR_A$; $C(O)OR_A$; $C(O)R_A$; $CONHR_A$; $N_3$; $NR_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; comprising the steps of a) preparing a glycolimide having the structure:

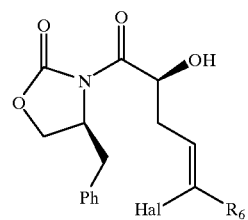

b) treating the glycolimide with a substituted hydroxylamine selected from the group consisting of N,O-(linear or branched chain $C_{1-8}$ alkyl,aryl) hydroxylamine, N,O-di-(linear or branched chain $C_{1-8}$) alkylhydroxylamine and N,O-aryl,arylhydroxylamine under suitable conditions to form an amide having the structure:

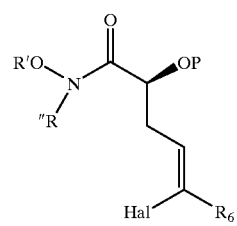

wherein R' and R" are each independently linear or branched chain $C_{1-8}$ alkyl or aryl; and c) reacting the amide with a substituted organometallic reagent under suitable conditions to form the compound. In certain embodiments, P is $SiR_HR_JR_K$ and wherein $R_H$, $R_J$ and $R_K$ are each ethyl. In certain other embodiments, $R_6$ is methyl, ethyl, n- or iso-propyl, phenyl or benzyl. In yet other embodiments, Hal is iodo. In yet further embodiments, the substituted organometallic reagent is a Grignard reagent, including, but not limited to, MeMgBr or MeMgCl.

In still another aspect, the present invention provides a method of preparing a compound having the structure:

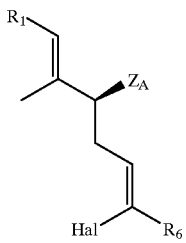

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic; wherein $Z_A$ is OP; wherein P is an oxygen protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; polymer; nitrogen protecting group; oxygen protecting group; sulfur protecting group; or carbon protecting group;which comprises the steps of:

a) preparing a phosphine oxide having the structure:

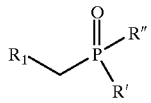

wherein R' and R" are independently $C_{1-8}$ linear or branched chain alkyl, or a substituted or unsubstituted phenyl; aryloxy; or alkoxy;

b) condensing the phosphine oxide with a ketone having the structure:

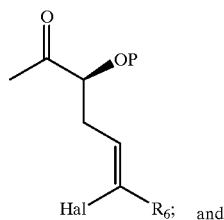

c) optionally reducing the ester formed in step b) under suitable conditions to form the compound.

In certain embodiments, P is $SiR_HR_JR_K$ and $R_H$, $R_J$ and $R_K$ are each ethyl. In still other embodiments $R_6$ is linear or branched, cyclic or acyclic, substituted or unsubstituted aliphatic or heteroaliphatic. In yet other embodiments, $R_6$ is methyl, ethyl, n- or iso-propyl, phenyl or benzyl. In still further embodiments, Hal is iodo. In certain embodiments, it will be appreciated that $R_1$ is hydrogen, linear or branched, substituted or unsubstituted, cyclic or acyclic, alkyl, heteroalkyl, phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl. In yet other embodiments, $R_1$ is substituted or unsubstituted 4-thiazolyl. In still other embodiments, 4-thiazolyl is substituted with one or two methyl groups in the -2 or -5 positions.

In yet another aspect, the present invention provides a method for preparing a compound having the structure:

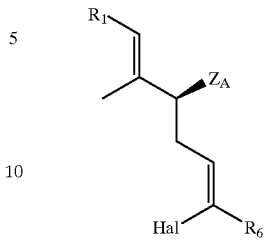

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic; wherein $Z_A$ is $N_3$ or NHP; wherein P is a nitrogen protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; which comprises the steps of:

a) preparing a phosphine oxide having the structure:

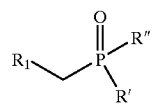

wherein R' and R" are independently $C_{1-8}$ linear or branched chain alkyl, or a substituted or unsubstituted phenyl; aryloxy; or alkoxy;

b) condensing the phosphine oxide with a ketone having the structure:

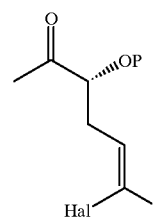

c) reacting the compound formed in step b) under suitable conditions to effect inversion to generate an azide, and optionally further treating the azide to generate a protected amine.

In certain embodiments, inversion is effected using Thompson's procedure. In certain other embodiments, the azide is reduced by Staudinger reduction to generate a protected amine. In yet other embodiments, P is $SiR_HR_JR_K$ and $R_H$, $R_J$ and $R_K$ are each ethyl. In still other embodiments, $R_6$ is linear or branched, cyclic or acyclic, substituted or unsubstituted aliphatic or heteroaliphatic. In yet other embodiments, $R_6$ is methyl, ethyl, n- or iso-propyl, phenyl or benzyl. In certain other embodiments, Hal is iodo. In still other embodiments of the invention, $R_1$ is hydrogen, linear or branched, substituted or unsubstituted, cyclic or acyclic, alkyl, heteroalkyl, phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl. In another subset of the invention, $R_1$ is substituted or unsubstituted 4-thiazolyl.

In still another aspect, the present invention provides a method of preparing a compound having the structure:

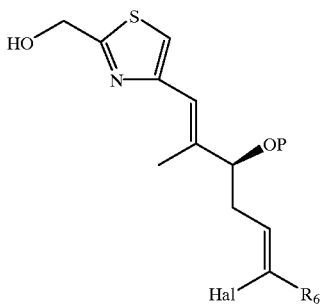

wherein P is a nitrogen protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; which comprises the steps of:

a) preparing a phosphine oxide having the structure:

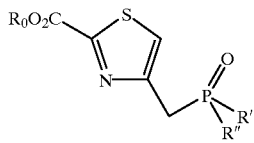

wherein $R_0$, R' and R" are independently $C_{1-8}$ linear or branched chain alkyl, or a substituted or unsubstituted phenyl; alkoxy; or aryloxy;

b) condensing the phosphine oxide with a ketone having the structure:

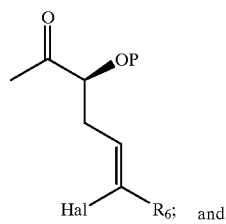

c) reducing the ester formed in step b) under suitable conditions to form the compound.

In certain embodiments for the method as described above, P is $SiR_HR_JR_K$ and $R_H$, $R_J$ and $R_K$ are each ethyl. In still other embodiments, $R_6$ is linear or branched, cyclic or acyclic, substituted or unsubstituted aliphatic or heteroaliphatic. In yet other embodiments, $R_6$ is methyl, ethyl, n- or iso-propyl or phenyl or benzyl. In certain embodiments, Hal is iodo.

In yet another aspect, the present invention provides a method preparing a compound having the structure:

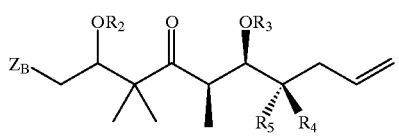

wherein $Z_B$ is $CO_2R_9$ or $COSR_9$, wherein $R_9$ is hydrogen or an oxygen or sulfur protecting group, wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; and wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroxyimino, or N-alkoxyimino, wherein $R_C$ and $R_D$ are each independently hydrogen, phenyl, benzyl, linear or branched chain alkyl; said method comprising:

protecting a ketoaldehyde having the structure:

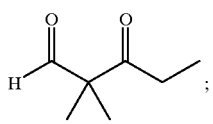

to generate a protected aldehyde and subsequently reacting said protected aldehyde with a compound having a structure:

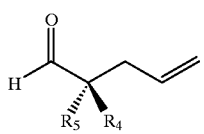

under suitable conditions to effect condensation to generate an aldol having the structure:

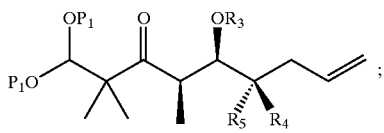

hydrolyzing the protected acetal group to generate a ketoaldehyde having the structure:

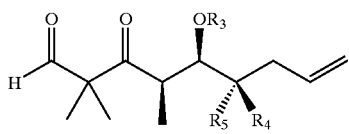

reacting said ketoaldehyde under suitable conditions to effect a second aldol reaction, and optionally protecting the C3 alcohol to generate a compound having the structure:

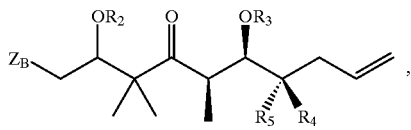

wherein $Z_B$, and $R_2$–$R_5$ are as defined above.

In certain embodiments, the step of reacting said ketoaldehyde under suitable conditions to effect a second aldol reaction comprises reacting said ketoaldehyde under stoichiometric conditions with a chiral titanium enolate. In certain other embodiments, the step of reacting said ketoaldehyde under suitable conditions to effect a second aldol reaction comprises reacting said ketoaldehyde with a catalytic reagent. In certain embodiments, the catalytic reagent employed is the Carreira catalyst. In certain other embodiments, the catalytic reagent employed is Mikami's chiral aldol catalyst.

In yet another aspect, the present invention provides a method for preparing a compound having the structure:

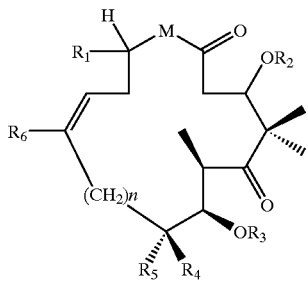

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic, or is —CY=CHX, wherein X is hydrogen, or is substituted or unsubstituted linear or branched, cyclic or acyclic, aliphatic, heteroaliphatic, aryl, heteroaryl, aryl substituted aliphatic or aryl substituted heteroaliphatic and wherein Y is hydrogen, or linear or branched chain alkyl; wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently H, phenyl, benzyl, linear or branched chain alkyl; wherein $R_6$ is independently hydrogen; $OR_A$; $SR_A$; $NR_AR_A$; $C(O)OR_A$; $C(O)R_A$; $CONHR_A$; $N_2$; $NR_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; wherein M is NH or O; and wherein n is 0, 1, 2 or 3; which method comprises:

providing a precursor having the structure:

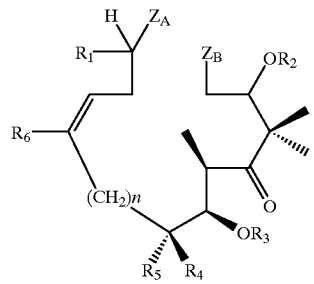

wherein $R_1$–$R_6$ are as defined above; $Z_A$ is $OR_7$, $NHR_8$, or $N_3$, and $Z_B$ is $CO_2R_9$ or $COSR_9$ wherein each occurrence of $R_7$, $R_8$, $R_9$, $R_{10}$, or $R_{11}$ is independently hydrogen, an oxygen protecting group or a nitrogen protecting group; and wherein the step of providing the precursor further comprises:

reacting a first compound having the structure

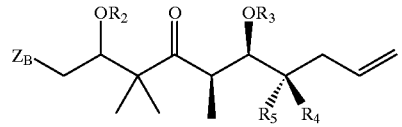

under suitable conditions with a second compound having the structure:

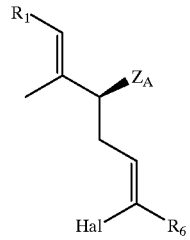

to effect coupling to generate the precursor; and subjecting said precursor to suitable conditions to effect macrocyclization and optionally deprotection to generate the desired compound.

In certain embodiments, the method includes a step of deprotection to generate a compound wherein $R_2$ and $R_3$ are hydrogen. In certain other embodiments, $R_1$ is —CY=CHX or hydrogen, substituted or unsubstituted, linear or branched, cyclic or acyclic, alkyl, heteroalkyl, phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl, wherein X is hydrogen, linear or branched, substituted or unsubstituted, cyclic or acyclic, alkyl, heteroalkyl, phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl. In still other embodiments, the aliphatic, heteroaliphatic, aryl or heteroaryl group is further substituted with a photoactivatable group or with one or more of hydroxy, thio, amino, substituted amino, aldehyde, carboxylic acid, alkenyl, iminio, or diazo. In yet other embodiments, M is O, $R_1$ is —CY=CHX, Y is methyl and X is 4-thiazolyl substituted at the 2-position by —(C=O)H, methyl, or —$(CH_2)_n$OH, and n is 0–5. In still other embodiments, X is 4-thiazolyl substituted at the 2- and 5-positions by methyl. In yet other embodiments, $R_7$-$R_{11}$ are each independently selected from the group consisting of hydrogen, linear or branched alkyl, alkoxyalkyl, aryloxyalkyl, or $Si(R_A)_3$, wherein each occurrence of $R_A$ is independently branched or unbranched, substituted or unsubstituted aliphatic or heteroaliphatic, or substituted or unsubstituted aryl or heteroaryl. In still other embodiments, the step of subjecting said first and second sectors to suitable conditions comprises subjecting said sectors to conditions to effect Suzuki coupling. In yet other embodiments, M is NH or O, and $R_6$ is a substituted or unsubstituted, cyclic or acyclic, branched or unbranched aliphatic or heteroaliphatic moiety, having 2 or more carbon atoms.

In certain embodiments for the method as described above, the present invention provides for the synthesis of the precursor compound having the following structure:

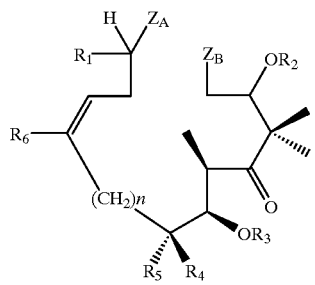

wherein $R_1$ is hydrogen, or is substituted or unsubstituted, linear or branched, cyclic or acyclic, aliphatic, heteroaliphatic, aryl, heteroaryl, aryl substituted aliphatic, or aryl substituted heteroaliphatic, or is —CY═CHX, wherein X is hydrogen, or is substituted or unsubstituted linear or branched, cyclic or acyclic, aliphatic, heteroaliphatic, aryl, heteroaryl, aryl substituted aliphatic or aryl substituted heteroaliphatic and wherein Y is hydrogen, or linear or branched chain alkyl; wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently H, phenyl, benzyl, linear or branched chain alkyl; wherein $R_6$ is independently hydrogen; $OR_A$; $SR_A$; $NR_AR_A$; $C(O)OR_A$; $C(O)R_A$; $CONHR_A$; $N_2$; $NR_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl; polymer; nitrogen protecting group; oxygen protecting group; sulfur protecting group; or carbon protecting group; wherein n is 0, 1, 2 or 3; wherein $Z_A$ is $OR_7$, $NHR_8$, or $N_3$, and $Z_B$ is $CO_2R_9$ or $COSR_9$, wherein each occurrence of $R_7$, $R_8$, $R_9$, $R_{10}$, or $R_{11}$ is independently hydrogen, an oxygen protecting group or a nitrogen protecting group, said method comprising:

providing a first sector having the structure:

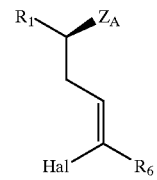

wherein $R_1$, $R_6$, and $Z_A$ are as defined above; providing a second sector having the structure:

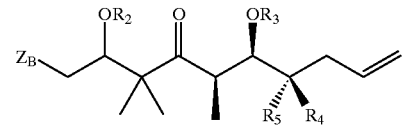

wherein $R_2$, $R_3$, $R_4$, and $R_5$ are as defined above, and wherein $Z_B$ is $CO_2R_9$ or $COSR_9$; wherein the step of providing a second sector further comprises:

protecting a ketoaldehyde having the structure:

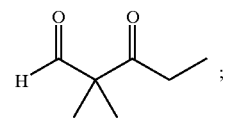

to generate a protected aldehyde and subsequently reacting said protected aldehyde with a compound having a structure:

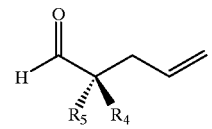

under suitable conditions to effect condensation to generate an aldol having the structure:

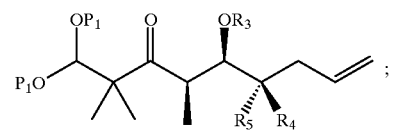

hydrolyzing the protected acetal group to generate a ketoaldehyde having the structure:

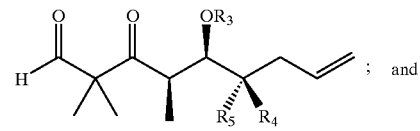

and reacting said ketoaldehyde under suitable conditions to effect a second aldol reaction, and optionally protecting the C3 alcohol to generate the second sector having the structure:

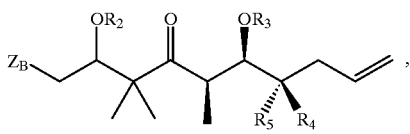

wherein $Z_B$, and $R_2$–$R_5$ are as defined above;

reacting said first and second sectors under suitable conditions to effect coupling to generate the precursor. In certain embodiments of the invention, $R_1$ is CY=CHX, Y is hydrogen or alkyl, and X is 4-thiazolyl substituted at the 2-position by linear or branched alkyl or generate the precursor. In certain embodiments of the invention, $R_1$ is CY=CHX, Y is hydrogen substituted by —(CH$_2$)$_n$OH, n is 0–5; and $R_6$ is independently hydrogen; OR$_A$; SR$_A$; NR$_A$R$_A$; C(O)OR$_A$; C(O)R$_A$; CONHR$_A$; N$_3$; N$_2$R$_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl. In still other embodiments of the invention, M is NH or O, and $R_6$ is a substituted or unsubstituted, cyclic or acyclic, branched or unbranched aliphatic or heteroaliphatic moiety, having 2 or more carbon atoms. In certain embodiments, $Z_A$ is N$_3$, and the method optionally further comprising a step of reacting the azide under suitable conditions to generate a protected amine. In certain other embodiments, the method further comprises a step of deprotecting the precursor compound to generate a free hydroxy acid precursor, or an amino acid precursor.

DEFINITIONS

Figure 1:
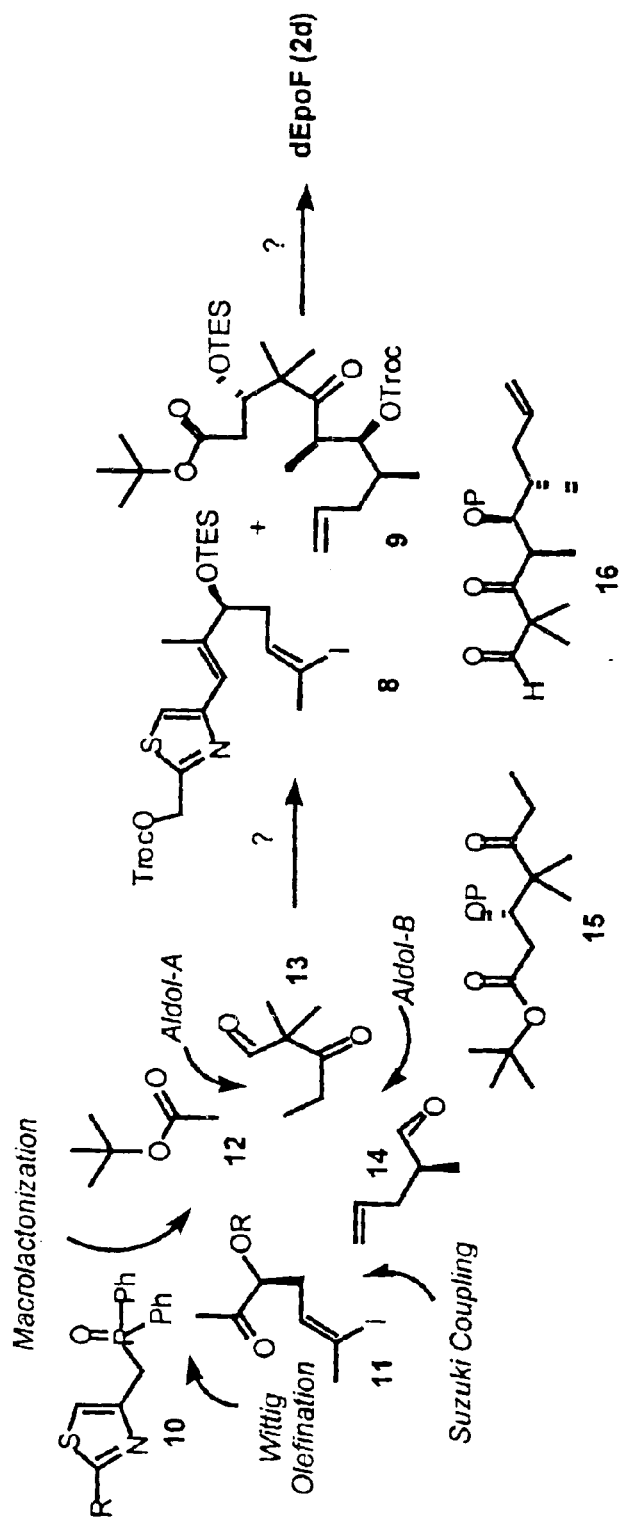
FIG. 1 depicts a modular plan for the synthesis of epothilones and analogues thereof using an aldol coupling reaction for the synthesis of the acyl sector.

As discussed above, the present invention provides a novel class of compounds useful for the treatment of cancer and other proliferative conditions related thereto. Compounds of this invention comprise those, as set forth above and described herein, and are illustrated in part by the various classes, subgenera and species disclosed elsewhere herein.

It will be appreciated by one of ordinary skill in the art that numerous asymmetric centers exist in the compounds of the present invention. Thus, inventive compounds and pharmaceutical compositions thereof may be in the form of an individual enantiomer, diastereomer or geometric isomer, or may be in the form of a mixture of stereoisomers. Additionally, in certain preferred embodiments, as detailed herein, the method of the present invention provides improved methods for the efficient synthesis of epothilones and analogues thereof.

Additionally, the present invention provides pharmaceutically acceptable derivatives of the foregoing compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of cancer and/or the inhibition of the growth of or the killing of cancer cells. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

Unless otherwise specified, alkyl and other aliphatic groups preferably contain 1–6, or 1–3, contiguous aliphatic carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to methylthio, ethylthio, propylthio, isopropylthio, n-butylthio, and the like.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$-$C_3$ alkylamino groups are utilized in the present invention.

Some examples of substituents of the above-described aliphatic (and other) moieties of compounds of the invention include, but are not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, -alkyl-amino, thio, aryl-thio, heteroarylthio, benzyl-thio, alkyl-thio, or methylthiomethyl. Additional examples of generally applicable substituents are illustrated by the specific embodiments shown in the Examples which are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted. F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quatemized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

"Labeled": As used herein, the term "labeled" is intended to mean that a compound has at least one element, isotope or chemical compound attached to enable the detection of the compound. In general, labels fall into three classes: a) isotopic labels, which may be radioactive or heavy isotopes, including, but not limited to, $^{67}$Ga, $^{99m}$Tc (Tc-99 m), $^{111}$In, $^{123}$I, $^{125}$I, $^{169}$Yb and $^{186}$Re; b) immune labels, which may be antibodies or antigens; and c) colored or fluorescent dyes. It will be appreciated that the labels may be incorporated into the compound at any position that does not interfere with the biological activity or characteristic of the compound which is being detected. In certain embodiments of the invention, photoaffinity labeling is utilized for the direct elucidation of intermolecular interactions in biological systems (e.g., to probe the epothilone binding site in a tubulin dimer). A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Polymer": The term "polymer", as used herein, refers to a composition comprising chains that may be open, closed, linear, branched or cross-linked of repeating units (monomers) that may be the same or different. It will be appreciated that in certain embodiments the term polymer refers to biopolymers, which, as used herein, is intended to refer to polymeric materials found in nature or based upon those materials found in nature, including, but not limited to nucleic acids, peptides, and mimetics thereof. In certain other embodiments, the term polymer refers to synthetic polymers, such as biodegradable polymers or other polymeric materials. It will be appreciated that polymeric solid supports are also encompassed by the polymers of the present invention. Inventive compounds can be attached to polymeric supports and thus certain synthetic modifications can be conducted on the solid phase. As used herein, the term "solid support" is meant to include, but is not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N-N'-bis-acryloylethylenediamine, and glass particles coated with a hydrophobic polymer. One of ordinary skill in the art will realize that the choice of particular solid support will be limited by the comparability of the support with the reaction chemistry being utilized. An exemplary solid support is a Tentagel amino resin, a composite of 1) a polystyrene bead crosslinked with divinylbenzene and 2) PEG (polyethylene glycol). Tentagel is a particularly useful solid support because it provides a versatile support for use in on-bead or off-bead assays, and it also undergoes excellent swelling in solvents ranging from toluene to water.

DETAILED DESCRIPTION OF THE INVENTION

As discussed above, the present invention provides novel epothilone analogues and methods for the synthesis thereof. In certain embodiments, the present invention provides 20- or 21- and 12-substituted epothilones and aza-analogues, pharmaceutical compositions, and methods of use of the epothilone analogues in the treatment of cancer. Unexpectedly, certain epothilones have been found to be effective not only in reversing multi-drug resistance in cancer cells, both in vitro and in vivo, but have been determined to be active as collateral sensitive agents, which are more cytotoxic towards MDR cells than normal cells, and as synergistic agents, which are more active in combination with other cytotoxic agents, such as vinblastin, than the individual drugs would be alone at the same concentrations. Remarkably, the desoxyepothilones of the invention have exceptionally high specificity as tumor cytotoxic agents in vivo, more effective and less toxic to normal cells than the principal chemotherapeutics currently in use, including Taxol®, vinblastin, adriamycin and camptothecin.

As disclosed previously, using totally synthetic derived drug, the present inventors were the first to conduct in vivo formulations of epothilone B. When it was found that EpoB itself exhibited worrisome toxicity profiles, the 12,13-desoxy compound was explored. Unexpectedly, dEpoB, while still highly cytotoxic and robust with respect to MDR activation, exhibited a more desirable toxicity profile. Significantly, experiments based on various mouse models have consistently demonstrated that dEpoB possesses remarkable therapeutic potential and is essentially curative against various sensitive and resistant tumors in xenografts. Due to its impressive in vivo profile, dEpoB has been advanced through toxicology evaluations in dogs, in expectation of human trials anticipating its development as an anticancer drug. Clearly, in building upon the inventors original pioneering recognition of the superior therapeutic profile of the 12,13-desoxy compounds, it was of interest to evaluate the in vivo efficacy of other analogues of epothilones. The ability to access significant quantities of these materials for biological evaluation, however, necessitated improved synthetic methodology. As disclosed herein, improved synthetic methods for the synthesis of a variety of epothilone macrolides, in particular 12,13-desoxyepothilones, are provided, which enables access to a variety of synthetic analogues of epothilones.

Inventive Epothilones and Analogues Thereof

Significantly, as discussed above, the present invention provides novel compounds and methodology that enables the efficient synthesis of epothilones and analogues thereof. In one aspect, the invention provides novel compounds having the structure:

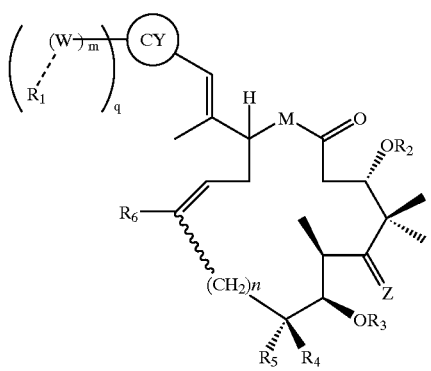

wherein M is NH or O;
wherein CY is an aryl or heteroaryl moiety;
wherein q is 1–5;
wherein each occurrence of W is independently absent; —NH—; C=O; C=S; —O—; —S—; or $C(V)_2$;
wherein each occurrence of V is independently hydrogen; halogen; —OH; —SH; amino; or substituted or unsubstituted alkyl, heteroalkyl, aryl or heteroaryl;
wherein each occurrence of m is independently 1–5;
wherein the bond W—$R_1$ represents a single bond or a double bond;
wherein each occurrence of $R_1$ is independently hydrogen; $OR_A$; $SR_A$; $NR_AR_A$; $C(O)OR_A$; $C(O)R_A$; $CONHR_A$; $N_3$; $N_2$; $N_2R_A$; halogen; substituted or unsubstituted, cyclic or acyclic, linear or branched aliphatic, heteroaliphatic, aryl, or heteroaryl; polymer; carbohydrate; photoaffinity label; or radiolabel; wherein each occurrence of $R_A$ is independently hydrogen; linear or branched, substituted or unsubstituted, cyclic or acyclic, aliphatic, heteroaliphatic, aryl or heteroaryl; nitrogen protecting group; carbon protecting group; oxygen protecting group; sulfur protecting group; polymer; carbohydrate; photoaffinity label; or radiolabel;
wherein $R_2$ and $R_3$ are each independently hydrogen; substituted or unsubstituted aliphatic, heteroaliphatic, aryl, or heteroaryl; acyl; aroyl; benzoyl; or $Si(R_B)_3$, wherein each occurrence of $R_B$ is independently substituted or unsubstituted, cyclic or acyclic, linear or branched aliphatic, heteroaliphatic, aryl or heteroaryl;
wherein $R_4$ and $R_5$ are each independently hydrogen; or substituted or unsubstituted, linear or branched, cyclic or acyclic aliphatic, heteroaliphatic, aryl, or heteroaryl, optionally substituted by one or more of hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently hydrogen, phenyl, benzyl, linear or branched chain alkyl;
wherein $R_6$ is independently hydrogen; $OR_A$; $SR_A$; $NR_AR_A$; $C(O)OR_A$; $C(O)R_A$; $CONHR_A$; $N_2$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; nitrogen protecting group; carbon protecting group; oxygen protecting group; sulfur protecting group; linear or branched, substituted or unsubstituted, cyclic or acyclic, aliphatic, heteroaliphatic, aryl or heteroaryl; polymer; carbohydrate; photoaffinity label; or radiolabel;

wherein Z is O, $N(OR_E)$ or $N-NR_FR_G$; wherein $R_E$, $R_F$, and $R_G$ are each independently a substituted or unsubstituted, linear or branched, cyclic or acyclic aliphatic moiety; and
wherein n is 0, 1, 2, or 3.

It will be appreciated that the present invention encompasses any stereoisomers and/or double bond isomers of the compounds depicted above. In certain embodiments, compounds having the structure below are provided:

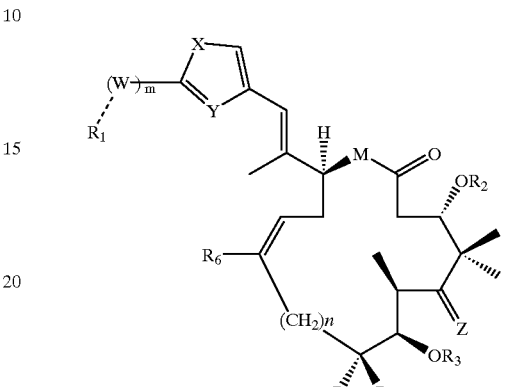

In certain embodiments, X is S; Y is N; m is 1; and n is 3. In certain other embodiments, $R_6$ is methyl or ethyl. In still other embodiments, M is O. It yet other embodiments, the present invention includes those compounds wherein $R_6$ is H, methyl, ethyl, n-propyl, n-butyl, n-hexyl,

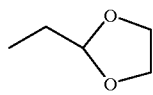

or $(CH_2)_p$—OH, wherein p is 1–6.

It will also be appreciated that the present invention also includes those compounds in which $R_6$ is a substituted or unsubstituted, cyclic or acyclic, branched or unbranched aliphatic or heteroaliphatic moiety, having 2 or more carbon atoms. In still other embodiments, $R_6$ is ethyl, n-propyl, n-butyl, n-hexyl,

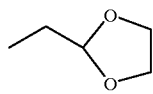

or $(CH_2)_p$—OH, wherein p is 1–6. Also provided herein are those compounds as described above and herein, wherein $R_1$ is $OR_A$ and $R_A$ is hydrogen, linear or branched, substituted or unsubstituted, cyclic or acyclic aliphatic or heteroaliphatic, or substituted or unsubstituted aryl or heteroaryl; W is —$CH_2$—; and m is 1. In still other embodiments, W is (C=O), m is 1, and $R_1$ is hydrogen. In yet other embodiments, W is —CH2— and $R_1$ is $NR_AR_A$, wherein each occurrence of $R_A$ is independently a nitrogen protecting group, hydrogen or lower alkyl. In still other embodiments, W is —$CH_2$— and $R_1$ is an alkyl or alkylene moiety substituted by one or more hydroxyl moieties. In certain other embodiments, for each of the compounds as described above and herein, $R_2$ and $R_3$ are each hydrogen; $R_4$ is methyl and $R_5$ is hydrogen; and Z is O. In yet other embodiments, $R_1$ is a photoaffinity label, and in certain embodiments the photoaffinity label is the photoactivatable group o-, m- or p-azidobenzoyl, substituted by one or more halogen moieties. In certain embodiments, the photoactivatable group is 4-azido-2,3,5,6-tetrafluorophenylacyl.

It will also be appreciated that the present invention provides certain isomers of epothilones including those compounds having the structure:

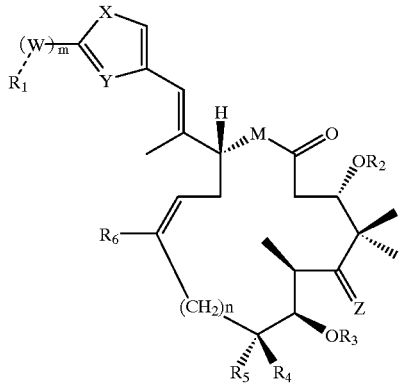

In certain other embodiments, isomers having the following structure are provided:

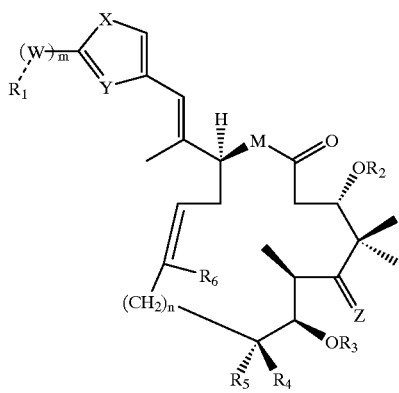

In still other embodiments, isomers having the following structure are provided:

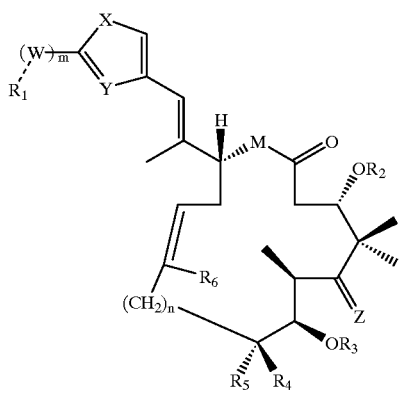

In certain other embodiments of the present invention, 21-hydroxylated compounds are provided, which compounds have the following structure:

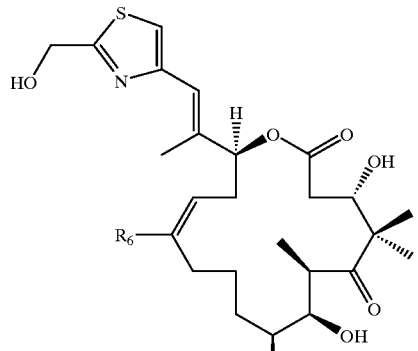

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel. In certain embodiments of the present invention, compounds are provided in which $R_6$ is a substituted or unsubstituted, cyclic or acyclic, branched or unbranched aliphatic or heteroaliphatic moiety, having 2 or more carbon atoms. In certain other embodiments, compounds are provided in which $R_6$ is H, methyl, ethyl, n-propyl, n-butyl, n-hexyl,

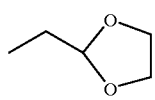

or $(CH_2)_p$—OH, wherein p is 1–6. In still other embodiments, compounds are provided in which $R_6$ is ethyl, n-propyl, n-butyl, n-hexyl,

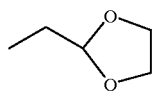

or $(CH_2)_p$—OH, wherein p is 1–6.

In still another embodiment of the present invention, $R_6$ is methyl and the compound has the structure:

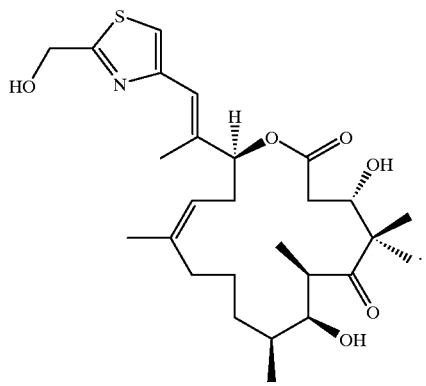

In still other embodiments, $R_6$ is ethyl and inventive compounds have the structure:

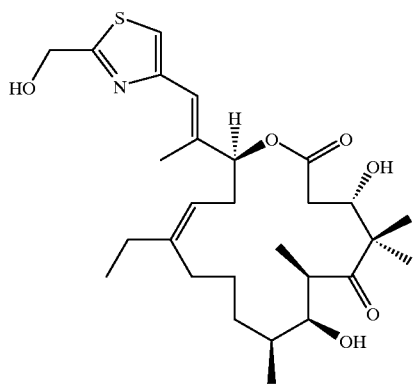

In yet other embodiments, inventive compounds have the structure:

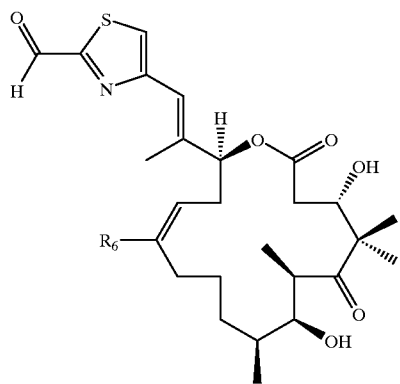

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel.

In still other embodiments, the present invention provides compounds having the general structure:

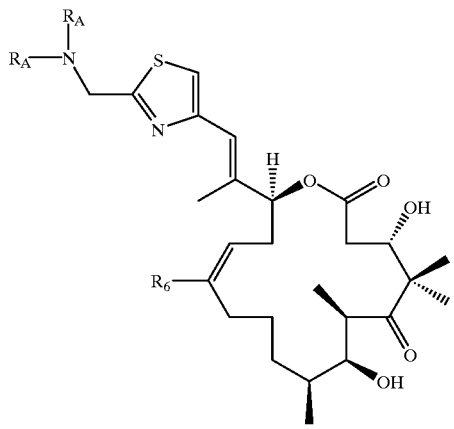

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; nitrogen protecting group; polymer; carbohydrate; photoaffinity label; or radiolabel.

It will be appreciated that the the ability to access large quantities of functionalized compounds enables further attachment to polymeric and/or therapeutic moieties. Thus, in another embodiment, the present invention contemplates the attachment of the compounds as described herein to polymers; carbohydrates; photoaffinity labels; or radiolabels. In one embodiment, compounds having the following formula are provided:

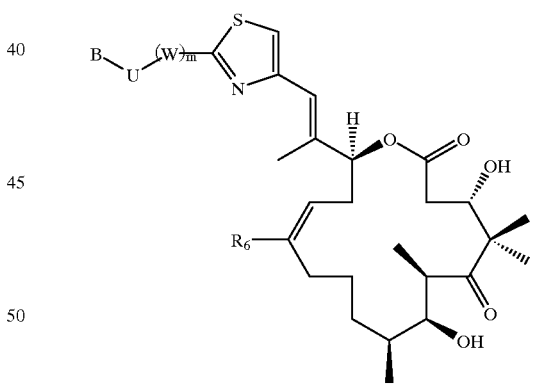

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel; wherein W or U are each independently absent; —NH—; C=O; C=S; —O—; —S—; or $C(V)_2$; wherein each occurrence of V is independently hydrogen; halogen; —OH; —SH; amino; or substituted or unsubstituted alkyl, heteroalkyl, aryl or heteroaryl; and
wherein B is a polymer; carbohydrate; photoaffinity
label; or radiolabel.

In another aspect, the present invention provides multiply presented compounds, and in one embodiment the present invention provides a composition comprising a polymeric backbone; and
- two or inventive compounds, wherein the two or inventive compounds are the same or different, whereby said two or more compounds are linked to the polymeric backbone directly or through a linker, and wherein the two or more compounds are linked through the 12-position, the 20-position or the 21-position of the compound.

In certain embodiments, the polymeric backbone is a dendrimer, a peptide, or a biodegradable polymer.

In certain other embodiments, a dimeric desoxyepothilone having the following structure is provided:

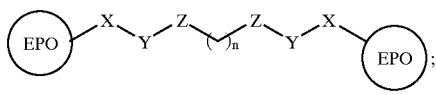

wherein EPO comprises a compound of claim 1, linked through functionality present in the 12- 20- or 21-position; wherein X is methylene , (C=O), or is absent; wherein Y is (C=O), O, NH or is absent; wherein Z is (C=O), NH, O, or is absent; and n is 0–5.

In certain other embodiments, EPO has the structure:

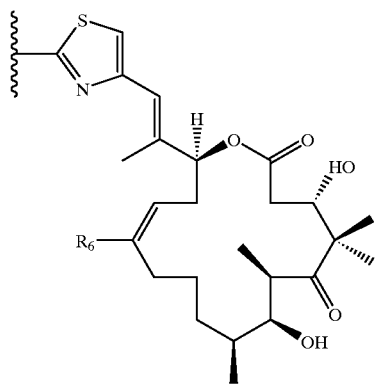

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; polymer; carbohydrate; photoaffinity label; or radiolabel.

In still other embodiments, $R_6$ is a substituted or unsubstituted, cyclic or acyclic, branched or unbranched aliphatic or heteroaliphatic moiety, having 2 or more carbon atoms.

In yet other embodiments, X is methylene, Y is O, and Z is (C=O).

In still other embodiments, X is methylene, Y is NH, and Z is absent. In still further embodiments, X is (C=O), Y is O or NH, and Z is absent.

Novel Synthetic Methodology

As described above, also provided by the present invention is novel methodology that enables the efficient synthesis of epothilones and related compounds and enables access to a variety of analogues. In general, the present invention provides novel methods by which the necessary acyl and alkyl sectors for macrocyclization can be provided in significant quantities, representing improved methods from previously reported synthetic methodologies as disclosed in Ser. Nos. 08/986,025 and 09/257,072, the entire contents of which are hereby incorporated by reference.

Figure 2:
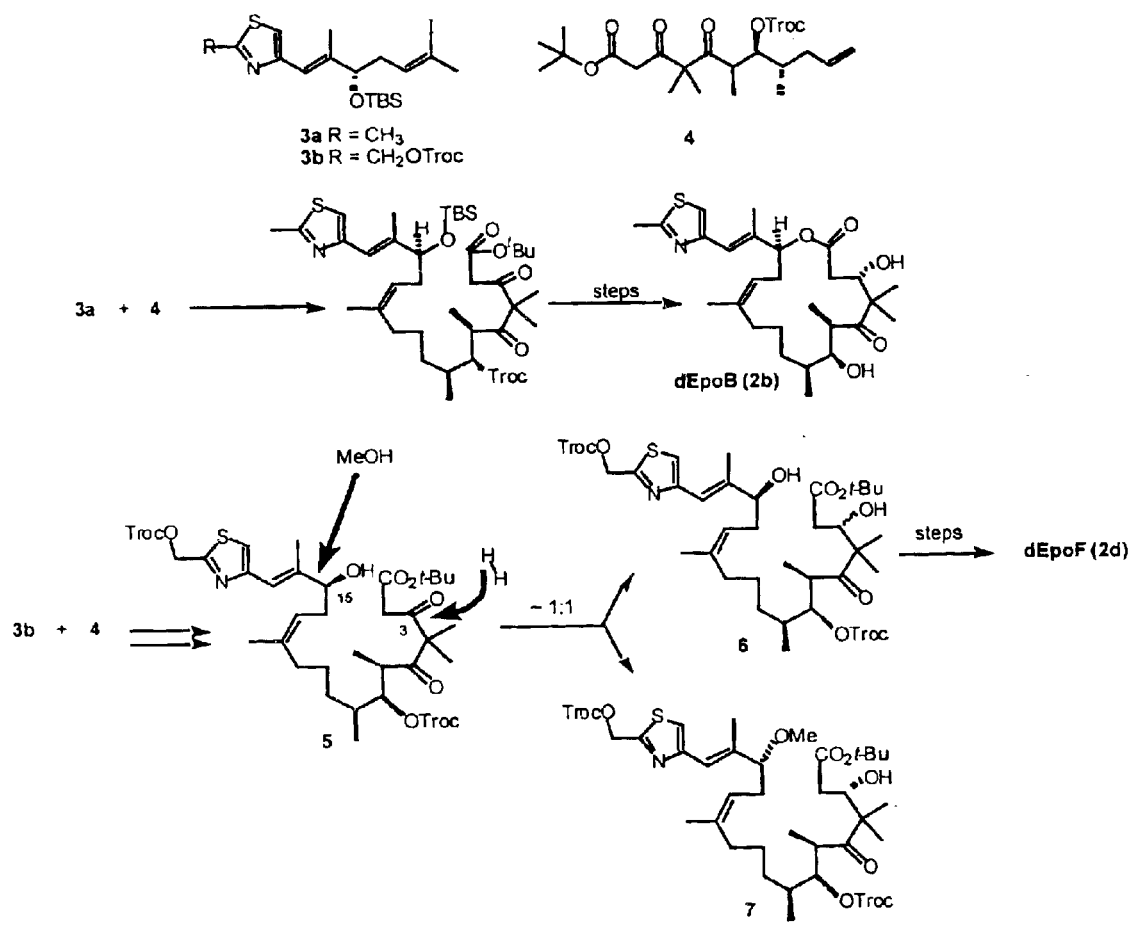
FIG. 2 depicts the synthesis of desoxyepothilone F via Suzuki coupling, Noyori reduction and macrolactonization.

As depicted in FIG. 1 (and as described in Example 2 for the alternative syntheses of dEpoF and dEpoB), the present invention provides, in one aspect, a novel synthesis for epothilones and analogues thereof. This approach involves the use of an acyl sector, as described herein, wherein the C3 in the acyl sector is already reduced and poised for coupling with the alkyl sector. Additionally, a more convenient and modular approach to the alkyl sector is provided. The two fragments can then be coupled, in certain embodiments by a B-alkyl Suzuki coupling reaction, and then advanced to macrolactone or macrolactam by a macrocyclization reaction. In certain embodiments, a Yamaguchi macrocyclization is utilized similarly to the reaction employed for previous syntheses of dEpoB (as described in pending patent application Ser. Nos. 08/986,025 and 09/257,072, the entire contents of which are hereby incorporated by reference) and dEpoF (as described in Example 1, and as shown in FIG. 2).

Thus, in one aspect of the present invention, efficient methods for preparing an intermediate for the O-Alkyl segment is provided, which intermediate compound has the structure:

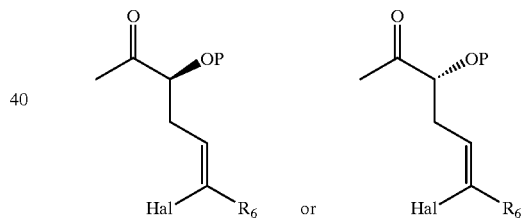

wherein P is an oxygen protecting group; wherein Hal is a halogen; and wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; polymer; nitrogen protecting group; oxygen protecting group; sulfur protecting group or carbon protecting group; or linear or branched, substituted or unsubstituted, cyclic or acyclic, aliphatic, heteroaliphatic, aryl or heteroaryl.

Figure 3:
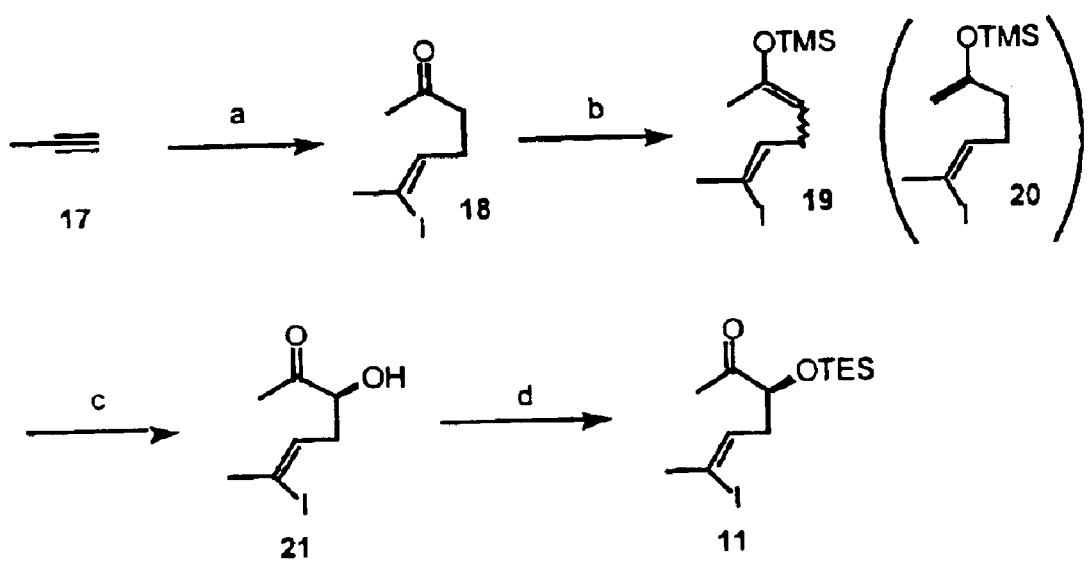
FIG. 3 depicts a catalytic asymmetric route to ketone 11: Reagents and conditions: (a) i) 9-BBN-I, Hexanes, ii) methyl vinyl ketone, iii) 3 N NaOH, Toluene, 100° C., 65%; (b) TMSI-HMDS, CH$_2$Cl$_2$, –20° C. to rt; (c) 1 mol % OsO$_4$, AD-mix-α, MeSO$_2$NH$_2$, t-BuOH-H$_2$O (1:1), 55% for two steps; (d) TESCl, imidazole, DMF, 85%.

It will be appreciated that the synthesis of these structures can be achieved in one embodiment via asymmetric catalytic oxygenation (see, FIG. 3 for the synthesis of one isomer). In this method, an asymmetric catalytic oxygenation method is employed to install the C15 center and iodoboration of an alkyne is effected to implement the (Z)-alkene geometry. In general, the method of the invention comprises:

a) providing a haloketone having the structure:

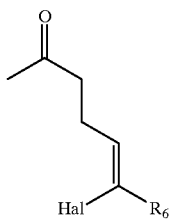

b) subjecting said haloketone to conditions to generate enol ethers and subsequently hydroxylating under suitable conditions to prepare a hydroxyketone having the structure:

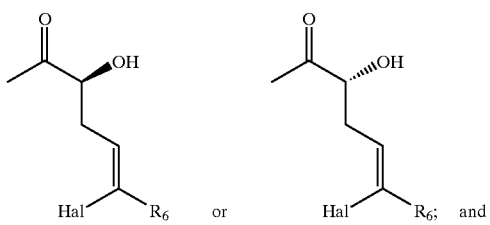

c) protecting the hydroxyketone under suitable conditions to form the compound:

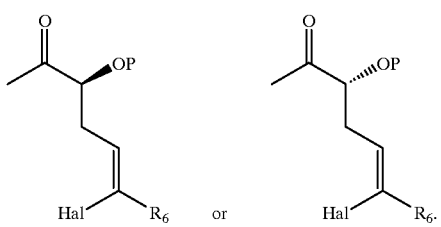

It will be appreciated that, depending on the reagent employed in the asymmetric hydroxylation reaction, either stereoisomer can be provided, as detailed above, for use in the preparation of inventive epothilones and analogues thereof. In certain embodiments, the step of hydroxylating comprises reacting the haloketone using asymmetric catalyst to effect asymmetric dihydroxylation, preferably in the presence of $OsO_4$ and AD-mix-α, to generate a compound having the structure:

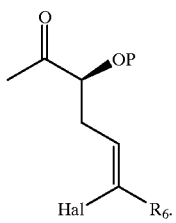

In certain other embodiments, the step of hydroxylating comprises reacting the haloketone using asymmetric catalyst to effect asymmetric dihydroxylation, preferably conducted in the presence of $OsO_4$ and AD-mix-β, to generate a compound having the structure:

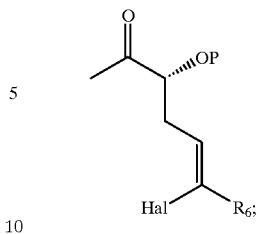

which compound is particularly useful for the synthesis of lactam derivatives, as described in more detail herein. It will also be appreciated that the present invention additionally contemplates those methods wherein the silyl enol ether is first provided.

In certain embodiments, for compounds employed in the method as described above, and herein, P is —$SiR_HR_JR_K$, wherein $R_H$, $R_J$, and $R_K$ are each ethyl. In certain other embodiments, for compounds employed in the method as described above, and herein, $R_6$ linear or branched, cyclic or acyclic, substituted or unsubstituted aliphatic or heteroaliphatic. In still other embodiments, $R_6$ is methyl, ethyl, n- or iso-propyl, phenyl or benzyl. In yet other embodiments, Hal is iodo.

As described in the Examples herein, and as depicted in FIG. 3, in one embodiment, this approach involves reacting propyne (17) with B-iodo-9-BBN and adding the resulting vinyl borant to methyl vinyl ketone to furnish ketone (18). Subsequent treatment of this compound with a reagent such as TMSI/HMDS afforded a 88:12 mixture of two silyl ether regioisomers 19 and 20. Asymmetric dihydroxylation of the mixture, using AD-mix-α, generated hydroxyketone 21. Significantly, it is possible using this procedure, to sustain the potentially vulnerable iodoalkene functionality during the osmium mediated dihydroxylation. Finally, triethylsilylation of 25 produced 18, completing the sequence in only 4 steps.

Figure 4:
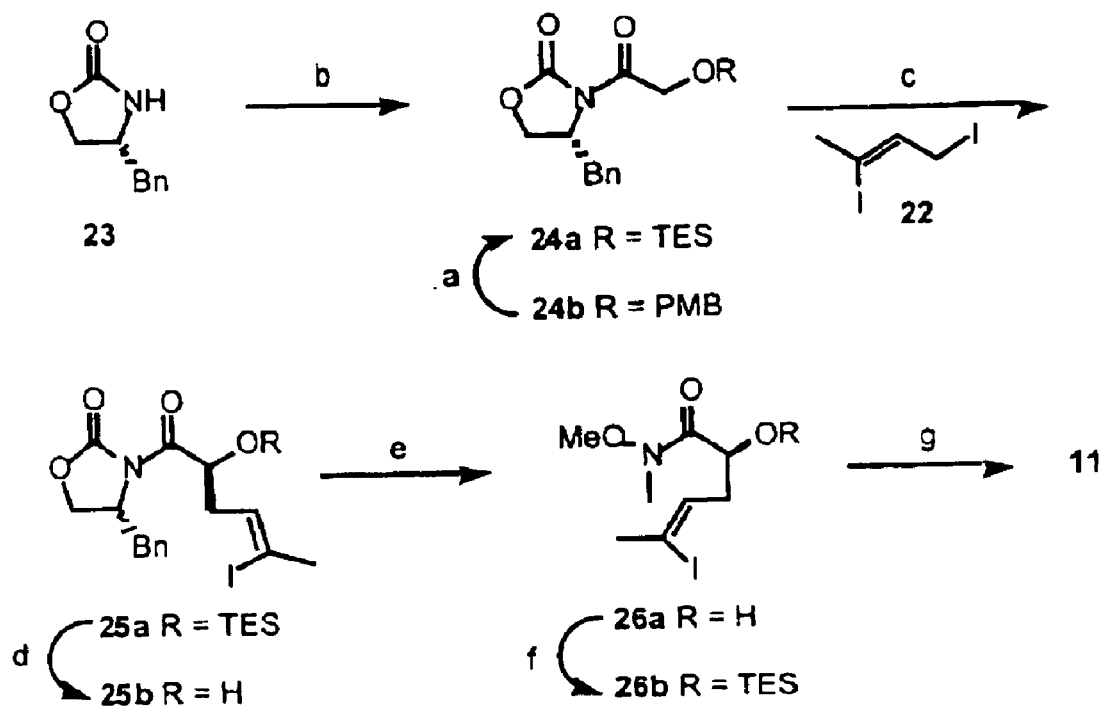
FIG. 4 depicts the stereoselective alkylation route to ketone 11: Reagents and conditions: (a) i) TiCl$_4$, CH$_2$Cl$_2$, DIPEA, 87%, ii) TESCl, Imidazole, DMF, 84%; (b) i) Glycolic acid, TESCl, NaH-TEA, ether, 0° C., then t-BuCOCl, –78° C., ii) n-BuLi, –78 ° C. to rt, 38~41%; (c) LHMDS, –78° C., THF, 81%; (d) AcOH:H$_2$O:THF (3:1:1), 86%; (e) i) CH$_3$ONHCH$_3$, AlMe$_3$, CH$_2$Cl$_2$ ii) TESCl, Imidazole, DMF, 88%; (g) MeMgBr, 0° C., 93%.

In still other embodiments of the present invention, it will be appreciated that the ketone can also be generated using an asymmetric alkylation reaction to establish the C15 configuration, as depicted in one embodiment, in FIG. 4.

In general, the method of the invention comprises the steps of:

a) preparing a glycolimide having the structure:

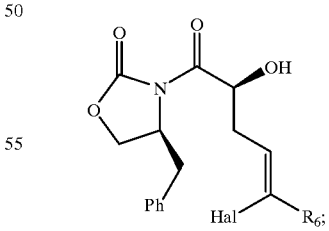

b) treating the glycolimide with a substituted hydroxylamine selected from the group consisting of N,O-(linear or branched chain $C_{1-8}$ alkyl,aryl) hydroxylamine, N,O-di-(linear or branched chain $C_{1-8}$) alkylhydroxylamine and N,O-aryl,arylhydroxylamine under suitable conditions to form an amide having the structure:

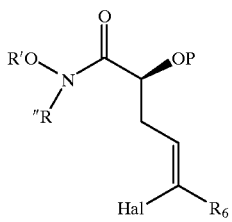

wherein R' and R" are each independently linear or branched chain $C_{1-8}$ alkyl or aryl; and c) reacting the amide with a substituted organometallic reagent under suitable conditions to form the compound.

In certain embodiments, P is $SiR_HR_JR_k$ and wherein $R_H$, $R_J$ and $R_K$ are each ethyl. In certain other embodiments, for compounds employed in the method as described above, and herein, $R_6$ linear or branched, cyclic or acyclic, substituted or unsubstituted aliphatic or heteroaliphatic. In still other embodiments, $R_6$ is methyl, ethyl, n- or iso-propyl, phenyl or benzyl. In yet other embodiments, Hal is iodo. In still other embodiments of the invention, the substituted organometallic reagent is a Grignard reagent, including, but not limited to MeMgBr or MeMgCl.

As depicted in FIG. 4, in one embodiment of the invention, ketone 18 was provided using asymmetric alkylation starting with the synthesis of the silylated glycolate from a known PMB derivative 24b which was obtained from 23 in 3 steps. In certain embodiments, 23 can be converted to 24a in multi-gram scales by a one flask procedure involving in situ formation of a mixed anhydride. Subsequent treatment of lithio 24a with diiodide 22 at −78° C. affords the desired 25a as a single isomer. After removal of the TES group, formation of Weinreb amide 26a is effected by simultaneous detachment of the chiral auxiliary, and subsequent protection and Grignard addition affords 11.

The ability to access large quantities of either stereoisomer of the ketone as described above also enables the synthesis of large quantities of the vinyl halide depicted below:

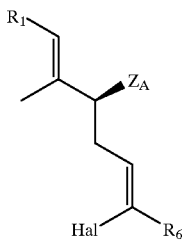

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic; wherein $Z_A$ is OP, SP, $N_3$ or NHP; wherein P is an oxygen, sulfur, or nitrogen protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; or polymer.

In certain embodiments, where $Z_A$ is OP, the method of the invention comprises:

a) preparing a phosphine oxide having the structure:

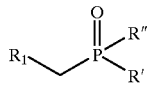

wherein R' and R" are independently $C_{1-8}$ linear or branched chain alkyl, or a substituted or unsubstituted phenyl; aryloxy; alkoxy;

b) condensing the phosphine oxide with a ketone having the structure:

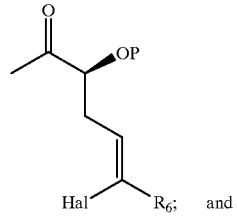

c) optionally reducing the ester formed in step b) under suitable conditions to form the compound.

In certain other embodiments of the present invention, where $Z_A$ is $N_3$ or NHP, the method of the invention comprises:

a) preparing a phosphine oxide having the structure:

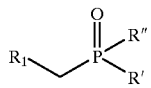

wherein R' and R" are independently $C_{1-8}$ linear or branched chain alkyl, or a substituted or unsubstituted phenyl; alkoxy; or aryloxy;

b) condensing the phosphine oxide with a ketone having the structure:

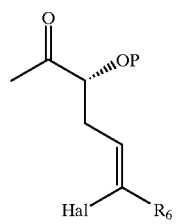

c) reacting the compound formed in step b) under suitable conditions to effect inversion to generate an azide, and optionally further treating the azide to generate a protected amine.

In certain embodiments, the inversion is effected using Thompson's procedure. In certain other embodiments, the azide is reduced by Staudinger reduction to generate a protected amine.

It will also be appreciated that the methodology as described above can be applied to a variety of analogues of epothilones, as described above and herein. For example, in certain embodiments, $R_1$ is hydrogen, linear or branched, substituted or unsubstituted, cyclic or acyclic, alkyl, heteroalkyl, phenyl, 4-thiazolyl, 2-furanyl, 3-furanyl, 4-furanyl, 2-pyridyl, 3-pyridyl, 4-pyridyl, imidazolyl, 4-oxazolyl, 3-indolyl or 6-indolyl. It will also be appreciated that each of these substituents can be substituted with one or more moieties, as described herein, and in certain embodiments of the invention, as described in more detail in the Examples herein, $R_1$ is substituted or unsubstituted 4-thiazolyl, and in certain embodiments, includes thiazolyl moieties substituted with one or two methyl functionalities at one or both of the 2- or 5-positions.

In one embodiment of the invention, and as described in more detail in Examples 1 and 2, the methodology as described above is utilized to synthesize 21-hydroxy analogues having the following structure:

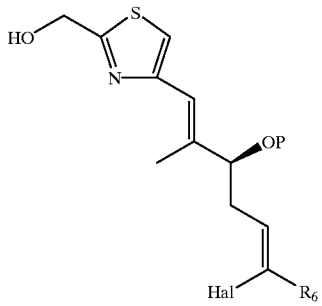

wherein P is a nitrogen protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; or polymer. The method comprises the steps of:

a) preparing a phosphine oxide having the structure:

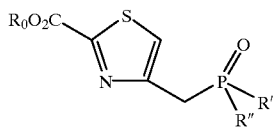

wherein $R_o$, R' and R" are independently $C_{1-8}$ linear or branched chain alkyl, or a substituted or unsubstituted phenyl; aryloxy; alkoxy;

b) condensing the phosphine oxide with a ketone having the structure:

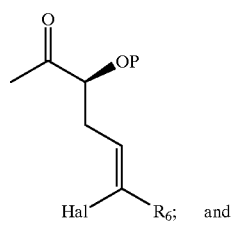

and c) reducing the ester formed in step b) under suitable conditions to form the compound.

It will be appreciated that for each of the vinyl halides and intermediates described above, in certain embodiments P is $SiR_HR_JR_K$ and $R_H$, $R_J$ and $R_K$ are each ethyl. In certain other embodiments, $R_6$ is linear or branched, cyclic or acyclic, substituted or unsubstituted aliphatic or heteroaliphatic. In still other embodiments, $R_6$ is methyl, ethyl, n- or iso-propyl, phenyl or benzyl. In yet other embodiments, Hal is iodo.

As discussed above, in yet another aspect of the present invention, a novel route to the O-Acyl fragment is provided, which fragment comprises the structure:

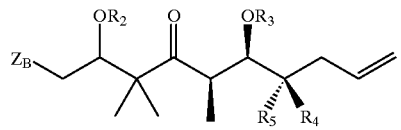

wherein $Z_B$ is $CO_2R_9$ or $COSR_9$, wherein $R_9$ is hydrogen or an oxygen or sulfur protecting group, wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; and wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroxyimino, or N-alkoxyimino, wherein $R_C$ and $R_D$ are each independently hydrogen, phenyl, benzyl, linear or branched chain alkyl; said method comprising:

protecting a ketoaldehyde having the structure:

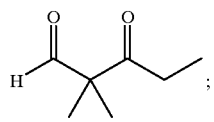

to generate a protected aldehyde and subsequently reacting said protected aldehyde with a compound having a structure:

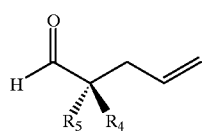

under suitable conditions to effect condensation to generate an aldol having the structure:

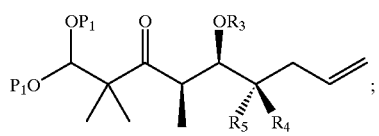

hydrolyzing the protected acetal group to generate a ketoaldehyde having the structure:

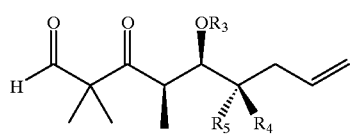

reacting said ketoaldehyde under suitable conditions to effect a second aldol reaction, and optionally protecting the C3 alcohol to generate a compound having the structure:

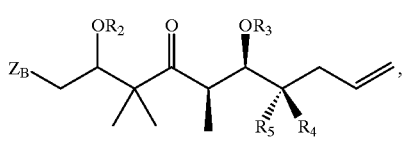

wherein $Z_B$, and $R_2$–$R_5$ are as defined above.

In certain embodiments, the step of reacting said ketoaldehyde under suitable conditions to effect a second aldol reaction comprises reacting said ketoaldehyde under stoichiometric conditions with a chiral titanium enolate. In certain other embodiments, the step of reacting said ketoaldehyde under suitable conditions to effect a second aldol reaction comprises reacting said ketoaldehyde with a catalytic reagent. It will be appreciated that a variety of catalytic reagents can be employed, including, but not limited to the Carreira catalyst and Mikami's chiral aldol catalyst. For example, an asymmetric aldol reaction can be utilized for construction of the right wing sector. (Duthaler, R. O.; Herold, P.; Lottenbach, W.; Oretle, K.; Reidiker, M. *Angew. Chem. Int. Ed. Engl.* 1989, 28, 495.). This method utilized a stoichiometric chiral additive for the aldol reaction.

In but one example, the first scheme below represents a catalytic Mukaiyama-type aldol reaction employing the Carreira catalyst (Carreira, E. M.; Singer, R. A.; Lee, W. *J. Am. Chem. Soc.* 1994, 116, 8837). EE's are generally high with this method using silyl ketene acetals with low catalyst loading (2–5 mol %). In this case a methyl ester will be produced which can be hydrolzed after the subsequent Suzuki coupling with aqueous base.

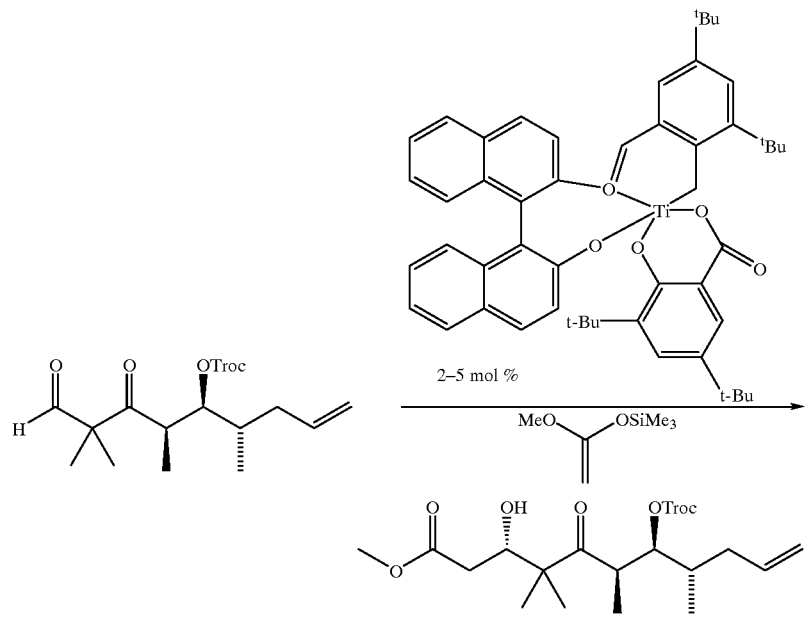

An additional method that can be utilized is based on Mikami's chiral aldol catalyst (Mikami, K.; Matsukawa, S. *J. Am. Chem. Soc.* 1994, 116, 4077). The catalyst in this series is easily prepared and the reaction is generally run at 0° C. and provides high enantioselectivity. This method produces a thioester which is easily hydrolysable after the subsequent Suzuki coupling.

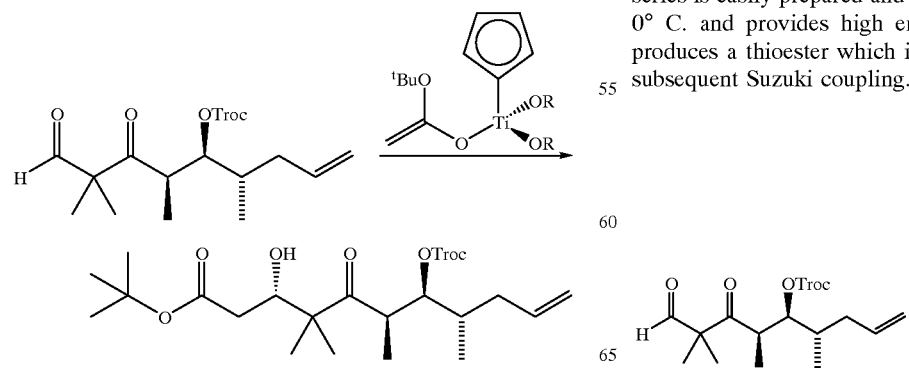

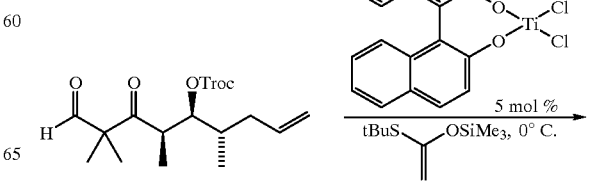

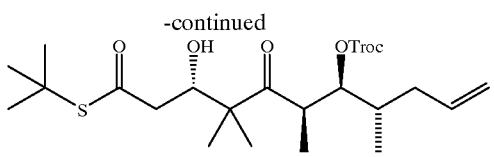

It will be appreciated that although the novel methodologies are described herein with reference to dEpoB and dEpoF and certain analogues thereof, the novel methodologies can also be employed for the synthesis of a wide range of other analogues including, but not limited to, oxazolinyl, pyridyl, and phenyl analogues and substituted derivatives thereof. It will be appreciated that the phosphine oxide, as described herein for the dEpoB and dEpoF precursor compounds, can also be prepared utilizing the appropriate oxazolinyl, pyridyl or phenyl starting materials, or materials for other analogues, as described herein. These phosphine oxides can be reacted with the ketone, as described herein, which ketone can also be diversified to generate 12-modified analogues. As described herein, the present invention provides efficient and modular syntheses of the ketone moiety and the acyl sector which can then be employed, utilizing appropriate phosphine oxides, for the syntheis of the macrocyclization precursor (via Suzuki coupling). Moreover, the ability to easily generate the modular ketone enables the synthesis of a variety of C12 analogues and thus the method enables the simultaneous modification of the 12-position and the aryl or heteroaryl sector during the course of the synthesis.

Thus, in another aspect, the novel methodologies as described herein can be utilized to synthesize compounds having the following general structure:

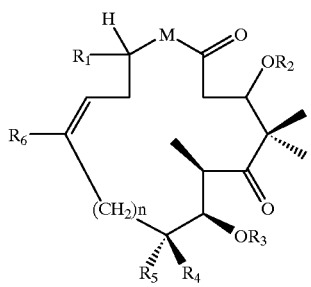

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic, or is —CY=CHX, wherein X is hydrogen, or is substituted or unsubstituted linear or branched, cyclic or acyclic, aliphatic, heteroaliphatic, aryl, heteroaryl, aryl substituted aliphatic or aryl substituted heteroaliphatic and wherein Y is hydrogen, or linear or branched chain alkyl; wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently H, phenyl, benzyl, linear or branched chain alkyl; wherein $R_6$ is independently hydrogen; $OR_A$; $SR_A$; $NR_AR_A$; $C(O)$ $OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; nitrogen protecting group; oxygen protecting group; sulfur protecting group; carbon protecting group; polymer; carbohydrate; photoaffinity label; or radiolabel; wherein M is NH or O; and wherein n is 0, 1, 2 or 3.

In general, the inventive compounds are prepared by:

providing a precursor having the structure:

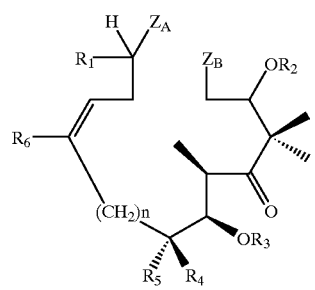

wherein $R_1$–$R_6$ are as defined above; $Z_A$ is $OR_7$, $NHR_8$, or $N_3$, and $Z_B$ is $CO_2R_9$ or $COSR_9$ wherein each occurrence of $R_7$, $R_8$, $R_9$, $R_{10}$, or $R_{11}$ is independently hydrogen, an oxygen protecting group or a nitrogen protecting group; and wherein the step of providing the precursor further comprises:

reacting a first compound having the structure:

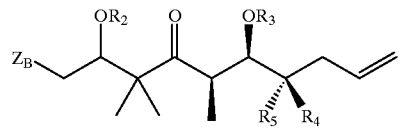

under suitable conditions with a second compound having the structure:

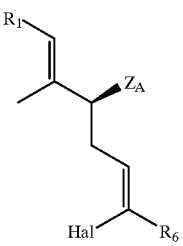

to effect coupling to generate the precursor; and subjecting said precursor to suitable conditions to effect macrocyclization and optionally deprotection to generate the desired compound.

It will be appreciated that the inventive precursors having the structure as depicted below, are, according to the method of the present invention, generally prepared using the novel acyl and alkyl sectors as described herein. For example, the precursor:

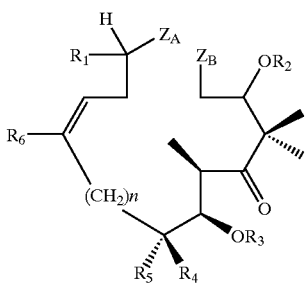

wherein $R_1$ is hydrogen, or is substituted or unsubstituted, linear or branched, cyclic or acyclic, aliphatic, heteroaliphatic, aryl, heteroaryl, aryl substitued aliphatic, or aryl substituted heteroaliphatic, or is —CY═CHX, wherein X is hydrogen, or is substituted or unsubstituted linear or branched, cyclic or acyclic, aliphatic, heteroaliphatic, aryl, heteroaryl, aryl substituted aliphatic or aryl substituted heteroaliphatic and wherein Y is hydrogen, or linear or branched chain alkyl; wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_C R_D$, N-hydroximino, or N-alkoxyimino, wherein $R_C$ and $R_D$ are each independently H, phenyl, benzyl, linear or branched chain alkyl; wherein $R_6$ is independently hydrogen; $OR_A$; $SR_A$; $NR_A R_A$; $C(O)OR_A$; $C(O)R_A$; $CONHR_A$; $N_3$; $N_2 R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; or polymer; wherein n is 0, 1, 2 or 3; wherein $Z_A$ is $OR_7$, $NHR_8$, or $N_3$, and $Z_B$ is $CO_2 R_9$ or $COSR_9$ wherein each occurrence of $R_7$, $R_8$, $R_9$, $R_{10}$, or $R_{11}$ is independently hydrogen, an oxygen protecting group or a nitrogen protecting group, is generally prepared by:

providing a first sector having the structure:

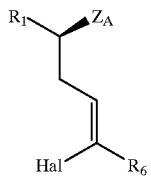

wherein $R_1$, $R_6$, and $Z_A$ are as defined above; providing a second sector having the structure:

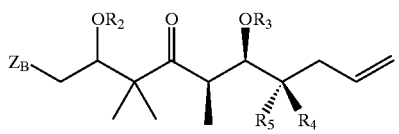

wherein $R_2$, $R_3$, $R_4$, and $R_5$ are as defined above, and wherein $Z_B$ is $CO_2 R_9$ or $COSR_9$; and reacting said first and second sectors under suitable conditions to effect coupling to generate the precursor.

In certain embodiments, as described above and herein, $R_1$ is CY═CHX, Y is hydrogen or alkyl, and X is 4-thiazolyl substituted at the 2-position, 5-position or both the 2- and 5-position by linear or branched alkyl or substituted by —$(CH_2)_n OH$, wherein n is 0–5; and $R_6$ is indepently hydrogen; $OR_A$; $SR_A$; $NR_A R_A$; $C(O)OR_A$; $C(O)R_A$; $CONHR_A$; $N_3$; $N_2 R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl; or polymer.

In certain other embodiments, M is NH, and $R_6$ is a substituted or unsubstituted, cyclic or acyclic, branched or unbranched aliphatic or heteroaliphatic moiety, having 2 or more carbon atoms. In still other embodiments, M is O, and wherein $R_6$ is a substituted or unsubstituted, cyclic or acyclic, branched or unbranched aliphatic or heteroaliphatic moiety, having 2 or more carbon atoms.

As described previously, in certain embodiments, the novel methodology is utilized to prepare macrolactam derivatives, and thus the method of the invention, when $Z_A$ is $N_3$, optionally further comprises a step of reacting the azide under suitable conditions to generate a protected amine. Additionally, the method of the invention optionally further comprises a step of deprotecting the precursor compound to generate a free hydroxy acid precursor, or an amino acid precursor, which precursors are then poised for macrolactamization or macrolactonization reactions, as described in more detail herein. The present invention further contemplates subjecting the cyclized compounds to steps of deprotecting and optionally further contemplates reacting the cyclized compounds under suitable conditions to generate the photoaffinity labeled, radiolabeled, carbohydrate-linked or polymer-linked compounds as described in more detail herein.

Synthesis of Functionalized Epothilone Analogs

As demonstrated herein, the ability to access large quantities of 21-hydroxy functionalized compounds (or other reactive analogues), provides a staging point for further functionalization and synthesis of each of the analogues as described generally and claimed herein. It will be appreciated that although certain hydroxy substituted thiazolinyl derivatives (based on dEpoB) are presented in certain exemplary embodiments herein, each of the methodologies as presented below and described herein, can also be applied to other novel analogues (e.g., hydroxyl substituted oxazolinyl, pyridyl, etc.), the syntheses of which are generally described above and herein.

Figure 5:
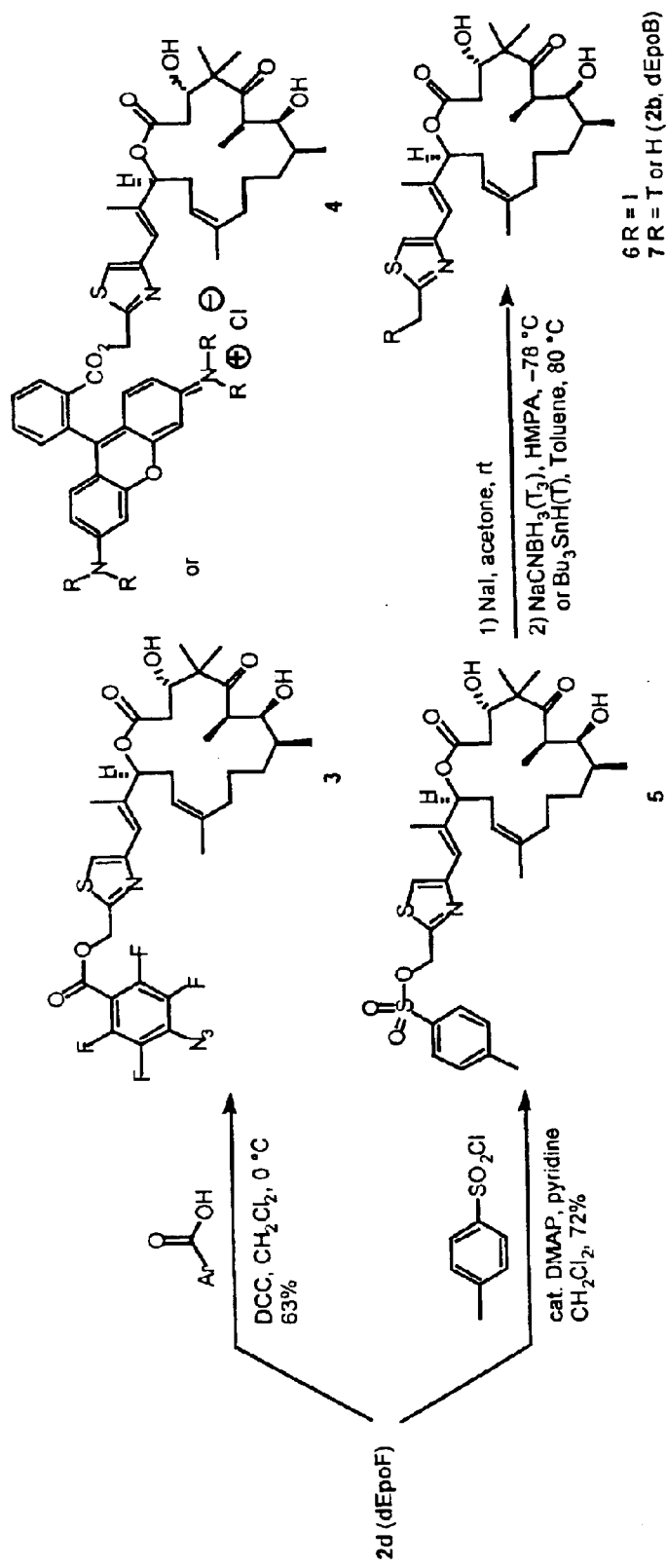
FIG. 5 depicts the synthesis and utilization of certain functionalized epothilone analogues.

In certain embodiments of the invention, labeled compounds are provided, and in certain embodiments, photoaffinity labeled or radiolabeled compounds are provided. It will be appreciated that a variety of photoaffinity radioactive reagents can be utilized. For example, in one embodiment of the invention, condensation of unprotected dEpoF with 4-azido-2,3,5,6-tetrafluorobenzoic acid is performed under the agency of DCC to afford photoaffinity labeled dEpoF 3 (as depicted in FIG. 5) which can be utilized to probe the epothilone binding site in a tubulin dimer. When a fluorescent aromatic acid (e.g., rhodamine) instead of the azidoacid is employed, the coupling reaction furnishes novel epothilone 4 containing a fluorophore. The fluorescent epothilone is particularly useful for binding studies and monitoring of subcelluar distribution of epothilone.

In certain other embodiments, a radioactive label is utilized. Significantly, the ability to functionalize 21-hydroxyl group without having recourse to the protection of the secondary hydroxyl groups provides efficient substitution at C21. Treatment of dEpoF with p-toluenebenzenesulfonyl chloride (p-TsCl) can be utilized to form C21-tosylate 5. Subsequent displacement with iodide yields 21-iodo-dEpoB 6, which in turn can be reduced with sodium cyanoborohydride or tributyltin hydride to dEpoB (2b). Thus, this sequence constitutes preparation of dEpoB via selective deoxygenation of dEpoF. Additionally, a radio-labeled epothilone (7, T-dEpoB) can be readily produced if a corresponding tritium reducing agent (e.g., $NaBT_3CN$, or $n-Bu_3SnT$) is employed as the hydride source. More importantly, a variety of nucleophiles can be introduced to C21 position by simple substitution reactions using tosylate 5 or iodide 6. In particular, the Staudinger reduction of 21-azido-epothilone ($R=N_3$ in 6), which has also been utilized for the synthesis of the ketones described above, permits an access to a new class of 21-amino-epothilone analogs ($R=NH_2$).

Figure 6:
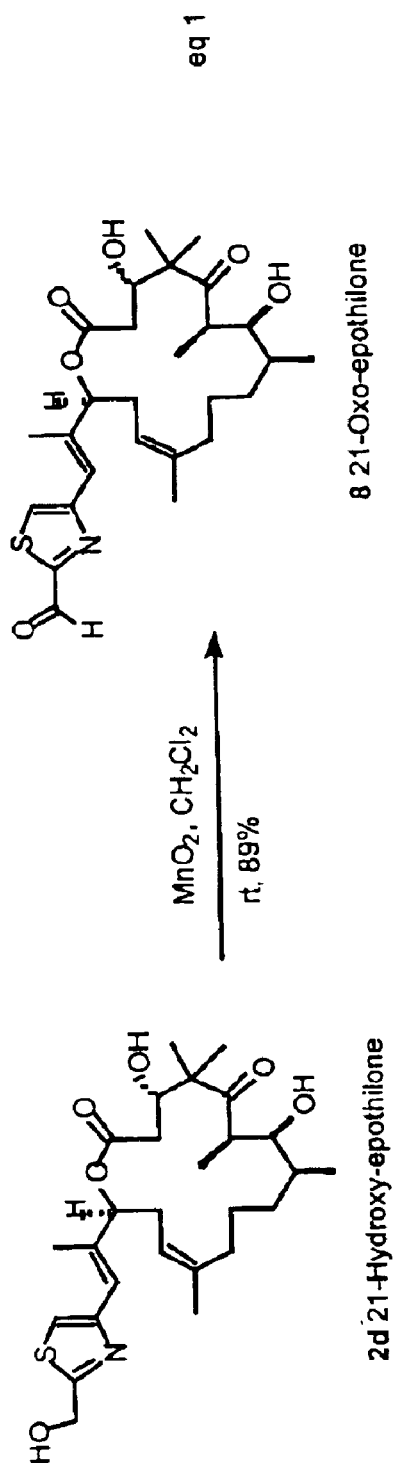
FIG. 6 depicts the conversion of 21-hydroxy-desoxyepothilone B to 21-oxo-desoxyepothilone B.

It will be appreciated that the selective functionalization at C21 is not limited to acylation or sulfonylation. For example, direct subjection of unprotected dEpoF (2d) to $MnO_2$ mediated oxidation conditions results in the formation of 21-oxo-epothilone B (8) in high yield as shown in FIG. 6, which is a useful analogue for further functionalization as depicted in FIG. 7

Figure 7:
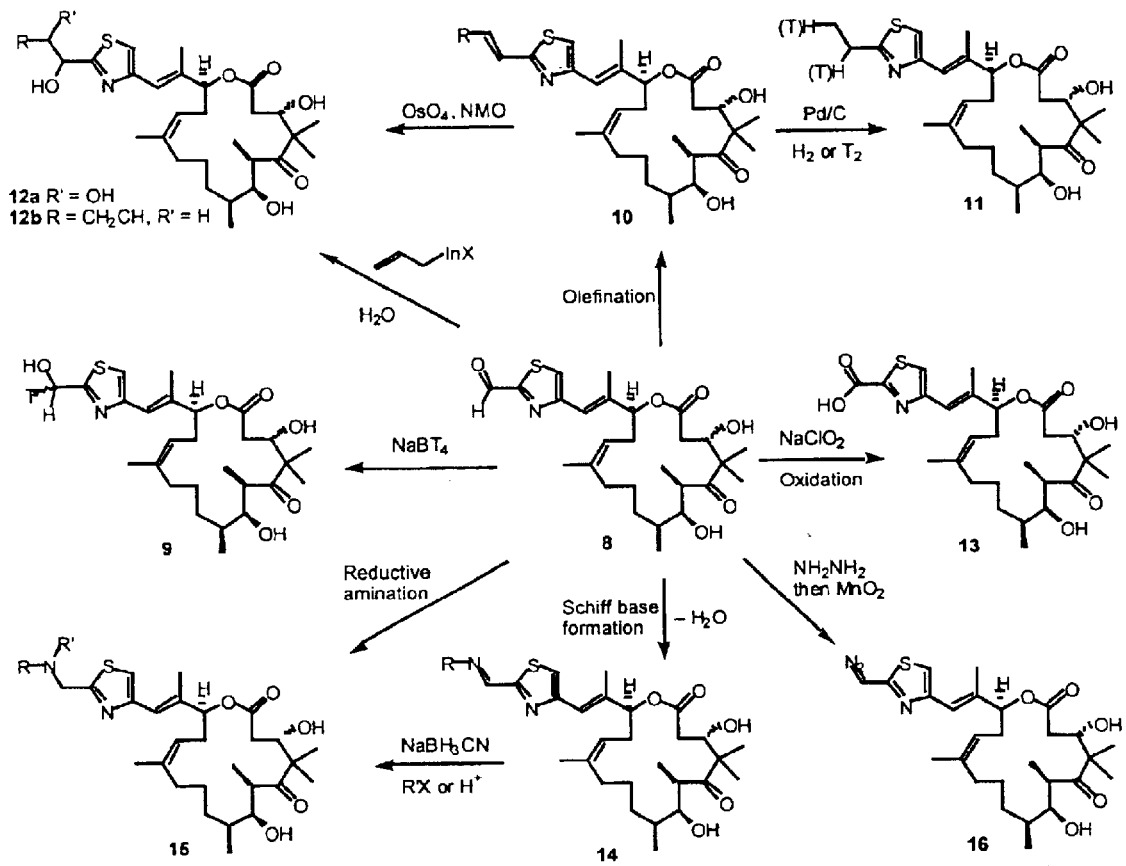
FIG. 7 depicts the synthesis of certain 21-functionalized 12,13-desoxyepothilone B analogues.

Thus, in other embodiments, epothilone derivatives can be accessed from the 21-oxo system as shown in FIG. 7. Simple reduction of aldehyde 8 with $NaBT_4$ (or $NaBCNT_3$, $NaB(OAc)_3T$) places a radioisotope in dEpoF such as 9. Wittig type olefination reactions generate 21-alkylidene-eopthilone 10 which can then be chemoselectively hydrogenated or dihydroxylated to give 11 and 12, respectively. Alternatively, an allyl unit can be readily added to unprotected aldehyde 8 in aqueous media to furnish 12b by the agency of an allylindium reagent. Once a terminal alkene function is installed such as 10 and 12b, its ability to participate in subsequent addition reactions can be utilized to produce more elaborated epothilone derivatives. For example, selective hydrogenation furnishes 11, which constitutes a "desoxy" analog of naturally occurring epothilone $B_{10}$. Isotopic labeling with tritium is also possible by employing $T_2$ instead of using hydrogen gas. On the other hand, 12a (or dihydroxylated 12b) is a water-soluble analog that provides advantages in formulation. A new epothilone with a carboxylic acid moiety, 13, is generated through the oxidation of aldehyde 8 by sodium chlorite.

In yet another embodiment, aldehyde 8 is reacted with an amine, and the corresponding Schiff base 14 is readily generated via dehydration. Schiff base 14 represents 21-imino-epothilone analogs, whose biological activity remains unreported. In particular, oxime derivatives (R=hydroxy or alkoxy in 14) are readily isolated and easily handled. Hydrazones ($R=NR_2$ in 14) derived form the reaction with hydrazine are another stable form of 21-imino-epothilones. Subsequent reduction with $NaBH_3CN$ readily converts imine 14 into 21-amino-epothilone 15. When methyl glycinate is employed as amine in this process, N-dEpoB-Gly methyl ester is formed as the product in good yield. Following the same protocol, the use of α-amino acid or oligopeptide for the reductive amination furnishes a novel epothilone-peptide conjugate that has many potential advantages.

Finally, addition of hydrazine to the aldehyde and subsequent oxidation of the resulting hydrazone generate 21-diazo-epothilone 16. Considering the lack of detailed information on the binding of epothilones to tubulin, the 21-diazo system may prove useful as a photoaffinity probe for the pertinent biological studies.

Synthesis of Water Soluble and Mutilply Presented Epothilone Analogs

The present invention additionally contemplates the formulation and/or funtionalization of the inventive compounds to permit more effective delivery of the therapeutic agent. One major problem in taxol chemotherapy arises from the hydrophobicity. Its marginal aqueous solubility necessitates recourse to formulation vehicles such as cremophores that pose their own risks and management issues. The relatively higher aqueous solubility imparted in epothilones and the additional increase by the hydroxy substitution at C21 have shown some promises. However, it would be more desirable if the aqueous solubility of epothilone is further enhanced to the extent that formulation epothilone in an aqueous medium is possible. The maintenance of biological activity by the C21-functionalized systems invites the possibility of attaching a solubility enhancer. It is anticipated that the auxiliary enhancer is cleaved and metabolized by cellular enzymes with concomitant release of the epothilone.

Figure 8:
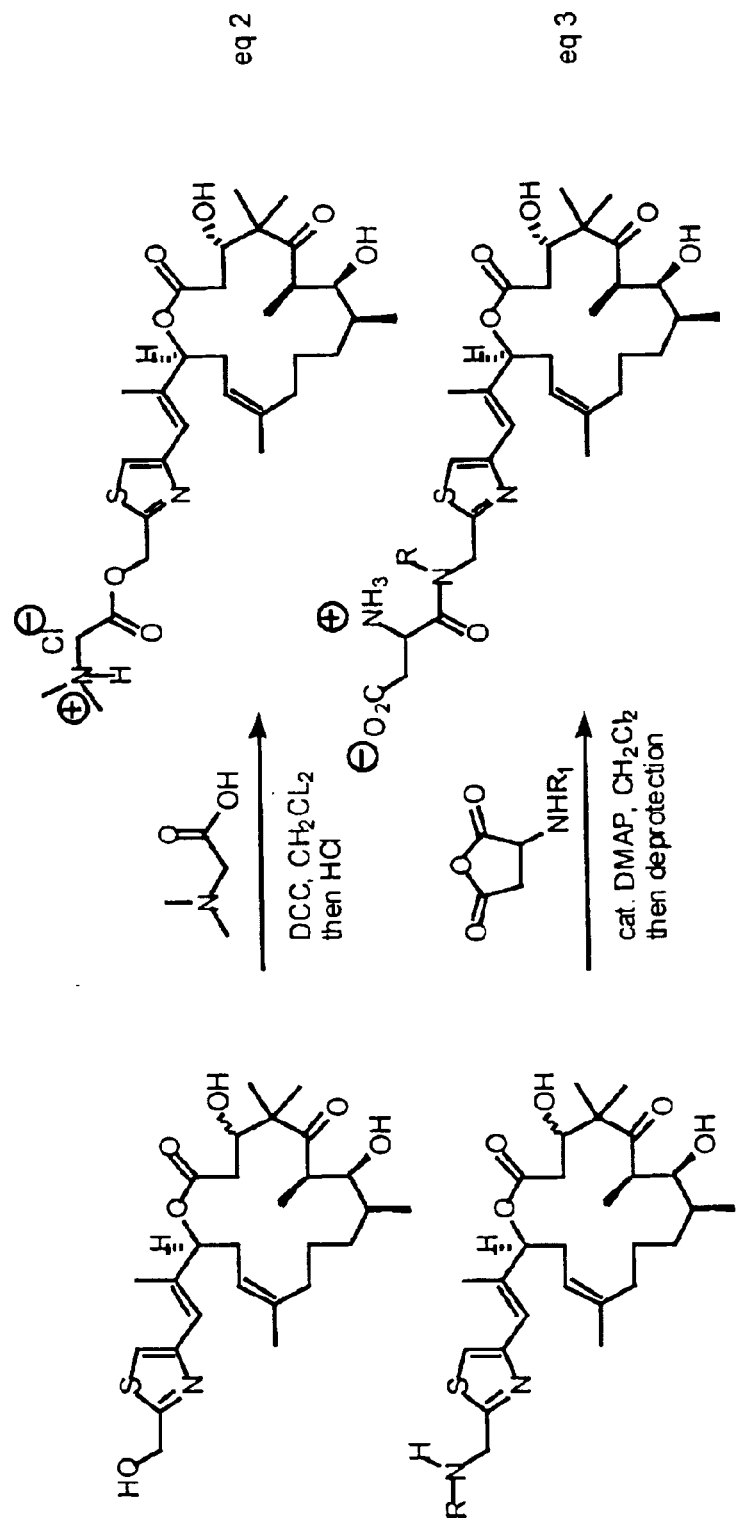
FIG. 8 depicts the synthesis of certain zwitter ions providing enhanced water solubility.

In one embodiment, the present invention provides novel compounds prepared by reacting dEpoF with N,N-dimethylglycine followed by hydrochloride salt formation as shown in FIG. 8. Another approach involves the use of aspartic anhydride as also shown in FIG. 8. Ring opening by the 21-amino group and liberation of the α-amino group by mild deprotection ($R_1$=Troc, Zn/AcOH) generate a zwitter ion which provides enhanced water solubility.

Figure 9:
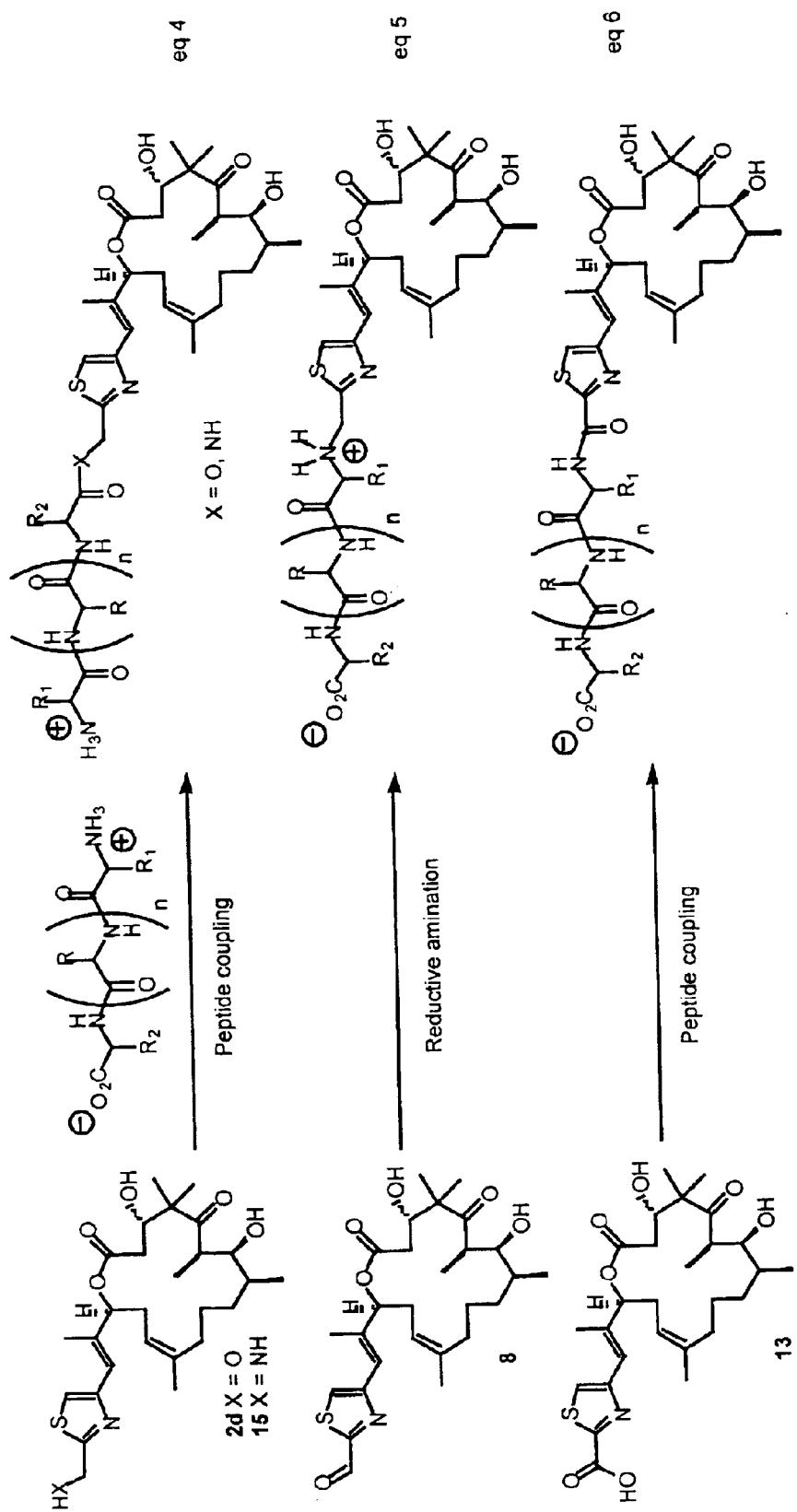
FIG. 9 depicts the conjugation of certain inventive compounds to peptides.

In other embodiments, the C21 functional groups lend themselves as a staging point for introduction of various α-amino acids or peptides containing hydrophilic side chains to increase the aqueous solubility. Referring to FIG. 9, using 21-hydroxy-(2d) or 21-amino compound (15), an N-protected oligopeptide can be attached to the epothilone domain through the C-terminal coupling. Alternatively, reductive amination and peptide coupling allow for the N-terminal coupling of carboxy-protected peptides to aldehyde 8 and acid 13, respectively. In addition to the aqueous solubility enhancement, the peptide-epothilone conjugate may provide an additional advantage of targeting tumor cells. Since tumors cells often over-express certain receptors to peptide ligands, the peptide attached to epothilone can be utilized as the recognition element. Thus, the ligand-receptor interaction can guide the peptide-epothilone to the tumor cells and facilitate endocytosis. For example, a segment of somatostatin can be used to deliver epothilone to the somatostatin receptor over-expressing cells, which are frequently found in several tumor types.

Figure 10:
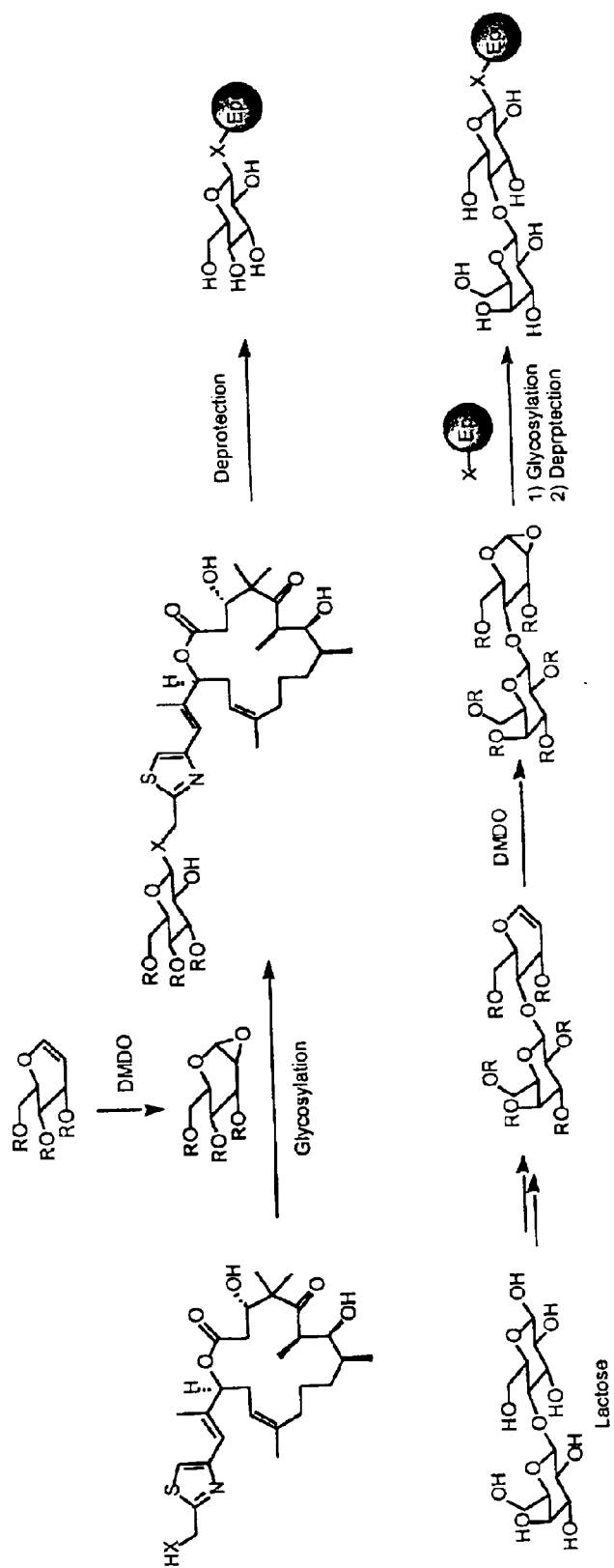
FIG. 10 depicts the synthesis of certain carbohydrate-epothilone conjugates.
Figure 11:
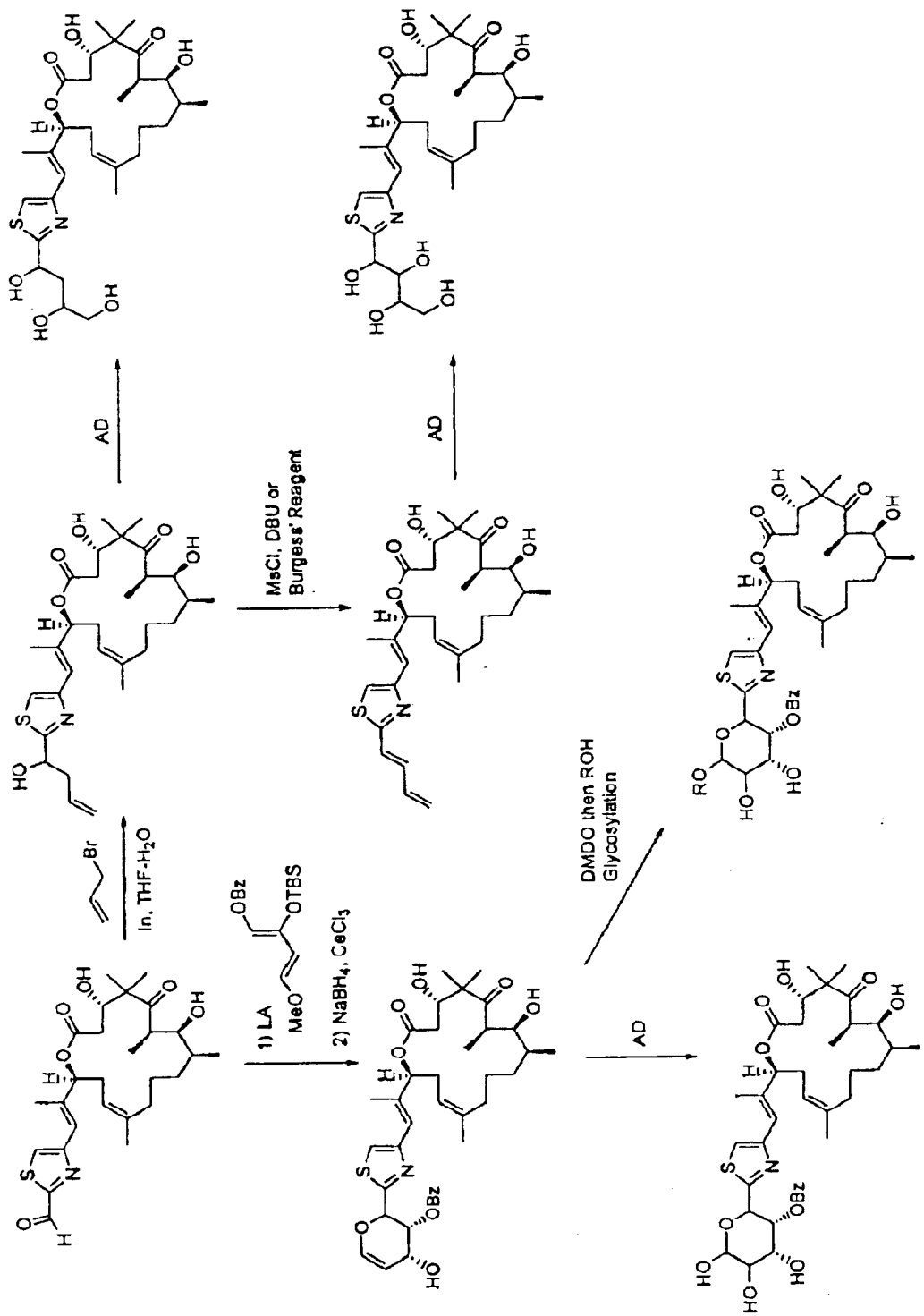
FIG. 11 depicts the synthesis of certain carbohydrate-epothilone conjugates attached via direct C—C linkage, and depicts certain other epothilone analogues.

In addition to the conjugation with peptides, another interesting class of water soluble epothilone analogs is generated by a novel glycosylation reaction. Taking advantage of glycosylation method using glucal epoxides, 21-funtionalized epothilones can be readily conjugated, in certain embodiments, with glucose or lactose as shown in FIG. 10. It should be noted that this conjugation strategy is applicable to a variety of oligosaccharides presenting a glycosyl donor unit at the reducing end. In yet other embodiments, as depicted in FIG. 11, epothilone carbohydrate conjugates having direct carbon-carbon linkages can be prepared as demonstrated. In one embodiment, Danishefsky diene is utilized and a hetero-Diels Alder reaction is effected.

In certain other embodiments, the present invention contemplates the formation of a polyvalent array. The low affinity binding of extracellular ligands can be significantly improved by covalently tethering many ligands together to form a polyvalent array. Since the initiating event of epothilone's anticancer activity involves noncovalent binding to microtubules, the formation of a dimer may enhance binding of the ligand (epothilone) to the biopolymer (microtubules). While the validity of polyvalency in an intracellular context is open to question, the multiple binding sites presented by microtubules offer a possibility of such advantage.

Figure 12:
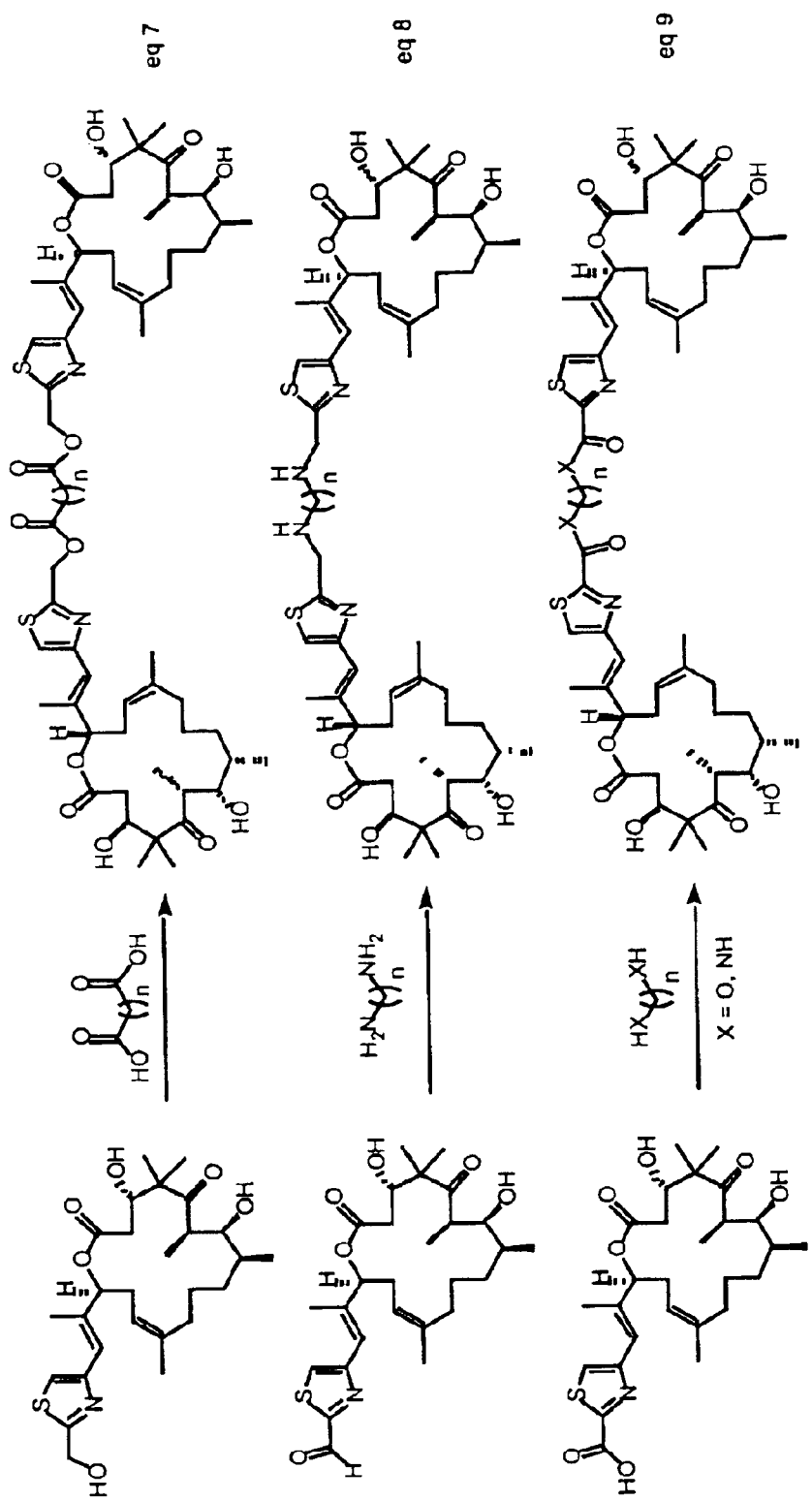
FIG. 12 depicts the synthesis of certain epothilone dimers.
Figure 13:
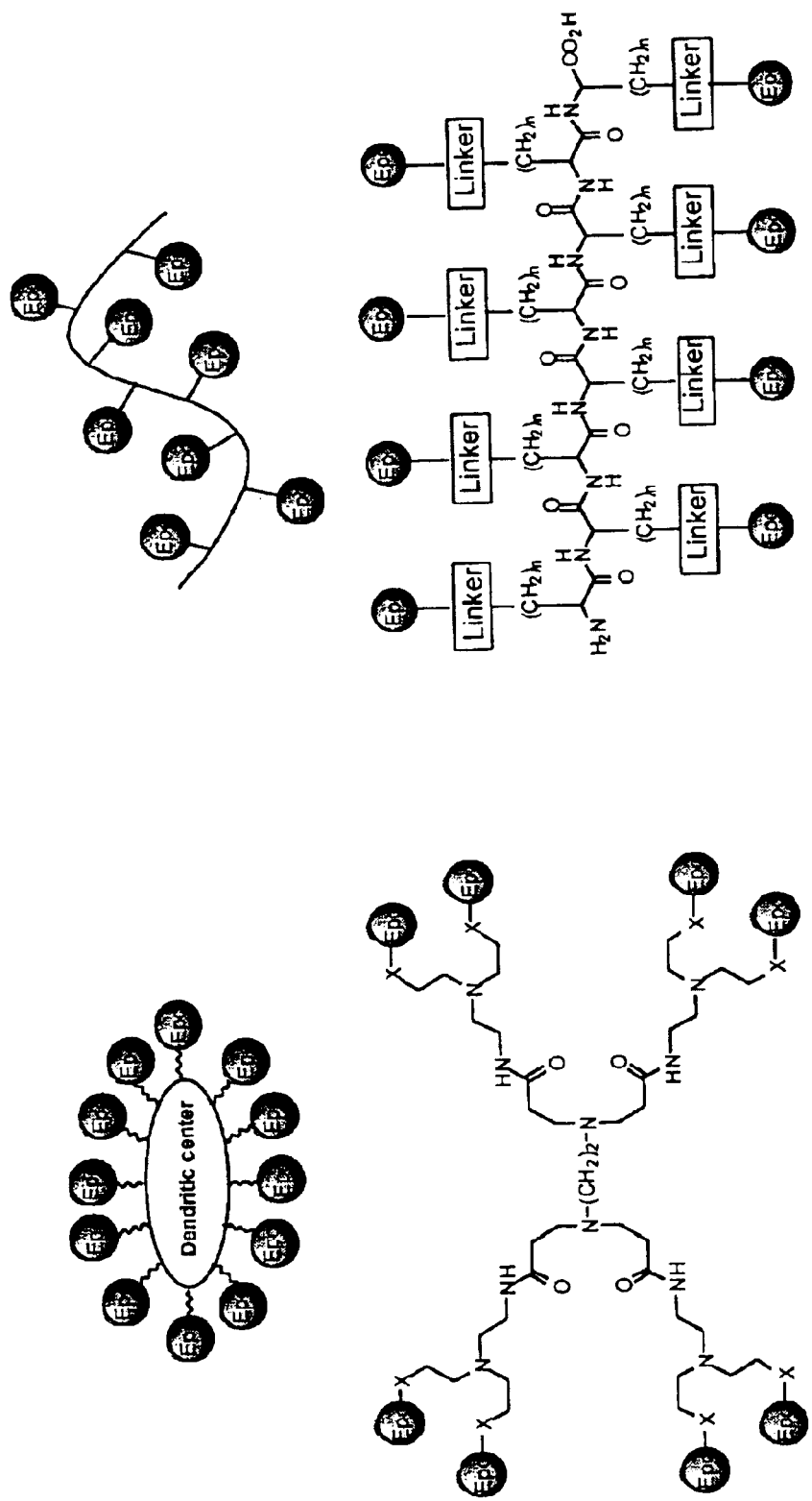
FIG. 13 depicts the multiple presentation of inventive epothilones on dendrimers and polymers.

As depicted in FIG. 12, the preparation of epothilone dimers is easily carried out by linking two halves of epothilones with a covalent tether. Taking advantage of the C21 functional groups as the functional handle, tethers such as α,ω-diacids, diamines, and diols with varied length (n=0, 1, 2, 3, etc.) can connect epothilones through a simple coupling reaction. In addition to potential enhancement in the cytotoxicity, the tubulin binding assay using the epothilone dimer may provide valuable information on the taxol (epothilone) binding site in a tubulin dimer or microtubules.

In other embodiments of the present invention, the concept of polyvalency in the context of a small molecule ligand (epothilone) and an intracellular receptor (microtubule) can be further tested by the multiple presentation of epothilones on a dendrimer or a polymer backbone. The interactions between the multiple binding sites located in microtubule and multiply presented epothilones can create a favorable situation of polyvalency, thereby ultimately leading to enhancement in antitumor activity. Following the same conjugation protocol described above, multiply presented epothilones can be readily synthesized using available functional groups on the backbone of a dendrimer or a polymer. Illustrated in FIG. 12 is presentation of eight epothilones on a commercially available PAMAM (Starburst®) dendrimer (X=$CO_2$ or NH) and an octapeptide (e.g., glutamate, lysine).

It will be appreciated that the present invention additionally contemplates the administration of epothilones via polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Synthetic and natural polymers can be used although synthetic polymers are preferred due to more uniform and reproducible degradation and other physical properties. Examples of synthetic polymers include polyanhydrides, polyhydroxyacids such as polylactic acid, polyglycolic acids and copolymers thereof, polyesters, polyamides, polyorthoesters, and some polyphosphazenes. Examples of naturally occurring polymers include proteins and polysaccharides such as collagen, hyaluronic acid, albumin and gelatin. When epothilone is administered via biopolymers or artificial functional polymers, it is possible to exploit the biological advantages of large molecule therapeutics. The ideal polymeric matrix would combine the characteristics of hydrophobicity, stability, organic solubility, low melting point, and suitable degradation profile. The polymer additionally is also preferably hydrophobic so that it retains its integrity for a suitable period of time when placed in an aqueous environment, such as the body, and be stable enough to be stored for an extended period before use. The ideal polymer must also be strong, yet flexible enough so that it does not crumble or fragment during use.

Figure 14:
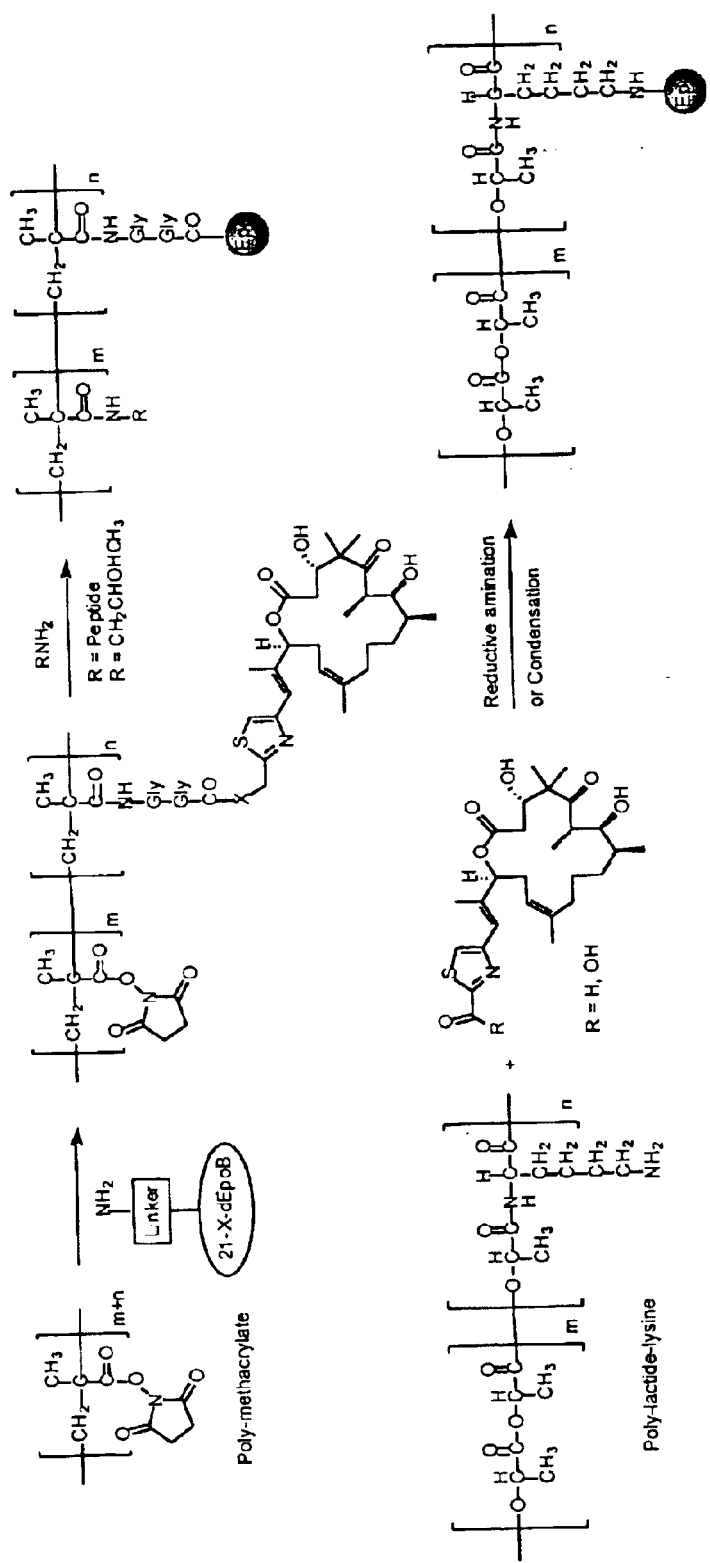
FIG. 14 depicts the synthesis of certain inventive epothilones bound to a biodegradable polymer.

It will be appreciated that a variety of biodegradable polymers can be used in the present invention, inter alia, containing a fashionable functional group, such as N-(hydroxypropyl)-methacrylamide (HPMA), glutamate, and lactide-lysine copolymers, (as shown in FIG. 14) can serve as an efficient vehicle. While polypeptides bearing a charged side chain are inherently water soluble, an engineered peptide linker as the solubility enhancer may be covalently incorporated between the polymer backbone and the epothilone analog in the case of nonpolar polymers. In certain embodiments, the compounds as described herein may be conjugated via suitable functionality to a water soluble chelator, or water soluble polymer, such as polyethylene glycol, poly(1-glutamic acid) or poly(1-aspartic acid), as described in U.S. Pat. No. 5,977,163, the entire contents of which are hereby incorporated by reference.

Figure 15:
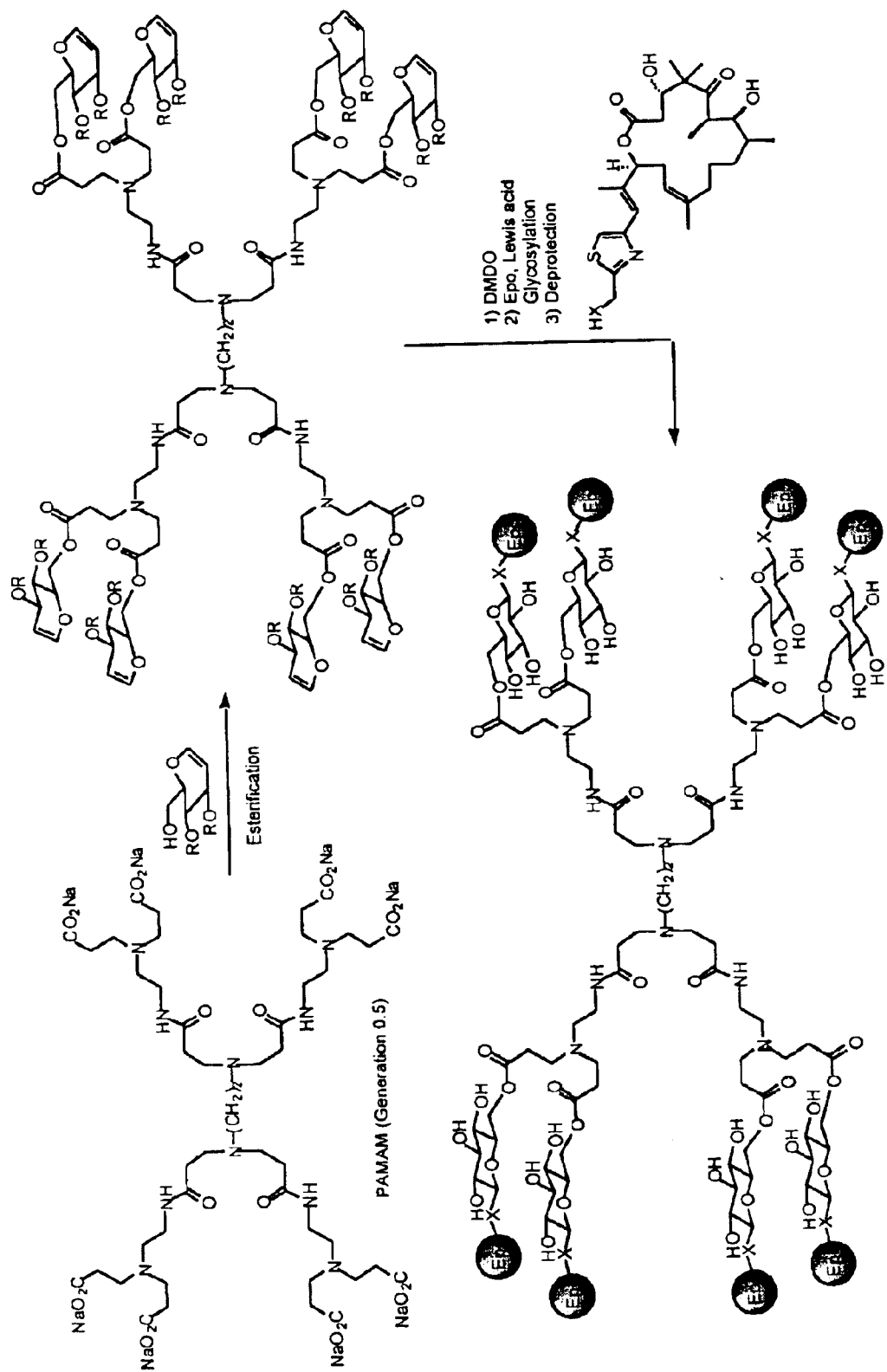
FIG. 15 depicts the synthesis of certain inventive water soluble epothilone derivatives.

In certain other embodiments, a strategy of multiply presenting epothilone on the sphere of a dendritic center is illustrated in FIG. 15. Starting from a half generation PAMAM (Starburst®), the 3,4-diprotected glucal is attached to the terminal carboxy groups. Depending on the generation of the dendrimer, the number (4, 8, 16, 32, etc.) and nature ($CO_2Na$, $NH_2$) of the terminal group can be changed. Using the glucal epoxide glycosylation protocol, the glycosidic bonds between the 21-functional groups (X=O, S, NH, etc.) of epothilones and the terminal glucose is achieved. Final deprotection of the protectective groups at C3' and C4' furnishes the water soluble, multiply presentated epothilone on the surface of the dendrimer. When additional hydrophilicity is required, an oligosaccharide unit rather than monosaccharide may be attached as the glycosyl donor to the terminal of the dendrimer.

Pharmaceutical Compositions

As discussed above, the present invention provides novel compounds having antitumor and antiproliferative activity, and thus the inventive compounds are useful for the treatment of cancer. Accordingly, in another aspect of the present invention, pharmaceutical compositions are provided, wherein these compositions comprise any one of the compounds as described herein, and optionally comprise a pharmaceutically acceptable carrier. In certain preferred embodiments, these compositions optionally further comprise one or more additional therapeutic agents. In certain other embodiments, the additional therapeutic agent is an anticancer agent, as discussed in more detail herein.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

In yet another aspect, according to the methods of treatment of the present invention, tumor cells are killed, or their growth is inhibited by contacting said tumor cells with an inventive compound or composition, as described herein. Thus, in still another aspect of the invention, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments of the invention, the inventive compounds as described herein are formulated by conjugating with water soluble chelators, or water soluble polymers such as polyethylene glycol as poly(1-glutamic acid), or poly(1-aspartic acid), as described in U.S. Pat. No. 5,977,163, the entire contents of which are hereby incorporated by reference. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

Exemplification

Figure 16:
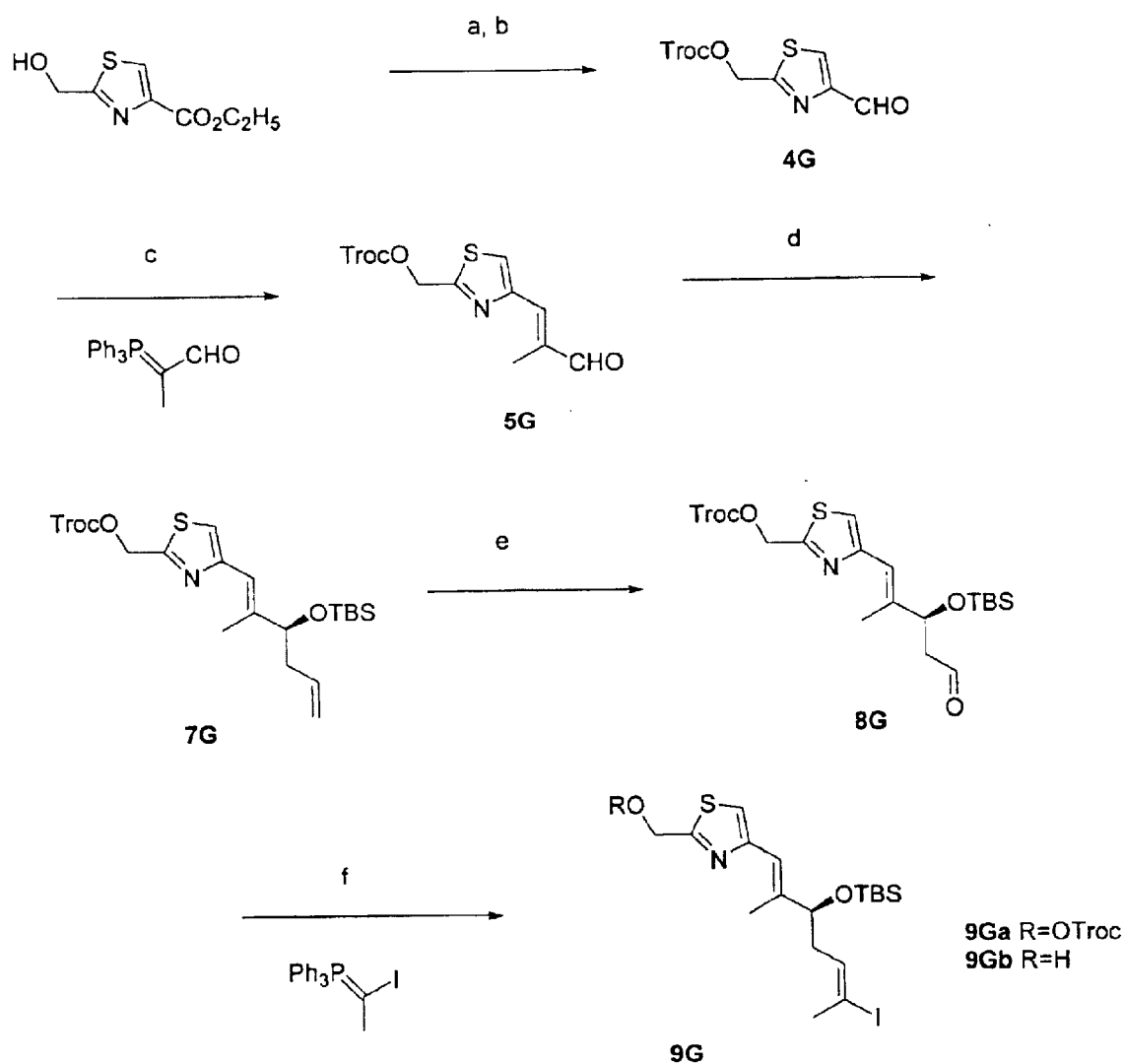
FIG. 16 depicts the synthesis of thiazolyl moiety 9G. Reagents and conditions: a) Cl$_3$CCH$_2$OCOCl, Pyr., CH$_2$Cl$_2$, 0° C., 0.5 h, 95%; b) Dibal-H, CH$_2$Cl$_2$, –78 0° C., 10 h, 80%; c) C$_6$H$_6$, 80° C., 3 h, 89%; d) (+)-Icp$_2$(allyl), pentane, –100° C., 74% (>95% ee); e) TBSOTf, 2,6-lutidine, CH$_2$Cl$_2$, –78° C. to rt, 2 h, 95%; f) (i) 1% OsO$_4$, NMO, H$_2$O-THF, 0° C., 12 h (ii) Pb(OAc)$_4$, EtOAc, 0° C., 1 h, 82%; g) THF, –78° C. to –30° C. then LiOH, THF-H$_2$O, rt, 61%; h) Cl$_3$CCH$_2$OCOCl, Pyr., CH$_2$Cl$_2$, 0° C., 95%.
Figure 17:
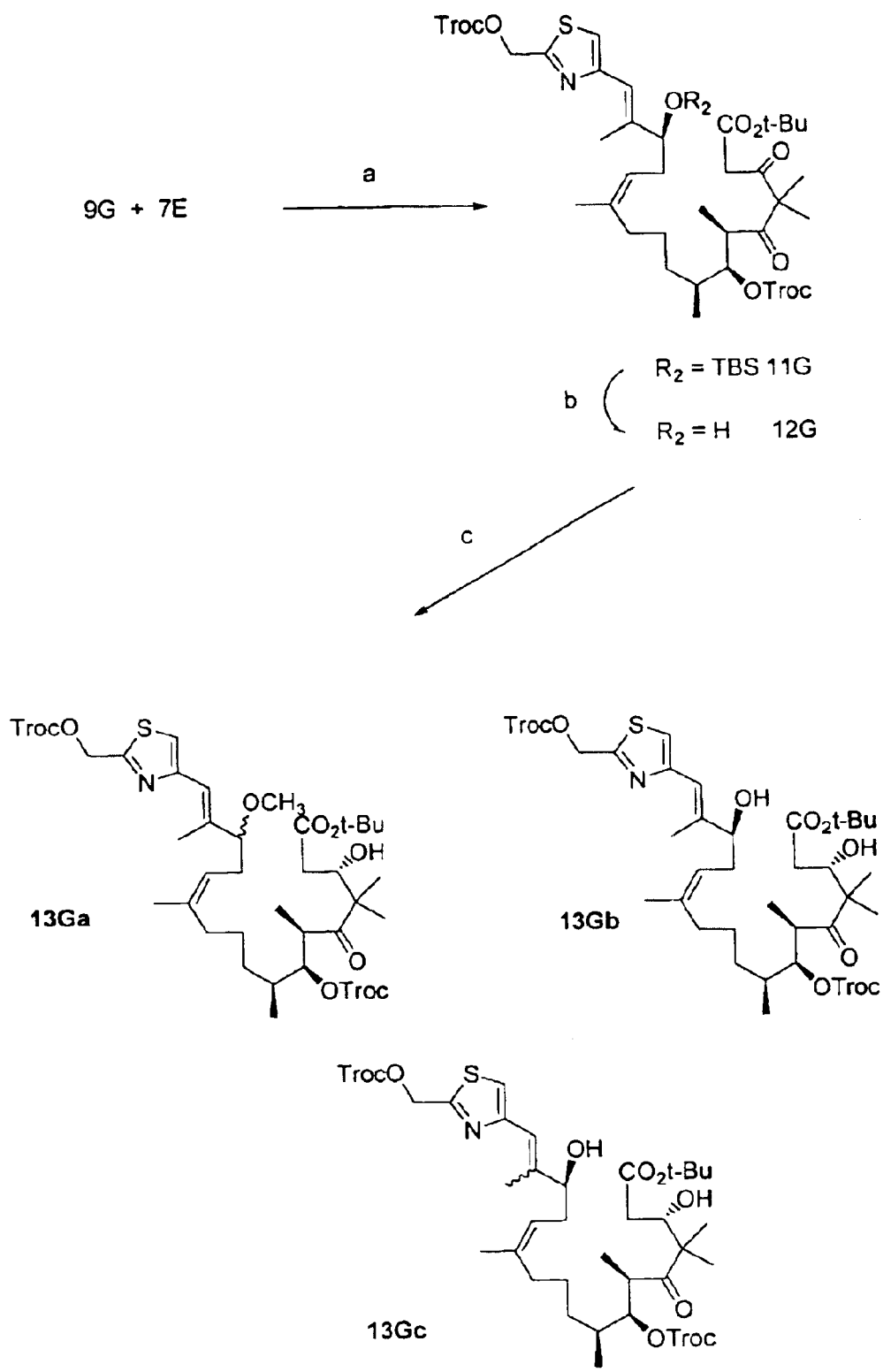
FIG. 17 depicts the synthesis of protected cyclization precursor 13Gc. Reagents and conditions: a) (dppt) PdCl$_2$CH$_2$Cl$_2$, AsPh$_3$, Cs$_2$CO$_3$, THF-DMF-H$_2$O, 2 h, 65%; b) HCl—CH$_3$OH, 2 h, 84%; c) 5% Et$_2$NH$_2$[{(R)-(BINAP)RuCl$_2$}$_2$Cl$_3$]HC$_1$—CH$_3$OH, H$_2$ (1,200 psi), rt, 8 h.
Figure 18:
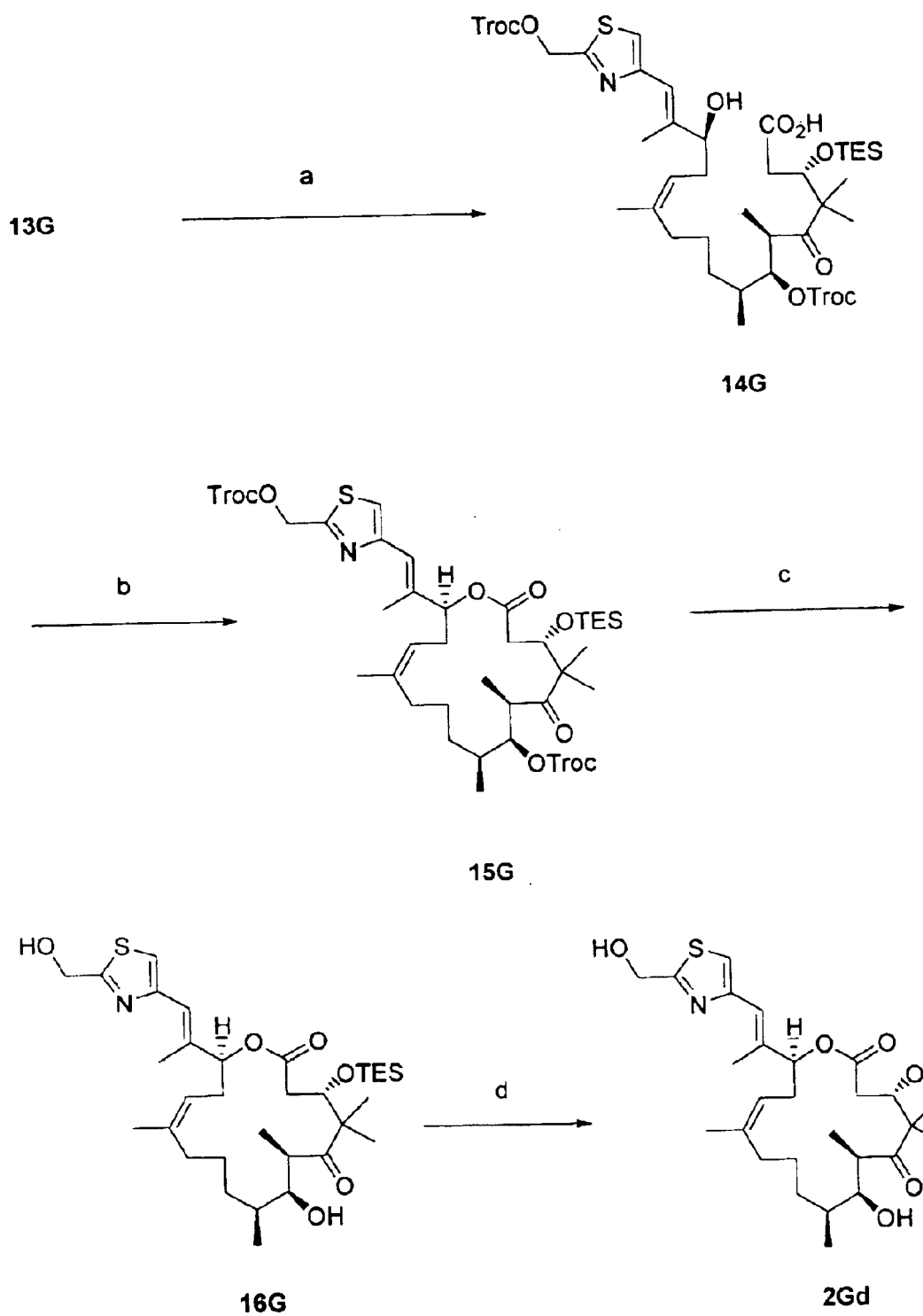
FIG. 18 depicts the synthesis of dEpoF (2Gd). Reaction conditions: a) (i) TESOTf, 2,6-lutidine, CH$_2$Cl$_2$, –78° C. to rt, 8 h, (ii) HCl—CH$_3$OH, 0° C., 70%; b) 2,4,6-trichlorobenzoic acid, (C$_2$H$_5$)$_3$ N then 4-DMAP, toluene, slow addition 3 h, 64%; c) Zn, AcOH-THF, rt, 1 h, 86% or cat. NiI$_2$/SmI$_2$, THF, –78 to –40° C., 87%; d) HF Pyridine, THF 0° C. to rt, 91%.

Example 1
Synthesis of 21-OH dEpoB (dEpoF) via Suzuki Coupling, Noyori Reduction and Macrolactonization (FIG. 2, and referring to FIGS. 16–18)

In one exemplary embodiment, a new epothilone analogue, 12,13-desoxyepothilone F (dEpoF, 21-hydroxy-12,13-desoxyepothilone B; FIG. 2), was synthesized using the convergent strategy previously used for the practical synthesis of 12,13-desoxyepothilone B (dEpoB), the synthesis of which is described in FIGS. 16–18. It will be appreciated, as discussed in further detail herein, that the new analogue containing an additional hydroxyl group provides certain advantages over other epothilones since it is more soluble in water and is readily functionalized for pertinent biological studies.

In one example, a method was utilized for the synthesis of dEpoF similar to the method used to prepare dEpoB as taught herein, in which two fragments of roughly equal complexity served as key building blocks (FIG. 2). As described herein, methodology was developed for the de novo construction of the thiazole moiety, and the right wing utilized in the previous synthesis of dEpoB was employed for the polypropionate domain for the synthesis of dEpoF.

As exemplified herein, the synthesis of the left wing was started from the protection of the known 2-substituted thiazole (Ciufolini, M. A.; Shen, Y. C. *J. Org. Chem.* 1997, 62, 3804) with Troc group which was removed simultaneously with the C7 hydroxy protection at a late stage of the synthesis (FIG. 16). The ethyl ester was reduced with Dibal-H to aldehyde which was then homologated to aldehyde. Asymmetric addition of the allyl unit was accomplished by the Brown protocol (Racherla, U. S.; Brown, H. C. *J. Org. Chem.* 1991, 56, 401), establishing the (S)-configuration at C15 with high ee (>95%). Selective dihydroxylation of the terminal olefin followed by the cleavage of the resultant diol gave rise to the aldehyde. The subsequent iodoethylenylation produced the desired vinyl iodide as a single geometric isomer. Stork, G.; Zhao, K. *Tetrahedron Lett.* 1989, 30, 2173; Chen, J. et al., *Tetrahedron Lett.* 1994, 35, 2827. The crude product was then directly treated with lithium hydroxide to give the alcohol in serviceable yield.

The union of the two key fragments was achieved by the Pd-catalyzed Suzuki coupling reaction to generate the diketone (FIG. 17). Miyaura, N.; Suzuki, A. *Chem. Rev.*, 1995, 95, 2457; Miyaura, N.,et al., *J. Am. Chem. Soc.*, 1989, 111, 314; Johnson, C. R.; Braun, M. P. *J. Am. Chem. Soc.*, 1993, 115, 11014. Alternatively, the free alcohol could be employed for the coupling to give the alcohol which was then converted back to the diketone. After removal of the TBS group, the diketone was subjected to ruthenium-catalyzed asymmetric hydrogenation conditions using a modified Noyori's catalyst. Ikariya, T., et al., *J. Chem. Soc., Chem. Commun.* 1985, 922; Taber, D. F.; Silverberg, L. J. *Tetrahedron Lett.* 1991, 32, 4227. Surprisingly, although the desired diol was produced as a single diastereomer, the C15 methyl ether was formed in a nearly 1:1 ratio. The use of commercially available Noyori's catalyst, $RuCl_2$ (BINAP) (Noyori, R. *Tetrahedron* 1994, 50, 4259), resulted in the formation of a complex mixture in which the major component was the C16–C17 reduced product. Under a variety of different conditions, the formation of the methyl ether could not be avoided. Since it was conceivable that methanolic HCl induced solvolysis of the C15 hydroxy group, employment of ethanol as solvent was expected to minimize the solvolysis process. While the yield of the diol was somewhat improved, the reaction suffered from a significantly longer reaction time and poor conversion. Changing the substrate from the diketone to the C15 TBS ether gave marginal improvement. These results sharply contrast with the synthesis of dEpoB where no such product formation from solvolysis was observed.

The asymmetric Noyori reduction using $Et_2NH_2[\{(BINAP)RuCl_2\}_2Cl_3]$ (Ohta, T., et al., *Orgnometal.* 1996, 19, 1521; Noyori, R., et al., *J. Am. Chem. Soc.* 1987, 109, 5856), as catalyst is known to be dependent on the amount of acid present in the reaction (King et al. *J. Org. Chem.* 1992, 57, 6689. In the case of dEpoB synthesis, the presence of stoichiometric HCl was required for both reduction at C3 and good diastereoselectivity. Harris, C. R., et al., *J. Amer. Chem. Soc.*, 1999, 121, 7050. Addition of stoichiometric acid apparently protonates the thiazole moiety, thereby preventing the inactivation of the ruthenium catalyst. Alternatively, this protonation of thiazole could have effectively protected the potentially vulnerable C15 allylic alcohol from solvolysis. The reduction of the C21 substituted derivatives could be carried out with substoichimetric HCl. However, the solvolysis still proceeded even with 20 mol % HCl, suggesting that the 2-hydroxymethyl substituted thiazole may not be an effective base to scavenge HCl. The substitution at the thiazole has a strong effect on the reactivity of a remote alcohol although this marked difference in reactivities could be largely of conformational origin.

Having established all of the necessary stereocenters, the t-butyl ester was unmasked with simultaneous protection of C3 and C15 alcohols by TESOTf (FIG. 18). Selective desilylation of the C15 TES group with methanolic HCl provided the hydroxy acid ready for macrolactonization. The macrolactonization by Yamaguchi's protocol afforded the fully protected macrolactone in 60~70% yield. Inanaga, J., et al., *Bull. Chem. Soc. Jpn.* 1979, 52, 1989; Mulzer, J., et al., *Synthesis* 1992, 215. The removal of the two Troc protective groups was performed through the agency of samarium (II) iodide (Evans, D. A., et al, *J. Am. Chem. Soc.* 1990, 112, 7001) or zinc both in good yields. Finally, standard HF-pyridine deprotection of the C3 TES group yielded 12,13-desoxyepothilone F.

Experimentals for Example 1
(Referring to FIGS. 16–18)

Ester (3G). To a solution of the known ethyl 2-(hydroxymethyl)thizole-4-carboxlyate (38.4 g, 0.205 mol) and pyridine (41 mL, 0.053 mol) in $CH_2Cl_2$ (100 mL) was slowly added 2,2,2-trichloroethyl chloroformate (32 mL, 0.23 mol) at 0° C. After stirring at 0° C. for 30 min, the reaction was quenched by the slow addition of aqueous $NaHCO_3$ (100 mL) The organic layer was separated, and the aqueous layer was extracted twice with $CH_2Cl_2$ (100 mL×2) The combined organic extracts were washed with 2 N HCl (100 mL) aqueous $NaHCO_3$ (50 mL) and brine. After drying over $Na_2SO_4$, the solvents were removed under reduced pressure. The residue was treated with ethanol (50 mL) to yield a light yellow solid (35 g). The mother liquor was concentrated and chromatographed to afford an additional amount (35 g) of the product (95%). Mp 82.9° C. IR (film): 2981, 1765, 1718, 1236 $cm^{-1}$. $^1H$ NMR (400 MHz, $CDCl_3$): d 8.22 (s, 1H), 5.64 (s, 2H), 4.85 (s, 2H), 4.55 (q, J=7.1 Hz, 2H), 1.45 (t, J=7.1 Hz, 3H). $^{13}C$ NMR (100 MHz, $CDCl_3$): d 164.4, 161.4, 153.9, 147.9, 129.2, 94.4, 77.6, 66.9, 62.2, 14.8. HRMS Calc'd for $C_{10}H_{10}Cl_3NO_5SNa$ (M+Na$^+$): 383.9242 Found: 383.9237.

Aldehyde (4G). To a solution of the ester (23 g, 0.063 mol) in $CH_2Cl_2$ (200 mL) was added a solution of Dibal-H (1.0 M in $CH_2Cl_2$, 120 mL) at −78° C. over 0.5 h. After the addition, the resulting mixture was placed in a refrigerator (−78° C.). After 10 h, the excess Dibal-H was quenched with acetic acid (5 mL), and the mixture was stirred with a saturated aqueous solution of potassium and sodium tartrate (150 mL) until the suspension disappeared to form a clear two-phased solution. The organic layer was washed with $NaHCO_3$, brine and then dried over $Na_2SO_4$. The solvents were removed in vacuo, and the residue was chromatographed on silica gel column to afford the desired aldehyde as a light yellow sticky oil (16 g, 80%). IR (film): 3016, 2966, 1762, 1699, 1384, 1281, 1233, 1060, 824 $cm^{-1}$. $^1H$ NMR (400 MHz, $CDCl_3$): d 9.97 (s, 1H), 8.17 (s, 1H), 5.49 (s, 2H), 4.77 (s, 2H). $^{13}C$ NMR (100 MHz, $CDCl_3$): d 184.7, 165.0, 155.3, 153.9, 153.5, 129.0, 94.3, 66.6. LRMS: Calc'd for $C_9H_9Cl_3NO_4SNa$ (M+Na$^+$): 353 Found 353.

Aldehyde (5G). To a solution of the aldehyde (21 g, 0.066 mol) in benzene (300 mL) was added 2-(triphenylphosphoranilidenyl)propionaldehyde (20.6 g, 0.066 mol). The resulting mixture was heated under reflux. After 3 h, the mixture was cooled to room temperature and concentrated under reduced pressure. Purification by flash column chromatography on $SiO_2$ (hexanes/ethyl acetate=4:1) yielded the desired aldehyde as a clear oil (21 g, 89%). IR (film): 1764, 1679, 1628, 1437, 1383, 1238 cm$^{-1}$. $^1$H NMR (400 MHz, CDCl$_3$): d 9.62 (s, 1H), 7.67 (s, 1H), 7.30 (s, 1H), 5.58 (s, 2H), 4.88 (s, 2H), 2.24 (s, 3H). LRMS Calc'd for $C_{11}H_{10}Cl_3NO_4S$ (M+H$^+$): 357 Found: 357.

Alcohol: Asymmetric Allylation (6G). The solution of the aldehyde (9.20 g, 25.7 mmol) was dissolved in anhydrous ether (50 mL) and cooled to $-100°$ C. by ether-liquid nitrogen bath. A pentane solution of (+)-diisopinocampheylallylborane (1.5 eq, 150 mL), prepared as the known procedure, was added dropwise to the vigorously stirred aldehyde solution. After the addition was complete, the reaction mixture stirred for 1.5 h and warmed to $-50°$ C. Then, 30% $H_2O_2$ (20 mL) and a saturated aqueous solution of NaHCO$_3$ (50 mL) were added, and the resulting turbid mixture was stirred for 8 h. The organic layer was separated and the aqueous layer was extracted with ether (100 mL×2). The combined organic layers were washed with aqueous $Na_2S_2O_3$ (100 mL) and brine, and dried over anhydrous MgSO$_4$. Purification by flash column chromatography on a silica gel (hexane/ethyl acetate=10:1) afforded the alcohol as a clear oil (7.65 g, 74%). The ee of the alcohol was determined to be 95% by derivatizing to the corresponding Mosher's ester. $[\alpha]_D$-2.5 (c 1.00, CHCl$_3$). IR (film): 3382, 2958, 1763, 1384, 1239, 820 cm$^{-1}$. $^1$H NMR (400 MHz, CDCl$_3$): δ 7.16 (s, 1H), 6.59 (s, 1H), 5.77~5.87 (m, 1H), 5.62 (s, 2H), 5,16 (d, J=17.0 Hz, 1H), 5.01 (d, J=11.0 Hz, 1H), 4.82 (s, 2H), 4.23 (m, 1H), 2.43~2.49 (m, 1H), 2.36~2.40 (m, 1H), 2.07 (s, 3H), 1.90 (s, 1H). HRMS Calc'd for $C_{14}H_{17}Cl_3N_1O_4Si$ (M+H$^+$): 399.9943 Found: 399.9927.

Silyl ether (7G). Procedure A: To mixture of the alcohol 7 (7.65 g, 19.1 mmol) and 2,6-lutidine (10 mL, 85.9 mmol) in CH$_2$Cl$_2$ (50 mL) was added dropwise TBSOTf (15 mL, 0.066 mol) at $-78°$ C. After the addition, the reaction mixture was allowed to warm to room temperature and stirred for 5 h. The reaction mixture was poured into a saturated aqueous solution of NaHCO$_3$ (50 mL) and extracted with ether (50 mL×3). The combined organic layers were washed with 2 N HCl (50 mL), aqueous NaHCO$_3$ (50 mL) brine, and dried over anhydrous Na$_2$SO$_4$. Flash chromatography on SiO$_2$ (hexane then hexane/ethyl acetate=95:5) provided 9.39 g of the TBS ether as a colorless oil (95%).

Procedure B: To a mixture of the alcohol (8.50 g, 25.0 mmol) and imidazole (3.40 g, 50.0 mmol) in DMF (50 mL) were added TBSCl (4.72 g, 31.3 mmol) and 4-DMAP (30 mg, 0.25 mmol). After stirring at room temperature for 8 h, the mixture was diluted with ether (250 mL) and washed successively with 2 N HCl (50 mL), aqueous NaHCO$_3$ (50 mL) and brine (50 mL). The organic layer was dried over anhydrous MgSO$_4$ and concentrated. Flash chromatography on SiO$_2$ afforded 11.0 g of the TBS ether (97%). $[\alpha]_D$-2.2 (c 1.00, CHCl$_3$). IR (film): 2954, 2920, 2855, 1767, 1239, 1076 cm$^{-1}$. $^1$H NMR (400 MHz, CDCl$_3$): d 7.14 (s, 1H), 6.49 (s, 1H), 5.79 (m, 1H), 5.52 (s, 2H), 5.04 (d, J=17.9 Hz, 1H), 5.01 (d, J=8.5 Hz, 1H), 4.82 (s, 2H), 4.16 (t, J=6.1 Hz, 1H), 2.30~2.39 (m, 2H), 2.01 (s, 9H), 0.06 (s, 3H), 0.01 (s, 3H). $^{13}$C NMR (100 MHz, CDCl$_3$): d 160.1, 152.8, 152.6, 142.1, 134.0, 116.9, 116.0, 115.5, 92.9, 77.0, 65.5, 40.2, 24.6, 17.1, 12.9, -5.7, -6.0. HRMS Calc'd for $C_{20}H_{31}C_{13}NO_4SSi$ (M+H$^+$): 514.0808 Found: 514.0790.

Aldehyde (8G). Dihydroxylation. To a solution of the olefin (20.6 g, 0.040 mol), N-methylmorpholine-N-oxide (50% in THF, 10 mL, 0.048 mol) and H$_2$O (21 mL) in t-BuOH (155 mL) was added OsO$_4$ solution (1 wt % in THF, 20.3 mL, 0.78 mmol) at 0° C. After stirring for 12 h, Na$_2$SO$_3$ (~10 g) and water (5 mL) were added, and the resulting solution was stirred for 30 min. Then, the mixture extracted with ether (100 mL×3) and washed with brine. The combined organic extracts were dried over anhydrous Na$_2$SO$_4$. Removal of the solvents and purification by flash chromatography on a silica gel column provided 18.8 g of the 1:1 diastereomeric diol mixture as a colorless viscous oil (85%). IR (film): 3396, 2953, 2928, 2856, 1764, 1384, 1240, 1068, 836 cm$^{-1}$. $^1$H NMR (400 MHz, CDCl$_3$): δ 7.26 (s, 0.5H), 7.16 (s, 0.5H), 6.61 (s, 0.5H), 6.53 (s, 0.5H), 5.51 (s, 2H), 4.82 (s, 2H), 4.49~4.45 (m, 1H), 3.94 (m, 1H), 3.61 (m, 1H), 3.45 (m, 1H), 2.04 (s, 3H), 1.55~1.92 (m, 4H), 0.93 (s, 4.5H), 0.92 (s, 4.5H), 0.14 (s, 1.5H), 0.13 (s, 1.5H), 0.07 (s, 1.5H), 0.04 (s, 1.5H). HRMS Calc'd for $C_{20}H_{32}O_6Cl_3$ NSSiNa (M+Na$^+$): 570.0682 Found: 570.0694.

Aldehyde Formation. Procedure A: To a suspension of the diol (18 g, 0.032 mol) and sodium carbonate(8.67 g, 0.081 mol) in benzene (500 mL) was added lead tetraacetate (19.1 g, 0.043 mol) in several portions at 0° C. over 5 min. After stirring for 15 min, the mixture was filtered through a short silica gel pad with the aid of 4:1 hexane-ethyl acetate mixture. Removal of the solvents under reduced pressure afforded 14 g of the desired aldehyde (82%). Procedure B: To a solution of the diol (11.8 g, 24.2 mmol) in ethyl acetate (100 mL) was added lead tetraacetate (95%, 12.5 g, 26.8 mmol) in several portions at 0° C. The resulting yellow suspension was vigorously stirred for 1 h, at which point TLC analysis indicated the complete consumption of the starting material. The reaction mixture was then filtered with a short pad of silica gel with the aid of 1:1 ether/hexanes mixture. The filtrate was concentrated and purified by flash chromatography to give 7.95 g of the aldehyde as a light yellow oil (72%). $[a]_D$-11.0 (c 1.00, CHCl$_3$). IR (film): 2954, 2929, 2856, 1765, 1724, 1678, 1384, 1239, 1079, 836, 778 cm$^{-1}$. $^1$H NMR (400 MHz, CDCl$_3$): δ 9.80 (s, 1H), 7.16 (s, 1H), 6.58 (s, 1H), 5.51 (s, 2H), 4.82 (s, 2H), 4.69 (dd, J=6.5, 3.2 Hz, 1H), 2.74 (ddd, J=12.6, 6.5, 2.3 Hz, 1H), 2.53 (ddd, J=12.5, 3.2, 1.6 Hz, 1H), 2.06 (s, 3H), 0.89 (s, 9H), 0.09 (s, 3H), 0.04 (s, 3H). $^{13}$C NMR (100 MHz, CDCl$_3$): d 162.0, 154.0, 153.8, 142.0, 118.9, 118.3, 94.5, 77.5, 74.1, 66.9, 50.5, 26., 18.5, 14.7, -4.4, -4.7. HRMS Calc'd for $C_{19}H_{29}Cl_3NO_5SSi$ (M+H$^+$): 516.0601 Found: 516.0604.

Vinyl Iodide (9G). To a suspension of ethyltriphenylphosphonium iodide (7.90 g, 17.9 mmol) in THF (150 mL) was added n-butyllithium (7.17 mL, 2.5 M in hexane, 17.94 mmol) at ambient temperature. After disappearance of the solid material, the red solution was added to a vigorously stirred solution of iodine (4.54 g, 17.94 mmol) in THF (150 mL) at $-78°$ C. The resulting dark brown suspension was stirred for 5 min and allowed to warm gradually to $-30°$ C. A solution of sodium hexamethyldisilazide (17.34 mL, 1.0 M in THF, 17.34 mmol) was added dropwise to the suspension to give a dark red solution. Then, a solution of aldehyde 8G (3.10 g, 5.98 mmol) in THF (10 mL) was slowly added, and the stirring was continued at $-30°$ C. for 30 min. The reaction mixture was diluted with pentane (1000 mL), filtered through a pad of celite, and concentrated in vacuo. Purification of the residue by flash column chromatography (hexane/ethyl acetate=6:1) afforded 1.50 g of the vinyl iodide as a syrup (38%). $[\alpha]_D$+4.5 (c 1.00, CHCl$_3$). IR (film): 2953, 2927, 2855, 1764, 1249, 1067, 835 cm$^{-1}$. $^1$H NMR (400 MHz, CDCl$_3$): δ 7.08 (s, 1H), 6.45 (s, 1H), 5.43 (s, 2H), 4.75 (s, 2H), 4.15 (dd, J=12.2, 5.7 Hz, 1H), 2.42 (s, 3H), 2.34~2.37 (m, 2H), 2.00 (s, 3H), 0.83 (s, 9H), 0.05 (s, 3H), 0.01 (s, 6H). $^{13}$C NMR (100 MHz, CDCl$_3$): d 161.6, 154.3, 154.0, 143.3, 132.4, 18.5, 7.8, 7.4, 102.9, 77.5, 67.0, 44.0, 34.1, 26.2, 18.6, 14.7, 14.3. FAB-HRMS Calc'd for C$_{21}$H$_{31}$Cl$_3$INO$_4$SSi (M+H$^+$): 653.9311 Found: 653.9931.

Vinyl iodide (9Gb). To a suspension of (ethyl) triphenylphosphonium iodide (5.05 g, 12.1 mmol) in THF (30 mL) was added a solution of sodium hexamethyldisilazide (12 mL, 1.0 M in THF) at ambient temperature. After stirring for 5 min, the dark red solution was cooled to −78° C. and cannulated into a vigorously stirred solution of iodine (3.02 g, 11.9 mmol) in THF (50 mL) at −78° C. to form a dark brown suspension. After 5 min, a solution of sodium hexamethyldisilazide (11 mL, 1.0 M in THF) was added, and the resulting red solution was stirred for 0.5 h. A solution of the aldehyde (3.12 g, 6.04 mmol) in THF (30 mL) was added via a cannula, and the mixture was allowed to warm to −20° C. over 1 h, at which point TLC analysis indicated complete consumption of the starting aldehyde. The reaction was quenched by the addition of a saturated aqueous solution of NH$_4$Cl (0.5 mL) and hexanes (50 mL), and the resulting precipitates were filtered with a short pad of silica gel. The filtrate was concentrated under reduced pressure to give 4.05 g of light yellow oil.

The crude mixture, obtained from above, was dissolved in aqueous THF (1:1, 10 mL). Then, lithium hydroxide monohydrate (0.510 g, 12.2 mmol) was added at room temperature, and the resultant mixture was stirred. After 4 h, the two-phased solution was poured into a saturated aqueous NH$_4$Cl (15 mL) and extracted with ethyl acetate (25 mL×3). The combined organic layers were washed with aqueous NaHCO$_3$ and brine, and dried over anhydrous MgSO$_4$. After removing solvents, the remainder was purified on a silica gel column (hexanes/ethyl acetate=3:1) to afford 1.78 g of the alcohol as a light yellow oil (61%). [α]$_D$+6.4 (c 2.00, CHCl$_3$). IR (film): 3272, 1252, 1068, 836, 776 cm$^{-1}$. $^1$H NMR (400 MHz, CDCl$_3$): d 7.08 (s, 1H), 6.49 (s, 1H), 5.45 (td, J=6.6, 1.4 Hz, 1H), 4.94 (s, 2H), 4.21 (t, J=6.4 Hz, 1H), 2.48 (s, 3H), 2.43~2.31 (m, 2H), 2.02 (s, 3H), 0.89 (s, 9H), 0.06 (s, 3H), 0.01 (s, 3H). $^{13}$C NMR (100 MHz, CDCl$_3$): δ 169.5, 153.2, 142.4, 132.0, 118.4, 115.8, 102.5, 77.1, 62.1, 43.6, 33.6, 25.8, 18.2, 14.3, −4.7, −5.0. FAB-MS Calc'd for C$_{18}$H$_{31}$INO$_2$SSi (M+H$^+$): 480.0890 Found: 480.0908.

15-(t-Butyldimethylsilyloxy)-3-ketone (minor tautomer*) (11G). To a solution of 9-BBN dimer (0.774 g, 6.34 mmol) in THF (5 mL) was added a solution of the tricarbonyl (2.80 g, 5.43 mmol) in THF (5 mL). After stirring at 25° C. for 1 h, TLC analysis indicated the complete consumption of the starting olefin.

In a separate flask, containing the vinyl iodide (3.25 g, 4.53 mmol), (dppf)PdCl$_2$.CH$_2$Cl$_2$ (0.370 g, 0.453 mmol), AsPh$_3$ (0.139 g, 0.454 mmol) and Cs$_2$CO$_3$ (2.21 g, 6.78 mmol) was added degassed DMF (5 mL). The resulting red suspension was purged with a stream of argon gas for 20 min. Water (2 mL) was added to the borane solution, prepared above, and the stirring was continued for 10 min to quench the excess 9-BBN. Then, the solution of the alkylborane was added rapidly to the vigorously stirred solution containing the vinyl bromide. After 2 h, the reaction mixture was diluted with ether (50 mL), washed with water (10 mL×2) and brine, and dried over anhydrous MgSO$_4$. After removal of solvents, the crude product was purified by flash column chromatography on a silica gel, being eluted with hexanes/ethyl acetate (10:1) to afford 3.26 g of the product as a light yellow sticky oil (65%). [α]$_D$−21.0 (c 4.46, CHCl$_3$). IR (film): 1759, 1721, 1698, 1462, 1384, 1251, 1155, 1067, 930, 836, 819, 778, 731 cm$^{-1}$. $^1$H NMR (400 MHz, CDCl$_3$): δ 12.60* (s, 1H), 7.12 and 7.10* (s, 1H), 6.46 (s, 1H), 5.49 (s, 2H), 5.10 (t, J=6.9 Hz, 1H), 4.86~4.80 (m, 3H), 4.74~4.67 (m, 2H), 4.05 (t, J=6.1 Hz, 1H), 3.47 (d, J=16.2 Hz, 1H), 3.40 (d, J=16.2 Hz, 1H), 3.35~3.25 (m, 1H), 2.25~2.15 (m, 2H), 1.99 (s, 3H), 1.99~1.86 (m, 2H), 1.73~1.60 (m, 5H), 1.48 (s, 3H), 1.48~1.27 (m, 15H), 1.09* and 1.07 (d, J=6.9 Hz, 3H), 0.93* and 0.90 (d, J=7.4 Hz, 3H), 0.86 (s, 9H), 0.02 (s, 3H), −002 (s, 3H). $^{13}$C NMR (100 MHz, CDCl$_3$): d 210.7, 209.6, 203.1, 178.4, 172.6, 166.2, 161.2, 154.2, 154.1*, 154.0, 153.6, 143.6, 136.6*, 136.5, 121.7, 117.9, 117.1, 94.7*, 94.6, 94.1, 90.6, 82.9*, 81.9, 81.6*, 78.7, 77.1, 66.6, 63.6, 54.3, 46.5, 41.9*, 41.5, 35.3, 34.8*, 34.6, 32.1, 31.7, 31.2*, 30.6*, 28.2, 27.9, 25.8, 25.1*, 25.0, 23.5*, 23.4, 22.7*, 22.1*, 21.5, 20.8, 18.8*, 18.2, 16.0*, 15.7, 14.1, 12.8*, 11.4. FAB-MS Calc'd for C$_{43}$H$_{66}$Cl$_6$NO$_{11}$SSi (M+H$^+$): 1042.2257 Found: 1042.2304.

15-Hydroxy-3-ketone (Suzuki product, minor tautomer*) (12G). The TBS ether (0.265 g, 0.254 mmol) was dissolved in 0.5 N HCl in MeOH (25 mL) at 25° C. The reaction was monitored by TLC for completion. After 2 h, the reaction mixture was poured into a solution of saturated aqueous NaHCO$_3$ (25 mL) and extracted with CH$_2$Cl$_2$ (40 mL×3). The combined organic extracts were washed with brine and dried over anhydrous MgSO$_4$. The alcohol was purified by flash column chromatography on a silica gel, eluting with hexanes/ethyl acetate (2:1) to give the pure alcohol (0.198 g, 84%) as a clear viscous oil. [α]$_D$−27.2 (c 1.33, CHCl$_3$). IR (film): 3545, 3411, 1759, 1717, 1698, 1456, 1385, 1251, 1153, 1061, 994, 927, 819, 730 cm$^{-1}$. $^1$H NMR (400 MHz, CDCl$_3$): d 12.60* (s, 1H), 7.16 (s, 1H), 7.13* (s, 1H), 6.57 (s, 1H), 5.50 (s, 2H), 5.15 (t, J=7.0 Hz, 1H), 4.87~4.81 (m, 4H), 4.81 (s, 2H), 4.76~4.68 (m, 2H), 4.13~4.10 (m, 1H), 3.48 (d, J=16.2 Hz, 1H), 3.41 (d, J=16.2 Hz, 1H), 3.35~3.26 (m, 1H) 4.13~4.10 (m, 2H), 2.05 (s, 3H), 2.03~1.99 (m, 2H), 1.75~1.61 (m, 5H), 1.59* and 1.49 (s, 3H), 1.41~1.39 (m, 11H), 1.36 (s, 3H), 1.34* (s, 3H), 1.28* (s, 3H), 1.10* and 1.08 (d, J=6.8 Hz, 3H), 0.92 and 0.88* (d, J=6.9 Hz, 3H). $^{13}$C NMR (100 MHz, CDCl$_3$): d 210.7*, 209.6, 203.2, 178.5*, 172.6*, 166.3, 161.3, 154.3, 154.2*, 153.8, 153.6, 142.7, 139.2*, 139.0, 120.4, 118.1, 117.6, 117.3*, 94.7*, 94.6, 94.1, 90.6*, 83.0*, 82.0, 81.7*, 77.2, 77.1, 66.6, 63.6, 54.3*, 46.6, 42.0*, 41.6, 34.8*, 34.7, 34.1, 32.1, 30.6, 28.3, 27.9, 25.1*, 25.0, 23.6, 22.7*, 22.2*, 21.6, 20.9, 16.0*, 15.7, 14.6, 13.6*, 12.9*, 11.5. LRMS Calc'd for C$_{37}$H$_{51}$Cl$_6$NO$_{11}$SNa (M+Na$^+$): 950.4 Found: 950.4.

3,15-Diol (Noyori product) (13G). The diketone (0.302 g, 0.325 mmol) was dissolved in 0.12 N HCl in MeOH (3.5 mL, 0.42 mmol) at 25° C. The Et$_2$NH$_2$[{(R)-(BINAP) RuCl}$_2$Cl$_3$] catalyst (0.048 M in THF, 0.034 mmol) was then added, and the mixture was transferred to a Parr apparatus. The vessel was purged with H$_2$ for 10 min and then pressurized to 1,200 psi. After 8 h at 25° C., the reaction was returned to atmospheric pressure and poured into a saturated solution of NaHCO$_3$ (15 mL). This mixture was extracted with CH$_2$Cl$_2$ (15 mL×3) and the combined organic layers were dried over anhydrous Na$_2$SO$_4$. The product mixture was separated by flash chromatography on a silica gel, eluting with hexanes/ethyl acetate (2:1) to give 0.152 g (49%) of the less polar methyl ether as a clear oil and 0.126 g (42%) of the more polar hydroxy ester as a green sticky oil. [α]$_D$+6.43 (c 2.54, CHCl$_3$). IR (film): 3518, 1759, 1726, 1704, 1453, 1383, 1249, 1153, 925, 819, 731 cm$^{-1}$. $^1$H NMR(400 MHz, CDCl$_3$): δ 7.16 (s, 1H), 6.57 (s, 1H), 5.50 (s, 2H), 5.14 (t, J=6.4 Hz, 1H), 4.86~4.80 (m, 4H), 4.71 (d, J=12.0 Hz, 1H), 4.15~4.10 (m, 2H), 3.49~3.40 (m, 1H), 2.39~2.20 (m, 5H), 2.04 (s, 3H), 2.04~1.98 (m, 2H), 1.73~1.68 (m, 1H), 1.68 (s, 3H), 1.49~1.44 (m, 2H), 1.44 (s, 9H), 1.19~1.13 (m, 10H), 1.09 (d, J=6.8 Hz, 3H), 0.94 (d, J=6.8 H). $^{13}$C NMR (100 MHz, CDCl$_3$): δ 216.0, 172.5, 161.4, 154.3, 153.7, 153.6, 120.3, 118.0, 117.6, 94.7, 83.1, 81.4, 77.1, 72.9, 66.5, 51.9, 41.5, 37.3, 34.7, 34.1, 32.2, 31.2, 28.1, 25.2, 23.6, 21.9, 19.2, 16.2, 14.6, 12.3. FAB-MS Calc'd for C$_{37}$H$_{53}$Cl$_6$NO$_{11}$SSiNa (M+Na$^+$): 952.1368 Found: 952.1383.

15-Hydroxy acid (14G). To a solution of the diol (0.495 g, 0.531 mmol) in CH$_2$Cl$_2$ (5 mL) were added successively 2,6-lutidine (0.870 mL, 7.47 mmol) and TESOTf (0.840 mL, 3.72 mmol) at −78° C. The reaction mixture was stirred at −78° C. for 0.5 h and then allowed to warm to room temperature over 3 h. After stirring at room temperature for 8 h, the reaction mixture was diluted with CH$_2$Cl$_2$ (40 mL) and poured into 1 N HCl (20 mL). The organic layer was separated and washed with a buffer solution (20 mL, pH=7). After drying over anhydrous Na$_2$SO$_4$ and concentration in vacuo, the crude product was subjected to the next set of reaction conditions.

The crude bis(triethysilyl)ether was dissolved in THF (5 mL) and then cooled to 0° C. A solution of 0.1 N HCl in MeOH (2.2 mL) was added while the reaction was closely monitored by TLC. Methanolic HCl was in small portions, and approximately 5 mL of 0.1 N HCl was required for completion. The reaction mixture was diluted with CH$_2$Cl$_2$ (30 mL) and washed with buffer (10 mL, pH=7) and dried over anhydrous Na$_2$SO$_4$. After the removal of solvents, the crude product was purified on a silica gel column (hexanes/ethyl acetate=1:1) to give 0.370 g of the acid as a colorless sticky oil (70%). [α]$_D$−30.3 (c 2.34, CHCl$_3$). IR (film): 3389, 1759, 1734, 1705, 1456, 1384, 1251, 1093 1063, 993, 926, 818, 780, 732 cm$^{-1}$. $^1$H NMR (400 MHz, CDCl$_3$): δ 7.17 (s, 1H), 6.62 (s, 1H), 5.50 (s, 2H), 5.11 (t, J=6.6 Hz, 1H), 4.87 (d, J=12.0 Hz, 1H), 4.81 (s, 2H), 4.73 (dd, J=8.0, 3.6 Hz, 1H), 4.65 (d, J=12.0 Hz, 1H), 4.31 (dd, J=7.4, 2.4 Hz, 1H), 4.14~4.10 (m, 1H), 3.44~3.40 (m, 1H), 2.58 (d, J=16.8 Hz, 1H), 2.32~2.23 (m, 3H), 2.02 (s, 3H), 2.02~1.96 (m, 2H), 1.74~1.67 (m, 1H), 1.67 (s, 3H), 1.46~1.35 (m, 2H), 1.32~1.23 (m, 2H), 1.23 (s, 3H), 1.14~1.06 (m, 1H), 1.08 (s, 3H), 1.06 (d, J=6.8 Hz, 3H), 0.97~0.92 (m, 12H), 0.62 (q, J=7.5 Hz, 6H). $^{13}$C NMR (100 MHz, CDCl$_3$): d 215.2, 175.9, 161.7, 154.2, 153.6, 142.7, 139.1, 120.4, 118.0, 117.4, 94.8, 81.9, 77.2, 77.1, 76.8, 73.9, 66.4, 54.0, 41.4, 39.5, 34.7, 34.1, 32.1, 31.7, 24.7, 23.5, 22.5, 19.3, 15.7, 14.8, 14.2, 11.2, 6.9, 5.0. FAB-MS Calc'd for C$_{39}$H$_{60}$Cl$_6$NO$_{11}$SSi (M+H$^+$): 988.1788 Found: 988.1755.

7,21-Bis(2,2,2-trichloroethyloxycarbonyl)-3-triethylsilyloxy-12,13-desoxyepothilone F (15G). Triethylamine (0.360 mL, 2.60 mmol) and 2,4,6-trichlorobenzoic acid (0.528 g, 2.15 mmol) were added to a solution of the hydroxy acid (0.426 g, 0.430 mmol) in THF (9.0 mL). The reaction mixture was stirred for 15 min at room temperature and then diluted with toluene (40 mL). The resultant solution was taken up in a syringe and added to a previously prepared solution of DMAP (0.525 g, 4.30 mmol) in toluene (400 mL) via syringe pump over 3 h. After the addition was complete, the reaction was stirred for 1 h and then filtered with a short pad of celite. The filtrate was concentrated in vacuo, and flash chromatography on SiO$_2$ (hexanes/ethyl acetate=21:1) afforded 0.196 g of the desired macrolactone as a white foam (64%). Mp 71.7~72.9° C. [α]$_D$+1.5 (c 0.98, CHCl$_3$). IR (film): 1762, 1736, 1700, 1382, 1245, 1107, 928 cm$^{-1}$. $^1$H NMR (400 MHz, CDCl$_3$): δ 7.17 (s, 1H), 6.54 (s, 1H), 5.49 (s, 2H), 5.20~5.16 (m, 2H), 5.04 (d, J=10.1 Hz, 1H), 4.84 (d, J=12.0 Hz, 1H), 4.81 (s, 2H), 4.76 (d, J=12.0 Hz, 1H), 4.06 (d, J=10.0 Hz, 1H), 3.35~3.27 (m, 1H), 2.77~2.63 (m, 2H), 2.47 (t, J=9.9 Hz, 1H), 2.12 (s, 3H), 2.04 (dd, J=14.5, 7.8 Hz, 1H), 1.76~1.66 (m, 4H), 1.66 (s, 3H), 1.19 (s, 3H), 1.14 (s, 3H), 1.12 (d, J=6.7 Hz, 3H), 1.04~0.97 (m, 5H), 0.88 (t, J=8.1 Hz, 9H), 0.58 (q, J=7.9 Hz, 6H). $^{13}$C NMR (100 MHz, CDCl$_3$): d 212.7, 170.7, 161.5, 154.6, 153.3, 140.5, 139.6, 119.2, 118.3, 94.8, 86.5, 80.1, 77.1, 76.1, 66.5, 53.6, 45.6, 39.2, 35.5, 32.3, 31.7, 31.2, 27.4, 24.7, 23.4, 23.0, 18.7, 16.3, 14.8, 6.9, 5.2. FAB-MS Calc'd for C$_{39}$H$_{58}$Cl$_6$NO$_{10}$SSi (M+H$^+$): 970.1682 Found: 970.1648.

3-Triethylsilyloxy-12,13-desoxyepothilone F (16G). Procedure A: The mixture of samarium metal (126 mg, 0.838 mmol) and iodine (170 mg, 0.838 mmol) in THF (8 mL) was stirred vigorously at reflux for 2 h. During this period of time, the reaction mixture progressed from a dark orange to an olive green to deep blue color. The deep blue solution was cooled to room temperature, and a catalytic amount of nickel iodide (2.6 mg, 0.0083 mmol) was added. After 5 min stirring at room temperature, the mixture was cooled to −78° C. A solution of the macrolactone (81.5 mg, 0.0838 mmol) in THF (2 mL) was cannulated to the SmI$_2$/NiI$_2$ solution, and the stirring was continued for 1 h. After stirring at −40° C. for 2 h, the reaction mixture was poured into 1 N HCl (10 mL) and extracted with ethyl acetate (10 mL×3). The combined organic layers were washed with a saturated aqueous NaHCO$_3$ (10 mL) and brine, and dried over anhydrous MgSO$_4$. After evaporation of the solvents in vacuo, flash chromatography on a silica gel column (hexanes/ethyl acetate=2:1) yielded 45.3 mg of the diol as a colorless oil (87%). Procedure B: To a suspension of activated zinc dust (0.261 g, 3.84 mmol) in acetic acid (2 mL) was added a solution of the macrolactone (0.196 g, 0.201 mmol) in THF (1.0 mL) at room temperature. After stirring for 1.5 h, the reaction mixture was diluted with ethyl acetate (30 mL) and filtered with a plug of cotton to remove the excess zinc. The filtrate was then washed with a saturated aqueous NaHCO$_3$ (15 mL) and brine, and dried over anhydrous MgSO$_4$. After removal of the solvents, purification of the crude product by flash chromatography afforded 0.108 g of the diol as a colorless sticky oil (86%). [α]$_D$−52.0 (c 1.38, CHCl$_3$). IR (film): 3374, 1742, 1693, 1456, 1379, 1200, 1107, 1008, 977, 733 cm$^{-1}$. $^1$H NMR (400 MHz, CDCl$_3$): δ 7.09 (s, 1H), 6.54 (s, 1H), 5.15 (dd, J=9.9, 5.6 Hz, 1H), 5.06 (d, J=9.9 Hz, 1H), 4.93 (s, 2H), 4.09 (dd, J=9.8, 3.0 Hz, 1H), 3.87 (t, J=2.8 Hz, 1H), 3.09~3.03 (m, 2H), 2.80~2.64 (m, 4H), 2.47~2.40 (m, 1H), 2.09 (s, 3H), 2.09~2.06 (m, 1H), 1.88~1.63 (m, 3H), 1.63 (s, 3H), 1.42~1.12 (m, 4H), 1.15 (s, 3H), 1.13 (d, J=6.6 Hz, 3H), 1.12 (s, 3H), 1.01 (d, J=7.0 Hz, 3H), 0.88 (t, J=8.0 Hz, 9H), 0.65~0.50 (m, 6H). $^{13}$C NMR (100 MHz, CDCl$_3$): δ 218.3, 170.8, 169.8, 152.4, 139.3, 139.2, 120.3, 118.9, 116.5, 79.3, 77.2, 75.8, 73.6, 62.1, 53.6, 43.0, 39.5, 39.0, 32.8, 32.3, 31.2, 26.1, 24.2, 22.6, 22.5, 16.5, 15.3, 14.2, 14.0, 7.0, 5.3. LRMS Calc'd for C$_{33}$H$_{55}$NO$_6$SSiNa (M+Na$^+$): 656.4 Found: 656.4.

12,13-Desoxyepothilone F (dEpoF) (2Gd). The triethylsilyl ether (82 mg, 0.132 mmol) was dissolved in THF (2 mL) in a polyethylene vessel and cooled to 0° C. in an ice bath. The resultant solution was treated with HF-pyridine (1.5 mL) while closely monitored by TLC. After stirring at 0° C. for 1 h and at room temperature for 0.5 h, the reaction mixture was diluted with ethyl acetate (30 mL) and poured into a saturated aqueous solution of NaHCO$_3$ (20 mL). The organic layer was separated and washed once with a saturated aqueous solution of NaHCO$_3$ (20 mL) with 1 N HCl (20 mL) and brine, and dried over anhydrous MgSO4. Flash chromatography on a silica gel column with hexanes/ethyl acetate (1:2) mixture yielded 61 mg of desoxyepothilone F as a white foam (91%). Mp 172.4~174.0° C. [α]$_D$−63.3 (c 1.83, CHCl$_3$). IR (film): 3408, 1729, 1688, 1468, 1451, 1252, 1149, 1063, 1008, 978, 912, 733 cm$^{-1}$. $^1$H NMR (400

MHz, CDCl$_3$): d 7.09 (s, 1H), 6.58 (s, 1H), 5.24 (d, J=8.8 Hz, 1H), 5.12 (dd, J=9.5 4.8 Hz, 1H), 4.87 (d, J=4.5 Hz, 1H), 4.87 (d, J=4.5 Hz, 2H), 4.44 (br s, 1H), 4.32~4.28 (m, 1H), 3.78 (d, J=5.8 Hz, 1H), 3.68 (m, 1H), 3.12 (qd, J=6.8, 1.9 Hz, 1H), 3.07 (d, J=1.6 Hz, 1H), 2.60 (dt, J=15.2, 9.8 Hz, 1H), 2.45 (dd, J=14.4, 11.2 Hz, 1H), 2.32~2.22 (m, 3H), 2.04 (s, 3H), 1.92~1.85 (m, 2H), 1.75~1.64 (m, 2H), 1.64 (s, 3H), 1.32 (s, 3H), 1.29~1.21(m, 4H), 1.18 (d, J=6.8 Hz, 3H), 1.04 (s, 3H), 0.99 (d, J=7.0 Hz, 3H). $^{13}$C NMR (100 MHz, CDCl$_3$): d 220.7, 170.3, 170.0, 152.3, 139.7, 138.4, 120.9, 118.4, 116.4, 78.7, 74.2, 72.0, 61.4, 53.7, 41.5, 39.6, 38.5, 32.4, 31.7, 31.5, 25.2, 23.1, 22.9, 17.6, 16.1, 15.6, 13.4. HRMS Calc'd for C$_{22}$H$_{42}$NO$_6$S (M+H$^+$): 508.2733 Found: 508.2739.

2-Ethoxycarbonyl-4-chloromethyl(thiazole) (3H). The 1:1 mixture of ethyl aminothioxoacetate (0.145 g, 1.09 mmol) and 1.3-dichloroacetone (0.138 g, 1.09 mmol) in acetone (2 mL) was heated under reflux for 24 h. The dark brown solution was cooled to room temperature, diluted with ethyl acetate (10 mL), washed with saturated aqueous NaHCO$_3$ (3 mL) and brine, and dried over anhydrous MgSO4. After removal of the solvent, the remainder was purified by flash chromatography on a silica gel column eluted with hexane-ethyl acetate (3:1) to afford 0.187 g of thiazole 3H as a light yellow sticky oil (83%). IR (film): 3104, 2978, 2927, 1732, 1714, 1456, 1302, 1251, 1087 cm-1. $^1$H NMR (400 MHz, CDCl3): δ 7.63 (s, 1H), 4.77 (s, 2H), 4.48 (q, J=7.1 Hz, 2H), 1.41 (t, J=7.1 Hz, 3H). 13C NMR (100 MHz, CDCl$_3$): δ 159.7, 158.8, 154.7, 123.4, 62.9, 40.4, 14.3. LRMS: Calc'd for C$_7$H$_8$ClNO$_2$SNa (M+Na+): 227.7 Found 227.7.

2-Ethoxycarbonyl(thiazole)-4-methyl diphenylphosphine oxide (4H). To a solution of chloride (2.65 g, 12.9 mmol) in methylene chloride (13 mL) were added diphenylphosphine oxide (3.13 g, 15.5 mmol), cesium carbonate (5.88 g, 18.0 mmol) and a catalytic amount of tetrabutylammonium iodide (95 mg, 0.26 mmol). The resulting suspension was stirred at room temperature for 48 h. After TLC analysis indicated the complete consumption of the starting chloride, the reaction mixture was poured into a separatory funnel containing saturated aqueous NaHSO$_4$ (50 mL) and extracted with methylene chloride (50 mL×3). The combined organic layers were washed with saturated aqueous NaHCO$_3$ (50 mL) and brine, dried over anhydrous Na$_2$SO$_4$, and concentrated in vacuo. Purification by column chromatography on a silica gel column (ethyl acetate-methylene chloride=1:1) afforded 3.28 g of the Wittig reagent as a light viscous oil (68%). IR (film): 3055, 2982, 1736, 1710, 1438, 1302, 1251, 1195, 1120, 1088, 696 cm-1. $^1$H NMR (400 MHz, CDCl$_3$): δ 7.74~7.69 (m, 4H), 7.49~7.37 (m, 7H), 4.41 (q, J=7.1 Hz, 2H), 4.01 (d, J=13.3 Hz, 2H), 1.38 (t, J=7.1 Hz, 3H). $^{13}$C NMR (100 MHz, CDCl$_3$): d 159.7, 157.1, 149.0, 148.9, 132.4, 132.04, 132.01, 131.4, 131.0, 130.9, 123.6, 123.5, 62.5, 33.9, 33.2, 14.2. LRMS: Calc'd for C$_{19}$H$_{18}$NO$_3$PSNa (M+Na+): 394.0 Found 394.0, Calc'd for C$_{19}$H$_{19}$NO$_3$PS (M+H+): 372.0 Found 372.0.

Vinyl iodide 6H. To a solution of the Wittig reagent (70 mg, 0.19 mmol) in THF (2 mL) was added dropwise lithium hexamethyldisilazide (1.0 M in THF, 0.15 mL) at −78° C. The initially light yellow solution turned to a deep red solution immediately. After 10 min, a solution of the ketone in THF was slowly added to the red solution via a cannula. Upon completion of the addition, the reaction mixture was allowed to warm to 0° C. over 0.5 h at which point TLC analysis indicated the completion of the reaction. The mixture was poured into saturated aqueous NaHSO$_4$ (5 mL) and extracted with ether (5 mL×3). The combined organic layers were washed with saturated aqueous NaHCO$_3$ (5 mL) and brine, dried over anhydrous MgSO4, and concentrated in vacuo. Purification by column chromatography on a silica gel column (hexanes-ethyl acetate=20:1) afforded 52 mg of the ethyl ester as a colorless oil (80%). $^1$H NMR (400 MHz, CDCl$_3$): δ 7.39 (s, 1H), 6.65 (s, 1H), 5.44 (td, J=6.6, 1.4 Hz, 1H), 4.48 (q, J=7.1 Hz, 2H), 4.24 (t, J=6.2 Hz, 1H), 2.47 (s, 3H), 2.44~2.32 (m, 2H), 2.03 (s, 3H), 1.43 (t, J=7.1 Hz, 3H), 0.93 (t, J=7.9 Hz, 9H), 0.59 (q, J=8.0 Hz, 6H).

Alcohol 7H. To a slurry of lithium aluminum hydride (4.0 mg, 0.10 mmol) in ether (0.5 mL) was added dropwise a solution of the ethyl ester (52 mg, 0.10 mmol) at 0° C. After the addition, the reaction mixture was allowed to warm to room temperature and stirred for 2 h. The mixture was then poured into saturated aqueous NaHSO$_4$ (5 mL) and extracted with ether (5 mL×3). The combined organic layers were washed with saturated aqueous NaHCO$_3$ (5 mL) and brine, dried over anhydrous MgSO4, and concentrated in vacuo. Purification by column chromatography on a silica gel column (hexanes-ethyl acetate=5:1) afforded 24 mg of the alcohol as a clear oil (50%). 1H NMR (400 MHz, CDCl$_3$): δ 7.08 (s, 1H), 6.50 (s, 1H), 5.44 (t, J=6.7 Hz, 1H), 4.96 (s, 2H), 4.20 (t, J=6.3 Hz, 1H), 2.50 (s, 3H), 2.40~2.33 (m, 2H), 2.02 (s, 3H), 0.92 (t, J=7.8 Hz, 9H), 0.66 (q, J=7.9 Hz, 6H).

Glycolimide 10Ha. To a solution of PMB-protected imide (9.23 g, 26.0 mmol) in dichloromethane (90 mL) cooled to 0° C. was added TiCl$_4$ (5.05 g, 27.3 mmol). The solution was stirred at 0° C. for 5 min. after which diisopropylethyl amine (3.53 g, 27.3 mmol) was added dropwise and stirring continued for 1 h. The reaction was quenched with a sat. NaHCO$_3$ solution and extracted using dichloromethane (3×60 mL). The combined organic layers were washed with brine (1×50 mL) then dried over MgSO$_4$. The solution was then filtered and concentrated in vacuo. Chromatography on silica gel (70% EtOAc/hexanes) provided glycolimide 10Ha (5.5 g, 87%) as a clear oil.

Glycolimide 11H. To a solution of glycolimide X (4.75 g, 20.2 mmol) in DMF (20 mL) was added imidazole (1.65 g, 24.3 mmol) followed by TESCl (3.35 g, 22.2 mmol). The mixture was stirred at room temperature for 12 h. The solution was then poured into H$_2$O (200 ml) and extracted with EtOAc (4×100 mL). The combined organic layers were washed with H$_2$O (2×100 mL) and dried over MgSO$_4$. The solution was then filtered and concentrated in vacuo. Chromatography on silica gel (25% EtOAc/hexanes) provided TES-protected glycolimide 11H (5.93 g, 84%) as a clear oil. R$_f$=0.33 in 20% EtOAc/hexanes; IR (neat) 2954, 2876, 1780, 1717, 1394, 1350, 1149 cm$^{-1}$; $^{13}$C NMR (100 MHz, CDCl$_3$) δ 171.6, 153.5, 135.0, 129.4, 129.0, 127.4, 67.2, 63.9, 54.9, 37.7, 6.7, 4.3; LRMS (+electrospray): 372.0 [M+Na]+, 350.2 [M+H]+.

Alkylated Glycolimide (12H). TES-protected glycolimide 11H (1.11 g, 3.18 mmol) was dissolved in THF (20 mL) and cooled to −78° C. LHMDS (1.0M THF solution, 3.50 mmol) was added dropwise and stirred at −78° C. for 30 min. 1,3-diiodo-3-butene (1.08 g, 3.5 mmol) in THF (5 mL) was added to the cooled enolate via cannula after which the solution was slowly warmed to room temperature over 12 h. The solution was quenched with a sat. NaCO$_3$ solution and extracted with EtOAc (3×30 mL). The combined organic extract were washed with brine (50 mL), dried over MgSO$_4$, filtered, and concentrated in vacuo. Chromatography on silica gel (10% EtOAc/hexanes) provided alkylated glycolimide 12H (1.27 g, 81%) as a light yellow oil. R$_f$=0.47 in 20% EtOAc/hexanes; IR (neat) 2954, 2876, 1778, 1714, 1455, 1392, 1349, 1327, 1208, 1010 cm$^{-1}$; $^{13}$C NMR (100

MHz, CDCl$_3$) δ 173.0, 153.1, 135.1, 130.3, 129.4, 129.0, 127.4, 103.6, 69.8, 66.9, 55.1, 42.6, 37.9, 33.8, 6.7, 4.6; LRMS (+electrospray): 552.1 [M+Na]+, 530.1 [M+H]+.

Alkylated TES-Protected N,O-dimethamide (12Ha). Alkylated TES-protected glycolimide 12H (5.29 g, 10.0 mmol) was dissolved in HOAc:THF:H$_2$O (3:1:1, 150 mL) and stirred at room temperature for 4 h. The solvent was then removed in vacuo. The oily residue was dissolved in EtOAc (100 mL) and washed with sat. NaCO$_3$ (2×50 mL), and brine (50 mL). The organic layer was dried over MgSO$_4$, filtered, and concentrated in vacuo. This material was used for the subsequent reaction without further purification. N,O-Dimethyl hydroxylamine hydrochloride (4.87 g, 50.0 mmol) was suspended in THF (60 mL) and cooled to 0° C. A 1.0 M solution of AlMe$_3$ in toluene (25 mL, 50 mmol) was added dropwise. After the addition was complete the ice bath was remove and the solution was stirred at room temperature for 2 h. This solution was then cannulated into a solution of the crude alkylated glycolimide (prepare above) in THF (100 mL) at 0° C. After the addition was complete the ice bath was remove and the mixture was stirred at room temperature for 6 h. The reaction was quenched by the addition of a 1N tartaric acid solution (100 mL) and stirred 1 h. The organic layer was removed and the aqueous layer was extracted with EtOAc (3×100 mL). The combined organic layers were dried over MgSO$_4$, filter, and concentrated in vacuo. Chromatography on silica gel (20% acetone/hexanes) provided N,O-dimethylamide 12Ha (2.67 g, 91% for two steps) as a clear oil. R$_f$=0.42 in 40% acetone/hexanes; IR (neat) 3439, 2962, 1659, 1438, 1371, 1196, 1092, 1061, 991, 884, 824 cm$^{-1}$; $^{13}$C NMR (100 MHz, CDCl$_3$) δ 173.8, 130.4, 103.3, 67.8, 61.5, 41.6, 33.8, 32.5; LRMS (+electrospray): 321.7 [M+Na]+, 299.8 [M+H]+.

TES-Protected N,O-dimethylamide (13H). To a solution of N,O-dimethylamide 12Ha (2.53 g, 8.47 mmol) in DMF (15 mL) was added imidazole (0.69 g, 10.2 mmol) followed by TESCl (1.40 g, 9.32 mmol). The solution was stirred at room temperature for 5 h. The solution was then poured into H$_2$O (150 mL) and extracted with EtOAc (4×100 mL). The combined organic layers were washed with H$_2$O (2×100 mL) and dried over MgSO$_4$. The solution was then filtered and concentrated in vacuo. Chromatography on silica gel (15% acetone/hexanes) provided TES-protected N,O-dimethylamide 13H (3.39 g, 97%) as a yellow oil. R$_f$=0.66 in 40% acetone/hexanes; IR (neat) 2954, 2876, 1682, 1459, 1435, 1324, 1240, 1104, 1002, 743 cm$^{-1}$; LRMS (+electrospray): 435.9 [M+Na]+, 414.1 [M+H]+.

TES-Protected methyl ketone (14H). To a solution of TES protected N,O-dimethylamide 13H (3.27 g, 7.91 mmol) in THF (80 mL) cooled to 0° C. was added methyl magnesium bromide (3.0M in diethylether, 23.7 mmol). The solution was stirred at 0° C. for 15 min and then quenched with a sat. NH$_4$Cl solution (50 mL). The organic layer was removed and the aqueous layer was extracted with EtOAc (3×50 mL). The combined organic layers were dried over MgSO$_4$, filtered, and concentrated in vacuo. Chromatography on silica gel (15% acetone/hexanes) provided TES-protected methyl ketone 14H (2.72 g, 93%) as a yellow oil. R$_f$0.35 in 20% acetone/hexanes; IR (neat) 2955, 2877, 1718, 1458, 1415, 1352, 1239, 1101, 1005, 812, 742 cm$^{-1}$; $^{13}$C NMR (100 MHz, CDCl$_3$) δ 210.9, 130.0, 103.7, 77.5, 41.8, 33.7, 25.2, 6.7, 4.7; LRMS (+electrospray): 390.9 [M+Na]+.

Hydroxy Ketone (17H). A solution of ketone 16H (3.10 g, 13.0 mmol) in CH$_2$Cl$_2$ (70 mL) was cooled to −17° C. and treated successively with HMDS (10.0 mL, 47.4 mmol) and then TMSI (5.5 mL, 38.6 mmol). The resulting yellow suspension was warmed to rt after 5 min. and magnetically stirred for 3 h, after which the reaction mixture was diluted with Et$_2$O (100 mL) and washed with cold saturated NaHCO$_3$ (2×50 mL). The aqueous layer was back-extracted with Et$_2$O (2×50 mL). The combined Et$_2$O extracts were dried over Na$_2$SO$_4$, filtered, and concentrated. The resulting yellow oil was used in the following step without further purification.

A solution of AD-mix-α (16.49 g) and OsO$_4$ (1.55 mL, 0.152 mmol) in 1:1 t-BuOH:H$_2$O (124 mL) was cooled to 0° C. and treated with the crude silyl enol ether. After 2 h the reaction was quenched with saturated Na$_2$SO$_3$ (100 mL), warmed to rt, and stirred for 1 h. The reaction mixture was extracted with EtOAc (3×100 mL). The combined organic extracts were dried over MgSO$_4$, filtered, and concentrated. Silica gel chromatography (5:1 hexanes:EtOAc) provided 17H (1.60 g, 48% overall) as a clear oil. IR (neat) 3447, 2950, 2913, 1716, 1653, 1558, 1540, 1419, 1360, 1279, 1242, 1181, 1092, 1061 cm$^{-1}$; $^1$H NMR (400 MHz, C$_6$D$_6$) δ 5.32 (td, J=1.3, 5.2 Hz, 1H), 3.77–3.73 (m, 1H), 3.52 (d, J=4.4 Hz, 1H), 2.43–2.36 (m, 1H), 2.17–2.10 (m, 4H), 1.56 (s, 3H); $^{13}$C NMR (100 MHz, C$_6$D$_6$), δ 208.4, 130.5, 103.8, 75.6, 40.9, 33.5, 24.8; LR-ESI calcd for C$_7$H$_{11}$IO$_2$: 254.0, found 288.6 [M−Cl]−.

TES-Protected Hydroxy Ketone (14H). A solution of hydroxy ketone 17H (1.383 g, 5.44 mmol) in DMF (10 mL) was treated with imidazole (0.822 g, 12.1 mmol) and TESCl (1.00 mL, 5.95 mmol). After 3 h the reaction was diluted with H$_2$O (20 mL) and extracted with EtOAc (3×20 mL). The combined organic extracts were washed with H$_2$O (1×20 mL) and brine (1×20 mL), then dried over MgSO$_4$, filtered, and concentrated. Silica gel chromatography (20:1 ® 5:1 hexanes:EtOAc) provided 14H (1.72 g, 86%) as a clear oil.

Example 2

Synthesis of Desoxyepothilone F via Presentation of Acyl Sector for Coupling in Reduced Form and Novel Methodologies for the Synthesis of Right and Left Wings In another embodiment, the total synthesis of dEpoF was accomplished, as shown in FIG. 1, and as detailed herein. Specifically, in an effort to improve the efficiency of the synthetic techniques employed, a novel and improved total synthesis of the promising antitumor agent, dEpoF was developed utilizing an acyl sector for Suzuki coupling with C3 already reduced (rather than performing the Noyori reduction after Suzuki coupling). In the context of this effort, a more convergent and modular route to both the acyl and alkyl sectors was developed. The new synthesis features a convergent and modular nature strategy with strong stereoselectivities at each step. The conciseness of the syntheses of the key intermediates readily allow for large scale preparation and easy structural variation in each synthetic segment.

Figure 19:
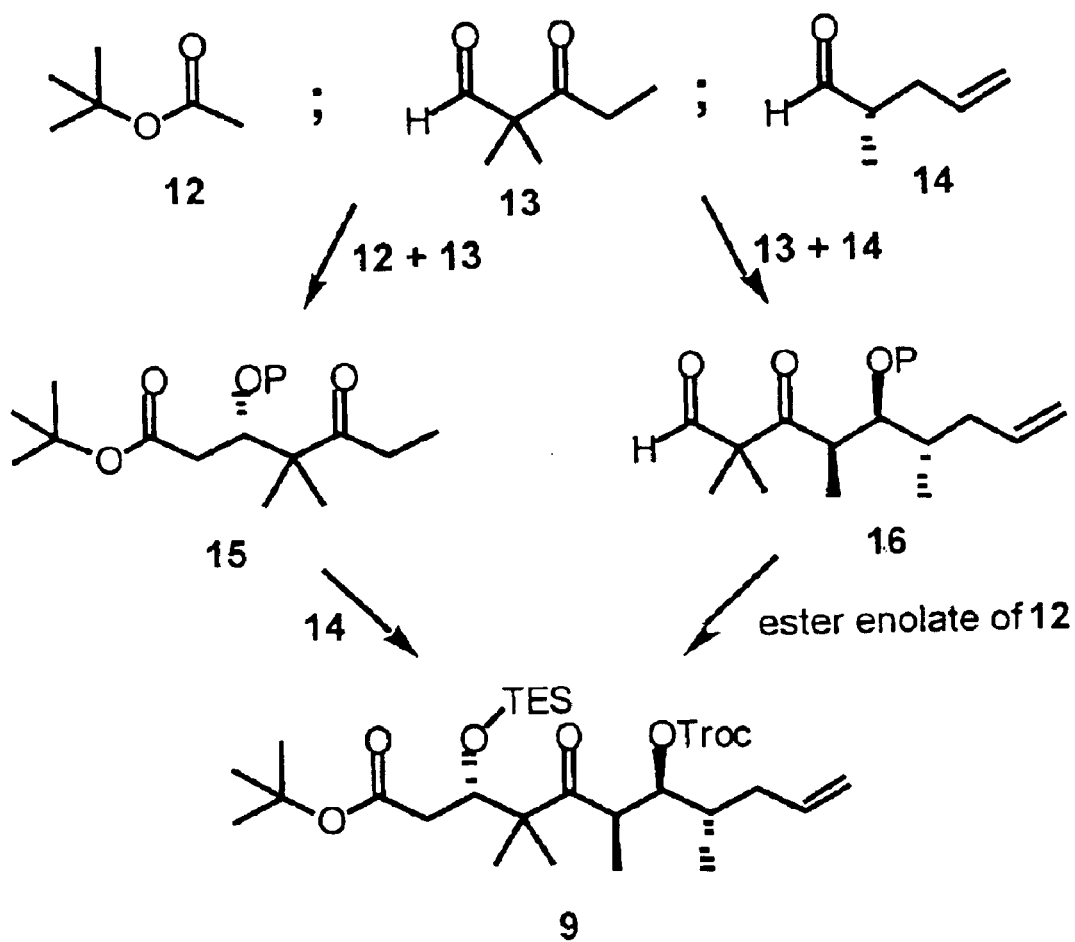
FIG. 19 depicts the synthetic plan for the O-Acyl Wing by sequential aldol reactions.

More specifically, for the synthesis of the O-alkyl wing of dEpoF, the Homer-like condensation conveniently conjoined the thiazole moiety and the segment possessing the critical C15 stereochemistry and (Z)-12,13-alkene function. The stereoselective aldol reactions en route to the O-acyl wing were investigated in some detail. As depicted in FIG. 19, it was demonstrated that a subtle variation in factors affecting the transition state has remarkable influence on the long range transmission of stereochemical information. In these studies (see also Wu et al., *Angew. Chem. Int. Ed.* 2000, 39, 4505–4508), the entire contents of which are hereby incorporated by reference, the implicatinons of ste reochemical matching of components in an aldol condensation were probed at a kinetic level. A remarkable instance of the consequences of molecular recognition in covalent bond formation has been demonstrated via kinetic resolution. As depicted in FIG. 19, for the synthesis of the O-Acyl wing 16, it was anticipated that sterselective aldol reactions of ketoaldehyde 19 with acetate 20 and aldehyde 11 in an appropriate order would assemble the necessary carbon units with control of the configuration at the relevant chiral centers (see, FIG. 18). It was believed that in this scenario a stereogenic center of an early aldol product (A or B) could potentially influence on the diastereoselectivity of the emerging C-C bond by a late aldol process. It was also demonstrated that a subtle variation in factors affecting the transition state has a remarkable influence on the long range transmission of stereochemical information.

Given the high degree of intolerance found in the SAR map of the polypropionate region, the new O-acyl wing fragment may serve as a widely applicable intermediate for accessing various analogues. Both the in vitro and in vivo evaluations of dEpoF, as described in more detail, revealed a highly promising antitumor activity for this compound.

In addition to the general synthetic methodology as provided above, the present invention additionally provides novel methods for the preparation of methyl ketone 11 by two independent sequences. The first approach involves an asymmetric catalytic oxygenation method to install the C15 center and iodoboration of an alkyne to implement the (Z)-alkene geometry (FIG. 3). As shown in FIG. 3, in one embodiment of the invention, propyne (17) reacted with B-iodo-9-BBN and the resultant vinyl borane was added to methyl vinyl ketone to furnish ketone 18. Subsequent treatment of this compound with TMSI/HMDS afforded an 88:12 mixture of two silyl ether regioisomers 19 and 20. Asymmetric dihydroxylation of the mixture, using AD-mix-α, generated hydroxyketone 21 in 55% yield and in 87% enantiomeric excess. It is noteworthy that it was possible to sustain the potentially vulnerable iodoalkene functionality during the osmium mediated dihydroxylation. Finally, triethylsilylation of 25 produced 18, completing the sequence in only four steps.

In yet another embodiment of the invention, a route involving an asymmetric alkylation reaction to establish the C15 configuration (FIG. 4) was investigated. Carbon-carbon bond formation was effected using a chiral glycolate enolate as a nucleophile and the required (Z)-2,4-diiodo-2-butene (22) could be readily prepared from 2-butyn-4-ol. Previously, asymmetric synthesis of glycolates had been accomplished by oxygenation of the "chiral enolate" (i.e. one armed with an auxilliary acyl group) rather than by alkylation. Examples involving the alkylation of a glycolate of the general type 24 tended to require a robust O-protecting group. Hence, the feasibility of using silyl protected 24 in these alkylations was examined. Synthesis of the silylated glycolate began with the known PMB derivative 24b which was obtained from 23 in 3 steps. In certain other embodiments 23 could be converted to 24a in multi-gram scales by a one flask procedure involving in situ formation of a mixed anhydride. Subseqent treatment of lithio 24a with diiodide 22 at −78° C. afforded the desired 25a as a single isomer (>98% d.e.) in good yield. In certain embodiments TES function was preferentially used as the protecting device, and the asymmetric alkylation of 24a could be routinely performed in multi-gram scales to give enantiopure 25a. After removal of the TES group, the formation of Weinreb amide 26a was effected by simultaneous detachment of the chiral auxiliary, and subsequent protection and Grignard addition afforded 11.

Figure 20:
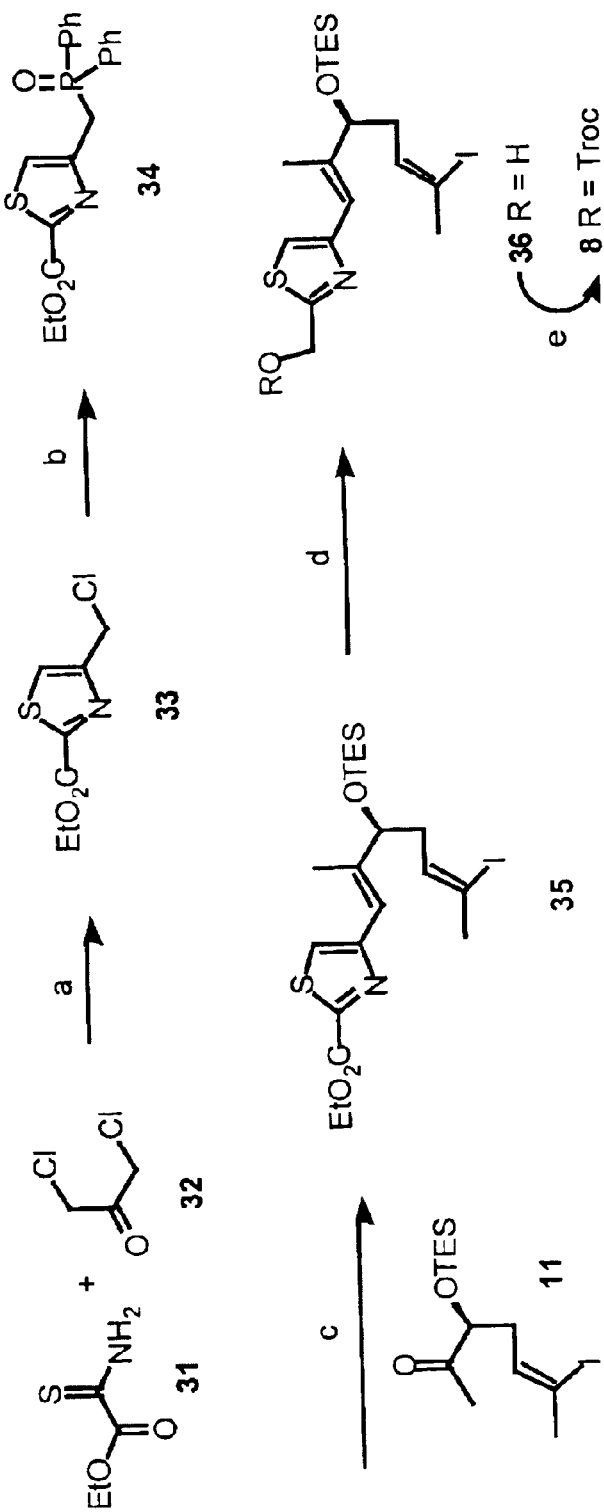
FIG. 20 depicts the synthesis of the O-Alkyl wing via Homer Condensation. Reagents and conditions: (a) Toluene, 110° C., 2 h, 96%; (b) HOPPh$_2$, Cs$_2$CO$_3$, cat. TBAI, CH$_2$Cl$_2$, rt, 48 h, 82%; (c) LHMDS, THF, –78° C., 52%; (d) 2.5 eq Dibal-H, CH$_2$Cl$_2$, 0° C., 98%; (e) Cl$_3$CCH$_2$OCOCl, Pyridine, CH$_2$Cl$_2$, 86%.
Figure 21:
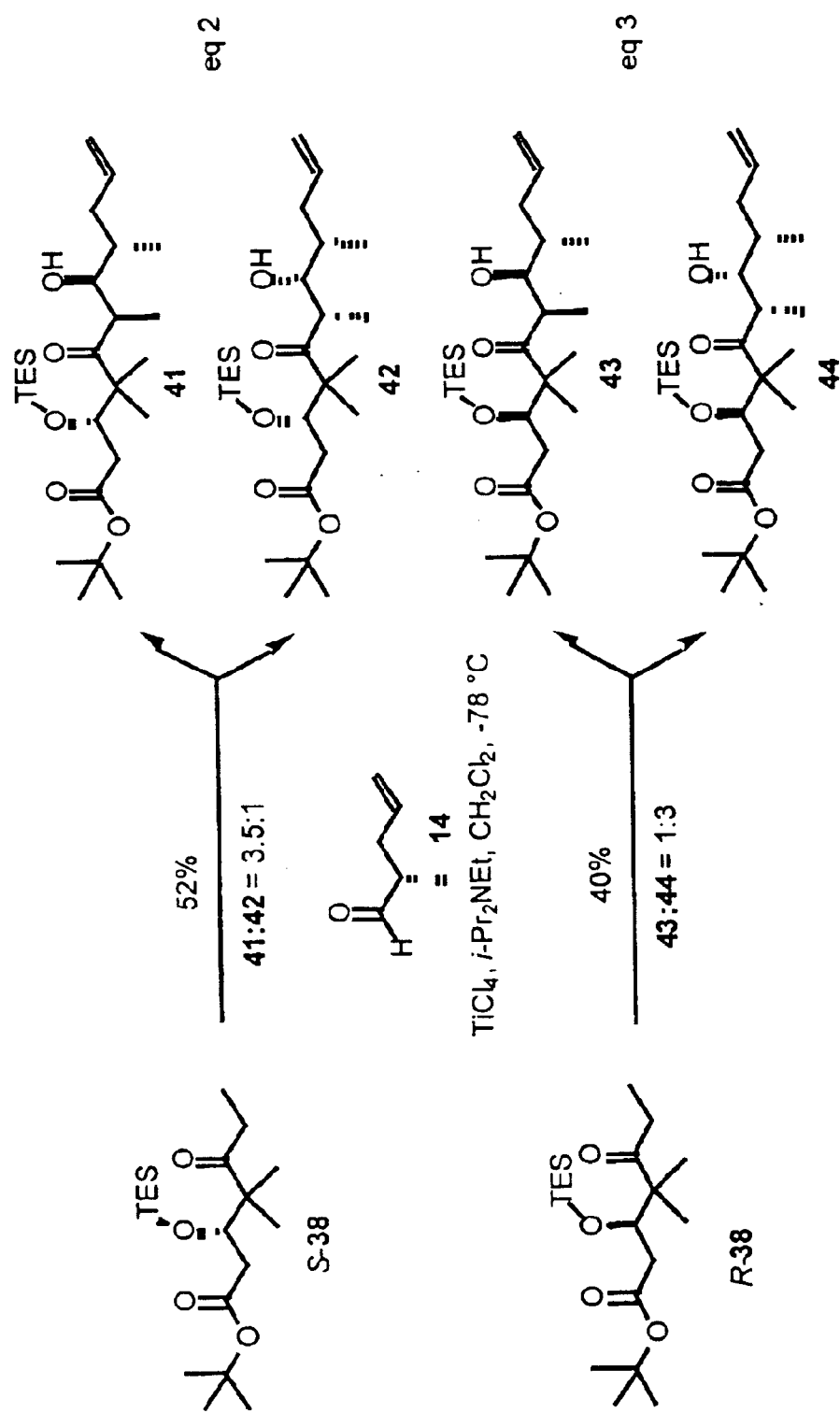
FIG. 21 depicts the aldol condensation of TES ether antipodes 38.

After the preparation of the requisite ketone 11, as described in certain exemplary embodiments above, preparation of the completed left wing moiety was achieved. Specifically, as shown in FIG. 20, ethyl thiooxamate (31) was condensed with 1,3-dichloroacetone (32) to provide 2,4-disubstituted thiazole 33 in excellent yield. 35 can then be effected, in certain embodiments via Arbuzov reaction using $Ph_2POEt$ or direct P-alkylation with $HOPPh_3$. Upon treatment with LHMDS, thiazole 34 and ketone 11 condensed smoothly to furnish 35 as a single geometric isomer. Finally, reduction of ester 35 with Dibal-H generated alcohol 36 which was protected with a Troc group to yield the desired O-alkyl moiety 8. The new route is significantly shorter and more convergent than the previous sequence which involved 10 linear transformations.

New Synthetic Route to the O-Acyl Fragment

Having successfully prepared the O-alkyl building block 8 in quantity, attention was then turned to the development of a route to the O-acyl fragment 9. As described earlier, use of the segment used in our previous synthesis (see, example 1), led certain solvolysis problems at C15 during the Noyori reduction. Hence, the major point of improvement was focused on the establishment of the C3 carbinol center prior to the Suzuki merger. In one embodiment, attempts to realize an asymmetric Reformatsky reaction (eq 1, Table 1), were investigated. Addition reactions of "zincated" of t-butyl bromoacetate to ketoaldehyde 13 were performed in the presence of chiral amino alcohol 39 (Soal et al. *J. Chem. Soc. Perkin Trans.* 1994, 1257; Soal et al. *Chem. Rev.* 1992, 92, 833). The reactions gave rise to the expected aldol adduct in excellent yields, and thus it will be appreciated that the reaction can be applied to a variety of other two carbon nucleophiles, although the enantioselectivities did not reach synthetically desirable levels (entries 1 and 2). While decreasing the reaction temperature increased the enantioselectivities significantly, reactions conducted this way suffered from less efficient conversion (entry 3).

In yet another embodiment, stereocontrol was achieved by the reaction of a chiral titanium enolate derived from t-butyl acetate. Following literature protocol (Dunthaler et al. *Angew. Chem. Int. Ed. Engl.* 1989, 28, 495), both enantiomers of β-hydroxy t-butyl ester 37 were prepared in good yields with high enantioselectivity (entries 4 and 5). The ee and sense of the absolute stereoselectivity was determined by derivatization of 37 to the corresponding Mosher's ester, and corroborated by certain events in our program (see, Dale et al. *J. Am. Chem. Soc.* 1973, 95, 512).

TABLE 1
Asymmetric Synthesis of C3 Stereogenic Center
| Entry | Nucleophile | Additive | Temp (° C.) | % Yield[a] | er[b] (S-37:R-37) |
|---|---|---|---|---|---|
| 1 | t-BuOCCH$_2$Br<br>Zn, TMSCl | 39 (Ph, Ph, OH, N-Me pyrrolidine) | 0 | 91 | 3:1 |
| 2 | t-BuOCCH$_2$Br<br>Zn, TMSCl | 39 | −40 | 93 | 5:1 |
| 3 | t-BuOCCH$_2$Br<br>Zn, TMSCl | 39 | −78 | 22 | 11:1 |
| 4 | t-BuOCCH$_3$<br>LDA | L-40<br>R = L-DIPGFc | −78 | 80 | >20:1 |

TABLE 1-continued

Asymmetric Synthesis of C3 Stereogenic Center

| Entry | Nucleophile | Additive | Temp (° C.) | % Yield[a] | er[b] (S-37:R-37) |
|---|---|---|---|---|---|
| 5 | t-BuOCCH$_3$ (O) | D-40 (Ti with Cp, Cl, OR, OR) | −78 | 85 | >1:20 |
|  | LDA | R = D-DIPGF[d] |  |  |  |

[a]Isolated yields.
[b]er = Enantiomeric ratio determined by $^1$H NMR integration of appropriate signals of the corresponding Mosher's ester.
[c]L-DIPGF = 1,2:5,6-di-O-isopropylidene-α-L-glucofuranos-3-O-yl.
[d]D-DIPGF = 1,2:5,6-di-O-isopropylidene-α-D-glucofuranos-3-O-yl.

Figure 22:
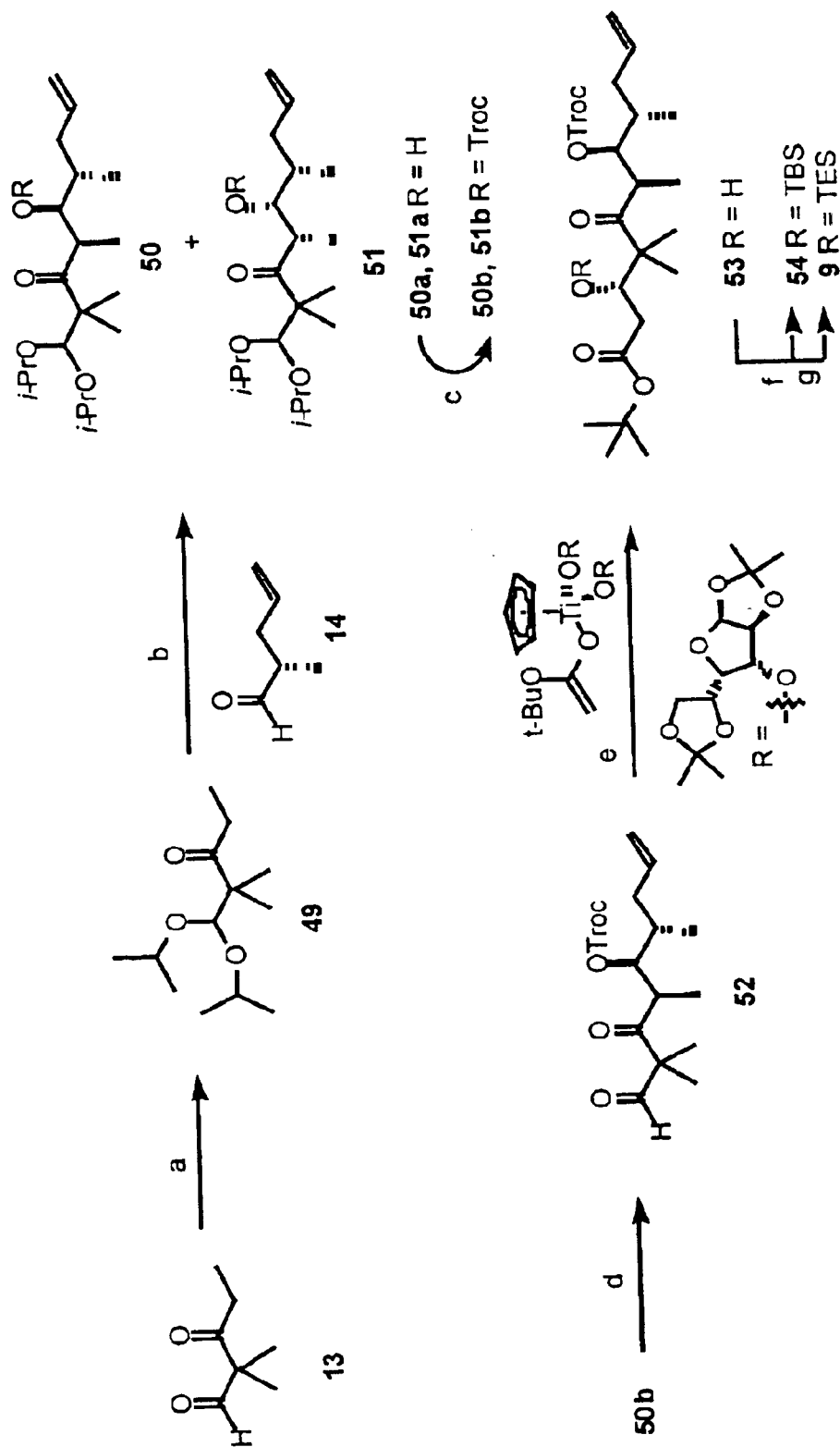
FIG. 22 depicts a novel synthetic route to the O-Acyl Wing. Reagents and conditions: (a) CH(Oi-Pr)$_3$, iPrOH, cat. TsOH, 88%; (b) LDA, –78° C., 85%, 46:47=4:1; (c) TrocCl, Pyridine, CH$_2$Cl$_2$, 0° C., 99%; (d) H$_2$O/THF, cat. TsOH, 88%; (e) THF, 89%, dr>20:1; (f) TBSOTf, 2,6-lutidine, CH$_2$Cl$_2$, –78° C., 81%; (g) TESCl, imidazole, DMF, 96%.

Having found a method to generate 37 in high enantiomeric excess, the double stereo-differentiation aldol reaction was investigated (For examples of aldol reactions of β-hydroxy ketones see Luke et al. *J. Org. Chem.* 1995, 60, 3013; Evans et al. *Tetrahedron Lett.* 1993, 34, 6871; McCarthy et al. *J. Org. Chem.* 1987, 52, 4681). In order to use protected 37 as the nucleophile, both enantiomeric aldol adducts were converted to corresponding TES ether antipodes 38. For the reaction, the titanium enolate of 38 for the same aldol reaction was utilized (Evans et al. *J. Am. Chem. Soc.* 1990, 112, 8215). Indeed, both (S)-38 and (R)-38 underwent the aldol condensation, giving mixtures of diastereomers, in moderate yields (FIG. 22). The stereochemical outcome of the major diastereomer from each reaction indicated that the configuration of C3 rather than C8 had a larger effect on the sense of the newly formed C6 and C7 centers.

During the course of the studies as described herein, certain other studies were performed to investigate the subtle variations in the long-range transmission of stereochemical information, during the course of the aldol reactions described herein. It was determined that, in the case of the lithio alkoxy enolates, a large kinetic advantage favoring the matched series has been demonstrated. It will be appreciated that these findings can be applied to other instances of long-range transmission of stereochemical bias. For a discussion of these results, see, Wu et al., *Angew. Chem. Int. Ed.* 2000, 39, 4505–4508, the entire contents of which are hereby incorporated by reference.

Thus, in certain other embodiments, an alternative sequence to 9 was sought wherein sequential "substrate-directed" and "reagent-controlled" aldol reactions would establish the requisite configurations at C6, C7 and C3 (FIG. 22).

Toward this end, ketoaldehyde 13 was protected as a diisopropyl acetal, and the resultant ketone 49 was subjected to an aldol reaction with 14. Upon deprotonation of 49 with LDA and reaction with 14, smooth condensation gave rise to a 4:1 mixture of aldol adducts 50 and 51. The major diastereomer 50 was very easily separated by flash chromatography and protected as a Troc group. Indeed, there was a significant advantage in this route in that the aldol condensation, unlike our earlier cases where C3 corresponded to an enol ether, went to completion. Furthermore, the reaction conditions are much less demanding technologically, since now the coupling is conducted at −78° C. rather than at −120° C. in the previous synthesis.

Referring to FIG. 22, hydrolysis of the diisopropyl acetal group of 50b under acid catalysis gave ketoaldehyde 52, setting the stage for the second aldol reaction. Following the same "titano" t-butyl ester method using a glucose derived auxiliary as in eq 1, the desired C3(S) 53 was obtained in high diastereoselectivity (dr>20:1). Protection of the C3 alcohol with a silyl group finally afforded the O-acyl wing 9 and the TBS derivative 54 whose spectral and chromatographic properties were identical to previously obtained material from other programs in these laboratories.

Figure 23:
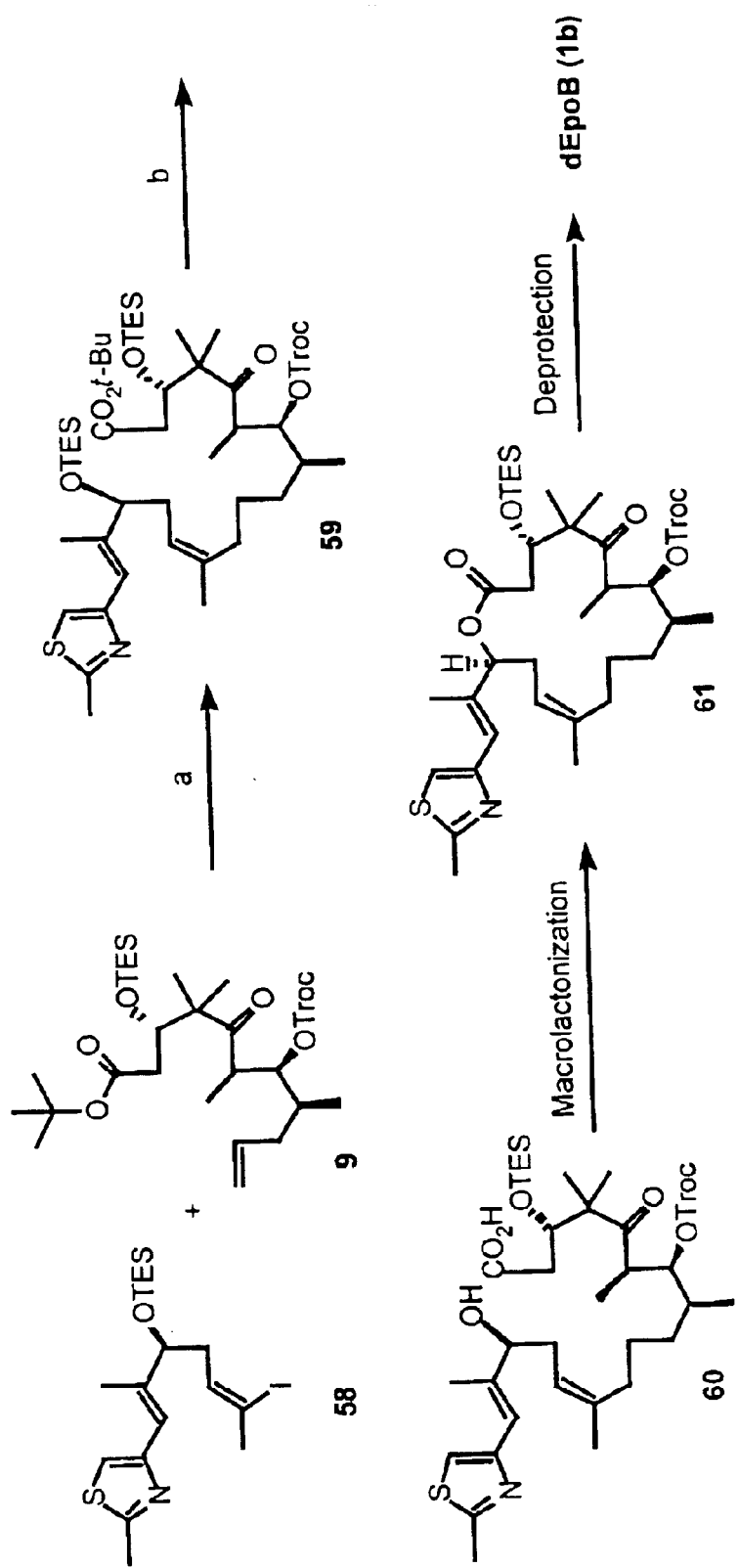
FIG. 23 depicts the total synthesis of dEpoB. Reagents and conditions: (a) i) 9-BBN-H, THF (ii) PdCl$_2$(dppf), AsPh$_3$, DMF-THF-H$_2$O, rt, 2 h, 72%; (b) TESOTf, 2,6-lutidine, CH$_2$Cl$_2$, –78° C. to rt, 8 h, (ii) HCl—CH$_3$OH, THF, 0° C., 69%.

Newly prepared 9 was then utilized in the formal total synthesis of dEpoB as illustrated in FIG. 23. The B-alkyl Suzuki coupling with the O-alkyl segment for EpoB series 58 proceeded to yield 59. Subsequently, treatment of 59 with TESOTf followed by selective desilylation afforded hydoxyacid 60 which had been advanced to dEpoB (2b) and EpoB (1b) in our previous syntheses. Accordingly, these studies unambiguously established the stereochemical outcomes of the various aldol reactions and constitute an alternate total synthesis of dEpoB. It will be appreciated that the "titanoacetate" based route to the C3S series in the acyl sector or the post-Suzuki (C3 keto→C3S hydroxy) route practiced previously, can be utilized depending on issues of costing and on susceptibility to scale up.

Finally, these findings were applied to a total synthesis of dEpoF. As explained above, a much improved total synthesis of this compound is important to advance to clinical evaluation.

Figure 24:
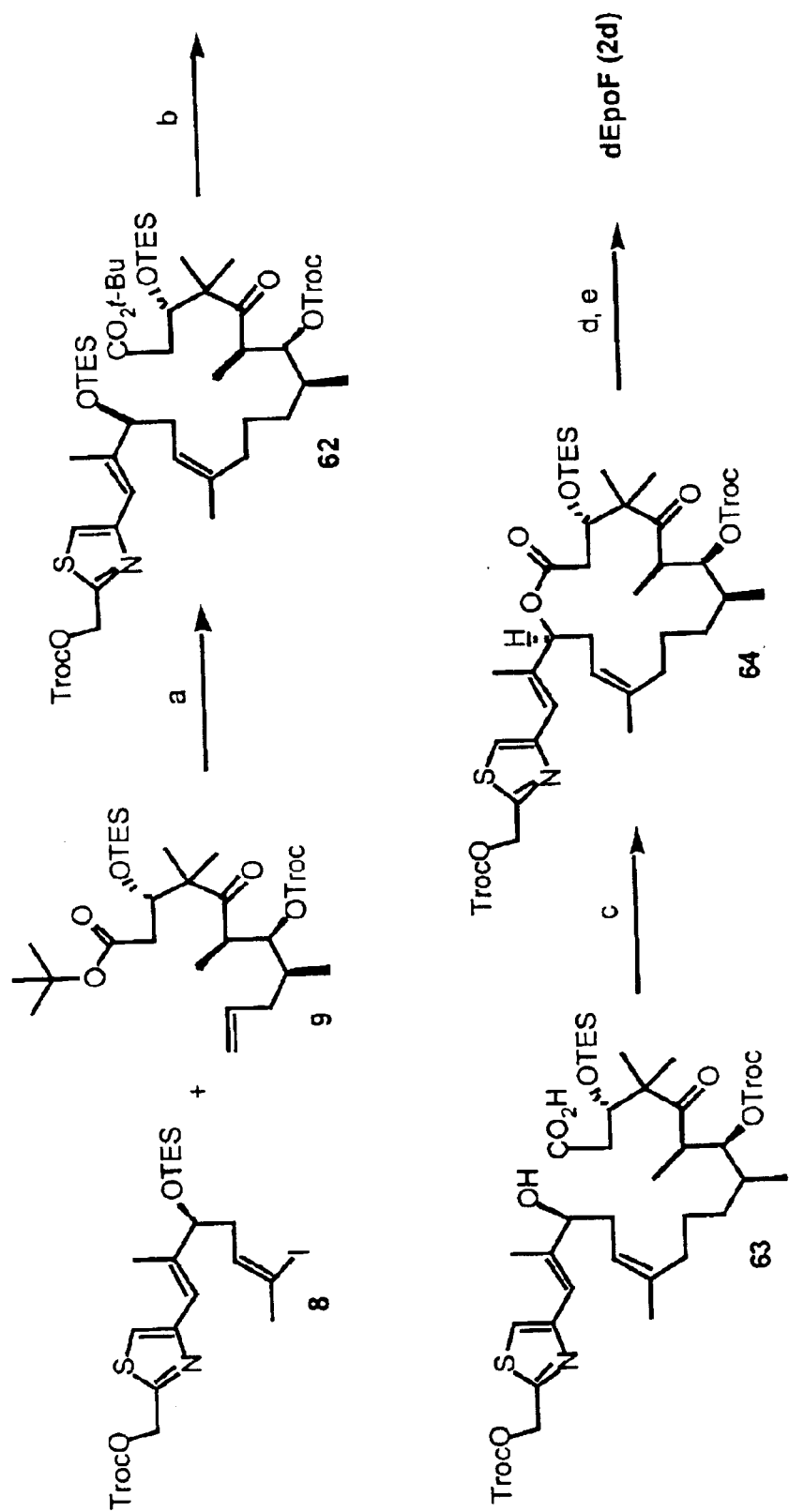
FIG. 24 depicts the completion of the total synthesis of dEpoF. Reagents and conditions: (a) i) 9-BBN-H, THF (ii) PdCl$_2$(dppf), AsPh$_3$, DMF-THF-H$_2$O, rt, 8 h, 89%; (b) TESOTf, 2,6-lutidine, CH$_2$Cl$_2$, –78° C. to rt, 8 h, (ii) HCl—CH$_3$OH, 0° C., 78; (c) 2,4,6-trichlorobenzoyl chloride, (C$_2$H$_5$)$_3$N then 4-DMAP, toluene, slow addition 3 h, 60–70%; (d) Zn, AcOH-THF, rt, 1 h, 90% (e) HF.Pyridine, THF 0° C. to rt, 91%.

As shown in FIG. 24, fragments 8 and 9 were conjoined via the B-alkyl Suzuki protocol to provide the seco ester 62. Conversion of the t-butyl ester 62 to the TES ester followed by acid catalyzed selective desilylation provided 63, which awaited macrolactonization. At this point, detailed spectral correlatons of 63 confirmed its identity with the previously synthesized intermediate. Following the same sequence as was used in our earlier synthesis, hydroxyacid 63 was cyclized to the fully protected macrolactone 64. Finally, sequential removal of the Troc and TES groups afforded 12,13-desoxyepothilone (2d, dEpoF) which again proved identical in all respects with the previously synthesized dEpoF.

Figure 25:
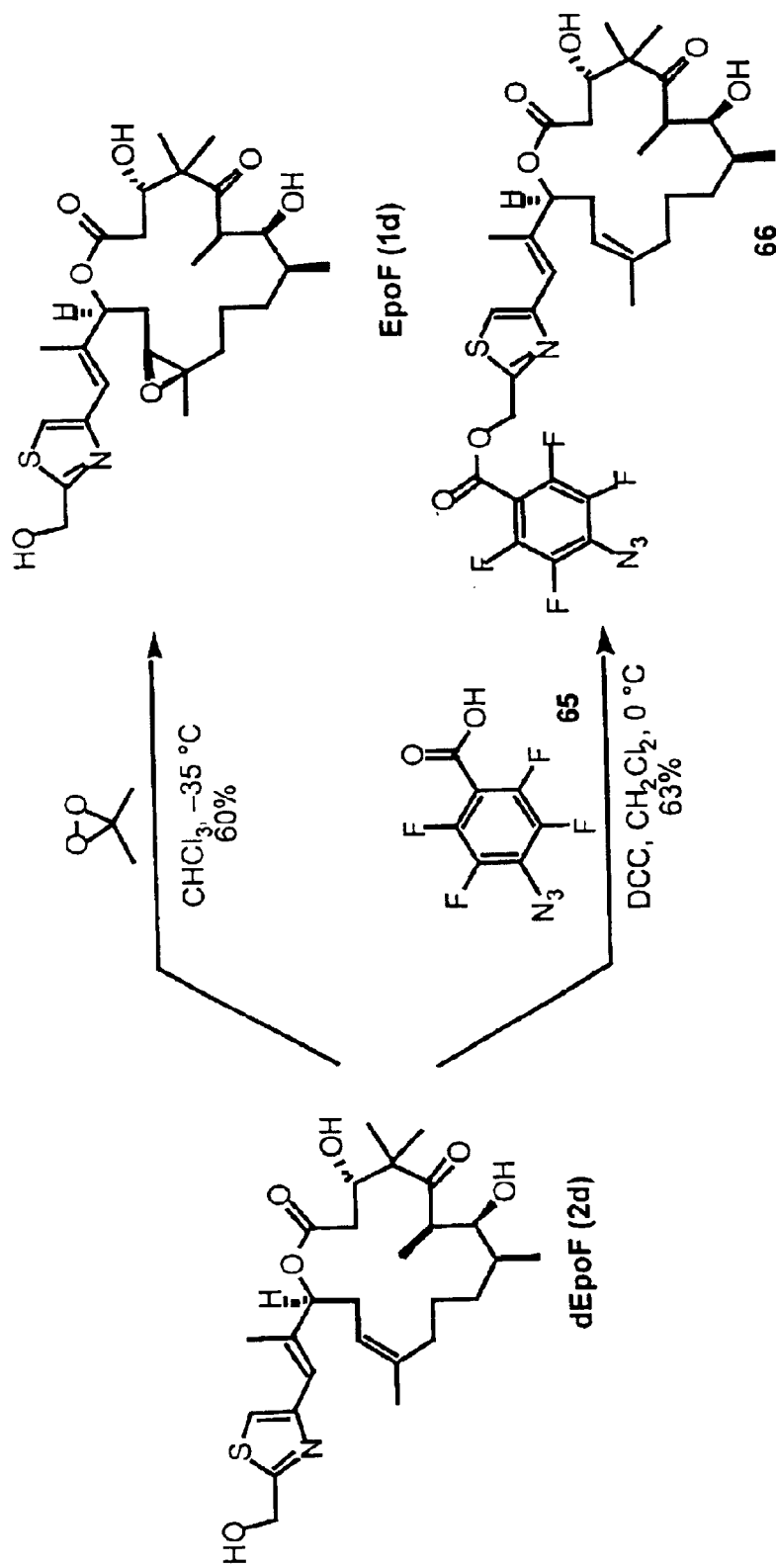
FIG. 25 depicts the synthesis of EpoF and photoaffinity labeled dEpoF.

With the completion of the synthesis of dEpoF, we also accomplished the synthesis of epothilone F itself (1d, EpoF) by epoxidation at the 12,13-alkene (FIG. 25). Treatment of the synthetic dEpoF with 2,2-dimethyldioxirane (DMDO) induced the formation of the 12,13-epoxide with natural stereochemistry to afford EpoF. Spectroscopic data and the observed $[\alpha]_D$ (c, MeOH) corresponded well to the naturally occurring EpoF, (Hofle et al. *Angew. Chem. Int. Ed* 1999, 38, 1971), $[\alpha]_D$ (c, EtOH). It was also demonstrated that the 21-hydroxyl group did increase the aqueous solubility of dEpoB by a factor of 2.5 (Swindell et al. *J. Med. Chem.* 1992, 34, 1176). In addition, its utility as a staging point for further functionalization was demonstrated. The condensation of unprotected dEpoF with azidoacid 65 was performed under the agency of DCC to afford the photoaffinity labeled dEpoF 66. While the tubulin-binding assay had shown that dEpoF retains 90% activity of dEpoB, the aroylated derivative 66 did not induce tubulin polymerization, thus underscoring the subtle nature of the thiazole region in effecting tubulin binding.

The fully synthetic dEpoF was first tested against various cell types to evaluate its antitumor potential. As shown in Table 2, dEpoF showed high cytotoxic activities against a broad range of sensitive and resistant tumor cell lines. In particular, dEpoF retained high potency and low cross-resistances against MDR cell lines and consistently outperformed other non-epothilone anticancer agents such as paclitaxel, vinblastine, etoposide, actinomycin, and adriamycin. These properties of dEpoF are closely comparable to those of the highly promising antitumor agent, dEpoB.

TABLE 2

Potency of dEpoF, dEpoB and Taxol against various tumor cell growth in vitro

| Tumor Cell Lines | $IC_{50}$ ($\mu$M)[a] | | | |
|---|---|---|---|---|
| | dEpoF | dEpoB | Taxol | Others |
| Human T-cell AL Leukemia | | | | |
| CCRF-CEM | 0.0027 | 0.0095 | 0.0021 | 0.00063[b], 0.0290[c] |
| CCRF-CEM/VBL$_{100}$ | 0.047 (17.4 x) | 0.017 (1.8 x) | 4.140 (1971 x) | 0.332[b] (527 x) |
| CCRF-CEM/VM$_1$ | 0.0049 (1.8 x) | 0.014 (1.5 x) | 0.0066 (3.18 x) | 3.44[c] (117 x) |
| CCRF-CEM/Taxol | 0.0053 (2.0 x) | 0.0162 (1.7 x) | 0.120 (57 x) | |
| Hamster Lung Fibroblasts | | | | |
| DC-3F | 0.0017 | 0.0019 | 0.0135 | 0.00025[d] |
| DC-3F/ADX | 0.0136 (8.0 x) | 0.0073 (3.8 x) | 0.583 (43.2 x) | 0.00153[d] (61 2 x) |
| DC-3F/ADII | 0.0223 (13.1 x) | 0.0288 (15.2 x) | 20.19 (1496 x) | 0.4092[d] (1637 x) |
| Human Promyelocytic Leukemia | | | | |
| HL-60 | 0.0007 | 0.0031 | 0.0011 | |
| Human CM Leukemia | | | | |
| K562 | 0.0021 | 0.0036 | 0.0029 | |
| Human Prostate Adenocarcinoma | | | | |
| PC-3 | 0.0119 | 0.0209 | 0.0280 | |
| Human Colon Adenocarcinoma | | | | |
| HT-29 | 0.0014 | 0.0048 | 0.0016 | |
| Human Mammary Adenocarcinoma | | | | |
| MCF-7 | 0.0069 | 0.0040 | 0.0024 | 0.081[e], 0.0094[b] |
| MCF-7/Adr | 0.0097 (1.4 x) | 0.00715 (1.4 x) | 0.0135 (5.6 x) | 0.280 (3.5 x), 0.025 (26.6 x) |
| Human Mammary Carcinoma | | | | |
| MX-1 | 0.0042 | 0.0221 | 0.0394 | 0.00184[f] |
| Human Ovary Carcinoma | | | | |
| SK-OV-3 | 0.0051 | 0.0035 | 0.0038 | 0.0016[f] |

TABLE 2-continued

Potency of dEpoF, dEpoB and Taxol against various tumor cell growth in vitro

| Tumor Cell Lines | IC$_{50}$ ($\mu$M)[a] | | | |
|---|---|---|---|---|
| | dEpoF | dEpoB | Taxol | Others |
| UL-3-C | 0.0048 | 0.0021 | 0.0016 | 0.00037[b], 0.00058[f] |
| UL-3-B/Taxol | 0.0067 (1.4 x) | 0.0070 (3.3 x) | 0.0107 (6.7 x) | 0.00310 (8.4 x)[b], 0.00124(2 1 x)[f] |

[a]Cell growth inhibition was measured by XTT tetrazonium assay after 72 h incubation for cell growth as described previously in ref. 15. The values were determined with six to seven concentrations of each drug using a computer program. The cross-resistance are shown in parentheses.
[b]Vinblastin (VBL).
[c]Etoposide (VM$_1$, VP-16).
[d]Actinomycin D (AD).
[e]Adriamycin (Adr)
[f]Epothilone B (EpoB).

Experimentals for Example 2

General. All commercial materials were used without further purification unless otherwise noted. The following solvents were obtained from a dry solvent system and used without further drying: THF, diethyl ether, methylene chloride, toluene and benzene. All reactions were performed under a positive pressure of prepurified dry argon gas. $^1$H and $^{13}$C NMR spectra were recorded in CDCl$_3$ solution at 300 or 400, and 75 or 100 MHz, respectively. Analytical thin-layer-chromatography was performed on E. Merck silica gel 60 F254 plates, and flash chromatography was performed using the indicated solvent on E. Merck silica gel 60 (40–63 $\mu$m) or Sigma H-type silica gel (10–40 $\mu$m).

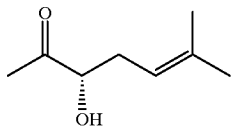

Compound 25. A solution of ketone 22 (3.10 g, 13.0 mmol) in CH$_2$Cl$_2$ (70 mL) was cooled to −17° C. and treated successively with HMDS (10.0 mL, 47.4 mmol) and then TMSI (5.5 mL, 38.6 mmol). The resulting yellow suspension was warmed to rt over 5 min and magnetically stirred for 3 h, after which the reaction mixture was diluted with ether (100 mL) and washed with cold saturated 10% NaHCO$_3$ (2×50 mL). The aqueous layer was back-extracted with ether (2×50 mL). The combined ethereal extracts were dried over Na$_2$SO$_4$, filtered, and concentrated. The resulting yellow oil was used in the following step without further purification.

A solution of AD-mix-α (16.49 g) and OsO$_4$ (1.55 mL, 0.152 mmol) in 1:1 t-BuOH: H$_2$O(124 mL) was cooled to 0° C. and treated with the crude silyl enol ether 23. After 2 h the reaction was quenched with saturated Na$_2$SO$_3$ (100 mL), warmed to rt, and stirred for 1 h. The reaction mixture was extracted with ethyl acetate (3×100 mL). The combined organic extracts were dried over MgSO$_4$, filtered, and concentrated. Silica gel chromatography (5:1 hexanes:ethyl acetate) provided 25 (1.60 g, 48% overall) as a clear oil: IR (neat) 3447, 2950, 2913, 1716, 1653, 1558, 1540, 1419, 1360, 1279, 1242, 1181, 1092, 1061 cm$^{-1}$; $^1$H NMR (400 MHz, C$_6$D$_6$) δ 5.32 (td, J=1.3, 5.2 Hz, 1H), 3.77–3.73 (m, 1H), 3.52 (d, J=4.4 Hz, 1H), 2.43–2.36 (m, 1H), 2.17–2.10 (m, 4H), 1.56 (s, 3H); $^{13}$C NMR (100 MHz, C$_6$D$_6$), δ 208.4, 130.5, 103.8, 75.6, 40.9, 33.5, 24.8; LR-ESI calcd for C$_7$H$_{11}$IO$_2$ (M-Cl$^-$) 254.0, found 288.6.

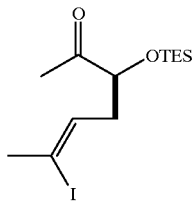

Compound 18. A solution of hydroxy ketone 25 (1.38 g, 5.44 mmol) in DMF (10 mL) was treated with imidazole (0.822 g, 12.1 mmol) and TESCl (1.00 mL, 5.95 mmol). After 3 h the reaction was diluted with H$_2$O(20 mL) and extracted with ethyl acetate (3×20 mL). The combined organic extracts were washed with H$_2$O(1×20 mL) and brine (1×20 mL), then dried over MgSO$_4$, filtered, and concentrated. Silica gel chromatography (20:1 to 5:1=hexanes:ethyl acetate) provided 18 (1.72 g, 86%) as a clear oil.

To a solution of TES protected N,O-dimethylamide 30b (3.27 g, 7.91 mmol) in THF (80 mL) cooled to 0° C. was added methyl magnesium bromide (3.0M in diethylether, 23.7 mmol). The solution was stirred at 0° C. for 15 min and then quenched with a sat. NH$_4$Cl solution (50 mL). The organic layer was removed and the aqueous layer was extracted with EtOAc (3×50 mL). The combined organic layers were dried over MgSO$_4$, filtered, and concentrated in vacuo. Chromatography on silica gel (15% acetone/hexanes) provided TES-protected methyl ketone 18 (2.72 g, 93%) as a yellow oil: R$_f$=0.35 in 20% acetone/hexanes; IR (neat) 2955, 2877, 1718, 1458, 1415, 1352, 1239, 1101, 1005, 812, 742 cm$^{-1}$; $^{13}$C NMR (100 MHz, CDCl$_3$) δ 210.9, 130.0, 103.7, 77.5, 41.8, 33.7, 25.2, 6.7, 4.7; LRMS 390.9 (M+Na$^+$).

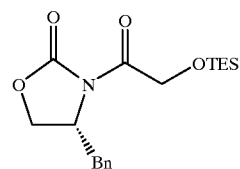

Compound 28a. Procedure A. To a solution of PMB-protected imide 28b (9.23 g, 26.0 mmol) in dichloromethane (90 mL) cooled to 0° C. was added TiCl$_4$ (5.05 g, 27.3 mmol). The solution was stirred at 0° C. for 5 min. after which diisopropylethyl amine (3.53 g, 27.3 mmol) was added dropwise and stirring continued for 1 h. The reaction was quenched with a sat. NaHCO₃ solution and extracted using dichloromethane (3×60 mL). The combined organic layers were washed with brine (1×50 mL) then dried over MgSO₄. The solution was then filtered and concentrated in vacuo. Chromatography on silica gel (70% EtOAc/hexanes) provided unprotected glycolimide (5.50 g, 87%) as a clear oil. To a solution of the compound obtained (4.75 g, 20.2 mmol) in DMF (20 mL) was added imidazole (1.65 g, 24.3 mmol) followed by TESCl (3.35 g, 22.2 mmol). The mixture was stirred at room temperature for 12 h. The solution was then poured into H₂O(200 ml) and extracted with EtOAc (4×100 mL). The combined organic layers were washed with H₂O(2×100 mL) and dried over MgSO₄. The solution was then filtered and concentrated in vacuo. Chromatography on silica gel (25% EtOAc/hexanes) provided TES-protected glycolimide 28a (5.93 g, 84%) as a clear oil Procedure B. In a 2 L three necked flask equipped with a mechanical stirrer and a nitrogen inlet were added sodium hydride (60% dispersion, 8.0 g, 0.200 mol) and ether (400 mL). To this suspension was added in several portions glycolic acid (15.21 g, 0.200 mol) at 0° C. After 20 min, triethylamine (30 mL, 0.215 mol) and TESCl (30.15 g, 0.200 mol) were added, and the mixture was stirred at rt for 2 h. After cooling the reaction mixture to −78° C., pivaloyl chloride (24.6 mL, 0.200 mol) was slowly added via syringe, and the stirring was continued for 1 h. To a separated flask containing 27 (17.7 g, 0.100 mol) in THF (400 mL) was slowly added n-BuLi (2.5 M in hexanes, 40 mL, 0.100 mol) at −78° C. After stirring for 0.5 h, the mixture was cannulated to the suspension prepared above with vigorous stirring. The mixture was allowed to warm to rt over 2 h and poured into 10% NaHSO₄ (500 mL). The organic layer was separated and the aqueous layer was extracted with ether (200 mL×3). The combined organic layers were washed with 10% NaHCO₃ and brine, dired, concentrated and filtered. Purification by flash chromatography on a silica gel column (hexanes/EtOAc=15:1) afforded 28a as a clear oil (12.85 g, 38%): R$_f$=0.33 in 20% EtOAc/hexanes; IR (neat) 2954, 2876, 1780, 1717, 1394, 1350, 1149 cm⁻¹; ¹³C NMR (100 MHz, CDCl₃) δ 171.6, 153.5, 135.0, 129.4, 129.0, 127.4, 67.2, 63.9, 54.9, 37.7, 6.7, 4.3; LRMS 372.0 (M+Na⁺) 350.2 (M+H⁺)

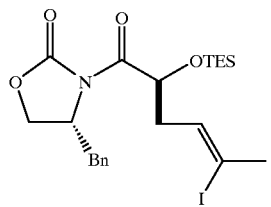

Compound 29a. TES-protected glycolimide 28a (1.11 g, 3.18 mmol) was dissolved in THF (20 mL) and cooled to −78° C. LHMDS (1.0M THF solution, 3.50 mmol) was added dropwise and stirred at −78° C. for 30 min. A solution of 1,3-diiodo-3-butene (26, 1.08 g, 3.5 mmol) in THF(5 mL) was added to the cooled enolate via cannula aftewhich the solution was slowly warmed to room temperature over 12 h. The solution was quenched with a sat. NaCO₃ solution and extracted with EtOAc (3×30 mL). The combined organic extract were washed with brine (50 mL), dried over MgSO₄, filtered, and concentrated in vacuo. Chromatography on silica gel (10% EtOAc/hexanes) provided alkylated glycolimide 29a (1.27 g, 81%) as a light yellow oil: R$_f$=0.47 in 20% EtOAc/hexanes; IR (neat) 2954, 2876, 1778, 1714, 1455, 1392, 1349, 1327, 1208, 1010 cm⁻¹; ¹³C NMR (100 MHz, CDCl₃) δ 173.0, 153.1, 135.1, 130.3, 129.4, 129.0, 127.4, 103.6, 69.8, 66.9, 55.1, 42.6, 37.9, 33.8, 6.7, 4.6; LRMS 552.1 (M+Na⁺), 530.1 (M+H⁻).

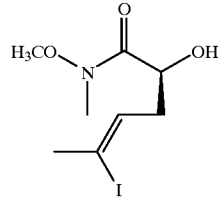

Compound 30a. Alkylated TES-protected glycolimide 29a (5.29 g, 10.0 mmol) was dissolved in HOAc:THF:H₂O (3:1:1, 150 mL) and stirred at room temperature for 4 h. The solvent was then removed in vacuo. The oily residue was dissolved in EtOAc (100 mL) and washed with sat. NaCO₃ (2×50 mL), and brine (50 mL). The organic layer was dried over MgSO₄, filtered, and concentrated in vacuo to give 29b. This material was used for the subsequent reaction without further purification.

N,O-dimethyl hydroxylamine hydrochloride (4.87 g, 50.0 mmol) was suspended in THF (60 mL) and cooled to 0° C. A 1.0M solution of AlMe₃ in toluene (25 mL, 50 mmol) was added dropwise. After the addition was complete the ice bath was remove and the solution was stirred at room temperature for 2 h. This solution was then cannulated into a solution of the crude alkylated glycolimide 29b (prepare above) in THF (100 mL) at 0° C. After the addition was complete the ice bath was remove and the mixture was stirred at room temperature for 6 h. The reaction was quenched by the addition of a1N tartaric acid solution (100 mL) and stirred 1 h. The organic layer was removed and the aqueous layer was extracted with EtOAc (3×100 mL). The combined organic layers were dried over MgSO₄, filter, and concentrated in vacuo. Chromatography on silica gel (20% acetone/hexanes) provided N,O-dimethylamide 30a (2.67 g, 91% for two steps) as a clear oil: R$_f$=0.42 in 40% acetone/hexanes; IR (neat) 3439, 2962, 1659, 1438, 1371, 1196, 1092, 1061, 991, 884, 824 cm⁻¹; ¹³C NMR (100 MHz, CDCl₃) δ 173.8, 130.4, 103.3, 67.8, 61.5, 41.6, 33.8, 32.5; LRMS 321.7 (M+Na⁺), 299.8 (M+H⁺).

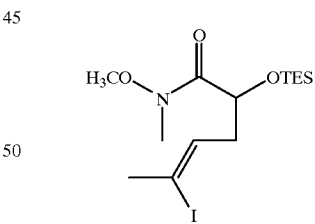

Compound 30b. To a solution of N,O-dimethylamide 30a (2.53 g, 8.47 mmol) in DMF (15 mL) was added imidazole (0.69 g, 10.2 mmol) followed by TESCl (1.40 g, 9.32 mmol). The solution was stirred at room temperature for 5 h. The solution was then poured into H₂O(150 mL) and extracted with EtOAc (4×100 mL). The combined organic layers were washed with H₂O(2×100 mL) and dried over MgSO₄. The solution was then filtered and concentrated in vacuo. Chromatography on silica gel (15% acetone/hexanes) provided TES-protected N,O-dimethylamide 30b (3.39 g, 97%) as a yellow oil: IR (neat) 2954, 2876, 1682, 1459, 1435, 1324, 1240, 1104, 1002, 743 cm⁻¹; LRMS 435.9 (M+Na⁺), 414.1 (M+H⁺).

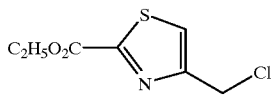

2-Ethoxycarbonyl-4-chloromethyl(thiazole), (34). The mixture of ethyl aminothioxoacetate (12.2 g, 91.6 mmol) and 1,3-dichloroacetone (13.4 g, 105 mmol) in toluene (100 mL) was heated under reflux for 2 h. The brown solution was cooled to rt, diluted with ethyl acetate (100 mL), washed with saturated aqueous NaHCO$_3$ (50 mL) and brine (50 mL), and dried over MgSO$_4$. After removal of the solvent, the remainder was purified by flash chromatography on a silica gel column (toluene-ethyl acetate=9:1) to afford thiazole 34 as a light yellow sticky oil (18.1 g, 96%): IR (film) 3104, 1732, 1714, 1456, 1251 cm$^{-1}$; $^1$H NMR (400 MHz, CDCl$_3$) δ 7.63 (s, 1H), 4.77 (s, 2H), 4.48 (q, J=7.1 Hz, 2H), 1.41 (t, J=7.1 Hz, 3H); $^{13}$C NMR (100 MHz, CDCl$_3$) δ 159.7, 158.8, 154.7, 123.4, 62.9, 40.4, 14.3; HRMS calcd for C$_7$H$_9$ClNO$_2$S (M+H$^+$) 206.0043, Found 206.0048.

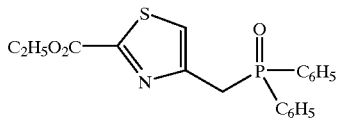

2-Ethoxycarbonyl(thiazole)-4-methyl diphenylphosphine oxide, (35). To a solution of chloride 34 (8.40 g, 40.8 mmol) in methylene chloride (60 mL) were added diphenylphosphine oxide (9.10 g, 45.0 mmol), cesium carbonate (16.3 g, 50.0 mmol), molecular sieve (4 Å, ~0.5 g) and a catalytic amount of tetrabutylammonium iodide (150 mg, 0.40 mmol). The resulting suspension was stirred at room temperature for 48 h. The reaction mixture was then poured into a separatory funnel containing saturated aqueous NaHSO$_4$ (50 mL) and extracted with ethyl acetate (50 mL×3). The combined organic layers were washed with saturated aqueous NaHCO$_3$ (50 mL) and brine, dried over anhydrous Na$_2$SO$_4$, and concentrated in vacuo. Purification by column chromatography on a silica gel column (ethyl acetate-methylene chloride=1:1) afforded Homer reagent 35 as a light viscous syrup (12.48 g, 82%): IR (film) 3055, 1736, 1710, 1438, 1088 cm$^{-1}$; $^1$H NMR (400 MHz, CDCl$_3$) δ 7.74–7.69 (m, 4H), 7.49–7.37 (m, 7H), 4.41 (q, J=7.1 Hz, 2H), 4.01 (d, J=13.3 Hz, 2H), 1.38 (t, J=7.1 Hz, 3H); $^{13}$C NMR (100 MHz, CDCl$_3$) δ 159.7, 157.1, 149.0, 148.9, 132.4, 132.04, 132.01, 131.4, 131.0, 130.9, 123.6, 123.5, 62.5, 33.9, 33.2, 14.2; LRMS calcd for C$_{19}$H$_{19}$NO$_3$PS (M+H$^+$) 372.0, found 372.0.

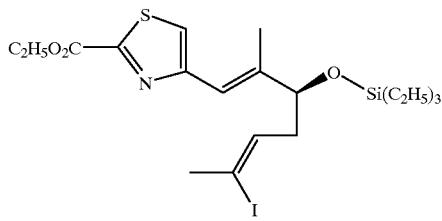

Compound 36. To a mixture of ketone 18 (5.45 g, 14.8 mmol) and phosphine oxide 35 (8.20 g, 22.1 mmol) and in THF (15 mL) was added dropwise a solution of lithium hexamethyldisilazide (1.0 M in THF, 18 mL) at −78° C. The initially light yellow solution gradually turned to deep red. After stirring at rt for 10 h, the reaction mixture was poured into saturated aqueous NH$_4$Cl (100 mL) and extracted with ether (100 mL×3). The combined organic layers were washed with 10% NaHCO$_3$ (50 mL) and brine, dried over MgSO$_4$, and concentrated in vacuo. Purification by column chromatography on a silica gel column (hexanes-ethyl acetate=40:1 to 10:1) afforded ethyl ester 36 as a colorless oil (4.01 g, 52%): [α]$_D$ +5.17 (c 2.65, CHCl$_3$); IR (film) 1740, 1716, 1456 cm$^{-1}$; $^1$H NMR (400 MHz, CDCl$_3$) δ 7.39 (s, 1H), 6.65 (s, 1H), 5.44 (d, J=6.6, Hz, 1H), 4.48 (q, J=7.1 Hz, 2H), 4.23 (t, J=6.2 Hz, 1H), 2.47 (s, 3H), 2.44–2.32 (m, 2H), 2.03 (s, 3H), 1.43 (t, J=7.1 Hz, 3H), 0.93 (t, J=7.9 Hz, 9H), 0.59 (q, J=8.0 Hz, 6H); $^{13}$C NMR (100 MHz, CDCl$_3$) δ 160.1, 156.9, 155.5, 143.9, 131.7, 121.4, 118.5, 102.6, 76.8, 62.6, 43.6, 33.7, 14.3, 6.8, 4.8; HRMS calcd for C$_{20}$H$_{33}$INO$_3$SSi (M+H$^+$) 522.0995, found 522.0977.

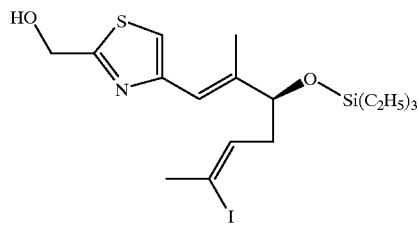

Compound 37. To a solution of ethyl ester 36 (4.01 g, 7.69 mmol) in THF (20 mL) was added a solution of Dibal-H (1.0 M in CH$_2$Cl$_2$, 19 mL) at 0° C. After the addition, the reaction mixture was allowed to warm to rt. After stirring for 2 h, a solution of 1.0 M Rochelle (100 mL) and ether (50 mL) were added to the reaction mixture, and the resulting suspension was stirred at rt for 2 h, at which point clear phase separation was achieved. The organic phase was separated and the aqueous phase was extracted with additional ether (50 mL×3). The combined organic layers were washed with saturated aqueous NaHCO$_3$ (5 mL) and brine, dried over MgSO$_4$, and concentrated in vacuo. Purification by column chromatography on a silica gel column (hexanes-ethyl acetate=5:1) afforded alcohol 37 as a clear oil (3.60 g, 98%): [α]$_D$ +5.57 (c 5.15, CHCl$_3$); IR (film) 3251, 1648, 1068 cm$^{-1}$; $^1$H NMR (400 MHz, CDCl$_3$) δ 7.05 (s, 1H), 6.49 (s, 1H), 5.44 (td, J=6.7, 1.4 Hz, 1H), 4.90 (s, 2H), 4.21 (t, J=6.3 Hz, 1H), 3.85 (br s, 1H), 2.46 (d, J=1.2 Hz, 3H), 2.40–2.34 (m, 2H), 1.99 (d, J=1.1 Hz, 3H), 0.93 (t, J=7.9 Hz, 9H), 0.58 (q, J=7.9 Hz, 6H); $^{13}$C NMR (100 MHz, CDCl$_3$) δ 170.0, 153.1, 142.4, 131.8, 118.4, 115.7, 102.4, 76.9, 61.8, 43.6, 33.6, 14.2, 6.8, 4.7; HRMS calcd for C$_{18}$H$_{31}$INO$_2$SSi (M+H$^+$) 480.0890, found 480.0890.

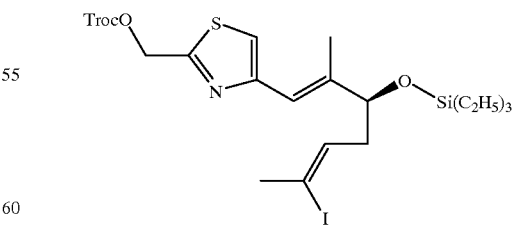

Compound 15. To a solution of alcohol 37 (3.40 g, 7.09 mmol) and pyridine (1.2 mL, 14.9 mmol) in CH$_2$Cl$_2$ (20 mL) was slowly added 2,2,2-trichloroethyl chloroformate (1.80 g, 8.50 mol) at 0° C. After stirring for 30 min, the reaction was quenched by the addition of 10% NaHCO$_3$ (30 mL) and extracted with ether (30 mL×3). The combined organic extracts were washed with 2 N HCl (20 mL), 10% aq. NaHCO$_3$ (20 mL) and brine, dried over MgSO$_4$, and concentrated. Purification on a silica gel column (hexanes-ethyl acetate 20:1) afforded of Troc ether 15 as a light yellow oil (3.93 g, 85%): $[\alpha]_D$ +6.10 (c 2.25, CHCl$_3$); IR (film) 1765, 1650, 1239 cm$^{-1}$; $^1$H NMR (400 MHz, CDCl$_3$) δ 7.15 (s, 1H), 6.51 (s, 1H), 5.50 (s, 2H), 5.45 (t, J=6.8 Hz, 1H), 4.81 (s, 2H), 4.21 (t, J=6.3 Hz, 1H), 2.47 (s, 3H), 2.37 (m, 2H), 2.03 (s, 3H), 1.99, 0.93 (t, J=8.0 Hz, 9H), 0.60 (q, J=7.9 Hz, 6H); $^{13}$C NMR (100 MHz, CDCl$_3$) δ 161.2, 153.9, 153.6, 142.9, 131.8, 118.1, 117.3, 102.5, 94.1, 77.1, 76.8, 66.6, 43.6, 33.7, 14.3, 6.9, 4.8; HRMS calcd for C$_{21}$H$_{32}$Cl$_3$INO$_4$SSi (M+H$^+$) 653.9932, found 653.9961.

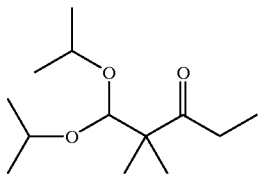

1,1-diisopropyloxy-2,2-dimethyl-3-pentanone (50). To a solution of keto aldehyde 19 (6.40 g, 50 mmol) in isopropanol (100 mL) was added triisopropyl orthoformate (16.7 mL, 75 mmol) and p-TsOH (951 mg, 5.0 mmol). After the mixture was stirred for 3 h, it was poured into brine (100 mL) and extracted with ether (3×100 mL). The combined organic layers were dried and concentrated in vacuo to give 50 as a pale yellow liquid (10.12 g, 88%: IR (neat) 2976, 2935, 1697, 1460, 1379, 1314, 1174, 1125, 1082, 1028 cm$^{-1}$; $^1$H NMR (300 MHz, CDCl$_3$) δ 4.58 (s, 1H), 3.80 (sept, J=6.1 Hz, 2H), 2.51 (q, J=7.2 Hz, 2H), 1.18 (d, J=6.2 Hz, 6H), 1.12 (s, 6H), 1.08 (d, J=6.2 Hz, 6H), 0.95 (t, J=7.2 Hz, 3H); $^{13}$C NMR (75 MHz, CDCl$_3$) δ 215.8, 104.0, 70.7, 53.4, 32.8, 23.8, 22.4, 20.3, 8.0; HRMS calcd for C$_{10}$H$_{19}$O$_2$ (M-C$_3$H$_7$) 171.1385, found 171.1377.

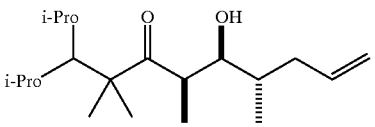

(4R,5S,6S)-1,1-diisopropyloxy-5-hydroxy-2,2,4,6-tetramethyl-8-none-3-one (51a). To a solution of LDA (15.70 mmol) in THF(20 mL) at −78° C. was added a solution of ketone 50 (3.29 g, 14.27 mmol) in THF (15 mL). The mixture was stirred at −78° C. for 0.5 h and then warmed to −40° C. After stirred at −40° C. for 0.5 h, it was recooled to −78° C. Then, a solution of aldehyde 11 in methylene chloride (2.2 mL, 73%, 16.36 mmol) was added. After stirred at −78° C. for 1 h, the reaction was quenched with saturated aqueous NH$_4$Cl solution (12 mL) and warmed to rt. The aqueous layer was extracted with ethyl acetate (3×50 mL). The combined organic layers was dried, filtered and concentrated in vacuo. The residue was purified by silica gel chromatography (2% EtOAc in hexane) to give 51a (3.06 g, 65%) and 52a (0.74 g, 16%) both as colorless oil: IR (neat) 3496, 3075, 2967, 2926, 1685, 1461, 1378, 1321, 1171, 1124, 1036, 994, 979 cm$^{-1}$; $^1$H NMR (300 MHz, CDCl$_3$) δ 5.82 (m, 1H), 5.03 (m, 2H), 4.56 (s, 1H), 3.85 (m, 2H), 3.64 (s, 1H), 3.51 (d, J=9.5 Hz, 1H), 3.38 (m, 1H), 2.55 (m, 1H), 1.91 (m, 1H), 1.65 (m, 1H), 1.15 (m, 18H), 1.04 (d, J=7.0 Hz, 3H), 0.83 (d, J=6.8 Hz, 3H); $^{13}$C NMR (75 MHz, CDCl$_3$) δ 222.5, 137.6, 116.6, 104.1, 74.4, 71.5, 69.9, 54.4, 41.8, 37.8, 35.5, 23.8, 23.7, 22.8, 22.0, 21.7, 20.6, 15.4, 9.8; HRMS calcd for C$_{16}$H$_{29}$O$_3$ (M-C$_3$H$_7$) 269.2117, found 269.2090.

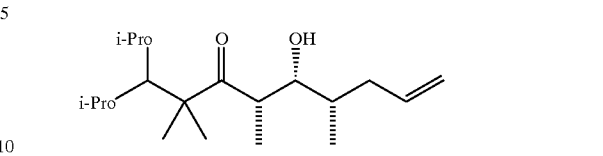

(4S,5R,6S)-1,1-diisopropyloxy-5-hydroxy-2,2,4,6-tetramethyl-8-none-3-one (52a). Characterization: IR (neat): 3496, 3076, 2978, 2936, 1685, 1461, 1378, 1321, 1171, 1124, 1083, 1030 cm$^{-1}$; $^1$H NMR (300 MHz, CDCl$_3$) δ 5.80 (m, 1H), 5.03 (m, 2H), 4.61 (s, 1H), 3.85 (m, 2H), 3.54 (m, 1H), 3.38 (m, 1H), 3.30 (d, J=2.0, 1H), 2.15 (m, 1H), 1.88 (m, 1H), 1.65 (m, 1H), 1.15 (m, 18H), 1.07 (d, J=7.0 Hz, 3H), 1.01 (d, J=6.7 Hz, 3H); $^{13}$C NMR (75 MHz, CDCl$_3$) δ 222.0, 137.1, 116.6, 103.9, 74.5, 71.4, 70.0, 54.3, 42.4, 38.1, 35.6, 23.8, 23.7, 22.7, 22.1, 21.5, 20.6, 16.1, 11.1; HRMS calcd for C$_{16}$H$_{29}$O$_3$ (M-C$_3$H$_7$) 269.2117, found 269.2104.

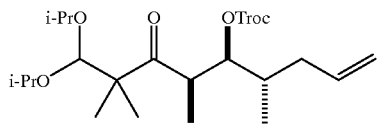

(4R,5S,6S)-1,1-diisopropyloxy-5-hydroxy-2,2,4,6-tetramethyl-5-(2,2,2-trichloroethoxyxarbonyl)-8-none-3-one (51b). To a solution of 51a (3.00 g, 9.13 mmol) in CH$_2$Cl$_2$ (40 mL) at 0° C. was added TrocCl (2.50 mL, 18.26 mmol, 2.0 equiv) and pyridine (2.95 mL, 26.5 mmol, 4.0 equiv). The mixture was stirred for 5 h. It was then poured into brine (20 mL) and extracted with CH$_2$Cl$_2$ (3×40 mL). The combined organic layers was dried, filtered and concentrated in vacuo. The residue was purified by silica gel chromatography (2% EtOAc in hexane) to give 51b (4.58 g, 99%): IR (neat) 3077, 2974, 1761, 1698, 1457, 1380, 1249, 1126, 1040, 995, 922 cm$^{-1}$; $^1$H NMR (300 MHz, CDCl$_3$) δ 5.75 (m, 1H), 5.05 (m, 2H), 4.95 (t, J=5.8 Hz, 1H), 4.80 (AB quartet, J=37.7, 12.0 Hz, 2H), 4.58 (s, 1H), ), 3.85 (m, 2H), 3.54 (m, 1H), 2.30 (m, 1H), 1.89 (m, 2H), 1.19 (m, 21H), 0.95 (d, J=6.6 Hz, 3H); $^{13}$C NMR (75 MHz, CDCl$_3$) δ 215.8, 154.6, 136.6, 117.2, 103.9, 95.2, 83.4, 71.3, 70.0, 54.3, 42.8, 36.3, 35.0, 23.8, 23.7, 22.7, 22.1, 21.9, 20.0, 16.6, 12.5; HRMS calcd for C$_{19}$H$_{30}$O$_5$Cl$_3$ (M-C$_3$H$_7$) 443.1160, found 443.1159.

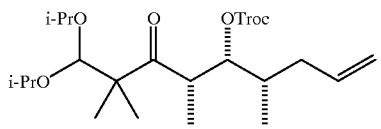

(4S,5R,6S)-1,1-diisopropyloxy-2,2,4,6-tetramethyl-5-(2,2,2-trichloroethoxyxarbonyl)-8-none-3-one, (52b). Following the procedure for 51b, Troc ether 52b (0.192 g, 90%) was prepared from 52a (0.140 g, 0.426 mmol), pyridine (138 μL, 1.70 mmol, 4.0 equiv) and TrocCl (117 μL, 0.85 mmol, 2.0 equiv): IR (neat) 3074, 2974, 2928, 1761, 1698, 1462, 1380, 1249, 1171, 1126.0, 1040, 995 cm$^{-1}$; $^1$H NMR (300 MHz, CDCl$_3$) δ 5.75 (m, 1H), 5.13 (dd, J=8.4, 3.4 Hz, 1H), 5.05 (m, 2H), 4.82 (s, 2H), 4.68 (s, 1H), 3.85 (m, 2H), 3.48 (m, 1H), 2.15 (m, 1H), 1.93 (m, 1H), 1.78 (m, 1H), 1.15 (m, 21H), 0.93 (d, J=6.8 Hz, 3H); $^{13}$C NMR (75 MHz, CDCl$_3$) δ 216.4, 154.7, 136.5, 117.2, 103.5, 95.2, 83.5, 70.9, 70.4, 54.2, 43.8, 38.9, 35.2, 23.8, 23.7, 22.4, 22.2, 21.4, 20.9, 14.5, 14.0; HRMS calcd for C$_{19}$H$_{30}$O$_5$Cl$_3$ (M-C$_3$H$_7$) 443.1154, found 443.1159.

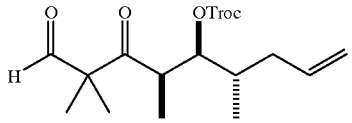

(4R,5S,6S)-3-oxo-2,2,4,6-tetramethyl-5-(2,2,2-trichloroethoxyxarbonyl)-8-nonenal (53). To a solution of 51b (4.58 g, 9.08 mmol) in THF (75 mL) and water (23 mL) was added p-TsOH (450 mg, 2.36 mmol). The reaction mixture was heated under reflux for 7 h and then poured into saturated aqueous NaHCO$_3$ solution (50 mL). The aqueous layer was extracted with EtOAc (3×100 mL) and the combined organic layers were dried, filtered and concentrated in vacuo. The residue was purified by silica gel chromatography (3% EtOAc in hexane) to give 53 (3.22 g, 88%): IR (neat) 3078, 2975, 2937, 2876, 1757, 1701, 1465, 1376, 1253, 1131, 1065, 999, 975, 928, 815 cm$^{-1}$; $^1$H NMR (300 MHz, CDCl$_3$) δ 9.62 (s, 1H), 5.70 (m, 1H), 5.02 (m, 2H), 4.79 (m, 3H), 3.29 (m, 1H), 2.35 (m, 1H), 1.89 (m, 2H), 1.39 (s, 3H), 1.35 (s, 3H), 1.08 (d, J=6.9 Hz, 3H), 0.92 (d, J=6.6 Hz, 3H); $^{13}$C NMR (75 MHz, CDCl$_3$) δ 209.6, 201.4, 154.6, 135.8, 117.7, 94.9, 81.7, 77.1, 61.7, 42.8, 36.6, 34.8, 20.0, 19.8, 16.1, 11.6; HRMS calcd for C$_{16}$H$_{24}$O$_5$C$_3$ (M+H$^+$) 401.0689, found 401.0672.

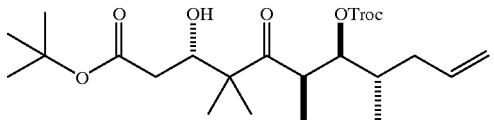

tert-Butyl (3S,6R,7S,8S)-3-hydroxy-5-oxo-4,4,6,8-tetramethyl-7-(2,2,2-trichloroethoxyxarbonyl)-10-undecenoate, (54). To a solution of LDA (7.52 mmol) in ether (30 mL) at −78° C. was added tert-butyl acetate (0.865 ml, 6.41 mmol) and stirred at −78° C. for 1 h. Titanium complex L-41 (8.34 mol) in ether (90 ml) was added dropwise over 40 min. After stirring at −78° C. for 0.5 h, the reaction mixture was warmed to −30° C., stirred for 45 min and recoled to −78° C. A solution of 53 (2.57 g, 6.41 mmol) in ether (15 mL) was added over 10 min and the mixture was stirred at −78° C. for 2 h. After quenching with a 5 M solution of water in THF (14 mL) and stirring for 1 h at rt, the mixture was filtered through a plug of celite. The filtrate was washed with brine (40 mL), the aqueous layer was extracted with ether (3×100 mL) and the combined organic layers were dried, filtered and concentrated in vacuo. The residue was purified by silica gel chromatography (7% EtOAc in hexane) to give 54 (2.95 g, 89%) as a clear oil: IR (neat) 3515, 3078, 2971, 2932, 1756, 1702, 1459, 1381, 1367, 1250, 1152, 924 cm$^{31\ 1}$; $^1$H NMR (300 MHz, CDCl$_3$) δ 5.70 (m, 1H), 5.01 (m, 2H), 4.80 (m, 3H), 4.12 (m, 1H), 3,45 (m, 1H), 3.32 (d, J=3.4 Hz, 1H) 2.27 (m, 3H), 1.89 (m, 2H), 1.45 (s, 9H), 1.19 (s, 3H), 1.15 (s, 3H), 1.11 (d, J=6.9 Hz, 3H), 0.93 (d, J=6.5 Hz, 3H); $^{13}$C NMR (75 MHz, CDCl$_3$) δ 216.3, 172.9, 154.6, 136.3, 117.4, 95.1, 82.9, 81.8, 77.1, 73.4, 52.3, 41.9, 37.7, 36.4, 34.8, 28.5, 22.3, 19.5, 16.5, 12.5; HRMS calcd for C$_{22}$H$_{36}$O$_7$Cl$_3$ (M+H$^+$) 517.1527, found 517.1535.

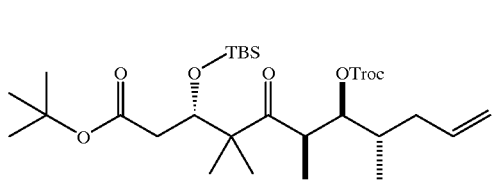

tert-Butyl (3S,6R,7S,8S)-5-oxo-3-tert-butyldemithylsilyloxy-4,4,6,8-tetramethyl-7-(2,2,2trichloroethoxyxarbonyl)-10-undecenoate, (54b). To a solution of 54a (126 mg, 0.243 mmol) in CH$_2$Cl$_2$ (3 mL) at −20° C. was added 2,6-lutidine (85 μL, 0.729 mmol, 3.0 equiv) and TBSOTf (62 μL, 0.269 mmol). The mixture was stirred and warmed to rt overnight. It was washed with brine (5 mL) and the aqueous layer was extracted with CH$_2$Cl$_2$ (3×10 mL). The combined organic layers was dried, filtered and concentrated in vacuo. The residue was purified with silica gel chromatography (2% EtOAc in hexane) to give 54b (110 mg, 72%): IR (neat) 3081, 2957, 2926, 2854, 1759, 1728, 1702, 1458, 1375, 1251, 1153, 1091, 1064, 993, 927, 836 cm$^{-1}$; $^1$H NMR (300 MHz, CDCl$_3$) δ 5.72 (m, 1H), 5.02 (m, 2H), 4.79 (m, 1H), 4.77 (AB quartet, J=55.3, 12.0 Hz, 2H), 4.20 (t, J=4.4 Hz, 1H), 3,50 (m, 1H), 2.55–2.05 (m, 3H), 1.91 (m, 2H), 1.44 (s, 9H), 1.36 (s, 3H), 1.07 (d, J=6.8 Hz, 3H), 1.02 (s, 3H), 0.95 (d, J=6.9 Hz, 3H), 0.88 (s, 9H), 0.15 (s, 3H), 0.08 (s, 3H); $^{13}$C NMR (75 MHz, CDCl$_3$) δ 216.5, 172.6, 154.5, 136.1, 117.5, 95.4, 82.0, 80.9, 77.1, 75.6, 54.0, 42.6, 41.4, 37.0, 34.7, 28.5, 26.4, 22.6, 21.2, 18.4, 16.0, 11.0, −4.2, −4.3; HRMS calcd for C$_{28}$H$_{49}$Cl$_3$O$_7$SiNa (M+Na$^+$) 653.2211, found 653.2191.

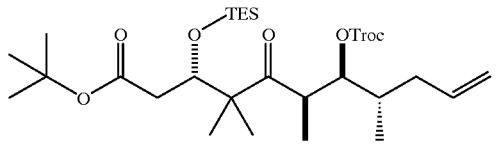

Compound 16. To a mixture of alcohol 54 (1.80 g, 3.48 mmol) and imidazole (0.48 g, 7.05 mmol) in DMF (5 mL) was added TESCl (0.68 g, 4.51 mmol). The mixture was stirred at rt for 2 h and poured into water (50 mL). Extracted with ether (30 mL×3), washed with brine, dired over MgSO$_4$, and concentrated, the crude product was purified by flash chromatography (toluene-ethyl acetate=20:1) to afford TES ether 16 as a colorless oil (2.12 g, 96%): [α]$_D$−61.7 (c 1.05, CHCl$_3$); IR (film) 1760, 1728, 1698 cm$^{-1}$; $^1$H NMR (400 MHz, CDCl$_3$) δ 5.76–5.65 (m, 1H), 5.03–4.99 (m, 2H), 4.83 (d, J=11.9 Hz, 1H), 4.74 (dd, J=7.9, 3.5 Hz, 1H), 4.66 (d, J=11.9 Hz, 1H), 4.18 (dd, J=6.5, 3.5 Hz, 1H), 3.51–3.44 (m, 1H), 2.48 (dd, J=17.4, 3.5 Hz, 1H), 2.29–2.24 (m, 1H), 2.07 (dd, J=17.4, 6.6 Hz, 1H), 1.93–1.82 (m, 2H), 1.42 (s, 9H), 1.34 (s, 3H), 1.06 (d, J=6.8 Hz, 3H), 1.01 (s, 3H), 0.96–0.91 (m, 12H), 0.66–0.59 (m, 6H); $^{13}$C NMR (100 MHz, CDCl$_3$) δ 215.3, 171.3, 154.0, 135.7, 117.1, 94.7, 81.8, 80.6, 75.0, 53.5, 42.2, 40.7, 36.6, 34.4, 28.0, 22.2, 20.9, 15.6, 10.6, 7.0, 4.9; LRMS calcd for C$_{28}$H$_{49}$Cl$_3$O$_7$Si (M+Na$^+$) 655.3, found 655.3.

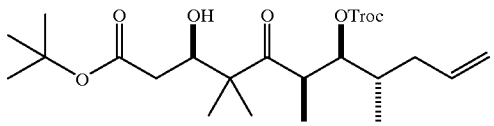
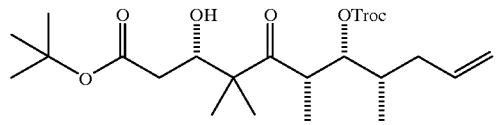

tert-Butyl (3R,6R,7S,8S)-3-hydroxy-5-oxo-4,4,6,8-tetramethyl-7-(2,2,2-trichloroethoxyxarbonyl)-10-undecenoate (56a). Following the procedure for 54a, (20.8 mg, 74%) of 56a was prepared from LDA (0.064 mmol), tert-butyl acetate (7.4 μL, 0.055 mmol), Titanium complex D-41 (0.0715 mmol) and aldehyde 55 (22 mg, 0.055 mmol): IR (neat) 3514, 3074, 2977, 2935, 1757, 1726, 1705, 1465, 1381, 1367, 1280, 1151, 1123 cm$^{-1}$; $^1$H NMR (300 MHz, CDCl$_3$) δ 5.73 (m, 1H), 5.04 (m, 2H), 4.93 (m, 1H), 4.80 (AB quartet, J=30.6, 12.0 Hz, 2H), 4.12 (m, 1H), 3,45 (m, 1H), 3.39 (d, J=3.5 Hz, 1H) 2.32 (m, 3H), 1.90 (m, 2H), 1.47 (s, 9H), 1.22 (s, 3H), 1.16 (s, 3H), 1.12 (d, J=6.9 Hz, 3H), 0.96 (d, J=6.5 Hz, 3H); $^{13}$C NMR (75 MHz, CDCl$_3$) δ 216.5, 173.0, 154.6, 136.3, 117.4, 95.0, 83.0, 81.9, 77.1, 73.2, 52.3, 42.0, 37.8, 36.4, 34.9, 28.5, 21.6, 19.8, 16.5, 12.6; HRMS calcd for C$_{22}$H$_{36}$O$_7$Cl$_3$ (M+H$^+$) 517.1527, found 517.1547.

tert-Butyl (3S,6S,7R,8S)-3-hydroxy-5-oxo-4,4,6,8-tetramethyl-7-(2,2,2-trichloroethoxyxarbonyl)-10-undecenoate, (58a). Following the procedure for 54, alcohol 58a (24 mg, 82%) was prepared from LDA (0.064 mmol), tert-butyl acetate (7.4 μL, 0.055 mmol), Titanium complex D-41 (0.0715 mmol) and aldehyde 57 (22 mg, 0.055 mmol): IR (neat) 3525, 3078, 2971, 2932, 1756, 1707, 1454, 1371, 1245, 1148, 919 cm$^{-1}$; $^1$H NMR (300 MHz, CDCl$_3$) δ 5.77 (m, 1H), 5.06 (m, 3H), 4.80 (AB quartet, J=15.0, 12.0 Hz, 2H), 4.19 (m, 1H), 3,4 (m, 1H), 3.30 (d, J=3.8 Hz, 1H) 2.30 (m, 3H), 1.95 (m, 1H), 1.75 (m, 1H), 1.45 (s, 9H), 1.22 (d, J=6.9 Hz, 3H), 1.20 (s, 3H), 1.15 (s, 3H), 1.12 (d, J=6.9 Hz, 3H), 0.96 (d, J=6.5 Hz, 3H); $^{13}$C NMR (75 MHz, CDCl$_3$) δ 216.8, 172.8, 154.8, 136.2, 117.4, 95.1, 83.0, 81.9, 77.0, 73.0, 52.3, 42.9, 38.8, 37.9, 35.3, 28.5, 22.2, 19.7, 14.3, 14.2; HRMS calcd for C$_{22}$H$_{36}$O$_7$Cl$_3$ (M+H$^+$) 517.1527, found 517.1535.

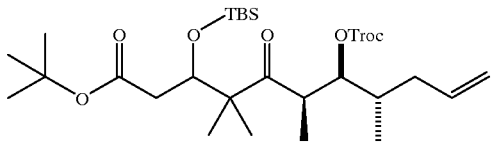
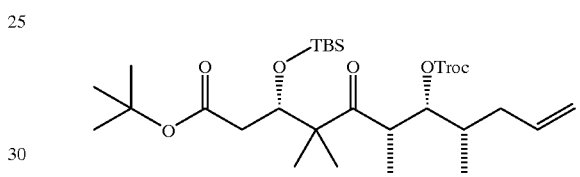

tert-Butyl (3R,6R,7S,8S)-5-oxo-3-tert-butyldemithylsilyloxy-4,4,6,8-tetramethyl-7-(2,2,2-trichloroethoxyxarbonyl)-10-undecenoate (56b). Following the procedure for 54b, TBS ether 56b (13 mg, 65%) was prepared from alcohol 56a (17 mg, 0.033 mmol), 2,6-lutidine (μL, 0.103 mmol), and TBSOTf (8.5 μL, 0.037 mmol). Both $^1$H NMR and TLC matched the sample obtained from the other route.

tert-Butyl (3S,6S,7R,8S)-5-oxo-3-tert-butyldemithylsilyloxy-4,4,6,8-tetramethyl-7-(2,2,2-trichloroethoxyxarbonyl)-10-undecenoate (58b). Following the procedure for 54b, TBS ether 58b (17 mg, 65%) was prepares from 58a (21 mg, 0.041 mmol), 2,6-lutidine (14 μL), and TBSOTf (10.5 μL). Both $^1$H NMR and TLC matched the sample obtained from the other route.

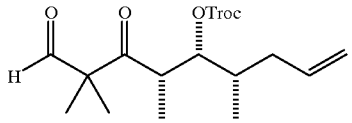
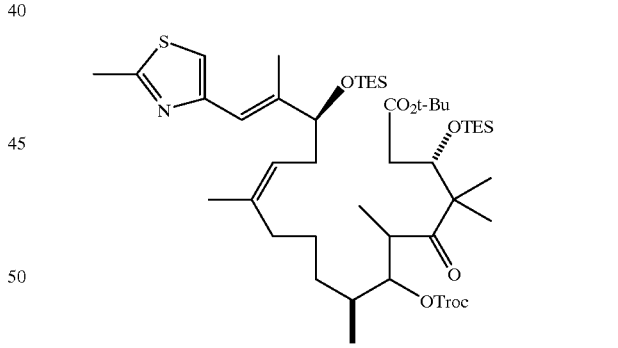

(4S,5R,6S)-3-oxo-2,2,4,6-tetramethyl-5-(2,2,2-trichloroethoxyxarbonyl)-8-nonenal (57). Following the procedure 55, aldehyde 57 (0.103 g, 81%) was prepared from 52b (0.16 g, 0.317 mmol), THF (3 mL), water (1 mL), p-TsOH (20 mg): IR (neat) 3078, 2975, 2937, 1757, 1701, 1460, 1380, 1277, 1248, 923 cm$^{-1}$; $^1$H NMR 9.60 (s, 1H), 5.75 (m, 1H), 5.02 (m, 3H), 4.78 (AB quartet, J=14.1, 12.0 Hz, 2H), 3.29 (quintet, J=6.9 Hz, 1H), 2.15 (m, 1H), 1.94 (m, 1H), 1.70 (m, 1H), 1.35 (s, 3H), 1.32 (s, 3H), 1.08 (d, J=6.9 Hz, 3H), 0.93 (d, J=6.6 Hz, 3H); $^{13}$C NMR (75 MHz, CDCl$_3$) δ 210.2, 200.9, 154.6, 135.8, 117.7, 95.1, 82.1, 77.1, 61.6, 43.8, 38.4, 35.3, 20.0, 19.9, 14.4, 13.4; HRMS calcd for C$_{16}$H$_{24}$O$_5$Cl$_3$ (M+H$^+$) 401.0689, found 401.0717.

tert-Butyl (3S,6R,7S,8S,12Z,15S,16E)-5-oxo-3,15-bis(triethylsilyloxy)-17-(2-methylthiazol-4-yl)-4,4,6,8,12,16-hexamethyl-(2,2,2-trichloroethoxyxarbonyl)pentadeca-12,16-dienoate, (60). To a solution of 9-BBN dimer (40 mg, 0.163 mmol) in THF (1.0 mL) was added olefin 16 (100 mg, 0.158 mmol) in THF (1.0 mL). After stirring at rt for 2 h, TLC analysis indicated the complete consumption of 16, at which point H$_2$O(30 mL) was added to quench the remaining 9-BBN. To a separate flask containing vinyl iodide 59 (73 mg, 0.158 mmol) in DMF (1.5 mL) was added successively with vigorous stirring Cs$_2$CO$_3$ (102 mg, 0.316 mmol), AsPh$_3$ (10 mg, 0.326 mmol), PdCl$_2$(dppf) (26 mg, 0.0318 mmol), and H₂O(0.13 mL). Then, the solution of the alkyl borane prepared above was added rapidly via syringe. After 4 h, the reaction mixture was poured into ether (20 mL) and washed with water (2×10 mL) and brine (8 mL). The organic layer was was dried, filtered and concentrated in vacuo. The residue was purified by silica gel chromatography (5% EtOAc in hexane) to give 60 (110.5 mg, 72%) as a light yellow oil: IR (CDCl₃) 2954, 2909, 2874, 1754, 1728, 1701, 1457, 1377, 1249, 1156, 1089, 1067, 1005, 925 cm$^{31\ 1}$; $^1$H NMR (300 MHz, CDCl₃) δ 6.92 (s, 1H), 6.46 (s, 1H), 5.12 (m, 1H), 4.80 (AB quartet, J=41.0, 12.0 Hz, 2H), 4.75 (m, 1H), 4.20 (m, 1H), 4.08 (t, J=11.5 Hz, 1H), 3.48 (m, 1H), 3.72 (s, 3H), 3.52–2.03 (m, 4H), 1.99 (s, 3H), 1.98 (m, 2H), 1.70 (m, 2H), 1.61 (s, 3H), 1.45 (s, 9H), 1.36 (s, 3H), 1.42–1.10 (m, 3H), 1.00 (m, 27H), 0.60 (m, 12H); $^{13}$C NMR (75 MHz, CDCl₃) δ 215.7, 171.7, 164.8, 154.8, 153.6, 142.8, 136.9, 122.0, 119.2, 115.4, 95.2, 82.6, 81.0, 79.1, 77.6, 75.4, 53.9, 42.5, 41.1, 35.7, 35.1, 32.6, 32.3, 28.5, 25.4, 23.9, 22.6, 21.3, 19.6, 16.1, 14.3, 11.1, 7.4, 7.3, 5.4, 5.2; HRMS calcd for C₄₆H₈₁O₈NCl₃Si₂S (M+H⁺) 968.4287, found 968.4282.

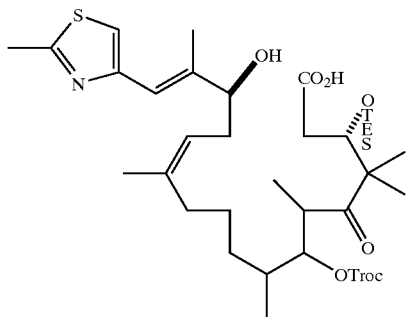

tert-Butyl-(3S,6R,7S,8S,12Z,15S,16E)-5-oxo-15-hydroxy-3-triethylsilyloxy-17-(2-methylthiazol-4-yl)-4,4,6,8,12,16-hexamethyl-(2,2,2-trichloroethoxyxarbonyl) pentadeca-12,16-dienoate, (61). To a solution of ester 60 (50 mg, 0.0517 mmol) in CH₂Cl₂ (1.0 mL) at −78° C. was added 2,6-lutidine (72 mL, 0.517 mmol) and TESOTf (71 mL, 0.31 mmol). The mixture was stirred overnight and warmed to rt. The reaction was quenched with saturated aqueous NH₄Cl solution (2 mL) and poured into CH₂Cl₂ (10 mL). The organic layer was washed with a buffer solution (pH 7.0) and concentrated. The residue was dissolved in THF (0.5 mL) and cooled to 0° C. Methanolic HCl (0.12 M, 0.5 mL) was added in portions and the reaction was carefully monitored by TLC. After 20 min, The reaction was quenched with saturated NaHCO₃ solution (5 mL) and extracted with EtOAc (3×10 mL). The combined organic layers was dried, filtered and concentrated in vacuo. The residue was purified by silica gel chromatography (30% EtOAc in hexane) to give 61 (28.2 mg, 68%) as a light yellow sticky oil.

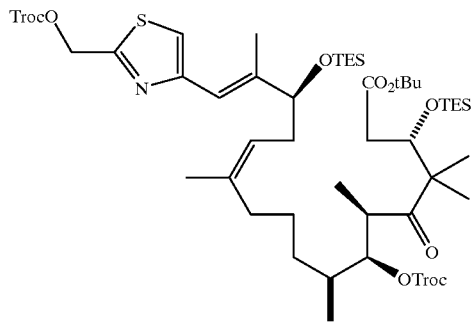

Compound 63. To a solution of 9-BBN-H dimer (0.490 g, 4.02 mmol) in THF (2 mL) was added a solution of olefin 16 (2.12 g, 3.35 mmol) in THF (4 mL). After stirring at rt for 1 h, TLC analysis indicated the complete consumption of the starting olefin 16. Water (0.25 mL) was added to the borane solution, prepared above, and the stirring was continued for 10 min to quench the excess 9-BBN-H. In a separate flask containing vinyl iodide 15 (2.00 g, 3.05 mmol), (dppf) PdCl₂·CH₂Cl₂ (0.250 g, 0.306 mmol), AsPh₃ (0.188 g, 0.614 mmol) and Cs₂CO₃ (1.49 g, 4.57 mmol) was added degassed DMF (2 mL). Then, the solution of the alkylborane was added rapidly to the vigorously stirred solution containing vinyl iodide 15 at 0° C. After stirring at rt for 15 h, the reaction mixture was poured into 10% NaHSO₄ (30 mL) and extracted with ethyl acetate (30 mL×3). The combined organic layers were washed with 10% NaHCO₃ (30 mL) and brine, dried over MgSO₄, and concentrated. Purification by flash column chromatography on SiO₂ (hexanes-ethyl acetate=10:1) gave 63 as a light yellow viscous oil (2.97 g, 84%): [α]$_D$−35.6 (c 2.10, CHCl₃); IR (film) 1760, 1727, 1703 cm⁻¹; $^1$H NMR (400 MHz, CDCl₃) δ 7.13 (s, 1H), 6.47 (s, 1H), 5.50 (s, 2H), 5.10 (t, J=6.8 Hz, 1H), 4.83 (d, J=12.0 Hz, 1H), 4.81 (s, 2H), 4.70 (dd, J=8.1, 3.6 Hz, 1H), 4.65 (d, J=12.0 Hz, 1H), 4.21–4.16 (m, 1H), 4.06 (t, J=6.4 Hz, 1H), 3.50–3.44 (m, 1H), 2.47 (dd, J=17.4, 3.4 Hz, 1H), 2.22 (t, J=6.7 Hz, 2H), 2.07 (dd, J=17.4, 6.6 Hz, 1H), 1.99 (s, 3H), 1.94 (t, J=7.3 Hz, 2H), 1.74–1.69 (m, 1H), 1.63 (s, 3H), 1.60 (m, 2H), 1.42 (s, 9H), 1.33 (s, 3H), 1.24 (m, 2H), 1.03 (d, J=6.7 Hz, 3H), 1.00 (s, 3H), 0.96–0.90 (m, 21H), 0.67–0.54 (m, 12H); $^{13}$C NMR (100 MHz, CDCl₃) δ 215.3, 186.6, 171.3, 154.2, 153.6, 143.6, 136.6, 121.4, 118.0, 94.7, 82.2, 80.6, 78.5, 77.2, 77.1, 75.0, 66.6, 53.5, 42.1, 40.7, 35.2, 34.6, 32.2, 31.9, 28.0, 25.0, 23.5, 22.2, 20.8, 15.7, 14.1, 10.6, 7.0, 6.8, 4.9, 4.8; LRMS calcd for C₄₉H₈₁Cl₆NO₁₁SSi₂Na (M+Na⁺) 1184.3, found 1184.3.

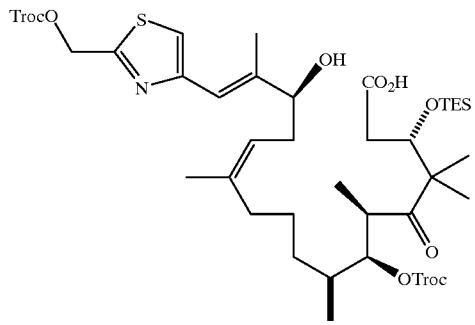

Compound 64. To a solution of tert-butyl ester 63 (2.86 g, 2.46 mmol) in CH$_2$Cl$_2$ (12 mL) were added 2,6-lutidine (0.86 mL, 7.37 mmol) and TESOTf (0.98 g, 3.71 mmol) at 0° C. The reaction mixture was stirred at 0° C. for 0.5 h and then allowed to warm to rt. After stirring at rt for 10 h, the reaction mixture was diluted with ethyl acetate (50 mL) and poured into 1 N HCl (20 mL). The organic layer was separated, washed with a phosophate buffer solution (20 mL, pH=7), dried (Na$_2$SO$_4$) and concentrated. The crude TES derivative was then dissolved in THF (5 mL) and treated with a solution of 0.1 N HCl in MeOH (0.5 mL) at 0° C. Additional methanolic HCl was added in small portions, and approximately 1.5 mL of 0.1 N HCl was required for completion. The reaction mixture was poured into phosphate buffer (15 mL pH=7) and extracted with ethyl acetate (20 mL×3). The combined organic layers were washed with brine, dried (Na$_2$SO$_4$), and concentrated. Purification on a SiO$_2$ column (hexanes-ethyl acetate=1:1) afforded acid 64 as a colorless sticky oil (1.78 g, 73%). Comparison of the chromatographic and spectroscopic data verified the identity of 64 with the previously synthesized compound.

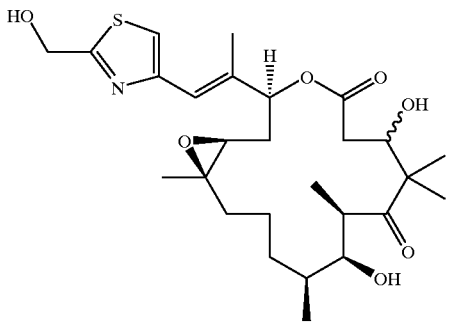

Epothilone F (1d, EpoF). To a solution of dEpoF (2d, 7.1 mg, 0.014 mmol) in CH$_2$Cl$_2$ (1 mL) was added a solution of 2,2-dimethyldioxirane (~0.04 M in CH$_2$Cl$_2$) at −78° C. The reaction mixture was warmed to −40° C. and stirred for 1 h. The reaction mixture was diluted with EtOAc (10 mL) and washed with 10% Na$_2$S$_2$O$_3$ (2 mL) and brine. The organic layer was dried (Na$_2$SO$_4$), filtered and concentrated. Purification by flash chromatography on a silica gel column (hexanes/ethyl acetate=1:1) afforded EpoF (1d) as a thin film (4.4 mg, 60%): [α]$_D$ −26.5 (c 0.35, CH$_3$OH); IR (film) 3420, 2967, 2935, 2876, 1734, 1685, 1451, 1381, 1252, 1148, 1063, 980, 913, 732 cm$^{-1}$; $^1$H NMR (400 MHz, CDCl$_3$): δ 7.12 (s, 1H), 6.59 (s, 1H), 5.43 (dd, J=7.4, 3.1 Hz, 1H), 4.92 (d, J=5.7 Hz, 2H), 4.21~4.13 (m, 1H), 4.05 (br s, 1H), 3.76 (m, 1H), 3.32~3.26 (m, 1H), 2.80 (dd, J=7.2, 5.0 Hz, 1H), 2.60 (br s, 1H), 2.54 (dt, J=14.2, 10.1 Hz, 1H), 2.38 (dd, J=14.1, 3.2 Hz, 1H), 2.09 (s, 3H), 2.06 (m, 1H), 1.97~1.89 (m, 2H), 1.72 (m, 2H), 1.49 (m, 2H), 1.43 (m, 1H), 1.35 (s, 3H), 1.27 (s, 3H), 1.16 (d, J=6.9 Hz, 3H), 1.07 (s, 3H), 0.99 (d, J=7.0 Hz, 3H); $^{13}$C NMR (100 MHz, CDCl$_3$) δ 220.6, 170.5, 170.0, 152.1, 137.6, 119.5, 116.9, 77.2, 74.3, 73.1, 62.1, 61.5, 61.3, 52.8, 43.1, 39.1, 36.4, 32.1, 31.9, 30.7, 22.7, 22.5, 21.2, 20.0, 17.1, 15.7, 13.8; LRMS calcd for C$_{27}$H$_{42}$NO$_7$S (M+H$^+$) 524.1, found 524.1.

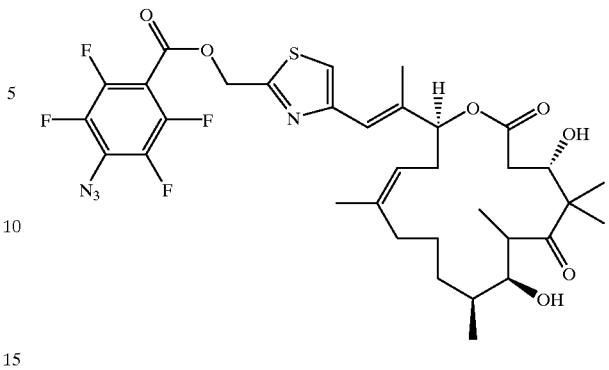

Compound 67. To a solution of azidoacid 66 (3.8 mg, 0.016 mmol) in CH$_2$Cl$_2$ (0.5 mL) was added DCC (3.3 mg, 0.016 mmol) and dEpoF (7.5 mg, 0.015 mmol) in CH$_2$Cl$_2$ (0.5 mL) at 0° C. After stirring for 2 h, the mixture was filtered with a short pad of silica gel and concentrated. Purification by flash chromatography on a silica gel column (hexane/ethyl acetate=5:1) afforded 67 as a clear sticky oil (6.8 mg, 63%): IR (film) 3582, 3472, 2933, 2128, 1738, 1688, 1647, 1489, 1255, 1187, 1007 cm$^{-1}$; $^1$H NMR (500 MHz, CDCl$_3$): δ 7.17 (s, 1H), 6.59 s, 1H), 5.62 (s, 2H), 5.22 (d, J=8.5 Hz, 1H), 5.14 (dd, J=4.9, 4.7 Hz, 1H), 4.22 (d, J=10.4 Hz, 1H), 3.72 (s, 1H), 3.14 (qd, J=6.9, 2.2 Hz, 1H), 2.92 (br s, 1H), 2.83 (br s, 1H), 2.66 (dt, J=15.0, 10.0 Hz, 1H), 2.46 (dd, J=15.0, 11.0 Hz, 1H), 2.34~2.30 (m, 2H), 2.26~2.19 (m, 1H), 2.10 (s, 3H), 1.94~1,86 (m, 2H), 1.75~1.66 (m, 2H), 1.66 (s, 3H), 1.60 (m, 1H), 1.33 (s, 3H), 1.24 (m, 2H), 1.19 (d, J=6.8 Hz, 3H), 1.07 (s, 3H), 1.01 (d, J=7.0 Hz, 3H); LRMS calcd for C$_{34}$H$_{40}$F$_4$NO$_7$SNa (M+Na$^+$) 747.3, found 747.3.

Example 3
Synthesis of Aza-Epothilones

Figure 26:
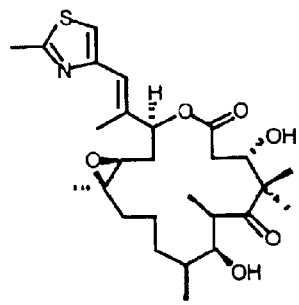
FIG. 26 depicts certain aza-analogues
Figure 26:
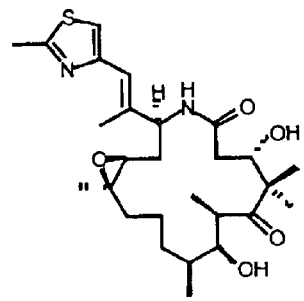
Figure 26:
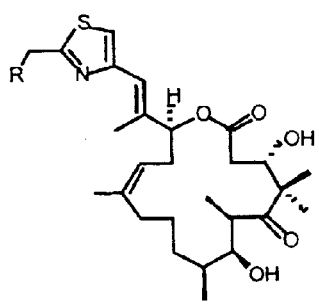
Figure 26:
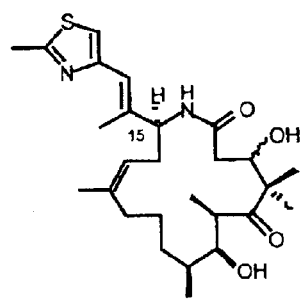

It will be appreciated that certain embodiments of the invention contemplate macrolactam analogues (see, for Example FIG. 26), and the following examples describe certain inventive aza-analogues.

Figure 27:
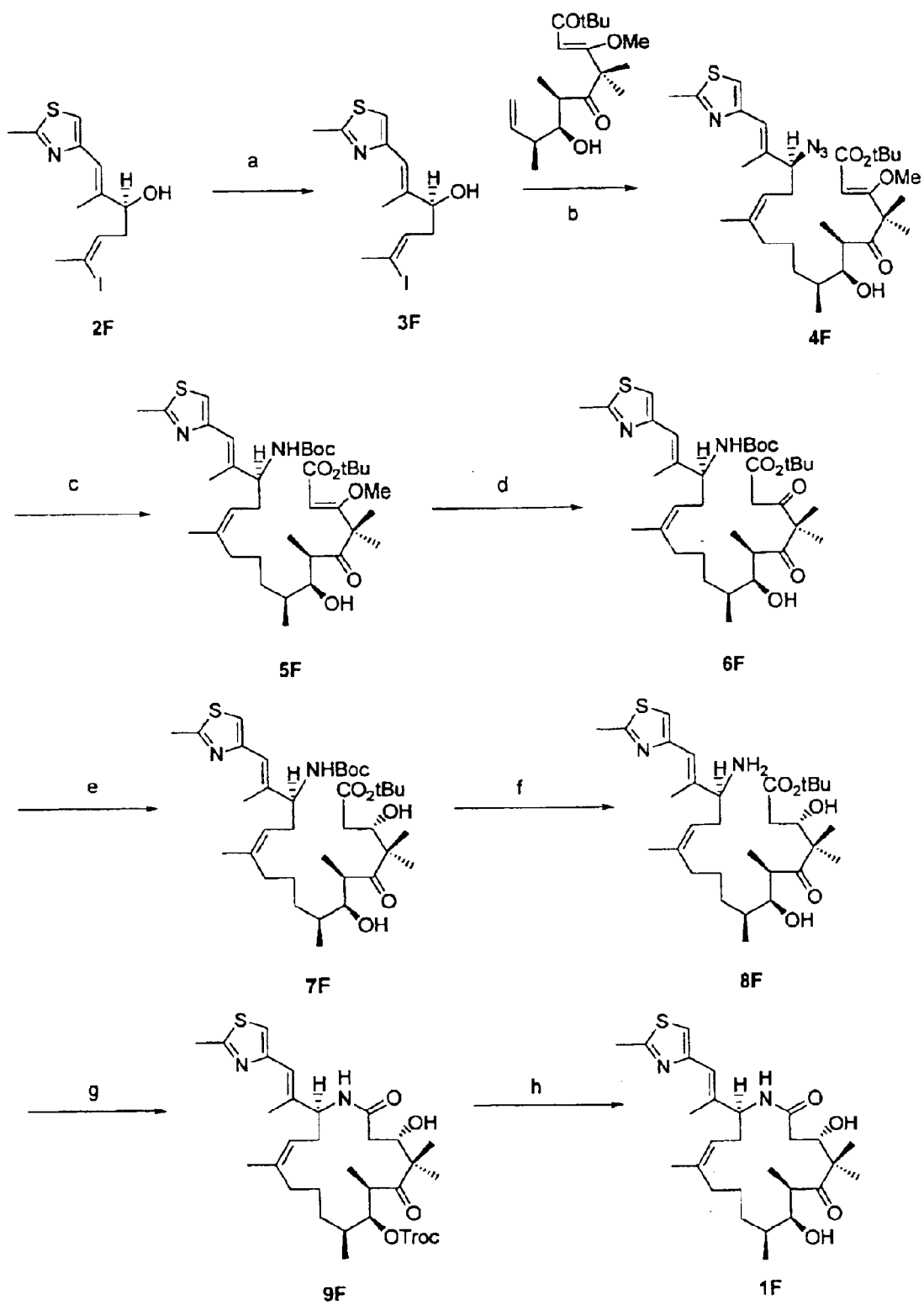
FIG. 27 depicts a synthetic pathway to prepare C15-epi-aza-desoxyepothilone B.

C15-Epi-aza-dEpoB (1F). In order to improve the biostability of desoxyepothilone B (dEpoB) the corresponding lactam analogue was synthesized. FIG. 27. The lactam would have increased biostability since it will not be susceptible to esterase cleavage in vivo. This synthesis represents the first total synthesis of C15-epi-aza-dEpoB. The methods described herein are also applicable to the synthesis of the requisite C15-(R)-aza-isomer.

Referring to FIG. 27, the synthesis of 1F begins with the previously reported (R)-hydroxy vinyl iodide 2F. Mitsunobu inversion of the C15 (epothilone numbering) alcohol using hydrazoic acid afforded azide 3F. Palladium-catalyzed Suzuki coupling of azide 2 with enol ether derived from 7E yielded azido ester 4F. Staudinger reduction of the azide with triphenylphosphine and protection of the nascent amine as its t-butoxycarbony derivative resulted in enol ether 5F in 52% overall yield from azide 4F. Subsequent hydrolysis of the methylenol ether using stoichiometric quantities of p-toluene sulfonic acid in acetone resulted in b-keto ester 6F in a gratifying 82% yield. Stereoselective reduction of the C-3 ketone was carried out under Noyori hydrogenation conditions to yield β-hydroxy ester 7F in 56% yield. The acidic hydrogenation conditions also resulted in some premature deprotection (~20%) of the amino-t-butoxycarbonyl group. Next, simultaneous deprotection of the t-Boc-amine and t-butyl ester was accomplished using trifluoroacetic acid in dichloromethane to afford amino acid 8F. Macrocyclic ring closure to produce the cyclic lactam was affected by treatment of the seco-amino acid with HATU and collidine in dichloromethane in 50% yield. Finally zinc mediated deprotection of the C7-Troc group afforded C15-epi-aza-desepoxyepothilone B (1F).

In another embodiment of the invention, aza-epothilones are prepared using methodology as described herein, and in more detail below. The results pertaining to a total synthesis of aza-dEpoB (4a) were recently communicated. Herein, we report the total synthesis of aza-EpoB (2) and provide indications of its likely value as an antitumor agent based on our own in vivo comparison.

Figure 28:
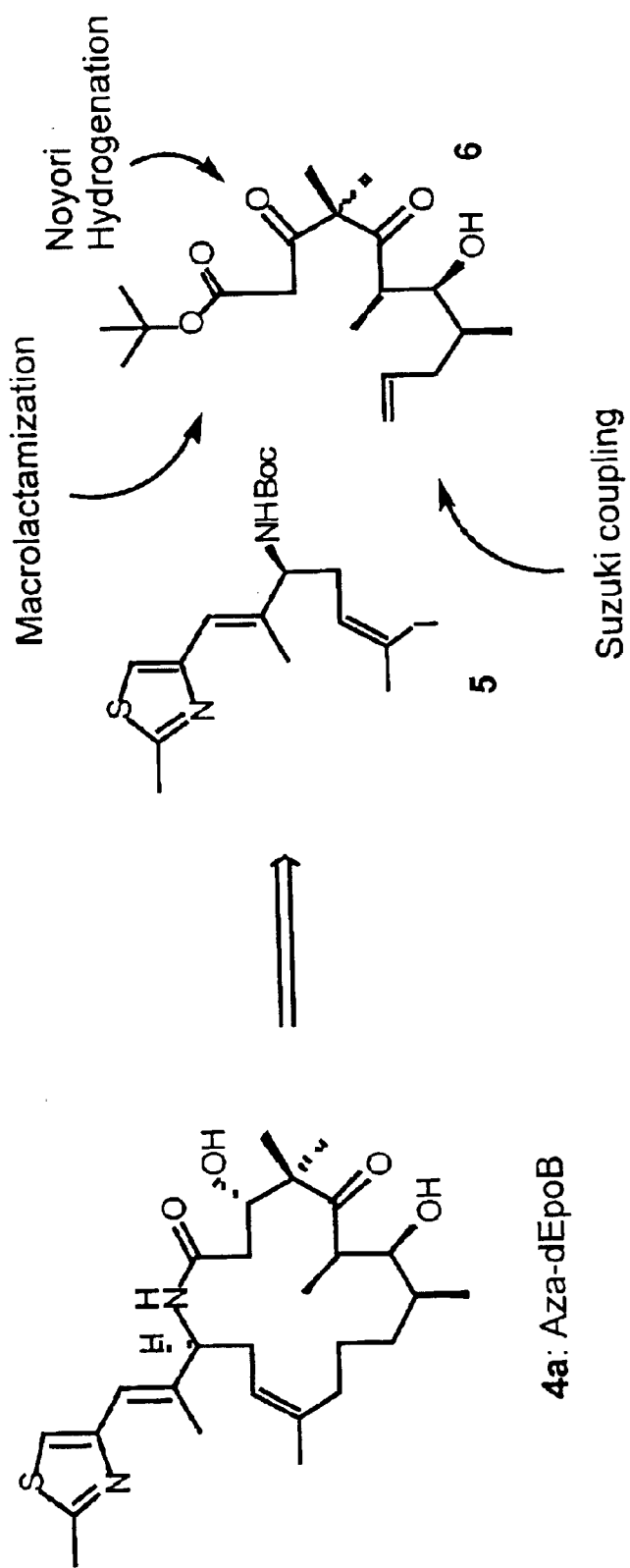
FIG. 28 depicts the synthesis of Aza-dEpoB via Suzuki coupling, Noyori Hydrogenation and Macrolactamization.

The total synthesis of aza-EpoB (4a) was recently achieved and was based on a convergent strategy similar to that employed in our synthesis of 12,13-desoxyepothilone B (3, dEpoB). Along these lines, fragments of roughly equal complexity served as key building blocks (FIG. 28). While the preparation of the alkyl sector 5 would require de novo construction to accommodate the new goal, we envisioned that the acyl sector 6, available from our previous synthesis of dEpoB, could serve for the polypropionate domain. The union of the two key fragments 5 and 6 was achieved through a palladium catalyzed B-alkyl Suzuki coupling. A ruthenium mediated asymmetric hydrogenation would provide highly selective access to the desired stereochemistry at C-3. Deprotection followed by macrolactamization would then lead to aza-dEpoB in short order. As will be seen, implementation of these ideas proved to be anything but straightforward in the lactam series.

Figure 29:
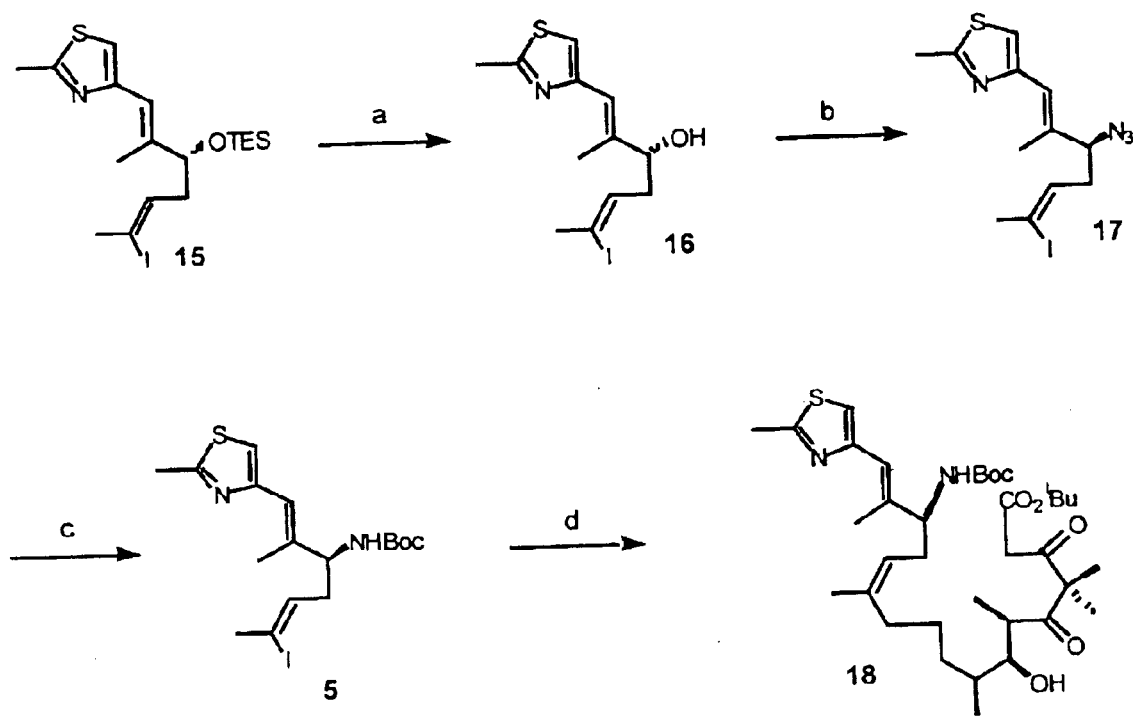
FIG. 29 depicts the Suzuki coupling of vinyl iodide 5 with acyl sector 6. Conditions: a) HOAc; THF: $H_2O$, 98%; b) DPPA, DBU, Toluene, 85%; c) i) $PPh_3$, THF, $H_2O$, 92%; ii) $Boc_2O$, MeCN, 65%; d) i) 6, 9-BBN, THF, ii) $Pd(dppf)Cl_{12}$, $AsPh_3$, $Cs_2CO_3$, DMF, 10%.

Although the required amine containing alkyl fragment 5 could be produced through a Homer-like olefination, the reaction was inefficient. To circumvent the olefination reaction, a Mitsunobu based strategy for the installation of the C-15 amine (epothilone numbering system) was developed based on the alkyl fragment used for the synthesis of dEpoB (3, FIG. 29). The opposite enantiomer (R instead of S hydroxyl configuration) of the TES-protected vinyl-iodide alkyl fragment (15) used in the synthesis of dEpoB is readily accessible though recently developed methods. Deprotection of the silyl ether (15) was easily accomplished using acetic acid:THF:water. It should be noted that the corresponding C-15 tert-butyldimethylsilyl ether was surprisingly resistant to deprotection and decomposition resulted under more forcing conditions. This finding suggested additional advantages for the use of triethylsilyl protection for the hydroxyl group instead of recourse to the more robust tert-butyldimethylsilyl ether. Transformation of the free alcohol (16) to the corresponding azide (17) was accomplished using Thompson's procedure. This protocol resulted in an 85% yield of the azide with complete inversion and minimal elimination product. In contrast, inversion using standard Mitsunobu conditions resulted in a 66% yield of the azide. This reaction was accompanied by significant amounts of elimination product. Next, triphenylphosphine mediated Staudinger reduction of the azide followed by protection of the nascent amine as the t-butyl carbamate yielded the requisite partner (5) for the subsequent B-alkyl Suzuki coupling. Unfortunately, the palladium catalyzed B-alkyl Suzuki reaction occurred in 10% yield. The low yield in the reaction is believed to result from the formation of a stable intermediate derived from intramolecular chelation of the palladium to the carbamate after oxidative insertion.

Figure 30:
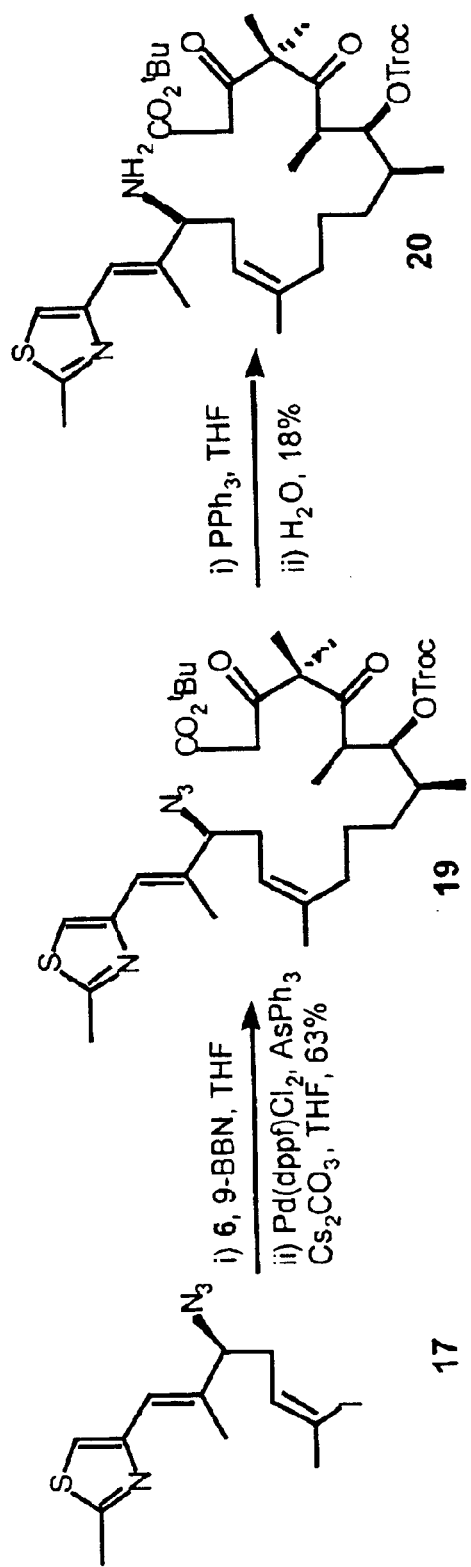
FIG. 30 depicts Suzuki coupling with Azide fragment.

In order to facilitate the B-alkyl Suzuki reaction, the cross-coupling was carried out using the corresponding azido-alkyl fragment 17. Gratifyingly, the palladium catalyzed cross-coupling proceeded smoothly producing the azido-ester 19 in 63% yield (FIG. 30). However, the subsequent Staudinger reduction of azide 19 afforded amino ester 20 in a disappointing 18% yield, presumably due to Schiff base formation, either inter- or intramolecularly, of the incipient amine with the β-keto ester.

Figure 31:
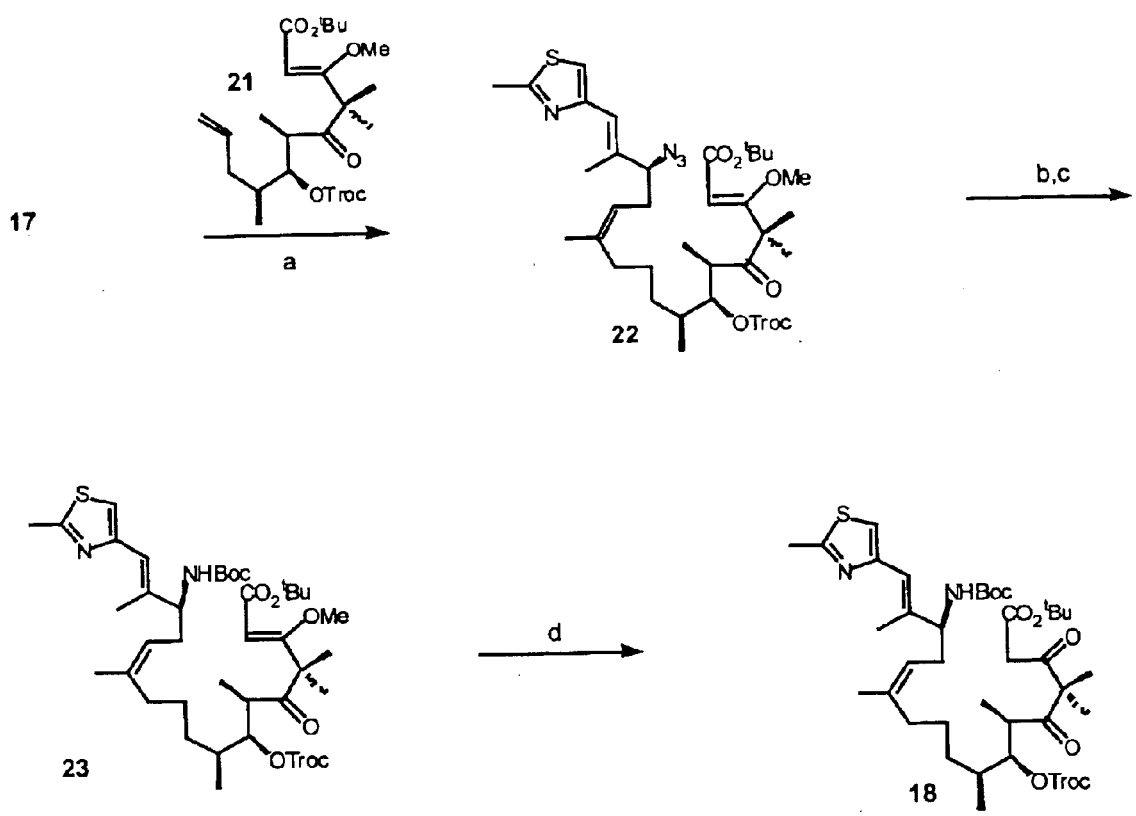
FIG. 31 depicts Suzuki coupling of azido vinyl-iodide 17 with methyl enol ether 21. Conditions: (a) i) 14, 9-BBN, THF; ii) $Pd(dppf)Cl_2$, $AsPh_3$, $Cs_2CO_3$, DMF, 78%; (b) PPhs, $H_2O$, THF, 98%, (c) $Boc_2$, MeCN, 70%; (d) p-TsOH, Acetone, 82%.

In order to increase efficiency, it was realized that the β-keto ester could be temporarily masked as the corresponding enol ether (FIG. 31). Since the penultimate step in the synthesis of the acyl fragment 6 involves the hydrolysis of the C2–C3 methyl enol ether, this circumvention actually shortened the synthesis. Significantly, the palladium catalyzed B-alkyl Suzuki cross-coupling reaction proceeded smoothly, and was effected in higher yield than with the corresponding β-keto ester, a result that was subsequently incorporated in a further improvement of the synthesis of dEpoB. As expected, by masking the β-keto ester as the corresponding enol ether, a 98% yield was obtained for the subsequent Staudinger reduction of azide 22 mediated by triphenylphosphine. After protection of the nascent amine as its t-butyl carbamate (23), the β-keto ester 18 could then be liberated by transfer hydrolysis.

Figure 32:
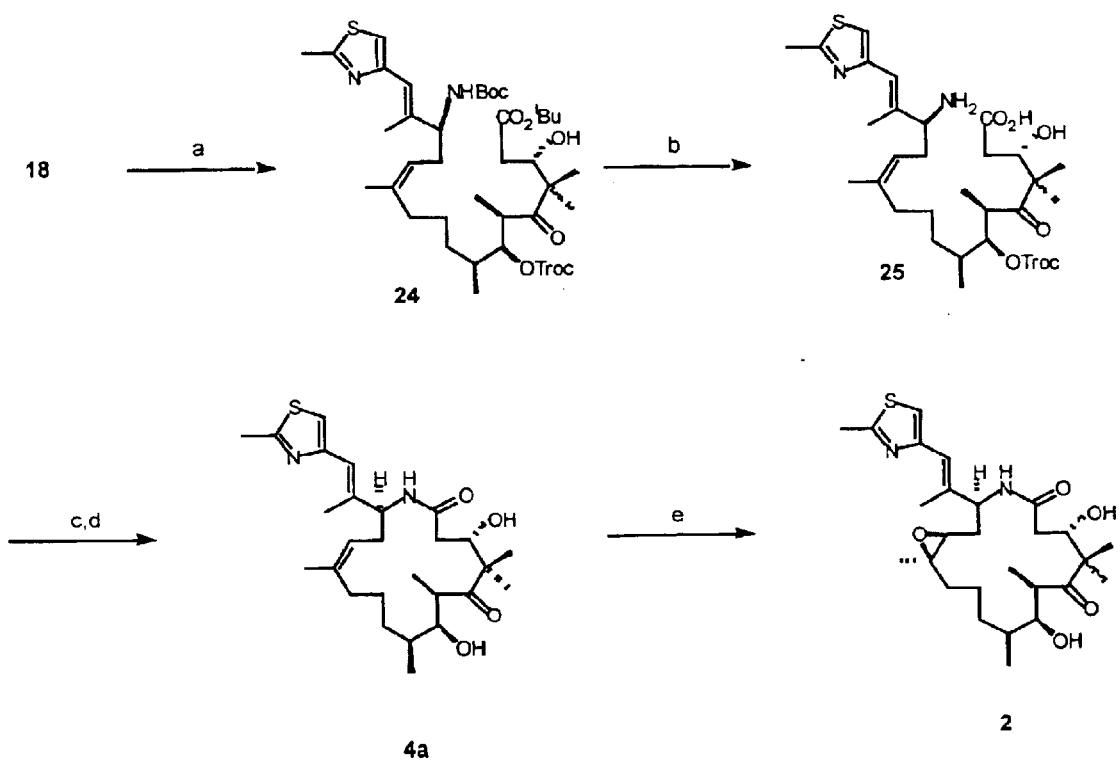
FIG. 32 depicts the synthesis of Aza dEpoB. Conditions: (a) 2% $Et_2NH_2(((R)-BINAP)RuCl)_2Cl_3$, HCl—MeOH, $H_2$, 1250 psi, 78%; (b) TFA, $CH_2Cl_2$; (c) HATU, Hoat, DIPEA, $CH_2Cl_2$, 90%; (d) Zn dust; HOAc, 88%; (e) DMDO, $CH_2Cl_2$, 70%.

The β-keto ester 18 was then subjected to a ruthenium-mediated asymmetric hydrogenation reaction in methanol using a modified Noyori catalyst (FIG. 32). Indeed, the desired diol 24 was produced as a single diastereomer in 78% yield. However, the necessity of acid in the hydrogenation medium (for protonation of the thiazole moiety) resulted in minor amounts of deprotected amine products. This undesired hydrolysis was circumvented by employing re-crystallized catalyst which results in an increased reaction rate, thus minimizing the time of exposure to the acidic solution. Simultaneous deprotection of the t-butyl carbamate and the t-butyl ester was performed through the agency of trifluoroacetic acid in dichloromethane to afford amino acid 25 that was used for the subsequent cyclization reaction without purification. Macrolactamization mediated by HATU in dichloromethane produced Troc-protected lactam in 90% yield. It should be noted that the use of other solvents (i.e. DMF, THF) for the macrolactamization also resulted in macrocyclization. However varying degrees of a by-product, which resulted from transfer of the tetramethyluronium fragment of HATU to the C3 hydroxyl of the cyclized adduct, limited access to the desired material. It was later determined that the by-product resulted from transfer of the tetramethyluronium fragment of HATU to the C3 hydroxyl of the cyclized adduct. Treatment of the urea adduct with aqueous acid (acetic acid: THF: water) released the cyclized product. Deprotection with zinc dust under the influence of sonication afforded fully deprotected 12,13,15-desoxy-15(S)-aza-epothilone B (4a) in 88% yield. Finally, epoxidation of the 12,13-olefinic linkage using 2,2-dimethyldioxirane at −50° C. yielded fully synthetic aza-epothilone B (2) as a single diastereomer.

To further probe the biological activity of the lactam series we synthesized the C15-(R) antipode, as described herein, by using the enantiomeric chiral auxiliary for the alkylation to produce the epimeric vinyl-iodide fragment. This diastereomer could then be assessed relative to the effects of inversion at C15 as seen in the corresponding lactone system (Harris et al. *J. Org. Chem.* 1999, 64, 8434).

Biological Evaluations of Aza-epothilones

Fully synthetic aza-epothilone B(2, aza-EpoB), 12,13,15-desoxy-15(S)-aza-epothilone B(4a, aza-dEpoB), and the epimeric 12,13,15-desoxy-15(R)-aza-epothilone B (4b, 15-epi-aza-dEpoB) have been evaluated in the context of a variety of cell types to evaluate their antitumor potential. As shown in Table 3, direct comparison of aza-EpoB with dEpoB showed that aza-EpoB was slightly more potent in vitro in our base leukemia cell line (CCRF-CEM), 0.0021 and 0.0095 μM respectively. However, aza-EpoB had markedly reduced activity in our multi-drug resistant cell lines (CCRF-CEM/$_{VBL100}$, CCRM-CEM/$_{VM1}$, and CCRF-CEM/$_{Taxol}$) as compared with dEpoB. Additionally, as we have noted with epothilone B (containing a C12,13 epoxide) compared with dEpoB (without epoxide), aza-dEpoB was about 10 fold less potent than the epoxide containing aza-EpoB. Also, 15-epi-aza-dEpoB displayed even further reduced activity in all cell lines tested.

P-glycoprotein (P-gp) substrate. Hence, the increased polarity of the lactam system compared to the lactone allows aza-dEpoB to be more efficiently removed from MDR cells by the P-gp receptor.

In summary, aza-dEpoB has been produced through total chemical synthesis, using the strategy based on the convergent merger of the two key fragments by B-alkyl Suzuki coupling and subsequent macrolactamization. aza-dEpoB was also successfully oxidized to aza-EpoB to study the in vitro activity. The synthesis has proven efficient and amenable to larger scale production to facilitate animal studies.

TABLE 3

Potency of dEpoB (3), aza-EpoB (2), aza-dEpoB (4a), 15-epi-aza-dEpoB (4b), and Taxol against various tumor cell growth in vitro.

| Tumor Cell Lines | IC$_{50}$ (μM)[a] | | | | |
| --- | --- | --- | --- | --- | --- |
|  | dEpoB | Aza-EpoB | Aza-dEpoB | 15-epi-aza-dEpoB | Taxol |
| Human T-cell AL Leukemia | | | | | |
| CCRF-CEM | 0.0095 | 0.0021 | 0.0278 | 0.119 | 0.0012 |
| CCRF-CEM/VBL$_{100}$ | 0.017 (5 x) | 2.99 (1423 x) | 0.997 (35.8 x) | 0.551 (4.6 x) | 5.17 (4308 x) |
| CCRF-CEM/VM$_1$ | 0.014 (1.5 x) | 0.039 (18.6 x) | NA | NA | 0.0066 (3.18 x) |
| CCRF-CEM/Taxol | 0.0162 (1.2 x) | 0.171 (81.4 x) | 0.791 (38.4 x) | NA | 0.339 (282.5 x) |
| Hamster Lung Fibroblasts | | | | | |
| DC-3F | 0.0025 | 0.0087 | NA | NA | 0.0135 |
| DDC-3F/ADX | 0.0091 (2.8 x) | 0.288 (33.1 x) | NA | NA | 0.583 (43.2 x) |
| DC-3F/ADII | 0.0484 (19.4 x) | 2.380 (274 x) | NA | NA | 20.19 (1496 x) |
| Human CM Leukemia | | | | | |
| K562 | 0.0069 | 0.0040 | 0.0024 | NA | 0.0029 |
| Human Mammary Carcinoma | | | | | |
| MX-1 | 0.0221 | 0.0024 | NA | NA | 0.0394 |

[a]Cell growth inhibition was measured by XTT tetrazonium assay after 72 h incubation for cell growth as described previously in ref. 23. The values were determined with six to seven concentrations of each drug using a computer program. The cross-resistance are shown in parentheses.
[b]Vinblastin (VBL). [c]Etoposide (VP-16). [d]Actinomycin D (AD). [e]Epothilone B (EpoB).

Figure 33:
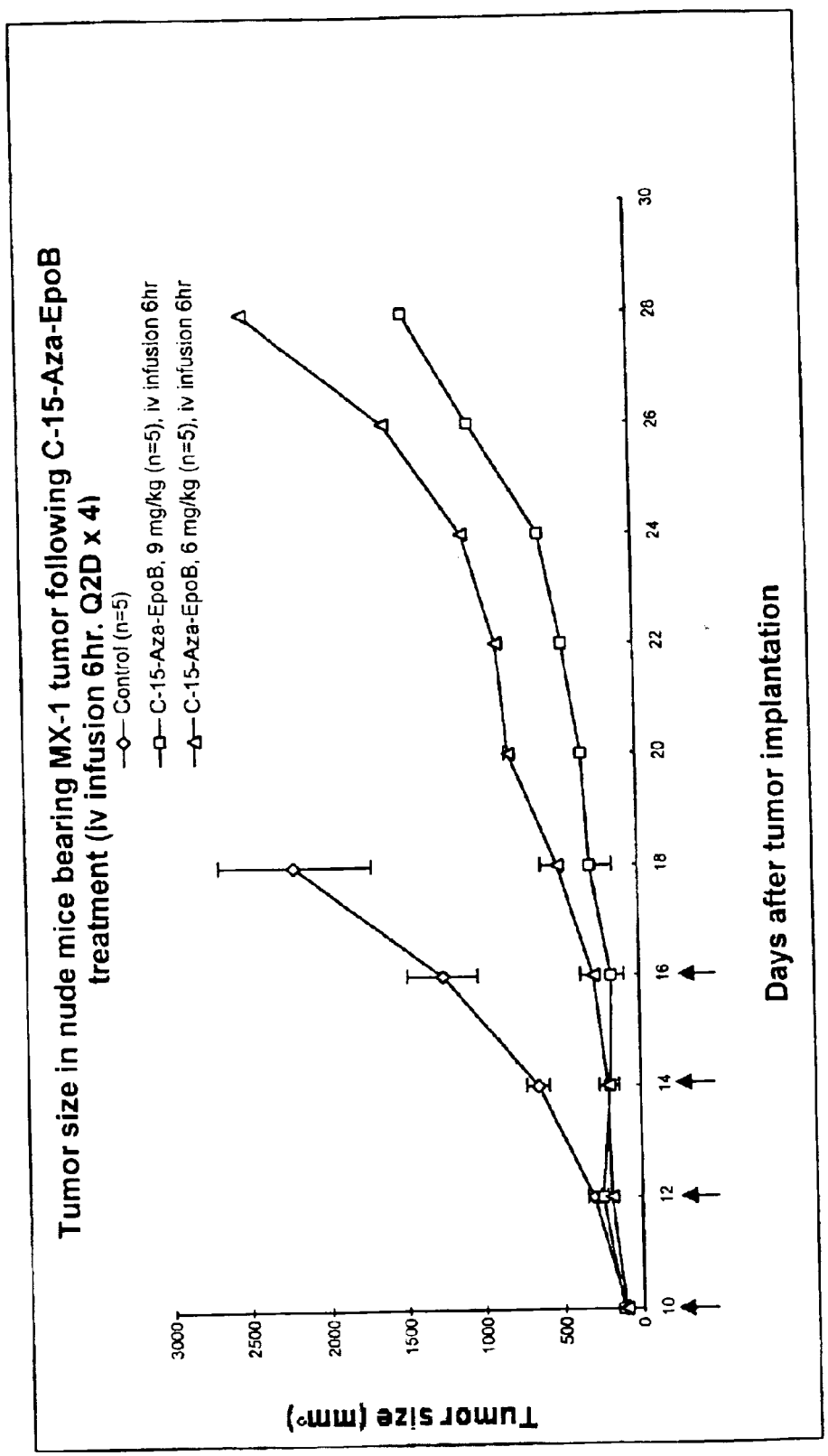
FIG. 33 depicts tumor size in nude mice bearing MX-1 tumor following C15. Aza-EpoB treatment (6 mg/kg and 9 mg/kg). MX-1 tumor cells ($1 \times 10^7$ in 0.2 mL) were inoculated to nude mice on day 0. Mice were treated with 6 or 9 mg/kg aza-EpoB, 6 h-i.v. infusion on days 10, 12, 14, and 16 (n=5). The control mice (n=5) received vehicle only.

Attentions were then turned to in vivo evaluations of aza-EpoB (2). Initially, the therapeutic effect of aza-EpoB was examined in nude mice bearing human mammary MX-1 xenograft (FIG. 33). The animal experiments were performed according to the slow IV infusion protocol developed in our previous studies. Dosage of 6 mg/kg demonstrated some inhibition in tumor growth but no reduction in tumor mass was noted and upon cessation of treatment the tumor regained its growth potential. At elevated dosage levels (9 mg/kg), approaching the maximally tolerated dose levels, similar inhibitory effects were seen, with no regression in tumor size.

Next, the therapeutic of aza-EpoB was evaluated in athymic mice bearing a human leukemia K562 xenograft.

Figure 34:
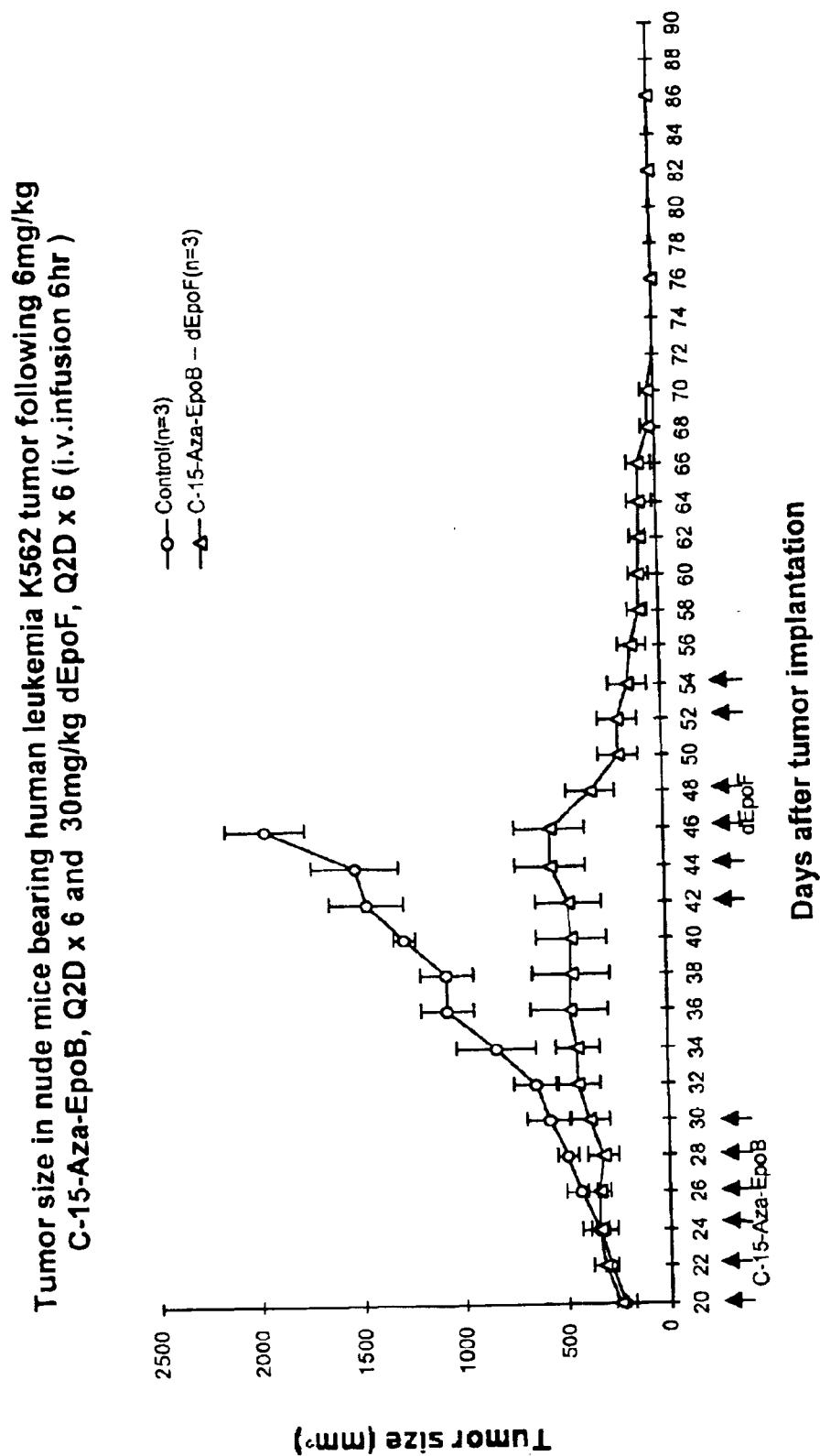
FIG. 34 depicts tumor size in nude mice bearing human leukemia K526 tumor following 6 mg/kg C-15-Aza-EpoB, Q2D×6 and 30 mg/kg dEpoF, Q2ED×6 (i.v. infusion 5 hr.). K562 tumor cells ($1 \times 10^7$ in 0.2 mL) were inoculated to nude mice on day 0. Mice were treated with 6 mg/kg aza-EpoB, 6 h-i.v. infusion on days 20, 22, 24, 26, 28 and 30 (Δ, n=3). The same group of mice were then treated with 30 mg/kg dEpoF, 6 h-i.v. infusion on days 42, 44, 46, 48, 52, and 54 (Δ, n=3). On days 76, all three mice were tumor free. The control mice (○, n=3) received vehicle only.

As depicted in FIG. 34 treatment of the mice with aza-EpoB (6 mg/kg) inhibited tumor growth but did not lead to a reduction in the size of the tumor. In contrast, further treatment of the same mice with dEpoF (30 mg/kg) readily induced reduction in the size of the tumor to the point of remission.

The aqueous solubility of aza-dEpoB using an HPLC-based method was then examined. Surprisingly, the lactam series was found to be approximately 25 times more water soluble than dEpoB. Considering this observation, and the apparent lack of activity against our MDR cell lines, we reinvestigated the activity of some of our previously prepared analogs. An apparent correlation was noticed between the polarity of the analogue and its ability to serve as a As such, aza-dEpoB was shown to exhibit similar activity to dEpoB, but was not effective towards resistant cell lines. Whereas, aza-EpoB was more active than dEpoB in non-resistant cell lines, it proved ineffective when extended to in vivo models.

Example 3

Experimental Section

General Procedures. All commercial materials were used without further purification unless otherwise noted. The following solvents were obtained from a dry solvent system and used without further drying: THF, diethyl ether, methylene chloride, toluene, and benzene. All reactions were performed under a positive pressure of prepurified dry argon gas. $^1$H and $^{13}$C NMR spectra were recorded in CDCl$_3$ solution at 400 and 100 MHz, respectively. Analytical thin layer chromatography was performed on E. Merck silica gel 60 F254 plates, and flash chromatography was performed using the indicated solvent on E. Merck silica gel 60 (40–63 μm) or Sigma H-type silica gel (10–40 μm).

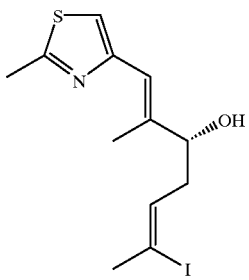

Preparation of 16. TES-protected alcohol 15 (2.28 g, 4.92 mmol) was dissolved in HOAc:THF:H$_2$O (3:1:1, 50 mL) and stirred at room temperature for 8 h. The solvent was then removed in vacuo. The oily residue was dissolved in EtOAc (100 mL) and excess acid was neutralized by the addition of sat. NaHCO$_3$ (50 mL). The organic layer was removed and the aqueous layer was extracted with EtOAc (3×50 mL). The combined organic layers were washed with sat. NaHCO$_3$ (1×50 mL), brine (1×50 mL), and then dried (MgSO$_4$). The solution was filtered and concentrated in vacuo. Chromatography on silica gel (30% EtOAc/hexanes) provided alcohol 16 (1.71 g, 99%) as a yellow oil: $[\alpha]_D$+4.9 (c 1.0, CHCl$_3$); R$_f$=0.19 in 40% EtOAc/hexanes; IR (neat) 3332, 2947, 1737, 1651, 1506, 1432, 1270, 1188, 1100, 1049, 969, 881, 732 cm$^{-1}$; $^1$H NMR (400 MHz, CDCl$_3$) δ 7.00 (s, 1H), 6.58 (s, 1H), 5.44 (t, J=6.5 Hz, 1H), 4.28 (t, J=6.4 Hz, 1H), 2.72 (s, 3H), 2.51 (s, 3H), 2.44 (m, 2H), 2.06 (s, 3H); $^{13}$C NMR (100 MHz, CDCl$_3$) δ 164.7, 152.4, 141.6, 131.5, 118.9, 115.5, 103.1, 76.1, 42.4, 33.7, 19.0, 14.4; LRMS (+electrospray): 371.9 [M +Na]$^+$, 349.9 [M +H]$^+$.

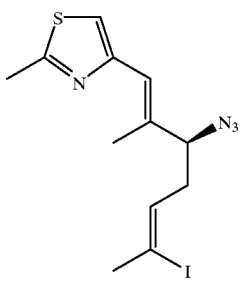

Preparation of 17. The allylic alcohol 16 (1.74 g, 4.99 mmol) was dissolved in toluene (30 mL) and cooled to 0° C. Diphenylphosphoryl azide (1.65 g, 5.98 mmol) was added followed by DBU (0.91 g, 5.98 mmol). The reaction mixture was stirred at 0° C. for 2 h. The solution was then warmed to 25° C. followed by the addition of ethyl acetate (100 mL). The organic layer was washed with H$_2$O (1×30 ml), sat. NaHCO$_3$ (1×50 mL), and brine (1×50 mL) sequentially. The organic layer was then dried over MgSO$_4$, filtered, and concentrated in vacuo. Chromatography on silica gel (7.5% EtOAc/hexanes) provided azide 17 (1.58 g, 85%) as a light yellow oil: $[\alpha]_D$-21.3 (c 1.0, CHCl$_3$); R$_f$=0.68 in 40% EtOAc/hexanes; IR (neat) 3104, 2914, 2094, 1650, 1504, 1427, 1243, 1183, 1103, 1031, 960, 877, 734 cm$^{-1}$; $^1$H NMR (400 MHz, CDCl$_3$) δ 7.01 (s, 1H), 6.52 (s, 1H), 5.44 (t, J=6.5 Hz, 1H), 4.07 (t, J=7.0 Hz, 1H), 2.70 (s, 3H), 2.49 (s, 3H), 2.41 (m, 2H), 2.10 (s, 3H); $^{13}$C NMR (100 MHz, CDCl$_3$) δ 164.7, 151.8, 136.1, 130.5, 122.2, 116.8, 103.8, 69.5, 40.0, 33.6, 19.2, 14.4; LRMS (+electrospray): 397.1 [M+Na]$^+$, 375.1 [M+H]$^+$, 332.0.

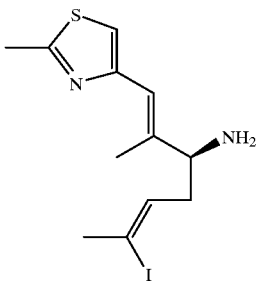

Preparation of 5. To a solution of azide 17 (0.074 g, 0.198 mmol) dissolved in THF (3 mL) was added triphenylphosphine (0.062 g, 0.237 mmol). The reaction mixture was stirred at 25° C. for 24 h. Water (0.014 g, 0.792 mmol) was then added and the reaction was heated to 65° C. for 4 h. The solution was cooled, acidified with 1N HCl, and extracted with ethyl acetate (3×30 mL). The aqueous layer was then basified using 1N NaOH followed by extraction with ethyl acetate (3×30 mL). The combined organic layers were dried over MgSO$_4$, filtered, and concentrated in vacuo. Chromatography on silica gel (5% methanol/chloroform) provided the free amine (0.069 g, 100%).

Characterization of amine: $[\alpha]_D$-7.7 (c 1.0, CHCl$_3$); R$_f$=0.30 in 10% MeOH/CHCl$_3$; IR (neat) cm$^{-1}$ 3368, 3287, 2912, 1650, 1504, 1432, 1182, 1063, 870, 731; $^1$H NMR (400 MHz, CDCl$_3$) δ 6.91 (σ, 1H), 6.48 (s, 1H), 5.45 (t, J=6.6 Hz, 1H), 3.53 (t, J=6.8 Hz, 1H), 2.69 (s, 3H), 2.48 (s, 3H), 2.34 (m, 2H), 2.03 (s, 3H); $^{13}$C NMR (100 MHz, CDCl$_3$) δ 164.4. 152.8, 142.9, 132.1, 118.8, 115.2, 103.1, 58.9, 42.6, 33.7, 19.1, 14.7; LRMS (+electrospray): 370.9 [M+Na]$^+$, 349.0 [M+H]$^+$, 331.9.

To a solution of free amine (0.069 g, 0.198 mmol), as prepared above, dissolved in acetonitrile (2 mL) was added di-tert-butyldicarbonate (0.065 g, 0.297 mmol) followed by triethylamine (0.024 g, 0.238 mmol). The reaction was stirred at 25° C. for 1.5 h. The solvent was then removed in vacuo. Chromatography on silica gel (15% EtOAc/Hexanes) provided the protected amine 5 (0.065 g, 73%) as a yellow oil: $[\alpha]_D$-8.0 (c 1.0, CHCl$_3$); R$_f$=0.58 in 40% EtOAc/hexanes; IR (neat) 3336, 2975, 2925, 1698, 1504, 1366, 1248, 1170, 1045, 873, 731 cm$^{-1}$; $^1$H NMR (400 MHz, CDCl$_3$) δ 6.93 (s, 1H), 6.46 (s, 1H), 5.37 (t, J=6.5 Hz, 1H), 4.68 (br s, 1H), 4.28 (br s, 1H), 2.70 (s, 3H), 2.45 (s, 3H), 2.39 (m, 2H), 2.06 (s, 3H), 1.43 (s, 9H); $^{13}$C NMR (125 MHz, CDCl$_3$) δ 165.0, 155.6, 153.1, 139.8, 131.6, 119.4, 116.1, 104.2, 79.9, 57.1, 41.4, 34.2, 28.8, 19.6, 16.5; LRMS (+electrospray): 470.9 [M+Na]$^+$, 448.8 [M+H]$^+$.

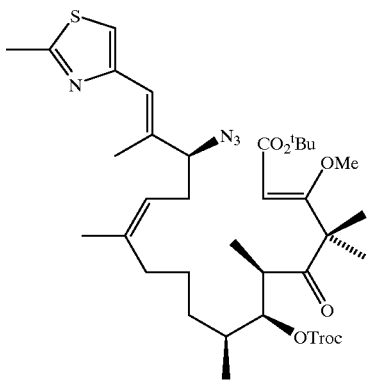

Preparation of 22. To a solution of enol ether 21 (5.80 g, 11.22 mmol) in THF (25 mL) was added 9-BBN dimer (2.10 g, 8.63 mmol). After the resulting mixture was stirred at 25° C. for 1 h, TLC analysis indicated the complete consumption of the starting olefin 21. In a separate flask containing vinyl iodide 17 (3.22 g, 8.63 mmol), (dppf)PdCl$_2$CH$_2$Cl$_2$ (0.705 g, 0.862 mmol), AsPh$_3$ (0.264 g, 0.862 mmol), and Cs$_2$CO$_3$ (4.21 g, 12.94 mmol) was added degassed DMF (30 mL). Water (5 mL) was added to the borane solution and stirring was continued for 10 min to quench the excess 9-BBN-H. Then, the solution of the alkylborane was added rapidly to the vigorously stirred solution containing the vinyl iodide. After 2 h, the reaction mixture was diluted with ethyl acetate (300 mL), washed with H$_2$O (1×250 mL), brine (1×100 mL), dried over MgSO$_4$, filtered, and concentrated in vacuo. Chromatography on silica gel (10% EtOAc/Hexanes) provide 22 as a yellow oil (4.56 g, 70%): [α]$_D$–13.8 (c 1.0, CHCl$_3$); R$_f$=0.38 in 20% EtOAc/hexanes; IR (neat) 2953, 2924, 2096, 1756, 1707, 1623, 1245, 1149, 972 cm$^{-1}$; $^1$H NMR (400 MHz, CDCl$_3$) δ 7.02 (σ1H), 6.53 (s, 1H), 5.23 (s, 1H), 5.12 (t, J=6.8 Hz, 1H), 4.89 (dd, J=12.0, 4.0 Hz, 1H), 4.84 (m, 1H), 4.72 (d, J=12.0 Hz, 1H), 3.97–3.91 (m, 2H), 3.93 (s, 3H), 3.27 (m, 1H), 2.73 (s, 3H), 2.41 (m, 1H), 2.22–2.15 (m, 2H), 2.10 (s, 3H), 2.00 (t, J=7.7 Hz, 1H), 1.92–1.78 (m, 2H), 1.70 (s, 3H), 1.50 (s, 9H), 1.58–1.41 (m, 2H), 1.34 (s, 3H), 1.27 (s, 3H), 1.13 (d, J=6.9 Hz, 3H), 0.95 (d, J=6.9 Hz, 3H); $^{13}$C NMR (125 MHz, CDCl$_3$) 211.6, 172.1, 165.0, 154.4, 152.4, 138.6, 137.6, 137.1, 122.3, 120.3, 116.8, 98.0, 95.0, 82.9, 80.3, 76.9, 71.1, 62.5, 56.2, 41.6, 35.0, 32.3, 31.7, 28.4, 25.2, 24.2, 23.7, 22.2, 19.4, 16.2, 14.6, 12.6; LRMS (+electrospray): 799.2 [M+Na]$^+$, 777.2 [M+H]$^+$.

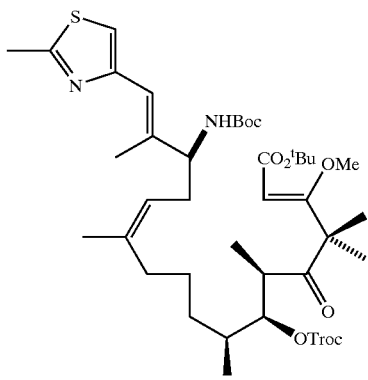

Preparation of 18. To a solution of Suzuki product 22 (4.10 g, 5.36 mmol) dissolved in THF (100 mL) was added triphenylphosphine (2.81 g, 10.71 mmol). The solution was heated to 40° C. for 19 h. Water (2 mL) was added followed by heating at 65° C. for 4 h. Silica gel (70 g) was added and the solvent removed in vacuo. Chromatography on silica gel (1.5% MeOH/chloroform containing 0.5% triethylamine) to afford the reduced amine (3.9 g, 98%): [α]$_D$–4.4 (c 1.0, CHCl$_3$); R$_f$=0.30 in 10% methanol/chloroform (containing 1% triethylamine); IR (neat) 2973, 2936, 1759, 1709, 1438, 1368, 1249, 1198, 1149, 1119 cm$^{-1}$; $^1$H NMR (500 MHz, CDCl$_3$) δ 6.91 (s, 1H), 6.48 (s, 1H), 5.20 (s, 1H), 5.11 (t, J=6.8 Hz, 1H), 4.86 (d, J=12.0 Hz, 1H), 4.81 (dd, J=7.7, 3.9 Hz, 1H), 4.70 (d, J=12.0, 1H), 3.90 (s, 3H), 3.39 (t, J=7.2 Hz, 1H), 3.25 (m, 1H), 2.69 (s, 3H), 2.24–2.11 (m, 2H), 2.02 (s, 3H), 2.00–1.94 (m, 2H), 1.70–1.61 (m, 1H), 1.67 (s, 3H), 1.49–1.40 (m, 4H), 1.47 (s, 9H), 1.37–1.20 (m, 2H), 1.31 (s, 3H), 1.24 (s, 3H), 1.10 (d, J=6.9 Hz, 3H), 0.91 (d, J=6.8 Hz, 3H); $^{13}$C NMR (100 MHz, CDCl$_3$) δ 211.6, 172.1, 165.0, 154.3, 153.4, 144.1, 137.8, 133.2, 122.0, 118.6, 115.1, 97.9, 95.0, 82.9, 80.3, 76.9, 62.5, 60.1, 56.2, 41.6, 35.0, 34.4, 32.4, 31.7, 28.4, 25.2, 23.7, 23.5, 23.1, 22.2, 19.4, 16.2, 15.1, 12.6; LRMS (+electrospray): 773.2 [M+Na]$^+$, 751.3 [M+H]$^+$.

To a solution of the amine (3.30 g, 4.48 mmol), as prepared above, dissolved in acetonitrile (100 mL) was added di-tert-butyldicarbonate (1,37 g, 6.27 mmol) followed by triethylamine (0.91 g, 8.57 mmol). The reaction mixture was stirred at RT for 16 h. The solution was then diluted with EtOAc (100 mL) and washed with 1N HCl (1×100 mL), sat. Na$_2$CO$_3$ (1×100 mL), brine (1×100 mL), dried over MgSO$_4$, filtered, and concentrated in vacuo. Chromatography on silica gel (10% EtOAc/hexanes) afforded 22 (2.66 g, 70%) as a white foam: [α]$_D$–14.5 (c 1.0, CHCl$_3$); R$_f$=0.60 in 40% EtOAc/hexanes; IR (neat) 2978, 2948, 1757, 1710, 1366, 1247, 1150 cm$^{-1}$; $^1$H NMR (400 MHz, CDCl$_3$) δ 6.91 (σ1H), 6.43 (s, 1H), 5.20 (s, 1H), 5.08 (t, J=6.0 Hz, 1H), 4.87 (d, J=12.0 Hz, 1H), 4.81 (dd, J=7.6, 3.8 Hz, 1H) 4.70 (d, J=12.0 Hz, 1H), 4.65–4.59 (m, 1H), 4.14–4.11 (m, 1H), 3.90 (s, 3H), 3.25 (dd, J=6.8, 3.8 Hz, 1H), 2.70 (s, 3H), 2.32 (m, 1H), 2.24–2.21 (m, 1H), 2.04 (s, 3H), 1.96–1.94 (m, 2H), 1.55–1.43 (m, 3H), 1.66 (s, 3H), 1.48 (s, 9H), 1.42 (s, 9H), 1.37–1.20 (m, 2H), 1.31 (s, 3H), 1.25 (s, 3H), 1.10 (d, J=6.9 Hz, 3H), 0.92 (d, J=6.8 Hz, 3H); $^{13}$C NMR (125 MHz, CDCl$_3$) δ 211.6, 172.2, 165.1 164.5, 154.4, 153.3, 120.5, 118.9, 115.5, 97.9, 95.0, 82.9, 80.4, 76.9, 62.5, 56.3, 41.6, 35.0, 32.2, 31.8, 28.6, 28.4, 25.3, 23.8, 23.5, 23.1, 19.4, 16.2, 12.6; LRMS (+electrospray): 873.2 [M+Na]$^{30}$, 851.2 [M+H]$^+$.

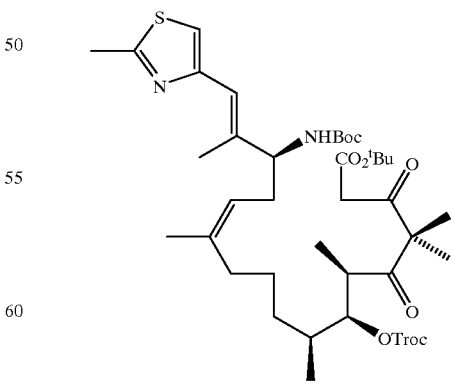

To a solution of enol ether 23 (0.309 g, 0.363 mmol) dissolved in acetone (9 mL) was added p-toluenesulfonic acid (0.083 g, 0.436 mmol). The solution was stirred at RT for 22 h. The reaction was neutralized by the addition of sat. NaHCO₃ and extracted with EtOAc (3×30 mL). The combined organic layers were dried over MgSO₄, filtered, and concentrated in vacuo. Chromatography on silica gel (15% EtOAc/Hexanes) afforded β-keto-ester 18 as a white foam (0.250 g, 82%): [α]$_D$−36.8 (c 1.0, CHCl₃); R$_f$=0.28 in 10% EtOAc/toluene; IR (neat) 2968, 2948, 1758, 1710, 1367, 1250, 1164, 1060, 927, 816, 733 cm⁻¹; ¹H NMR (400 MHz, CDCl₃) δ*12.61 (s, 1H), 6.91 (s, 1H), 6.43 (s, 1H), 5.14–5.07 (m, 1H), 4.88–4.66 (m, 4H), 4.11 (m, 1H), 3.49 (d, J=16.2 Hz, 1H), 3.42 (d, J=16.0 Hz, 1H), 3.31–3.29 (m, 1H), 2.69 (s, 3H), 2.33–2.17 (m, 2H), 2.04 (s, 3H), 2.04–1.96 (m, 2H), 1.72–1.61 (m, 2H), *1.65 and 1.63 (s, 3H), 1.45 (s, 9H), 1.42 (s, 9H), 1.24 (s, 9H), *1.10 and 1.08 (d, J=8.5 Hz, 3H), 0.92 and *0.88 (d, J=8.5 Hz, 3H); ¹³C NMR (100 MHz, CDCl₃) δ 209.8, 203.4, 178.7, 166.5, 164.5, 154.4, 153.2, 140.2, 138.3, 120.6, 118.9, 115.5, 94.9, 82.2, 77.3, 76.9, 63.8, 60.6, 46.8, 41.8, 34.9, 32.3, 32.2, 31.5, 28.6, 28.2, 23.7, 22.4, 21.8, 21.1, 19.4, 15.9, 14.4, 11.6; LRMS (+electrospray): 837.5 [M+Na]⁺, 859.6 [M+H]⁺.

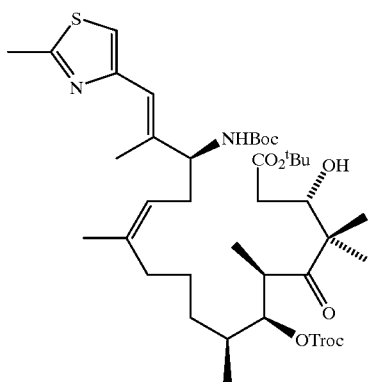

Preparation of 23. Diketone 18 (1.234 g, 1.48 mmol) was dissolved in 0.12 N HCl in MeOH (24.6 mL, 2.95 mmol) at 25° C. The solution was then sparged with argon gas for 30 min. The ruthenium catalyst (0.150 g, 0.089 mmol) was then added and the mixture was transferred to a Parr apparatus. The vessel was purged with H₂ for 10 min and then pressurized to 1200 psi. After 18 h at 25° C., the reaction was returned to atmospheric pressure and poured into satd. aq. NaHCO₃ (60 mL). After extraction with EtOAc (3×100 mL), the combined organic layers were dried over MgSO₄, filtered, and concentrated in vacuo. Chromatography on silica gel (20% EtOAc/Hexane) afforded the hydroxy ester 24 (0.955 g, 78%) as a white foam: [α]$_D$−33.5 (c 1.0, CHCl₃); R$_f$=0.20 in 20% EtOAc/hexanes; IR (neat) 3385, 2974, 2936, 1758, 1703, 1504, 1471, 1455, 1367, 1249, 1161, 1051, 926, 817, 733 cm⁻¹; ¹H NMR (500 MHz, CDCl₃) δ 6.90 (s, 1H), 6.42 (s, 1H), 5.08 (t, J=6.7 Hz, 1H), 4.85 (t, J=5.7 Hz, 1H), 4.82 (d, J=12.0 Hz, 1H), 4.71 (d, J=12.0 Hz, 1H), 4.66 (1br s, 1H), 4.15–4.09 (m, 2H), 3.46–3.39 (m, 2H), 2.79 (s, 3H), 2.39–2.21 (m, 4H), 2.03 (s, 3H), 1.98–1.94 (m, 2H), 1.73–1.71 (m, 1H), 1.65 (s, 3H), 1.44 (s, 9H), 1.42 (s, 9H), 1.37–1.20 (m, 2H), 1.18 (s, 3H), 1.16 (s, 3H), 1.09 (d, J=6.8 Hz, 3H), 0.94 (d, J=6.7 Hz, 3H); ¹³C NMR (100 MHz, CDCl₃) □ 216.2, 172.7, 164.4, 154.5, 153.2, 140.2, 138.3, 120.6, 120.5, 118.9, 115.5, 95.0, 83.3, 81.6, 77.3, 76.9, 73.2, 52.1, 41.7, 37.6, 35.0, 32.5, 32.3, 31.5, 28.6, 28.3, 25.4, 25.3, 23.7, 22.2, 19.3, 16.4, 12.4; LRMS (+electrospray): 861.2 [M+Na]⁺, 832.2 [M+H]⁺.

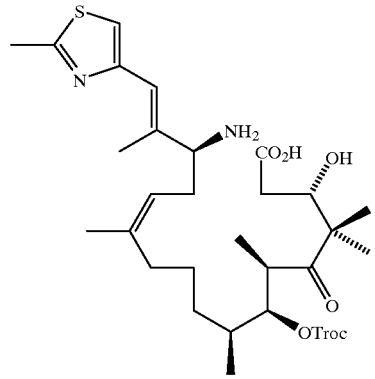

Preparation of 24. To a solution of the bis-Boc protected amino acid (0.738 g, 0.880 mmol) dissolved in CH₂Cl₂ (20 mL) was added trifluoroacetic acid (10 mL). The solution was stirred a RT for 2 h followed by concentration in vacuo. The crude material was used without further purification: [α]$_D$+3.4 (c=1.0, CHCl₃); R$_f$=0.5 in 75:15:10 ᵗBuOH: HCOOH: H₂O; IR (neat) 3076, 2971, 1757, 1668, 1378, 1255, 1187, 926, 818 cm⁻¹; ¹H NMR (400 MHz, DMFd₇) δ 8.61 (br s, 3H), 7.48 (s, 1H), 6.67 (s, 1H), 5.14 (t, J=6.8 Hz, 1H), 5.03 (d, J=12.4 Hz, 1H), 4.98 (d, J=12.3 Hz, 1H), 4.88 (t, J=6.6 Hz, 1H), 4.28 (dd, J=9.8, 1.1 Hz, 1H), 4.00 (m, 1H), 3.63–3.60 (m, 1H), 2.70 (s, 3H), 2.68–2.66 (m, 2H), 2.49 (dd, J=15.4, 2.0 Hz, 1H), 2.26 (s, 3H), 2.25–2.21 (m, 1H), 2.12–2.04 (m, 2H), 1.78–1.71 (m, 1H), 1.67 (s, 3H), 1.59–1.17 (m, 5H), 1.24 (s, 3H), 1.14 (s, 3H), 1.09 (d, J=6.7 Hz, 3H), 0.98 (d, J=6.7 Hz, 3H); ¹³C NMR (100 MHz, CDCl₃) δ 217.9, 171.6, 161.0, 161.3, 154.8, 143.9, 143.0, 142.9, 118.2, 116.7, 94.8, 83.9, 73.2, 58.8, 53.6, 52.2, 42.3, 36.5, 34.8, 32.2, 30.4, 27.8, 25.2, 23.8, 23.6, 22.5, 18.7, 16.4, 16.1, 14.1; LRMS (+electrospray): 705.1 [M+Na]⁺, 683.1 [M+H]⁺.

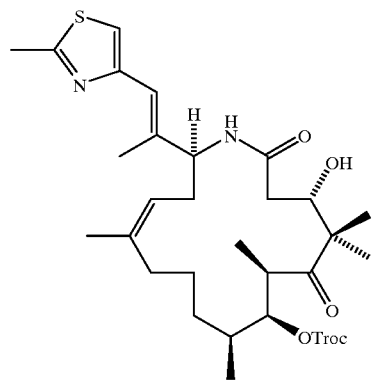

Preparation of Troc-protected 4a. The crude mixture, obtained from above, was dissolved in DMF (10 mL) and further diluted with CH₂Cl₂ (500 mL). Then HOAt (0.359 g, 2.64 mmol) was added followed by diisopropylethylamine (1.02 g, 7.92 mmol) and finally HATU (0.359 g, 2.64 mmol). The resultant mixture was stirred at 25° C. for 16 h. The reaction mixture was then washed with H₂O (1×100 mL). The organic layer was dried over MgSO₄, filtered, and concentrated in vacuo. The crude mixture was then dissolved in HOAc: THF:H₂O (3:1:1, 30 mL) for 30 min. The reaction mixture was concentrated in vacuo, neutralized with satd. aq. NaHCO₃ and extracted using EtOAc (3×100 mL). The combined organic layers were dried over MgSO$_4$, filtered, and concentrated in vacuo. Chromatography on silica gel (45% EtOAc/Hexanes) afforded Troc-protected aza-dEpoB (0.479 g, 79%) and Troc-protected C-15-epi-aza-dEpoB, from 88% ee asymmetric dihydroxylation, (0.065 g, 11%) as a white foam: Characterization for Troc-protected aza-dEpoB: $[\alpha]_D$-16.3 (c 1.0, CHCl$_3$); R$_f$=0.35 in 70% EtOAc/Hexanes; IR (neat) 3318, 2932, 1758, 1620, 1370, 1248, 1143, 1069, 926 cm$^{-1}$; $^1$H NMR (500 MHz, CDCl$_3$) δ 7.04 (s, 1H), 6.92 (d, J=7.80 Hz, 1H), 6.51 (s, 1H), 5.18 (t, J=7.8 Hz, 1H), 5.08 (d, J=7.7 Hz, 1H), 4.79 (s, 2H), 4.64–4.63 (m, 1H), 4.34 (dd, J=10.9, 7.0 Hz, 1H), 4.05 (d, J=9.0 Hz, 1H), 2.68 (s, 3H), 2.52–2.46 (m, 2H), 2.31–2.21 (m, 3H), 2.09 (s, 3H), 1.98–1.92 (m, 1H), 1.69 (s, 3H), 1.65–1.51 (m, 4H), 1.35 (s, 3H), 1.37–1.20 (m, 2H), 1.17 (d, J=6.8 Hz, 3H), 1.09 (s, 3H), 0.99 (d, J=6.8 Hz, 3H); $^{13}$C NMR (125 MHz, CDCl$_3$) δ 216.3, 170.7, 165.9, 154.5, 140.0, 139.6, 120.7, 118.4, 115.6, 94.9, 84.9, 76.8, 73.0, 56.4, 52.9, 43.8, 39.6, 38.7, 32.0, 31.8, 30.8, 27.2, 24.1, 22.0, 21.3, 19.2, 17.6, 16.9, 16.0; LRMS (+electrospray): 687.0 [M+Na]$^+$, 665.1 [M+H]$^+$.

Characterization for Troc-protected C-15-epi-aza-dEpoB: $[\alpha]^{22}_D$-1.50 (c 1.0, CHCl$_3$; R$_f$=0.61 in 70% EtOAc/Hexanes; IR (neat) 3315, 2966, 1759, 1696, 1646, 1526, 1466, 1382, 1248, 1183, 925, 733 cm$^{-1}$; $^1$HNMR (400 MHz, CDCl$_3$) δ 6.95 (s, 1H), 6.40 (s, 1H), 6.34 (d, J=5.8 Hz, 1H), 5.15 (t, J=7.0 Hz, 1H), 4.92 (d, J=12.0 Hz, 1H), 4.84–4.77 (m, 1H), 4.74 (d, J=12.0 Hz, 1H), 4.69–4.60 (m, 1H), 4.57–4.52 (m, 1H), 3.40–3.35 (m, 1H), 2.71 (s, 3H), 2.34–2.09 (m, 3H), 2.07 (s, 3H), 1.97–1.91 (m, 3H), 1.70 (s, 3H), 1.43–1.20 (m, 6H), 1.33 (s, 3H), 1.17 (d, J=6.9 Hz, 3H), 1.04 (s, 3H), 0.98 (d, J=7.1 Hz, 3H); $^{13}$C NMR (125 MHz, CDCl$_3$) δ 215.9, 172.5, 164.9, 154.8, 152.6, 139.7, 139.0, 120.8, 118.4, 115.8, 94.8, 77.1, 71.8, 55.9, 54.3, 53.6, 52.9, 45.9, 38.8, 34.7, 32.1, 31.8, 30.8, 24.7, 22.5, 19.3, 16.6, 15.7; LRMS (+electrospray): 687.0 [M+Na]$^+$, 665.2 [M+H]$^+$.

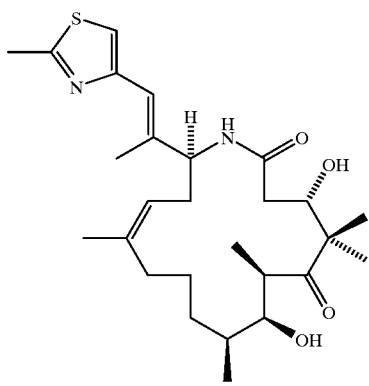

Preparation of 4a. To a solution of Troc-protected aza-dEpoB (0.038 g, 0.057 mmol) dissolved in THF:HOAc (1:3, 6 mL) was added a spatula tip of activated nanosized zinc. The reaction mixture was then sonicated at 25° C. for 2 h. The solution was filtered to remove the zinc metal followed by concentration in vacuo. The residue was then dissolved in EtOAc (20 mL) and neutralized with satd. aq. NaHCO$_3$ (10 mL). The aqueous layer was extracted using EtOAc (3×20 mL). The combined organic layers were dried over MgSO$_4$, filtered, and concentrated in vacuo. Chromatography on silica gel (60% EtOAc/Hexanes) afforded aza-dEpoB (0.025 g, 88%) as a white foam:

Characterization for aza-dEpoB (4a) $[\alpha]_D$-61.9 (c 0.5, CHCl$_3$); R$_f$=0.55 in 100% EtOAc; IR (neat) 3330, 2929, 1690, 1634, 1510, 1456, 1381, 1147, 732 cm$^{-1}$; $^1$H NMR (500 MHz, CDCl$_3$) δ 6.92 (s, 1H), 6.46 (s, 1H), 5.99 (d, J=6.5 Hz, 1H), 5.13 (t, J=7.6 Hz, 1H), 4.31 (dd, J=11.6, 6.8 Hz, 1H), 4.06 (d, J=8.9 Hz, 1H), 3.82–3.74 (m, 2H), 3.14 (q, J=6.9 Hz, 1H), 2.99 (s, 1H), 2.69 (s, 3H), 2.48–2.31 (m, 3H), 2.25–2.21 (m, 1H), 2.06 (s, 3H), 2.07–2.00 (m, 1H), 1.77–1.69 (m, 4H), 1.69 (s, 3H), 1.31 (s, 3H), 1.34–1.20 (m, 2H), 1.17 (d, J=6.9 Hz, 3H), 1.11 (s, 3H), 1.00 (d, J=7.1 Hz, 3H); $^{13}$C NMR (125 MHz, CDCl$_3$) δ 221.2, 170.6, 164.8, 152.8, 139.7, 120.8, 118.7, 115.7, 74.5, 73.9, 56.6, 53.1, 42.6, 40.5, 38.5, 32.7, 31.7, 31.5, 25.8, 23.3, 22.9, 20.2, 19.3, 16.8, 15.9, 13.7; LRMS (+electrospray): 513.2 [M+Na]$^+$, 491.1 [M+H]$^+$.

Characterization for 15 (R)-aza-dEpoB (4b): $[\alpha]^{22}_D$30.9 (c 1.0, CHCl$_3$); R$_f$=0.43 in 70% EtOAc; IR (neat) 3339, 2966, 1685, 1644, 1520, 1454, 1377, 1184, 979, 733 cm$^{-1}$; $^1$H NMR (400 MHz, CDCl$_3$) δ 6.94 (s, 1H), 6.31 (s, 1H), 5.77 (d, J=8.4 Hz, 1H), 5.06 (t, J=7.2 Hz, 1H), 4.98 (s, 1H), 4.71–4.68 (m, 1H), 4.22 (d, J=10.4 Hz, 1H), 3.51 (d, J=6.0 Hz, 1H), 3.16 (dd, J=11.9, 7.0 Hz, 1H), 2.96 (s, 1H), 2.71 (s, 3H), 2.47–2.40 (m, 2H), 2.17–2.02 (m, 2H), 2.08 (s, 3H), 1.96–1.87 (m, 2H), 1.77–1.75 (m, 1H), 1.70 (s, 3H), 1.58–1.50 (m, 2H), 1.34 (s, 3H), 1.34–1.20 (m, 2H), 1.14 (d, J=6.8 Hz, 3H), 1.07 (s, 3H), 0.94 (d, J=7.0 Hz, 3H); $^{13}$C NMR (125 MHz, CDCl$_3$) □221.3, 172.0, 164.7, 152.6, 140.3, 138.7, 119.4, 118.4, 115.7, 73.2, 72.2, 54.8, 54.0, 41.5, 39.0, 36.7, 32.0, 31.8, 31.2, 25.1, 24.2, 23.0, 19.3, 17.2, 15.5, 14.4, 12.4; LRMS (+electrospray): 513.0 [M+Na]$^+$, 491.1 [M+H]$^+$.

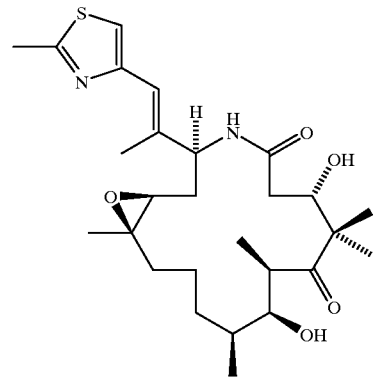

Preparation of 2. Aza-dEpoB (0.025 g, 0.051 mmol) was dissolved in CH$_2$Cl$_2$ (2 mL) and cooled to -78° C. 2,2-dimethyldioxirane (0.6M, 0.11 mmol) was added slowly. The reaction mixture was allowed to warm to -50° C. and stirred for 1 h. Excess DMDO was quenched at -50° C. by the addition of dimethylsulfide (0.1 mL) and warmed to RT. Chromatography on silica gel (80% EtOAc/Hexanes) afforded fully synthetic aza-EpoB (0.018 g, 69%) as a white foam: $[\alpha]_D$-34.1 (c 1.0, CHCl$_3$); R$_f$=0.4 in 100% EtOAc; IR (neat) 3319, 2931, 1661, 1643, 1536, 1453, 1372, 1185, 753 cm$^{-1}$; $^1$H NMR (500 MHz, CDCl$_3$) δ 6.97 (s, 1H), 6.83 (d, J=8.0 Hz, 1H), 6.55 (s, 1H), 4.66–4.64 (m, 1H), 4.25 (d, J=6.2 Hz, 1H), 4.03–4.01 (m, 1H), 3.83–3.81 (m, 1H), 3.38–3.33 (m, 1H), 2.81 (dd, J=7.2, 6.4 Hz, 1H), 2.70 (s, 3H), 2.62 (br s, OH, 1H), 2.43 (dd, J=14.7, 9.3 Hz, 1H), 2.32 (dd, J=14.7, 2.9 Hz, 1H), 2.13 (s, 3H), 2.04–1.97 (m, 4H), 1.69–1.38 (m, 5H), 1.34 (s, 3H), 1.27 (s, 3H), 1.17 (d, J=6.9 Hz, 3H), 1.12 (s, 3H), 0.99 (d, J=7.0 Hz, 3H); $^{13}$C NMR (125 MHz, CDCl$_3$) δ221.0, 170.6, 165.0, 152.6, 137.8, 119.4, 116.2, 75.0, 74.1, 61.4, 61.1, 54.7, 52.4, 43.9, 40.4, 38.0, 31.9, 31.8, 30.7, 23.9, 23.1, 21.7, 21.6, 19.4, 17.3, 17.1, 14.5; LRMS (+electrospray): 529.0 [M+Na]$^+$, 507.0 [M+H]$^+$.

Example 4

Biological Studies

Among naturally occurring molecules that stabilize microtubule assemblies, paclitaxel (Taxol®) is by far the most well known, extensively studied, and widely used front-line cancer chemotherapeutic agent, especially for treating solid tumors (Landino, L. M. & MacDonald, T. L. (1995) in: *The Chemistry and Pharmacology of Taxol and Its Derivatives*, ed. Favin, V. (Elsevier, N.Y.) Chap. 7.; Rose, W. C. (1992) *Anti. Cancer Drugs* 3, 311–321; Rowinsky, E. K., Eisenhauser, E. A., Chaudhry, V., Arbuck, S. G. & Donehower, R. C. (1993) *Semin, Oncol*, 20, 1–15). More recently discovered compounds with similar mechanisms of action include discordermolids (4,5), eleutherobins (6), laulimalides (7) and epothilones (8–14). Despite their supposed common binding site on tubulin assemblies (15–18), their chemical structures and/or pharmacological profiles are drastically different.

Epothilones A and B, along with other minor related constituents, are macrolides isolated from the myxobacterium *Sorangium cellulosum*, which were harvested off the shores of Zambezi River in the Republic of South Africa (8). Our recent studies on the effects of epothilone derivatives on the formation of microbule from tubulin indicated that 13 out of 16 epothilones (at 10 $\mu$M) showed 83–99% of the microtubule stabilization effect relative to EpoB (16). There was a correlation between cytotoxicity and the observed microtubule stabilization effect (10).

Pharmacological evaluations pointed to the fact that EpoB, although the most potent among epothilone series, gave poor therapeutic efficacy even a highly toxic or lethal doses (19). dEpoB (Z-12,13-desoxyepothilone B) which ranked lower in vitro cytotoxicity assays than EpoB, showed far higher therapeutic effects than EpoB (19,20). Structural activity-relationship (SAR) results suggested that 12,13-epoxymoiety in EopB contributed to the toxicity toward the host and yet offer little advantage toward the antineoplastic therapeutic effects.

In this paper we present the in vitro and in vitro pharmacologic properties of the lead compounds dEpoB (14) and 21-hydroxy-dEpoB (dEpoF)(21) along with 15-aza-EpoB (BMS 247550)(22) which is currently under clinical investigations. It is shown that both dEpoB and dEpoF have broad antitumor spectrum and yield curative effect in nude mice bearing human leukemia or mammary tumor xenografts. Preliminary toxicological profile of dEpoB showed that it is well tolerated at therapeutic doses, with limiting toxicity mainly occurred in the gastrointestinal tracts.

Results

Therapeutic Effects against Human Colon Carcinoma HCT-116 Xenografts

Figure 35:
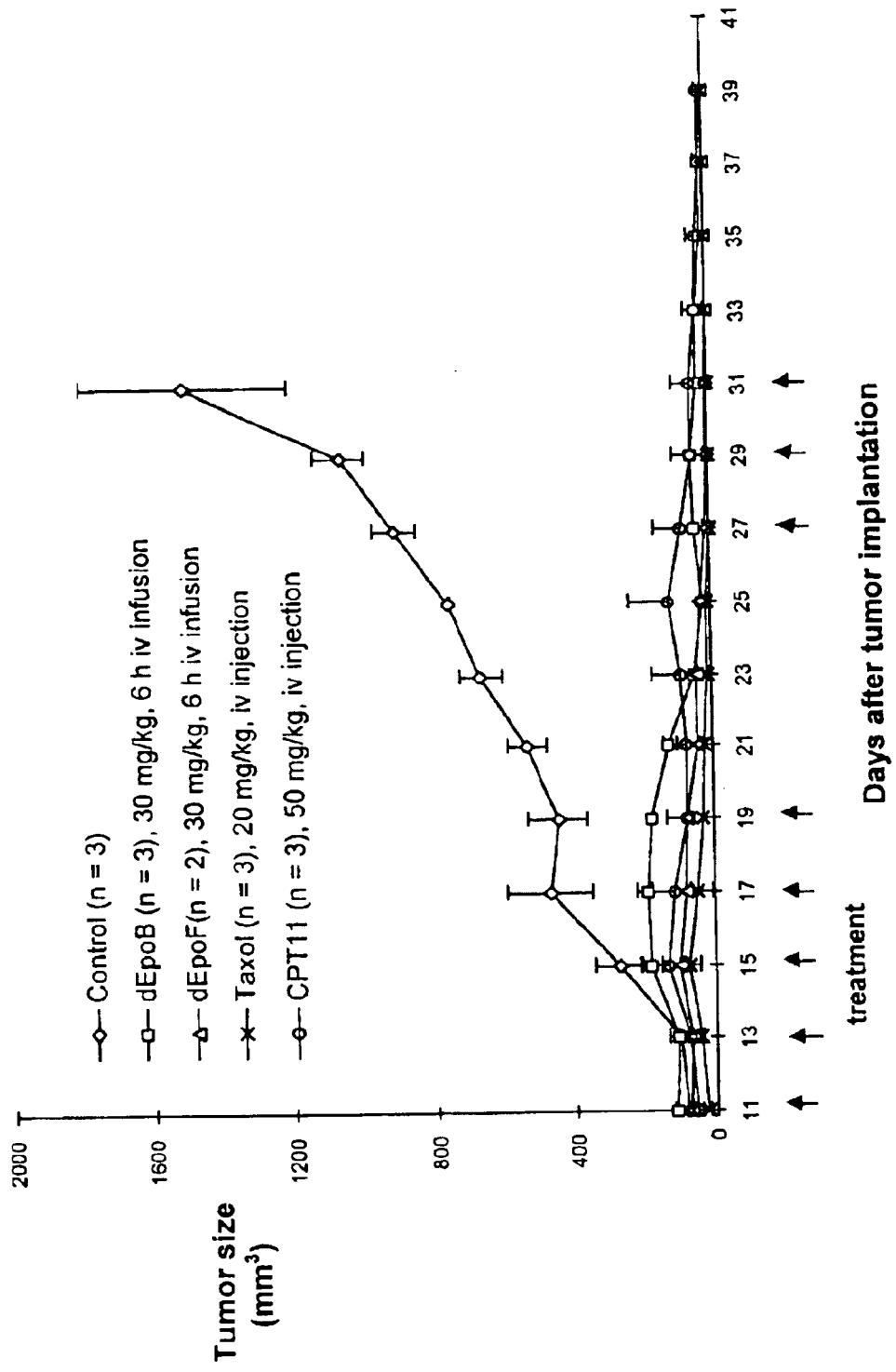
FIG. 35 depicts tumor size in nude mice bearing human colon carcinoma.

Therapeutic efficacy of cancer chemotherapeutic agents varies with various factors including the tumor models used and the dosage of drug and schedules and routes of administration. For human colon carcinoma HCT-116 xenografts in nude mice, dEpoB, dEpoF, paclitaxel and CPT-11 virtually showed similar curative effects against this tumor xenograft (FIG. 35). These results suggest that the doses of each drug to be used in the present studies are adequate and the routes of administration appropriate. In the present studies, we intended to compare the therapeutic effects of drugs near their maximal tolerated doses by measuring the extent of body-weight decreases and/or lethality.

Figure 36:
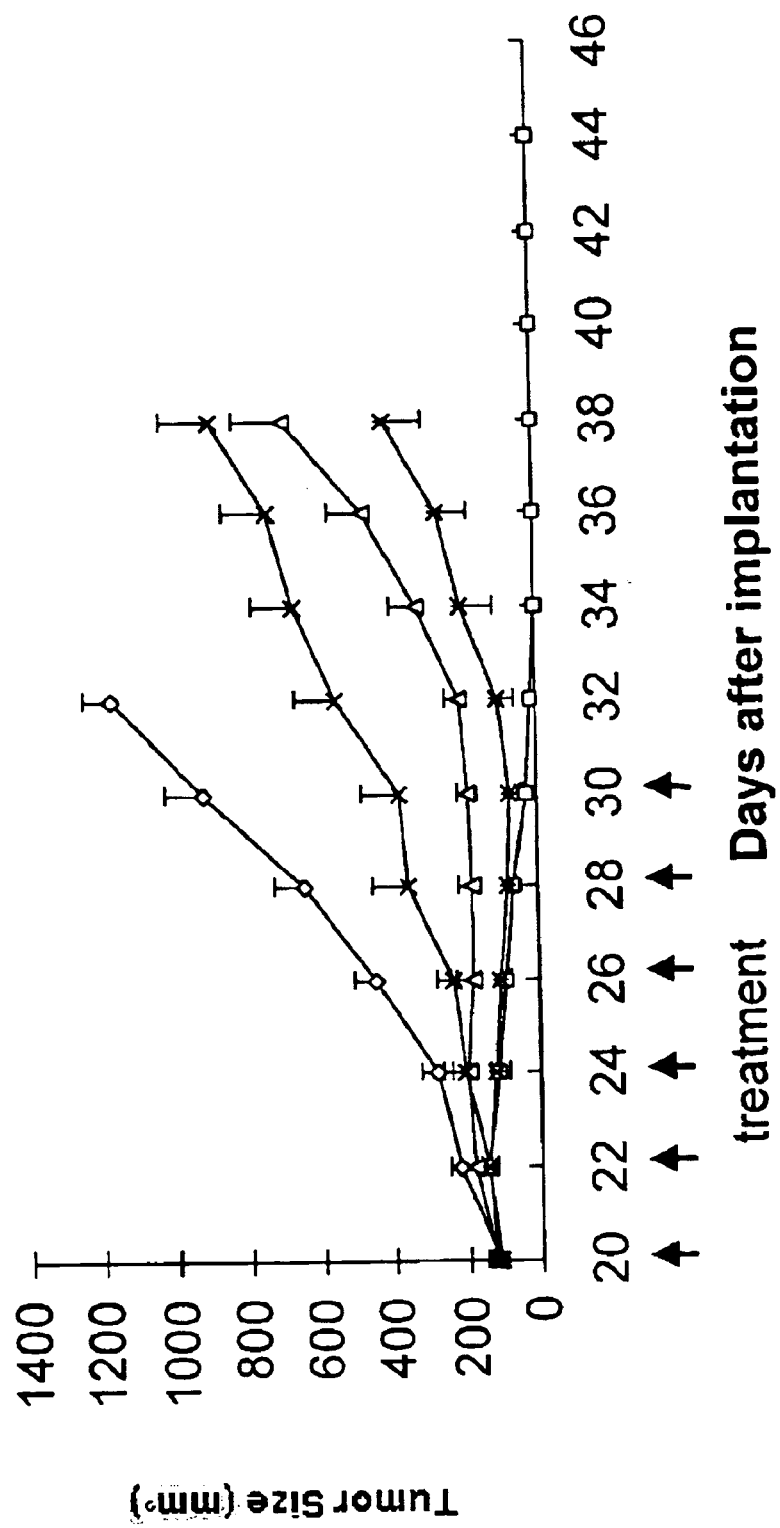
FIG. 36 depicts the therapeutic effect of dEpoB, paclitaxel (Taxol®), doxorubicin (Adriamycin), and vinblastine in nude mice bearing human chronic myelocytic leukemia tumor K562 xenograft. K562 tumor cells ($1 \times 10^7$, in 0.2 ml/mouse) were implanted s.c. on day 0. Every other day treatments were given starting on day 20 with 30 mg/kg of dEpoB, 6 hr i.v. infusion (□, n=5); 20 mg/kg of Taxol 6 hr i.v. infusion (Δ, n=3); 3 mg/kg of Adriamycin, i.v. injection, (X, n=4) and 2.5 mg/kg of vinblastine, i.v. injection (*, n=4). The control mice (○, n=4) received vehicle, Cremophor-ethanol (1:1), only. The vertical bars indicate mean tumor size in $mm^3 \pm S.E.$

Therapeutic Effects Against Human Leukemia K562 Xenografts a. Comparison among dEpoB, Pacliltaxel, Adriarnycin and Vinblastine As shown in FIG. 36, we observed that dEpoB was particularly effective against naive non-MDR human chronic myelocytic leukemia K562 xenografts in nude mice. Complete remission was achieved for dEpoB, whereas Adriamycin, paclitaxel and vinblastine showed only partial curative or remissive effects. This is in contrast with our earlier reports (19, 27, 28) that dEpoB showed superior therapeutic effects than paclitaxel in a broad range of drug-resistant tumors (e.g., tumors resistant to VBL, Adr, or paclitaxel), but had similar efficacy as paclitaxel, in non-drug resistant tumors.

b. Sequential Treatment with paclitaxel followed by dEpoB.

Figure 37:
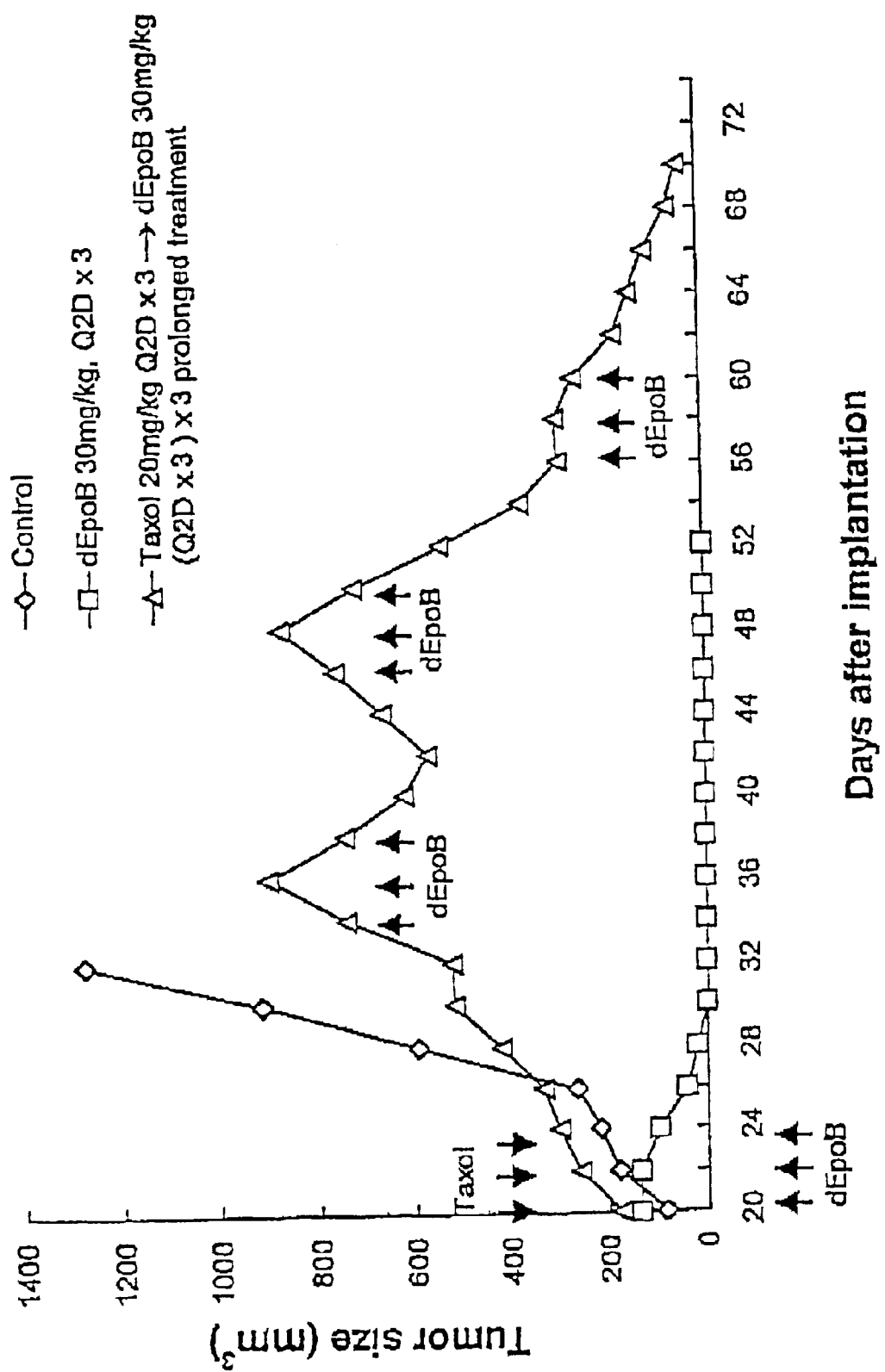
FIG. 37 depicts therapeutic effects of dEpoB and Taxol in nude mice bearing human leukemia K562 xenograft.

Single course treatment with dEpoB (30 mg/kg, Q2D×3) led to disappearance of K562 xenografts for four weeks. However, the same schedule of treatment with paclitaxel led to only partial therapeutic effects (FIG. 37). The later group of nude mice were subsequently treated with dEpoB for three cycles of treatment [30 mg/kg, (Q2D×3)×3] caused the established K562 tumor as large as 880 mm³ to shrink to less than 20 mm³ size. No further treatment with dEpoB was given due to damage to the tail vein following repeated needle insertions.

c. Sequential Treatment with azaEpoB and then dEpoF

Treatment of K562 xenografts with maximal tolerated dose of azaEpoB (6 mg/kg Q2D×6) strongly suppressed tumor growth but did not shrink the tumor. The same group of tumor-bearing nude mice with tumor size near 500 mm³ was subsequently treated with dEpoF (30 mg/kg Q2D×6). The tumor shrank during treatment and continue to shrink after cessation of treatment. The tumor mass eventually disappeared three weeks later.⁺

Figure 39:
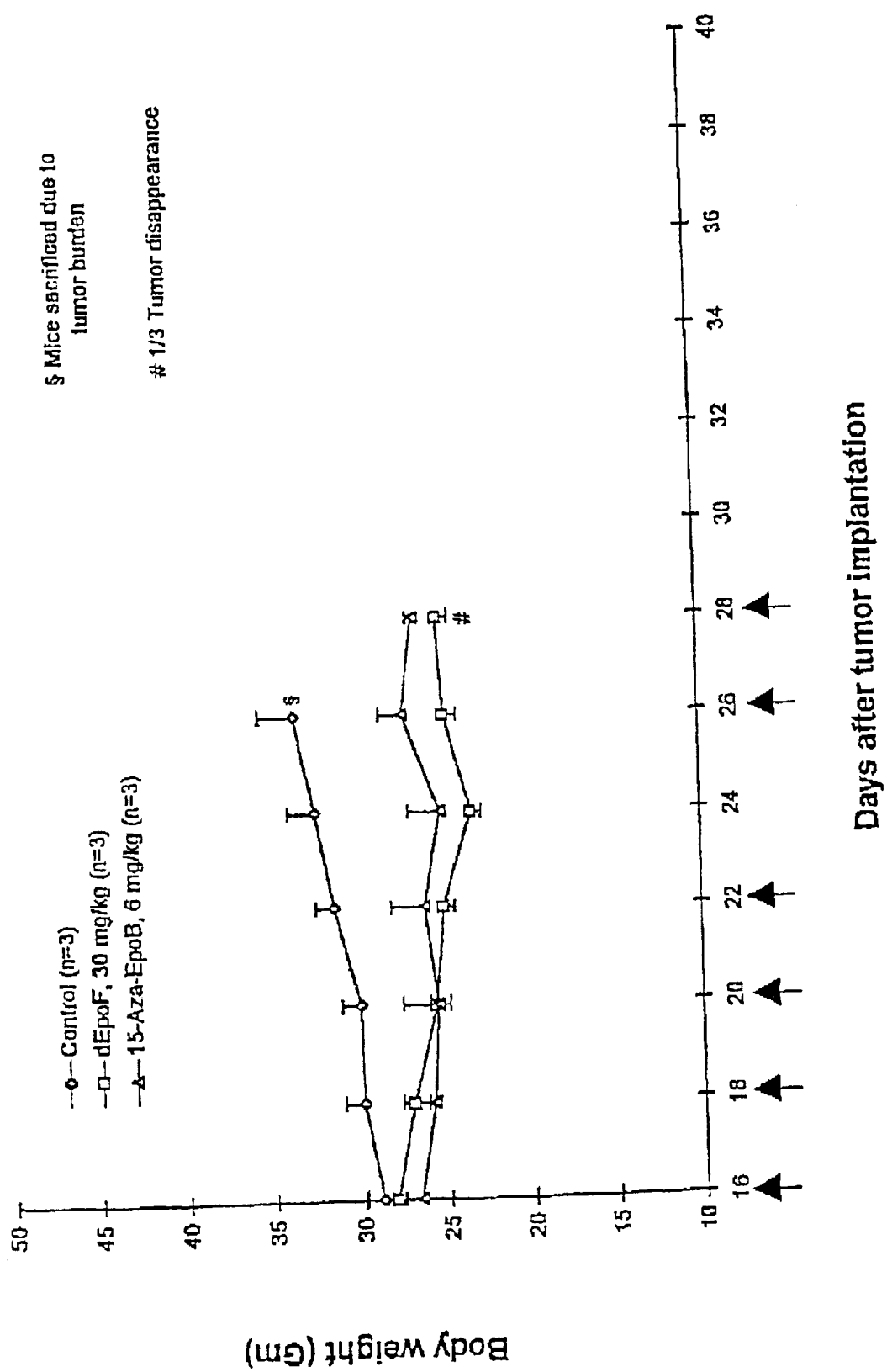
FIG. 39 depicts body weight in nude mice bearing CCRF-CEM tumor following 15-Aza-EpoB or dEpoF treatment (i.v. infusion 6 hr.).
Figure 40:
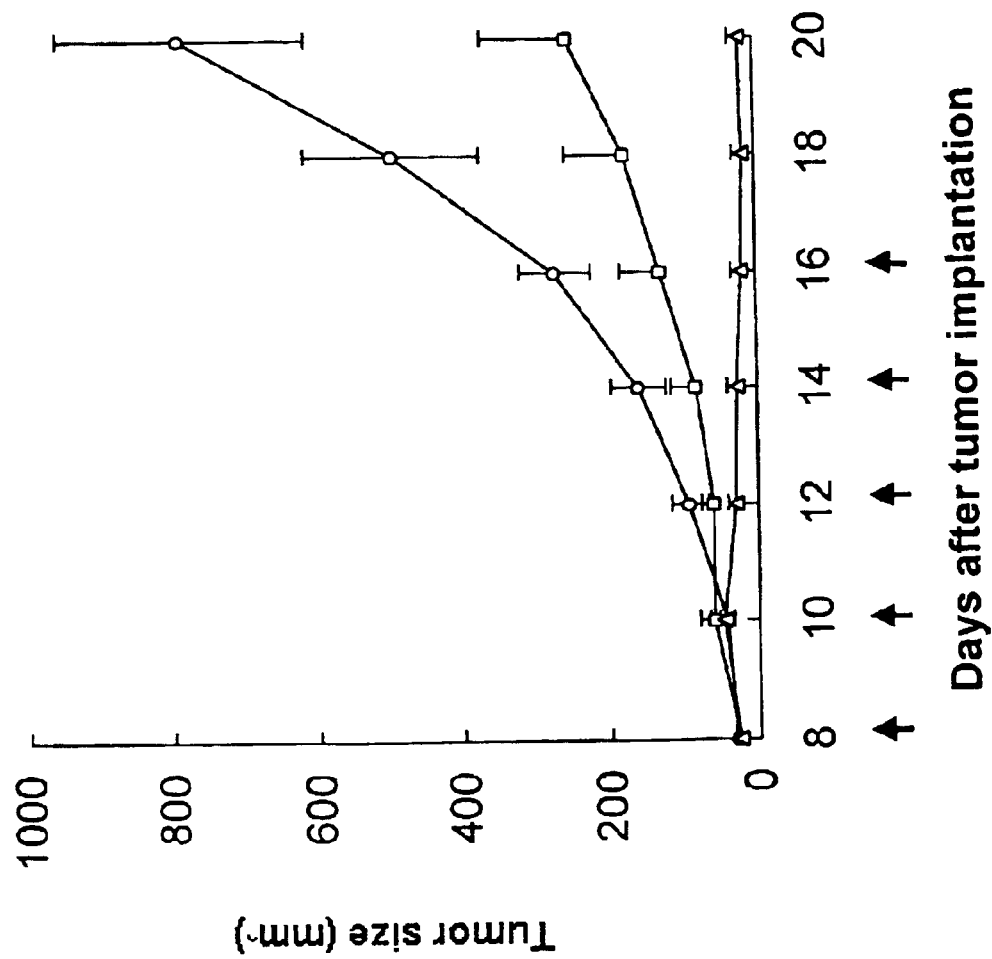
FIG. 40 depicts tumor size in nude mice bearing MX-1 following dEpoF (i.v. 6 hr. infusion (Q2D×5)). MX-1 tumor tissue (50 mg/mouse) was implanted s.c. into nude mice on day 0. The doses of 15 mg/kg (□, n=4) and 30 mg/kg (Δ, n=5) of dEpoF were given via 6 hr i.v. infusion on days 8, 10, 12, 14, and 16. For the 30 mg/kg group, three out of five mice were tumor free on days 16, 18, and 20, respectively. The vertical bars indicate mean tumor size in $mm^3 \pm S.E.$

Therapeutic Effects of dEpoF Against Human Mammary Adenocarcinoma M-1 Xenografts We showed earlier that both dEpoB and paxlitaxel had curative effects against M-1 xenographs (19, 27, and 28). We have now conducted a similar experiment with dEpoF. MX-1 tumor-bearing nude mice were treated at two dose levels of dEpoF (FIG. 39). At 15 mg/kg Q2D×5 6 hr-i.v. infusion, tumor growth was partially suppressed. At a higher dose of dEpoF (30 mg.kg, Q2D×5, 6 hr-i.v. infusion), the Mx-1 tumor was gradually shrunken, with tumor disappearance in three out of five mice.

Figure 38:
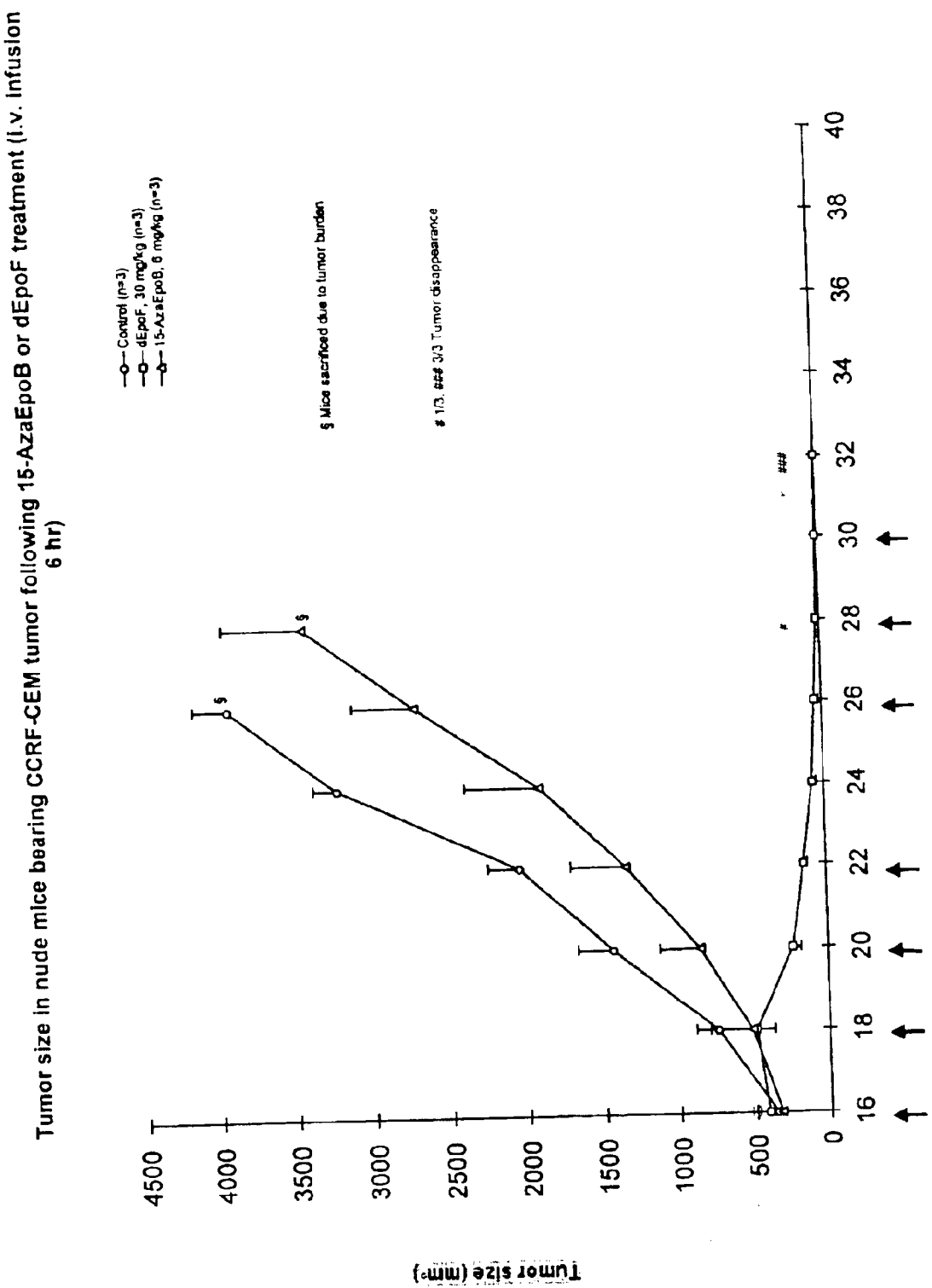
FIG. 38 depicts tumor size in nude mice bearing CCRF-CEM tumor following 15-Aza-EpoB or dEpoF treatment (i.v. infusion 6 hr.).

Comparison of Therapeutic Effect of dEpoF and 15-azaEpoB Against CCRF-CEM Xenographs Nude mice bearing well established CCRF-CEM tumor xenografts (average tumor size about 400 mm³) were treated with 30 mg/kg of dEpoB or with 6 mg/kg of 15-azaEpoB, 6 hr-i.v. infusion Q2D×6 as shown in FIG. 37. Moderate suppression of tumor growth by 15-azaEpoB was observed. However, dEpoF shrank tumor gradually and on day 28 (the 6$^{th}$ dose) one of three mice was tumor free and the other two mice had only residual tumors (FIG. 38). In this experiment, the control mice continued to gain body-weight whereas dEpoF or 15-azaEpoB treated mice reduced body-weight about 10% on day 28 (FIG. 39).

Figure 41:
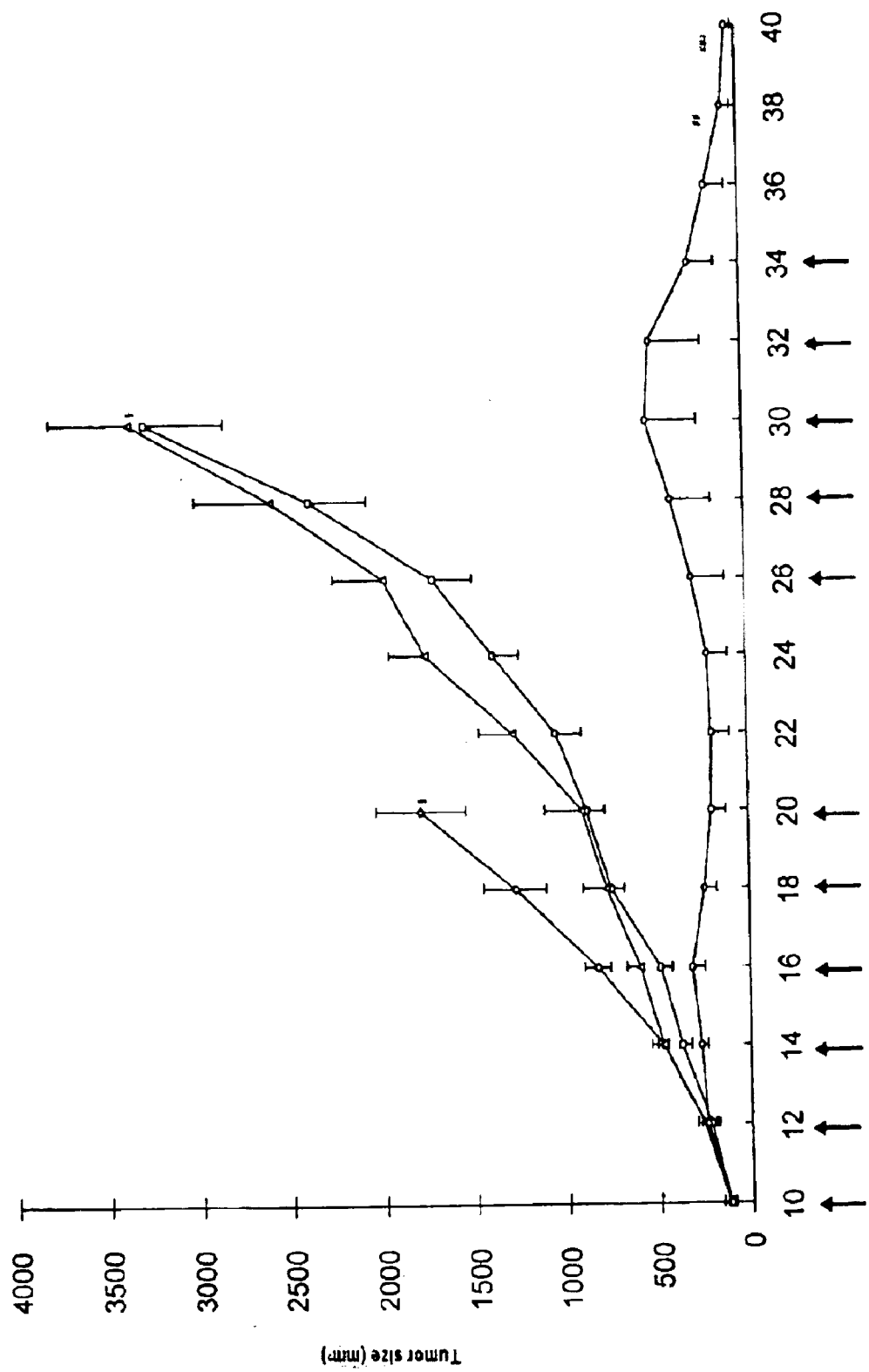
FIG. 41 depicts the therapeutic effect of dEpoB and aza-EpoB against MX-1 xenografts in nude mice. MX-1 tumor tissue (50 mg/mouse) was implanted s.c. onto nude mice on day 0. The control mice (◇, n=5) received vehicle only. Aza-EpoB 4 mg/kg (, n=5), 6 mg/kg (, n=5) and dEpoB 30 mg/kg (O, n=5) were given via 6 hr i.v. infusion Q2D×6 on day 10, 12, 14, 16, 18, and 20. On day 10, the average tumor size was 120 $mm^3$. The second cycle of treatments (Q2D×3) with aza-EpoB (4 mg/kg) and aza-EpoB (6 mg/kg) started on day 26, 28, and 30. On day 30, the mice on these two groups were sacrificed due to excessive tumor burden. The second cycle of treatments for dEpoB (30 mg/kg, Q2D×5) started on day 26 and ended on day 34. On day 22, one out of five mice in the group treated with aza-EpoB (6 mg/kg) died of toxicity. The three out of five mice treated with dEpoB exhibited tumor disappearance on days 32, 38, and 40. In aza-EpoB (6 mg/kg) treated group, one out of five mice died of toxicity on day 22.
Figure 42:
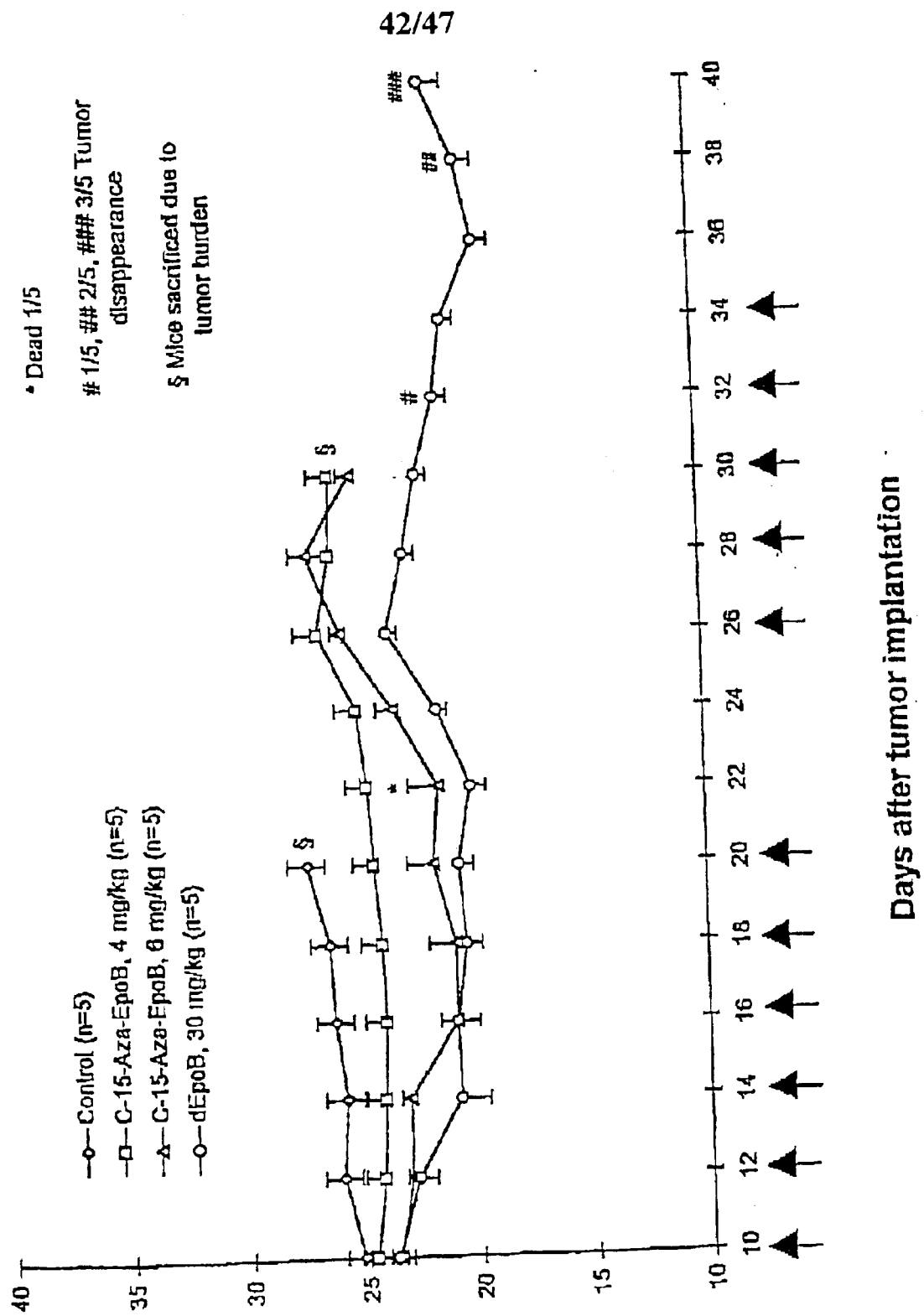
FIG. 42 depicts body weight in nude mice bearing MX-1 tumor following C-15-Aza-EpoB or dEpoB treatment.

Comparison of Therapeutic Effect of dEpoB and 15Aza-EpoB Against MX-1 Xenografts At about 100 mm³ MX-1 tumor size, treatment with azaEpoB 4 mg/kg or 6 mg/kg Q2D×6 (day 10–20) led to slowed down tumor growth but without tumor shrinkage. Additional treatment with Q2D×3 (day 26–30) yielded continued tumor progression and the animals were scarified due to tumor burden (FIG. 41). Little change in body-weight following azaEpoB 4 mg/kg doses but 6 mg/kg doses caused body-weight decreases of about 3 gm on day 18, and one out of five mice died of toxicity on day 22 (FIG. 42). At about 120 mm³ MX-1 tumor size, treatment with dEpoB 30 mg/kg Q2D×6 (day 10–20) showed initial slow down in tumor growth, followed by tumor shrinkage (FIG. 41). Continued treatment with dEpoB Q2D×5 (day 26–34) led to ⅕ tumor disappearance on day 22, ⅖ tumor disappearance on day 38 and ⅗ tumor disappearance on day 40. It is noted that tumors continued to shrink even on six days after the last dose of dEpoB (FIG. 41).

Body-weight decreased about 3.5 gm on day 22 after dEpoB 30 mg/kg Q2D (day 10–20), but recovered to the near control body-weight on day 26. When the second cycle of treatment started Q2D×5 (day 26–34), the body-weight dropped about 4.1 gm on day 36 and then gained about 2 gm body-weight during day 36–40, when tumor disappearance occurred. (FIGS. 41 & 42).

Comparison of Therapeutic Effect of dEpoB and Paclitaxel Against Various Human Tumor Xenografts Therapeutic effect of dEpoB and paclitaxel has been compared in nude mice bearing human tumor xenograft. In all, eight solid tumors [lung carcinoma (A549), mammary carcinoma (MX-1), colon adenocarcinoma (HT-29), colon carcinoma (HCT-116), prostate adenocarcinoma PC-3), ovary adenocarcinomas (SK-OV-3) and UL3-C)] and five leukemias (T-cell acute lymphoblastic leukemia (CCRF-CEM) and its sublines resistant to paclitaxel (CCRF-CEM/taxol), 57-fold resistance; resistant to vinblastine (CCRF-CEM/VBL$_{100}$), 761-fold resistance; chronic myeloblastic leukemia (K562) and promyelocytic leukemia (HL-60) had been used for subcutaneous implantation (Table 5). dEpoB 30–40 mg/kg and paclitaxel (Taxol®) 15–24 mg/kg both in Cremophor: EtOH (1:1) formulations were used for 6-hr i.v. infusion with the treatment schedules as indicated in Table 5. These doses of treatment led to 10–20% body-weight decrease without lethality. Depending on the tumor type, treatment started on day 10 to day 21 when subcutaneous tumor size reached 35–200 mm³, except otherwise indicated. Tumor size and body-weight were recorded every other day (Q2D) and, for humane reasons, the animals were sacrificed when tumor size reached ≧10% of body-weight. Each group, including untreated control, consisted of 3–5 animals unless otherwise indicated. The lowest average tumor size achieved during the course of treatment for the ratio of the treated group vs the untreated control group was given in Table 5. The proportion of mice in the treated group with tumor disappearance was also given in Table 5. For all three drug-resistant tumors tested (MCF-7/Adr, CCRF-CEM/taxol and CCRF-CEM/VBL$_{100}$) and for leukemia K562, dEpoB showed much greater (>>) or very much greater therapeutic effect (>>>) than taxol. For prostrate PC-3 and ovarian SK-OV-3, taxol showed much greater effect (>>) than dEpoB. Interestingly, for another ovarian tumor, UL3-C, dEpoB gave equal or slightly greater effect (≧) than taxol. Other tumors which dEpoB gave equal or slightly greater effect (≧) than taxol were: lung A549, mammary MX-1, CCRF-CEM; whereas those taxol gave equal or slightly greater effect than dEpoB were: colon HT-29, colon HCT-116 and leukemia HL-60. For mammary MCF-7/Adr, colon HT-29, prostrate PC-3 and ovarian UL3-C, tumors were shrunken by dEpoB or taxol treatment but none achieved tumor disappearance. For mammary MX-1 and leukemia CCRF-CEM tumor, both dEpoB and taxol achieved total tumor disappearance in all or most animals tested. For leukemias CCRF-CEM/taxol, CCRF-CEM/VBL$_{100}$ and K562, taxol slowed down tumor growth but did not yield tumor shrinkage nor tumor disappearance, whereas dEpoB yielded total tumor disappearance in all animals treated.

Comparison of Therapeutic Effect Among dEpoB, dEpoF, EpoB, azaEpoB or with Several Established Anticancer Agents in Animal Models Relative efficacy of chemotherapeutic effect of dEpoB were compared with paclitaxel (Taxol®), Adriamycin (ADR), vinblastine (VBL), camptothecin, Camptosar (CPT-11), etoposide (VP-16), dEpoF, , EpoB, or 15 aza-EpoB are summarized for 21 experiments using one murine tumor, eight human solid tumors and five human leukemias with different routes of administration (i.p., i.v., and i.v.-infusion) and different schedules of treatment (Table 6).

The comparisons were carried out at or near maximal tolerated doses with 10–20% decreases in body-weight but without lethality. Overall, dEpoB showed the broadest and most efficacious therapeutic effects, followed by taxol, and then followed by other cancer chemotherapeutic agents tested. dEpoF has a similar therapeutic effect as dEpoB but had not yet been compared directly with other established cancer chemotherapeutic agents. EpoB and azaEpoB showed moderate antitumor effect but appeared to have narrow therapeutic windows as indicated by the death at moderate decreases in body-weight (Ref. 19, tables 3 and 4 and this report FIGS. 38 and 39).

More detailed comparison between dEpoB and Taxol has been given in Table 5 and FIG. 37; comparison among dEpoB, dEpoF, taxol, CPT-11 for HCT-116 tumor in FIG. 35; among dEpoB, taxol, Adriamycin and vinblastine for K562 leukemia in FIG. 36; between 15-azaEpoB and dEpoF for K562 leukemia in FIGS. 38 and 39; and between 15-azaEpoB and dEpoB for MX-1 tumor in FIGS. 41 and 42.

Time-course of Development of Drug Resistance

Repeated exposure of human lung carcinoma A549 cells to sublethal concentrations of antitumor agents may lead to the development of drug resistance. In the present studies, exposure to VBL for 14.3 months led to 4848-fold resistance to VBL, to paclitaxel for 21.3 months led to 2858-fold resistance to paclitaxel, to adriamycin for 21.3 months led to 16.3-fold resistance to paclitaxel, and to dEpoB for 21.4 months led to 21-fold resistance to dEpoB (FIG. 8). Thus, comparing with other antitumor agents, dEpoB is not only more efficacious against drug-resistant tumor cells (Table 4) but also more difficult to develop drug resistance upon prolonged exposure to dEpoB.

Stability of dEpoB in Plasma

Figure 44:
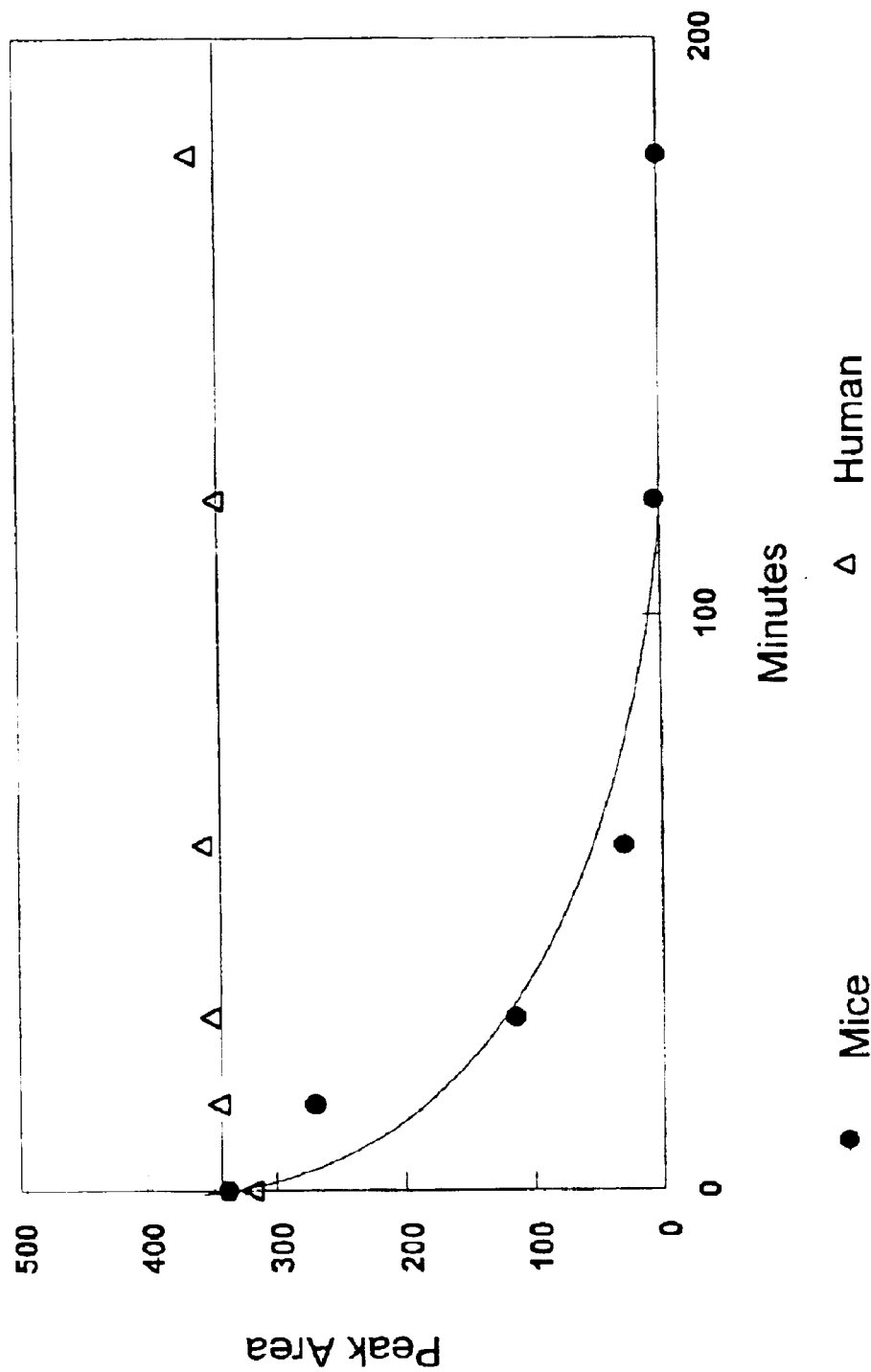
FIG. 44 depicts stability in plasma (mouse vs. human).

Despite of the remarkable therapeutic effect of dEpoB against various human tumor xenografts in nude mice, dEpoB showed relatively short half-life in nude mice plasma in vitro with $t_{1/2}$ about 20 min. (FIG. 44). Surprisingly, HPLC results indicated that dEpoB is stable in human plasma in vitro for a period of over 3 hrs. (FIG. 44).

Toxicity and Pharmacokinetics of dEpoB in Beagle Dogs dEpoB at doses of 2, 6, 12 and 20 mg/kg, were given to male beagle dogs (11.2–14 kg) via i.v. infusion. The infusion volume was 1 ml/kg for 10 min using the Harvard PHD2000 pump (Harvard Apparatus). dEpoB was formulated in Cremophor 3%, ethanol 3%, propyleneglycol 40% and 5% glucose 54%. The animal was pretreated at −30 min with Benadryl 5 mg/kg, i.v.; cimetidine 5 mg/kg i.m.; and dexamethasone 1 mg/kg, i.e. to minimize allergic reactions due to Cremophor administration.

No significant toxicity was observed at 2 or 6 mg/kg (40 and 120 mg/m²) of dEpoB. At 12 mg/kg. (240/m²) there were moderate diarrhea (without blood) and a drop in body-weight (1.3 kg) on day 3. The body-weight slowly recovered in 2–3 weeks. The white blood cell (WBC) counts slightly decreased (13%) which recovered in 9 days. No significant changes in platlet counts and in alanine aminotransferase (ALT) or aspartate aminotransferase (AST) were observed. No significant histopathologic lesions were found in 28 organs or tissues examined including: heart, lung, kidney, spleen, small and large intestine, liver, muscle, bone marrow and lymph nodes. When the dose of dEpoB was further escalated to 20 mg/kg (400/m²) i.v., there were severe bloody diarrhea and dehydration on day 2 and the body-weight loss of 0.9 kg on day 2 and 3.6 kg on day 3; and WBC dropped to 0.6 k/μl on day 3, accompanied by 3–6 fold increase in ALT and AST by day 4. The animal showed general weakness, loss of appetite, became less active, and eventually expired on day 4. There was a gross abnormality (reddish discoloration) of the intestinal mucosa from duodenum to the ileum. The small intestines contained blood tinged mucinous materials. Histopathological examination on bone marrow showed reduction in cellularity. Necrosis of intestinal mucosal epithelium with crypt cells most severely affected at this lethal dose.

Figure 45:
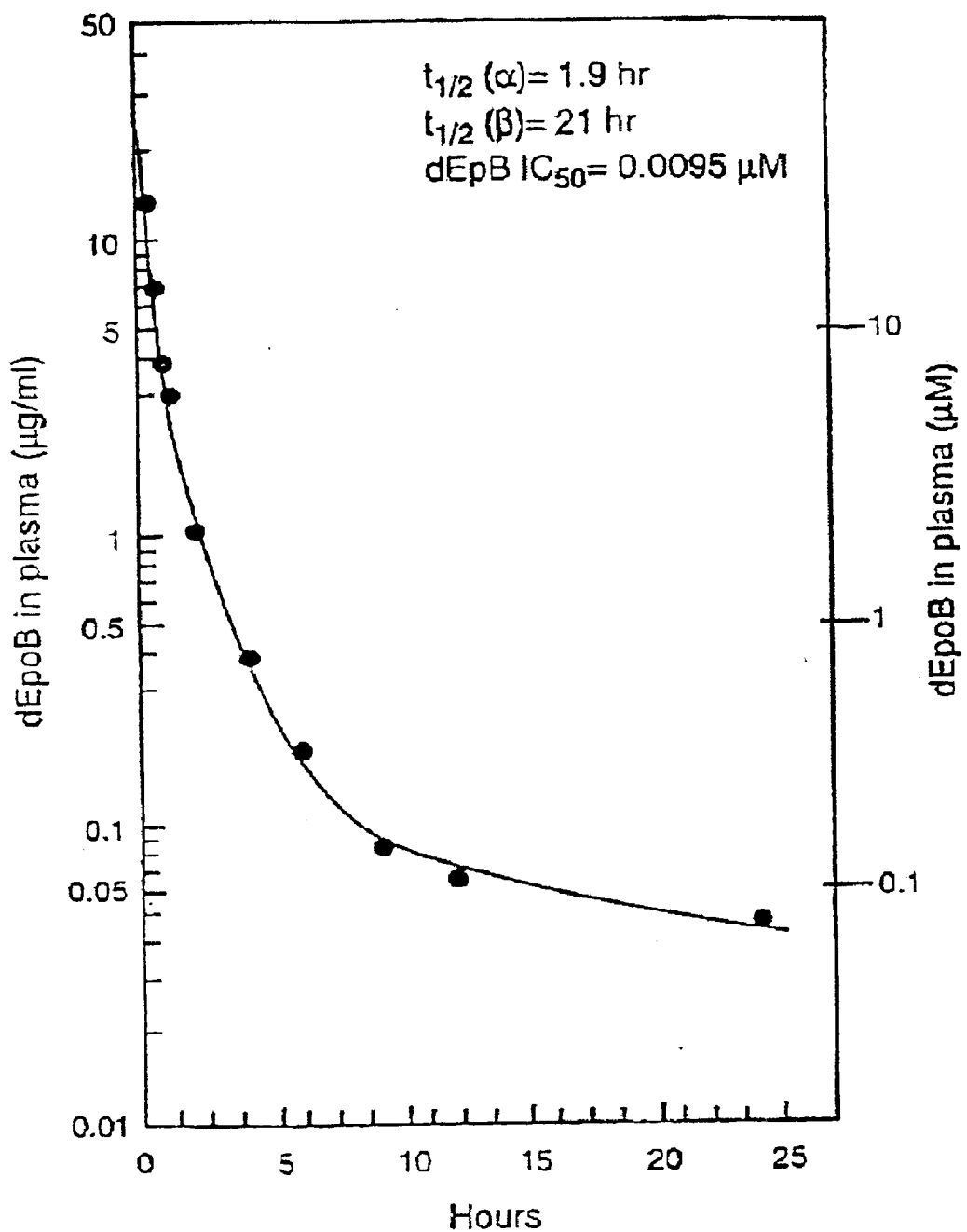
FIG. 45 depicts pharmacokinetics of dEpoB in dog following 6 mg/kg, i.v. infusion (10 minutes).

Pharmacokinetic studies were also carried out for of dEpoB in beagle dogs at 6 mg/kg (120 mg/m² body surface), with 10-min i.v. infusion. Serial blood samples were collected in 5 ml heparinized tubes intermittently from -15 min to 24 hours. Plasma concentrations of dEpoB were determined by HPLC as described in methods. The α-phase of $t_{1/2}$ was 1.9 hrs and the β-phase, 21 hrs (FIG. 45). At the end of 24-hr collection, dEpoB plasma concentration of 0.045 μg/ml or 0.092 μM was considerably higher than the $IC_{50}$ value of dEpoB, 0.0095 μM, for inhibiting CCRF-CEM cell growth in tissue culture.

In summary, despite similar microtubule stabilization effects, epothiolones (e.g., EpoA, EpoB and dEpoB) are distinct from taxanes (e.g., paclitaxel) in terms of their natural source, chemical structure, water solubility, Pgp-MDR profile, tolerance to structural modifications, difficulty in total synthesis, and anticancer spectrum. Results cumulated so far indicate that dEpoB has more favorable pharmacological features than paclitaxel both in vitro and in vivo, especially in terms of efficacy against drug-resistant cells or tumors (19, 29, Table 4).

EpoB, although more potent than EpoA, paclitaxel, and dEpoB, was shown to be highly toxic in nude mice and showed little therapeutic effect in mice bearing human tumor xenografts even at highly toxic doses when compared with dEpoB or paclitaxel (19). However, paclitaxel is a good substrate for Pgp-MDR and is ineffective against multiple-drug resistant tumors in which dEpoB achieved curative effect (19, 20, 28 and FIGS. 35 and 36).

In addition to our reports on the therapeutic effect of dEpoB (NSC-703147) against human tumor xenografts in nude mice, in vivo effects of EpoB (30, 31) and 15-aza-EpoB (BMS-247550) (32) have appeared. We now compare dEpoB, with another compound (dEpoF) as well as 15-aza-EpoB, and taxol® in the same experimental settings. The present results indicate that dEpoF and dEpoB have similar chemotherapeutic effects and are curative against human K562 tumor xenografts in nude mice (FIGS. 36–39). The therapeutic effect of dEpoB and dEpoF were superior than taxol® (FIGS. 36, and 37) or 15-aza-EpoB (FIGS. 38 and 39, 41 and 42), and some currently widely used cancer therapeutic agents such as dexombicin, vinblastine or CPT-11 (FIG. 35). The high efficacy of dEpoB against a broad spectrum of human tumor xenograft is apparent despite the fact that dEpoB has short half-life ($t_{1/2}$=15–20 min) in nude mice plasma in vitro (FIG. 44). The six-hour i.v. infusion of dEpoB to nude mice may have compensated the short half-life situations. The long half-life of dEpoB in human plasma (FIG. 44) and in beagle dog (FIG. 45) may reduce the necessity for i.v. infusion in humans and in dogs.

Essential features of useful cancer therapeutic agent involve not only high efficiency against cancer but also low toxicity toward the host, especially toward vital organs or functions [i.e. wide therapeutic window or high therapeutic index ($LD_{50}/ED_{50}$)]. One important toxicological finding is that dEpoF and dEpoB may render 23–29% drop in body-weight in nude mice during treatment without causing lethality whereas only 14–20% drop in body-weight due to EpoB or azaEpoB led to lethality. Furthermore complete tumor disappearances were achieved for dEpoB and dEpoF in the absence of lethality (FIGS. 36–42); whereas EpoB (19) or azaEpoB (FIGS. 41–42) caused lethality when only marginal therapeutic effects were achieved.

Materials and Methods

Chemicals. dEpoB (NSC-703147) (10, 14), dEpoF (21) and aza EpoB (BMS 247550) (22) used in this study were obtained in our Bio-Organic Chemistry Laboratory through total synthesis as described. For in vitro studies, paclitaxel (Taxol®), etoposide (VP-16), teniposide (VM-26) camptothecin (CPT), actinomycin D (AD) and vinblastine sulfate (VBL) were purchased from Sigma. All stock solutions of the above (except VBL in saline) were prepared by using dimethyl sulfoxide (DMSO) solvent and were further diluted to desired concentrations for experimental use. The final concentration of DMSO in tissue culture was 0.25% (vol/vol) or less to avoid solvent cytotoxicty. For in vivo studies, dEpoB, dEpoF and 15-Aza-EpoB were dissolved in Cremophor/EtOH (1:1) vehicle and then diluted with saline for i.v. infusion, for six hours. Cremophor EL was purchased from Sigma. Paclitaxel in Cremophor/EtOH formulation was obtained commercially from clinical preparation (Bristol-Myers Squibb). Solubility in water for paclitaxel, dEpoB and dEpoF was approximately 0.6 mg/ml, 10 mg/ml and 25 mg/ml, respectively. Vinblastine sulfate (VBL, Velban; Eli Lilly), etoposide (VP-16, Vepisid, Bristol-Myers Squibb), Camptosar (Irinotecan or CPT-11; pharmacia & Upjohn) and adriamycin (DX or Adr, Doxorubiane-HCl; Astra Pharmaceutical) were used in the manufacture's formulation and diluted with saline.

Tumor and Cell Line

Figure 43:
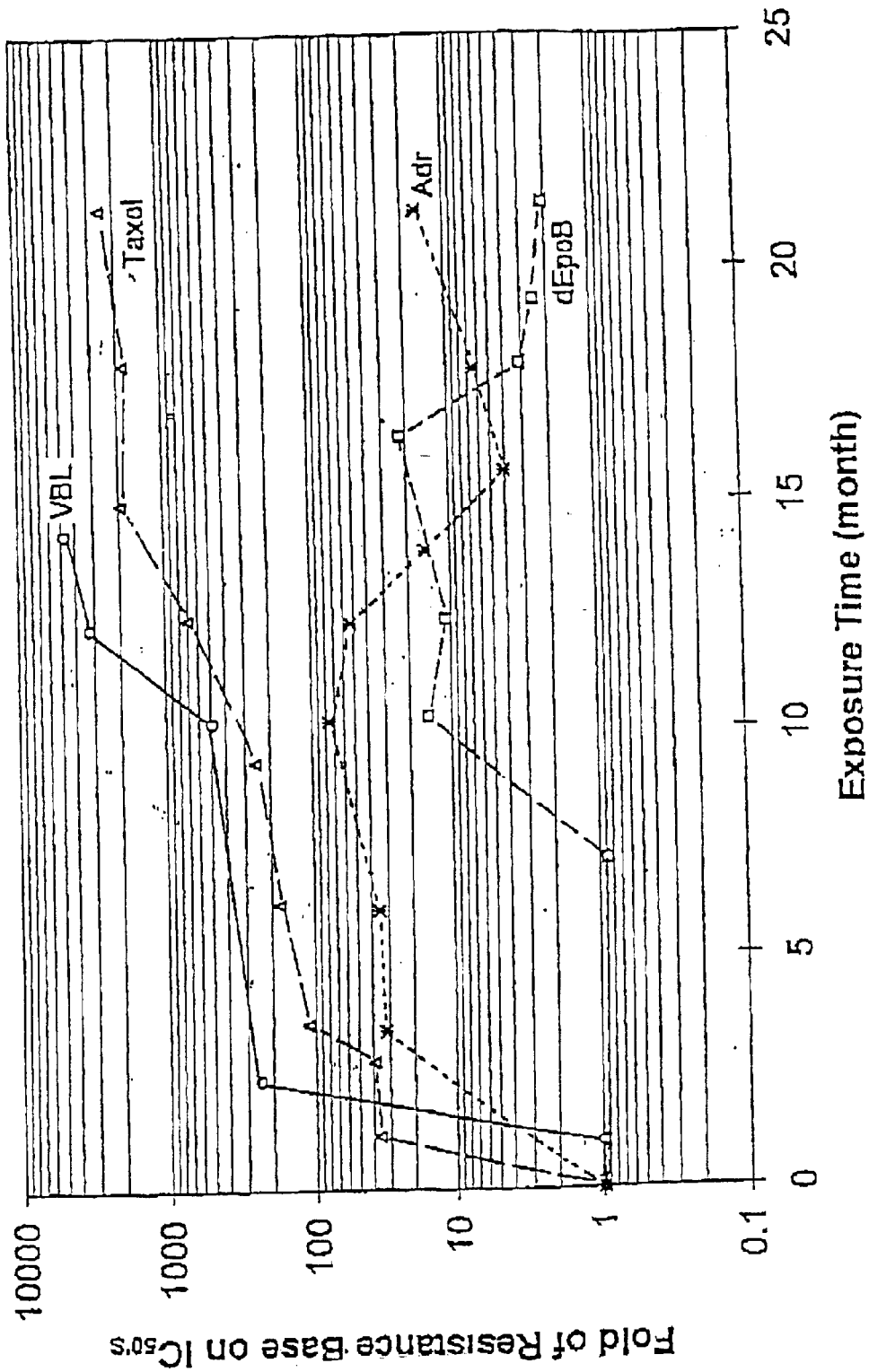
FIG. 43 depicts resistance to human lung carcinoma A549.

The CCRF-CEM human T cells acute lymphoblastic leukemic cells, its teniposide-resistant subline (CCRF-CEM/VM₁) and vinblastine-resistant subline (CCRF-CEM/VBL₁₀₀) were obtained from W. T. Beck (University of Illinois, Chicago, Ill.). These sublines were exposed to increasing sublethal concentrations ($IC_{50}$–$IC_{90}$) of vinblastine for 16 months, paclitaxel for 12 months, and teniposide for 12 months respectively (designated CCRF-CEM/VBL₁₀₀₀, CCRF-CEM/taxol, and CCRF-CEM/VM₂, respectively). The fresh medium containing each drug was replenished every 7–14 days. The resistant cells lines exhibited 4308-fold resistance to vinblastine ($IC_{50}$:0.9743 μM), 282-fold resistance to paclitaxel ($IC_{50}$:0.339 μM), and 69-fold resistant to VP-16 ($IC_{50}$:19.8 μM), respectively, when compared with the original CCRF-CEM cells at the beginning of the experiment (see Table 1). Similar procedure was used for the time-course of the development of drug-resistance to VBL, taxol, Adr and dEpoB in A549 human lung carcinoma cells (see FIG. 43). In each case, the drug-exposed cells were resuspended in fresh media for a minimum of 4 days before the experiments for the cell-growth inhibition was carried out. Ovarian adenocarcinoma UL3-C, UL3-B/taxol, hamster lung fibroblasts and its sublines DC-3F, DC-3F/ADII and DC-3F/ADX were obtained from the cell bank of this institution.

The following human cancer cells were obtained from American Type Culture Collection (ATCC, Rockville, Md.): mammary carcinoma, MX-1; mammary adenocarcinoma, MCF-7; ovarian adenocarcinoma, SK-OV-3; lung carcinoma, A549; colon adenocarcinoma, HT-29; colon carcinoma, HCT-116; prostate adenocarcinoma, PC-3; chronic myeloblastic leukemia, K562; and promyelocytic leukemia, HL-60.

Animals

Athymic nude mice bearing the nu/nu gene were used for all human tumor xenografts. Outbred, Swiss-background mice were obtained from Charles River Laboratories. Male mice 8 weeks or older weighing 22 g and up were used for most experiments. The drug was administered via the tail vein for 6 hr.-i.v. infusion. Each individual mouse was confined in a perforated Falcon polypropylene tube restrainer for drug administration. Tumor volume was assessed by measuring length×width×height (or width) using a caliper. The programmable Harvard PHD2000 syringe pump (Harvard Apparatus) with multi-track was used for i.v. infusion. Typically, the infusion volume for each drug in Cremophor/EtOH (1:1) was 100 $\mu$l+2.0 ml of saline for a 6-hr infusion. All animal studies were conducted in accordance with the guidelines of the National Institutes of Health "Guide for the Care and Use of Animals" and the protocol approved by the Memorial Sloan-Kettering Cancer Center's Institutional Animal Care and Use Committee. In keeping with the policy of this committee for the humane treatment of tumor-bearing animals, mice were euthanized when tumors reached $\geq$10% of their total body weight.

Cytoxicity Assays

The cells were cultured at an initial density of 2–5×10$^4$ cells per ml. They were maintained in a 5% $CO_2$-humidified atmosphere at 37° C. in RPMI mediun 1640 (GIBCO/BRL) containing penicillin (100 units/ml), streptomycin (100 $\mu$g/ml) (GIBCO/BRL), and 5% heat-inactivated fetal bovine serum. For solid tumor cells growing in a monolayer (such as MCF-7/Adr), cytotoxicitiy of the drug was determined in 96-well microtiter plates by using the sulforhodamine B method as described by Skehan et al (23) for measuring the cellular protein content. For cells that were grown in suspension (such as CCRF-CEM and its sublines), cytotoxicitiy was measured by using the 2,-3-bis(2-methoxy-4-nitro-5-sulfophenyl)-5carboxanilide)-2H terazodium hydroxide (XTT)-microculture tetrazonium method (24) in duplicate in 96-well microtiter plates. For both methods, the absorbance of each well was measured with a microplate reader (EL-340, Bio-Tek, Burlington, Vt.). Each run entailed six or seven concentrations of the tested drugs. Dose-effect relationship data were analyzed with the median-effect plot (25) by using a previously described computer program (26).

HPLC Analysis

Human blood plasma or nude mice plasma (300 $\mu$l) containing dEpoB (0.05–20 $\mu$g/ml) was added 30 $\mu$l of methanol and mixed for 2 min and then added 300 $\mu$l of methanol. The centrifuge supernatant was used for high performance liquid chromatography (HPLC). Nova-pak C18 column (15 cm) was used, with 50% acetonitrile/water with 0.8% triethylamine and 0.2% phosphoric acid as mobile phase. UV absorbance at 250 nm was measured.

Development of Drug Resistance in Vitro

Human lung carcinoma A549 cells were repeatedly exposed to $IC_{50}$–$IC_{90}$ of anticancer agents (dEpoB, paclitaxel, vinblastine or Adriamycin) during 14.3–21.4 month period. Every several weeks, cells were harvested for the dose-effect analysis to determine their folds of resistance (using SRB protein staining assay) based on comparing the $IC_{50}$ value with the $IC_{50}$ value of the untreated parent cells. Trypsinized/washed cells were used for propagating the cell lineage. Increasing drug concentration (1–2 fold of the new $IC_{50}$ concentrations) were added to the fresh culture medium containing drug weekly for continued exposure of cells to the drug.

Xenograft Studies

Human tumor cells (5×10$^6$) or tumor tissue (30–50 mg) were implanted s.c. flank in nu/nu mice (Charles River Laboratories, Wilmington, Mass.). When tumor grew to a specified size, treatment was started by every-other day×5 with 6 hr i.v.-infusion, unless otherwise indicated. Tumor volume was measured with calipers in three dimensions (length×width×height or width). Body-weight changes and lethality were monitored every other day.

The Following References are Cited Throughout Example 4

1. Gunasekera, S. P., Gunasekera, M., & Longley, R. E. (1990) *J. Org. Chem* 55, 4912–4915.
2. Haar, E. T., Kowalski, R. J., Hamel, E., Lin, C. M. Longley, R. E., Gunasekera, S. P., Rosenkranz, H. S., & Day, B. W. (1996) *Biochemiestry* 35, 243–250.
3. Lindel, T., Jensen, P. R. Fenical, W., Long, B. H., Casazza, A. M., Carboni, J., & Fairchild, C. R. *J. Am. Chem. Soc.* (1997) 119, 8744–8745.
4. Mooberry, S. L., Hernandez, T. G., Plubrukarn, A. & Davidson, B. S. (1999) *Cancer Res.* 59, 653–680.
5. Hoelfle, G., Bedorf, N., Steinmetz, H., Schumburg, D., Gerth, K. & Reichenbach, H. (1996) *Angew. Chem Int. Ed. Engl.* 35, 1567–1569.
6. Balog, A., Meng, D., Kamenecka, T., Bertinato, P., Su, D.-S., Sorensen, E. J. & Danishefsky, S. J. (1996) *Angew. Chem. Int. Ed. Engl.* 35, 2801–2803.
7. Su, D.-S., Meng, D., Bertinato, P., Balog, A., Soresen, E. J., Danishefsky, S. J., Zheng, Y.-H., Chou, T.-C., He, L. & Horwitz, S. B. (1997) *Angew. Chem. Int. Ed. Engl.* 36, 757–759.
8. Nicholaou, K. C., Winssinger, N., Pastor, J. A., Niniovic, S., Sarabia, F., He, Y., Vourloumis, D., Yang, Z., Li, T., Giannakakou, P. & Hamel, E. (1997) *Nature* (London) 387, 268–272.
9. Meng, D., Su, D-S., Balog, A., Bertinato, P., Sorensen, E. J., Danishefsky, S. J., Zheng, Y.-H., Chou, T.-C., He, L., & Horwitz, S. B. (1997) *J. Am. Chem. Soc.* 119, 2733–2734.
10. Meng, D., Bertinato, P., Balog, A., Su, D.-S., Kamenecka, T., Sorensen, E. J. & Danishefsky, S. J. (1997) *J. Am. Chem. Soc.* 119, 10073–10092.
11. Balog, A., Harris, C., Savin, K., Zhang, X.-G., Chou, T.-C. & Danishefsky, S. J. (1998)*Angew. Chem. Int. Ed. Engl.* 37, 2675–2678.
12. Bollag, D. M., McQuency, P. A., Zhu, J., Hensens, O., Koupal, L., Liesch, J., Goetz, M., Lazarides, E. & Woods, C. M. (1995) *Cancer Res.* 55, 2325–2333.
13. Su, D.-S., Balog, A., Meng, D., Bertinato, P., Danishefsky, S. J., Zheng, Y.-H., Chou, T.-C., He, L. & Horwitz, S. B. (1997)*Angew. Chem. Int. Ed. Engl.* 36, 2093–2096.
14. Kowalski, R. J., Giannakakou, P. & Hamel, E. (1997) *J. Biol. Chem.* 272, 2534–2541.
15. Nicolaou, K. C., Vourloumis, D., Li, T., Pastor, J., Winssinger, N., He, Y., Ninkovic, S. Sarabia, F., Vallberg, H., Roschangar, F., King, N. P., Finlay, M. R. V., Giannakakou, P., Verdier-Pinard, P. & Hamel, E. (1999) *Angew. Chem. Int. Ed. Engl.* 36, 2007–2103.

16. Chou, T.-C., Zhang, X.-G., Balog, A., Su, D. S., Meng., D., Savin, K., Bertino, J. R. & Danishefsky, S. J. (1998) *Proc. Natl. Acad. Sci. USA* 95, 9642–9647.

17. Balog, A., Harris, C., Savin, K. Zhang, X.-G., Chou, T.-C. & Danishefsky, S. J. (1998) *Angewante Chemie Int'l Ed. Engl.* 37:2675–2678.

18. Lee, C. B., Chou, T.-C., Zhang, X.-G., Wang, Z.-G., Kuduk, S. D., Chappell, M. D., Stachel, S. J. & Danishefsky, S. J. (2000) *J. Org. Chem.* 65, 6525–6533.

19. Stachel, S. J., Chappell, M. D., Lee, C. B. Danishefsky, S. J. Chou, T.-C., & Horwitz, S. B. (2000) *Org. Letters* 2:1637–1639.

20. Skehan, P., Storeng, R., Scudiero, D., Monks, A., McMahon, J., Vistica, D., Warren, J. T., Bokesch, H., Kenny, S. & Boyd, M. R. (1990) *J. Natl. Cancer Inst.* 82, 1107–1112.

21. Scudiero, D. A., Shoemaker, R. H., Paull, K. D. Monks, A., Tierney, S., Nofziger, T. H., Curreus, M. J., Scniff, D. & Boyd, M. R. (1988) *Cancer Res.* 46, 4827–4833.

22. Chou, T.-C., & Talalay, P. T., (1984) *Adv. Enzyme Regul.* 22-27–55.

23. Chou, T.-C. & Hayball, M. (1997) *CalcuSyn for Windows*, Multiple-drug doses effect analyzer and manual, Biosoft, Cambridge Place, Cambridge, UK.

24. Chou, T.-C., Zhang, X.-G. & Danishefsky, S. J. (1998) *Proc. Am. Assoc. Cancer Res.* 39, 163–164.

25. Chou, T.-C., Zhang, X,-G., Harris, C. R., Kuduk, S. D., Balog, A. Savin, K. & Danishefsky, S. J. (1998) *Proc. Nalt. Acad. Sci. USA* 95, 15798–15802.

26. Chappell M. D., Stachel S. J., Lee C.-B., & Danishefsky, S. J. (2000) *Org. Letters*, 2, 1633–1636.

27. Altmann, K.-H., Wartmann, K. & O'Reilly, T. (2000) *Biochemica et Biophysica Acta* 1479, M79–91.

28. Wartmann, M., Muller, M., Woods-Cook, K., Mett, H., Altman, K.-H., Fabbro, D., O'Reilly, F. (1998) *Proc. Am. Assoc. Cancer Res.*, 39, 163. (Abs.)

29. Botzilleri, R. M., Zheng, X., Schmidt, R. J., Johnson, J. A. Kim, S-H., DiMarco, J. D., Fairchild, C. R. Gougoutas, J. Z., Lee, F. Y. F., Long, B. H., & Vite, G. D. (2000) *J. Am. Chem. Soc.* 122, 8890–8897.

TABLE 4

Comparison of potency of dEpoB, dEpoF, 15-aza-EpoB and paclitaxel (Taxol ®) against various tumor cell growth in vitro

| Tumor Cell Lines | dEpoB | dEpoF ($IC_{50}$ in $\mu M$)[a] | 15-aza-EpoB | Paclitaxel | Others | |
|---|---|---|---|---|---|---|
| Human T-cell Acute Lymphocytic Leukemia[b] | | | | | | |
| | | | | | Vinblastine | 0.0063 |
| CCRF-CEM | 0.0095 | 0.0027 | 0.0021 | 0.0021 | VP-16 | 0.290 |
| CCRF-CEM/VBL$_{100}$ | 0.017$_{[1.8X]}$[c] | 0.047$_{[17.4X]}$ | 2.99$_{[1423X]}$ | 4.140$_{[1971X]}$ | Vinblastine | 0.332$_{[527X]}$ |
| CCRF-CEM/VM$_1$ | 0.014$_{[1.5X]}$ | 0.0049$_{[1.8X]}$ | 0.039$_{[118.6X]}$ | 0.0066$_{[3.18X]}$ | VP-16 | 3.44$_{[117X]}$ |
| CCRF-CEM/taxol | 0.0162$_{[1.7X]}$ | 0.0053$_{[2.0X]}$ | 0.171$_{[81.4X]}$ | 0.120$_{[57X]}$ | | |
| Hamster Long Fibroblasts[b] | | | | | | |
| DC-3F | 0.0025 | 0.0037 | 0.0087 | 0.0135 | Actinomycin D | |
| DC-3F/ADII | 0.0091$_{[2.8X]}$ | 0.0181$_{[4.9X]}$ | 0.288$_{[33.1X]}$ | 0.583$_{[43.2X]}$ | | 0.00031 |
| DC-3F/ADX | 0.0484$_{[19.4X]}$ | 0.0787$_{[21.3X]}$ | 2.380$_{[274X]}$ | 20.19$_{[1496x]}$ | | 0.0322$_{[10.4X]}$ |
| | | | | | | 0.4646$_{[1499X]}$ |
| Human Promyelocytic Leukemia | | | | | | |
| HL-60 | 0.0031 | 0.0007 | 0.0025 | 0.0011 | | |
| Human Chronic Myeloblastic Leukemia[b] | | | | | | |
| K562 | 0.0036 | 0.0021 | 0.060 | 0.0029 | | |
| Human Prostate Adenocarcinoma | | | | | | |
| PC-3 | 0.0209[d] | 0.0119 | 0.042 | 0.0280[d] | | |
| Human Colon Adenocarcinoma | | | | | | |
| HT-29 | 0.0048[d] | 0.0014 | 0.0032 | 0.0016[d] | | |
| Human Mammory Adenocarcinoma | | | | | | Adriamycin | 0.090 |
| MCF-7 | | | | | Vinblastine | 0.0094 |
| MCF-7/Adr | 0.0038 | 0.010 | 0.0043 | 0.0024 | Adriamycin | 0.316$_{[3.5X]}$ |
| | 0.0133$_{[3.5X]}$ | 0.0186$_{[1.9X]}$ | 0.0118$_{[2.7X]}$ | 0.0135$_{[5.6X]}$ | Vinblastine | 0.025$_{[76.6X]}$ |
| Human Mammary Carcinoma[b] | | | | | | |
| MX-1 | 0.0221 | 0.0042 | 0.0024 | 0.0394 | EpoB | 0.00184 |
| Human Ovary Adenocarcinoma | | | | | | |
| SK-0V-3 | 0.0035[d] | 0.0051 | 0.016 | 0.0038[d] | EpoB | 0.0016 |
| UL-3-C | | | | | Vinblastine | 0.00037 |
| | 0.0021 | 0.0048 | 0.0012 | 0.0015 | EpoB | 0.00058 |

TABLE 4-continued

Comparison of potency of dEpoB, dEpoF, 15-aza-EpoB and paclitaxel (Taxol ®) against various tumor cell growth in vitro

| Tumor Cell Lines | dEpoB | dEpoF ($IC_{50}$ in $\mu M$)[a] | 15-aza-EpoB | Paclitaxel | Others | |
|---|---|---|---|---|---|---|
| UL-3-B/Taxol | $0.0070_{[3.3X]}$ | $0.0067_{[1.4X]}$ | $0.015_{[12.5]}$ | $0.0134_{[8.9X]}$ | Vinblastine<br>EpoB | $0.00310_{[8.4X]}$<br>$0.00124_{[2.1X]}$ |

[a] Cell growth inhibition was measured by XTT tetrazonium assay (24) after 72 hours incubation for cell growth as described previously. The $IC_{50}$ values were determined from close-effect relationship six or seven concentrations of each drug using a computer program (25, 26).
[b] Preliminary results for dEpoB, dEpoF, and paclitaxel (except aza-EpoB) were reported in ref (12, 19).
[c] Numbers in brackets are fold of resistance compared with the corresponding $IC_{[50X]}$ of the parent cell line.
[d] Preliminary results were reported in Ref (28).

TABLE 5

Comparison of therapeutic effects between dEpoB and paclitaxel (Taxol ®) in nude mice bearing human tumor xenografts

| Tumor | Drugs | Doses Schedule | | Lowest Average Tumor Size (T/C) | Tumor Disappearance | Therapeutic Effects dEpoB vs Taxol | Ref. |
|---|---|---|---|---|---|---|---|
| A549 | dEpoB | 40 mg/kg | Q2Dx3 | 0.01 | 1/3 | ≈ | |
| Lung | Taxol | 15 mg/kg | Q2Dx3 | 0.01 | 2/4 | | # |
| MX-1 | dEpoB | 30 mg/kg | Q2Dx6 | 0 | 5/5 | ≈ | |
| Breast | Taxol | 15 mg/kg | Q2Dx6 | 0 | 5/5 | | 28 (FIG. 2) |
| MCF-7/Adr | dEpoB | 30 mg/kg | Q2Dx5 | 0.11 | 0/3 | >> | |
| Breast | Taxol | 24 mg/kg | Q2Dx5 | 0.71 | 0/4 | | 28 (FIG. 3) |
| HT-29 | dEpoB | 30 mg/kg | Q2Dx6 | 0.02 | 0/3 | ≦ | # |
| Colon | Taxol | 15 mg/kg | Q2Dx6 | 0.01 | 0/4 | | |
| HCT-116 | dEpoB | 30 mg/kg | Q2Dx5₁x3 | 0 | 1/2 | ≦ | FIG. 2 |
| Colon | Taxol | 20 mg/kg | Q2Dx5₁x3 | 0 | 3/3 | | |
| PC-3 | dEpoB | 40 mg/kg | Q2Dx3 | 0.12 | 0/3 | << | |
| Prostate | Taxol | 15 mg/kg | Q2Dx3 | 0.02 | 0/4 | | # |
| SK-OV-3 | dEpoB | 30 mg/kg | Q2Dx6 | 0.17 | 0/3 | << | |
| Ovary | Taxol | 15 mg/kg | Q2Dx6 | 0.02 | 1/4 | | # |
| UL3-C | dEpoB | 30 mg/kg | Q2Dx5 | 0.03 | 0/3 | ≧ | |
| Ovary | Taxol | 20 mg/kg | Q2Dx5 | 0.04 | 0/3 | | # |
| CCRF/CEM | dEpoB | 40 mg/kg | Q2Dx4 | 0 | 2/2 | ≈ | |
| Leukemia | Taxol | 20 mg/kg | Q2Dx4 | 0 | 2/2 | | # |
| CCRF/Taxol | dEpoB | 30 mg/kg | Q2Dx5 | 0 | 3/3 | >>> | |
| Leukemia | Taxol | 20 mg/kg | Q2Dx5 | 0.32 | 0/2 | | 28 (FIG. 4) |
| CCRF/VBL | dEpoB | 30 mg/kg | Q2Dx5 | 0 | 2/2 | >>> | |
| Leukemia | Taxol | 20 mg/kg | Q2Dx5 | 0.62 | 0/2 | | # |
| K562 | dEpoB | 30 mg/kg | Q2Dx5 | 0 | 5/5 | >>> | FIG. 3 |
| Leukemia | Taxol | 20 mg/kg | Q2Dx5 | 0.18 | 0/6 | | FIG. 4 |
| HL-60 | dEpoB | 30 mg/kg | Q2Dx5 | 0.01 | 2/3 | ≦ | |
| Leukemia | Taxol | 20 mg/kg | Q2Dx5 | 0 | 4/4 | | # |

Cremophor-EtOH (1:1) was used as a solvent for both dEpoB and taxol for 6-hr infusion with doses and schedules as indicated. The therapeutic effects were compared with the tumor size reduction or dissappearance of the maximally tolerated doses as measured by body weight decreases and lack of lethality. The relative therapeutic effects are indicated by: >, greater: >>, much greater: >>>, very much greater: ≈, almost equal; ≧, equal; or slightly greater; ≦, equal or slightly less. # Chou, T.-C., (unpublished results)

TABLE 6

Comparison of chemotherapeutic effect among dEpoB, dEpoF, EpoB, 15-aza-EpoB, paclitaxel (Taxol ®) and/or other cancer therapeutic agents in murine B16 melanoma or in nude mice bearing human tumor xenografts.

| Tumor | Route of Administration | Therapeutic Effect Rank Order | Ref. |
|---|---|---|---|
| B16 Melanoma[+] | i/p* | dEpoB>Taxol>>EpoB | # |
| MX-1 | i.p. | dEpoB>Camptothecin>Taxol>VBL, EpoB | 19 (Table 4) |
| MX-1 | i/p. | dEpoB>Adriamycin>Taxol | 19 (FIG. 2) |
| MCF-7/Adr | i.p. | dEpoB>Camptothecin>Adriamycin>Taxol | 19 (Table 5) |
| SK-OV-3 | i.v. or i.p. | dEpoB≈Taxol | 19 (Table 6) |
| PC-3 | i.v. or i/p. | Taxol>dEpoB>>Adriamycin | # |
| MX-1 | i.v. infusion* | Taxol≈dEpoB | 19 (Table 7) |

TABLE 6-continued

Comparison of chemotherapeutic effect among dEpoB, dEpoF, EpoB, 15-aza-EpoB, paclitaxel (Taxol ®) and/or other cancer therapeutic agents in murine B16 melanoma or in nude mice bearing human tumor xenografts.

| Tumor | Route of Administration | Therapeutic Effect Rank Order | Ref. |
|---|---|---|---|
| | | | 28 (FIG. 2) |
| MX-1 | i.v. infusion | dEpoB>>>15-azaEpoB | FIG. 7 |
| MCF-7/Adr | i.v. infusion | dEpoB>>VP-16, Taxol>VBL, Adriamycin | 28 (FIG. 3) |
| HT-29 | i.v. infusion | Taxol>dEpoB | # |
| HCT-116 | i.v. infusion | Taxol, CPT-11≈dEpoB, dEpoF | FIG. 2 |
| A549 | i.v. infusion | Taxol, dEpoB, VBL>VP-16 | # |
| PC-3 | i.v. infusion | Taxol, VBL>dEpoB>>VP-16 | # |
| SK-OV-3 | i.v. infusion | Taxol>>dEpoB | # |
| UL3-C | i.v. infusion | dEpoB≧Taxol | # |
| CCRF-CEM | i.v. infusion | dEpoB≈Taxol | # |
| CCRF-CEM | i.v. infusion | dEpoF>>>15-azaEpoB | FIG. 5 |
| CCRF-CEM/Taxol | i.v. infusion | dEpoB>>>Taxol | 28 (Table 4) |
| CCRF-CEM/VBL | i.v. infusion | dEpoB>>>Taxol | # |
| K562 | i.v. infusion | dEpoB>>>VBL>Taxol>Adriamycin | FIG. 3 & 4 |
| K562 | i.v. infusion | dEpoF>>>15-azaEpoB | # |
| HL-60 | i.v. infusion | Taxol≧dEpoB | # |

The therapeutic effects were compared with the tumor size reduction or disappearance at the maximal tolerated doses as measured by body weight decreases and lack of lethality. The relative therapeutic effects are indicated by: >, greater; >>, much greater; >>>very much greater; ≈, almost equal; ≧ equal; or slighter greater.
+Murine melanoma, all others are human tumor xenografts.
*DMSO was used as solvent for i.p. injecton whreas Cremophor-EtOH (1:1) was used for i.v. infusion for all dEpoB or EpoB studies. Clinical preparations were used for taxol, vinblastine, Adriamycin, VP-1y and camptothecin.
Chou, T.-C. et al (unpublished results)

Example 5
Additional Biological Data and Synthesis of Analogues

Stability of dEpoF in animal plasmas. A HPLC method is set up using a NovaPak C 18, 3.9×300 mm column with a mobile phase of 50% acetonitrile in 50 mM potassium dihydrogen phosphate with 0.01% triethylamine at a flow rate of 0.8 ml/min. dEpoF is monitored at a wavelength of 260 nm and has a retention time of about 10 min. The plasma stability is performed with mouse plasma and dog plasma purchased from Pel-Freeze and human plasma from the blood center in MSKCC. A small amount of dEpoF was dissolved in 50% methanol/water at a concentration of 500 $\mu$g/mL. An aliquot of 20 $\mu$L is then spiked to 2 mL of plasma to a final plasma concentration of 5 $\mu$g/mL. The plasma samples were kept at 37 degree. At the time point, 200 $\mu$L of the plasma was removed and added to 400 $\mu$L of methanol to precipitate the plasma protein. Twenty $\mu$L of the supernatant was analyzed by HPLC without further modification. dEpoF disappears rapidly with half life about one hour in the commercial frozen mouse plasma alone, but stable in dog and human plasma.

The Following Experimentals Refer to Compounds Depicted in FIG. 7

Tosylate (5). To a solution of dEpoF (4.2 mg, 0.0083 mmol) and pyridine (0.1 mL) in $CH_2Cl_2$ (0.2 mL) was added p-toluenesulfonyl chloride (2.4 mg, 0.013 mmol) at 0° C. The resulting solution was stirred for 1 h at which point TLC analysis indicated a small progress of the reaction. An additional amount of p-toluenesulfonyl chloride (1.0 mg) and 4-dimethylaminopyridine (0.1 mg) were further added, and the stirring was continued for 0.5 h. The reaction mixture was then diluted with EtOAc (5 mL), washed successively with aqueous 1 N HCl (2×2 mL), $NaHCO_3$ (2 mL), and NaCl (2 mL) solutions, dried over $MgSO_4$, and concentrated. Purification on a silica gel column (40% EtOAc-hexanes) afforded pure tosylate 5 (4.1 mg, 75%) as a sticky oil.

$^1$H NMR (500 MHz, $CDCl_3$) $\delta$ 7.83 (d, J=8.3 Hz, 2H), 7.35 (d, J=8.1 Hz, 2H), 7.13 (s, 1H), 6.53 (s, 1H), 5.29 (s, 2H), 5.21 (d, J=8.3 Hz, 1H), 5.13 (dd, J=9.7, 4.9 Hz, 1H), 4.23–4.20 (m, 1H), 3.72 (s, 1H), 3.14 (qd, J=6.8, 2.4 Hz, 1H), 2.94 (s, 1H), 2.86 (d, J=5.9 Hz, 1H), 2.64 (dt, J=15.1, 10.0 Hz, 1H), 2.49–2.43 (m, 1H), 2.45 (s, 3H), 2.34–2.28 (m, 2H), 2.21–2.16 (m, 1H), 2.05 (s, 3H), 1.92–1.85 (m, 1H), 1.78 (m, 1H), 1.69 (s, 3H), 1.32 (s, 3H), 1.26 (m, 2H), 1.19 (d, J=6.8 Hz, 3H), 1.07 (s, 3H), 1.01 (d, J=7.0 Hz, 3H).

Iodide (6). To 21-tosylate-dEpoB (5, 2.0 mg) in acetone (HPLC grade, 0.45 g) was added NaI (5 mg). After stirring for 15 min, two drops of saturated aqueous $Na_2S_2O_3$ was added to quench trace $I_2$, and the stirring was continued for 3 min. After addition of toluene (0.5 mL) and evaporation of acetone by a stream of nitrogen gas, the remainder was directly loaded on a silica gel column. Elution with hexane-EtOAc (4:1) gave 21-iodo-dEpoB (6, 1.5 mg) as light yellow oil.

$^1$H NMR (500 MHz, $CDCl_3$) $\delta$ 7.14 (s, 1H), 6.56 (s, 1H), 5.22 (dd, J=9.7, 1.5 Hz, 1H), 5.14 (dd, J=10.2, 4.7 Hz, 1H), 4.69 (s, 2H), 4.27–4.23 (m, 1H), 3.73 (m, 1H), 3.15 (qd, J=6.8, 2.3 Hz, 1H), 3.03 (d, J=5.9 Hz, 1H), 2.97 (s, 1H), 2.65 (dt, J=15.1, 10.0 Hz, 1H), 2.47 (dd, J=14.9, 11.0 Hz, 1H), 2.35–2.29 (m, 2H), 2.22 (d, J=15.1 Hz, 2H), 2.09 (s, 3H), 1.91–1.86 (m, 1H), 1.75 (m, 1H), 1.72–1.66 (m, 1H), 1.66 (s, 3H), 1.35 (s, 3H), 1.25 (m, 2H), 1.20 (d, J=6.8 Hz, 3H), 1.08 (s, 3H), 1.01 (d, J=7.0 Hz, 3H).

dEpoB (2 or 7). To 21-iodo-dEpoB (6, ca. 0.15 mg) in HMPA (0.15 mL) was added $NaBH_3CN$ (5 mg). In order to monitor the progress of the reaction, a small aliquot of reaction mixture was partitioned between water and ether, and the ether layer was taken for TLC. The reaction was completed in 3.5 h according to the TLC analysis. After quenching with water (3 mL), the reaction mixture was extracted three times with hexanes-$CH_2Cl_2$ (2:1, 2 mL) and once with hexanes-toluene (2:1, 2 mL). Purification by silica gel chromatography (50% ether in hexanes to pure ether)

gave the desired dEpoB (2b, ca. 0.05 mg). The identity of dEpoB was verified by chromatographic and spectroscopic comparison of the sample with previously obtained data.

Aldehyde (8). To a solution of dEpoF (10.0 mg, 0.0197 mmol) in $CH_2Cl_2$ (0.5 mL) was added manganese dioxide (pre-activated, 14 mg, 0.16 mmol). After stirring at rt for 2 h, the mixture was filtered through a short pad of silica gel column. The filtrate was concentrated to give aldehyde 8 (8.9 mg, 89%) as a viscous, colorless oil.

$^1$H NMR (400 MHz, $CDCl_3$) δ 9.99 (s, 1H), 7.53 (s, 1H), 6.65 (s, 1H), 5.26 (dd, J=9.7, 1.7 Hz, 1H), 5.15 (dd, J=9.6, 5.0 Hz, 1H), 4.21 (dd, J=10.8, 2.9 Hz, 1H), 3.74 (t, J=2.8 Hz, 1H), 3.15 (qd, J=6.8, 2.5 Hz, 1H), 2.70 (dt, J=14.9, 9.9 Hz, 1H), 2.49 (dd, J=15.1, 10.7 Hz, 1), 2.39–2.29 (m, 2H), 2.27–2.21 (m, 1H), 2.17 (s, 3H), 1.93–1.86 (m, 1H), 1.75–1.70 (m, 1H), 1.67 (s, 3H), 1.36 (s, 3H), 1.25 (m, 2H), 1.20 (d, J=6.8 Hz, 3H), 1.08 (s, 3H), 1.01 (d, J=7.0 Hz, 3H)

Biological Data for 21-oxo-dEpoB

As depicted in Table 4, the relative potency of 21-oxo-dEpoB was tested. Very highly resistant MDS cells were utilized (2766×resistant to Vinblastine). As depicted, dEpoF is slightly less potent than dEpoB and 21-oxo-dEpoB is about 3.7× less potent than dEpoB and shows a similar degree of low drug resistance as dEpoB. Specifially, in MDR CCRF-CEM/VBL cells, dEpoF is 4.5×less potent than dEpoB and 21-oxo-dEpoB is 5.1×less potent than dEpoB. Using [IC50 CCRF-CEM/VBL]/[IC50 CCRF-CEM] ratio, dEpoB is 8.6×resistant, 21-oxo-dEpoB is 11.9×resistant and dEpoF is 33.6×resistant.

TABLE 4

Relative potency of 21-oxo-dEpoB, dEpoB and dEpoF in vitro

| Compound | CCRF-CEM $IC_{50}$ in μM | CCRF-CEM/VBL $IC_{50}$ in μM | Fold of Resistance |
|---|---|---|---|
| Vinblastine | (A) 0.00073 | (B) 2.0195 | (B)/(A) 2766x |
| 21-oxo-dEpoB | 0.027 | 0.326 | 11.9x |
| dEpoB | 0.0074 | 0.637 | 8.6x |
| dEpoF | 0.0085 | 0.2873 | 33.6x |

Example 6

Figure 46:
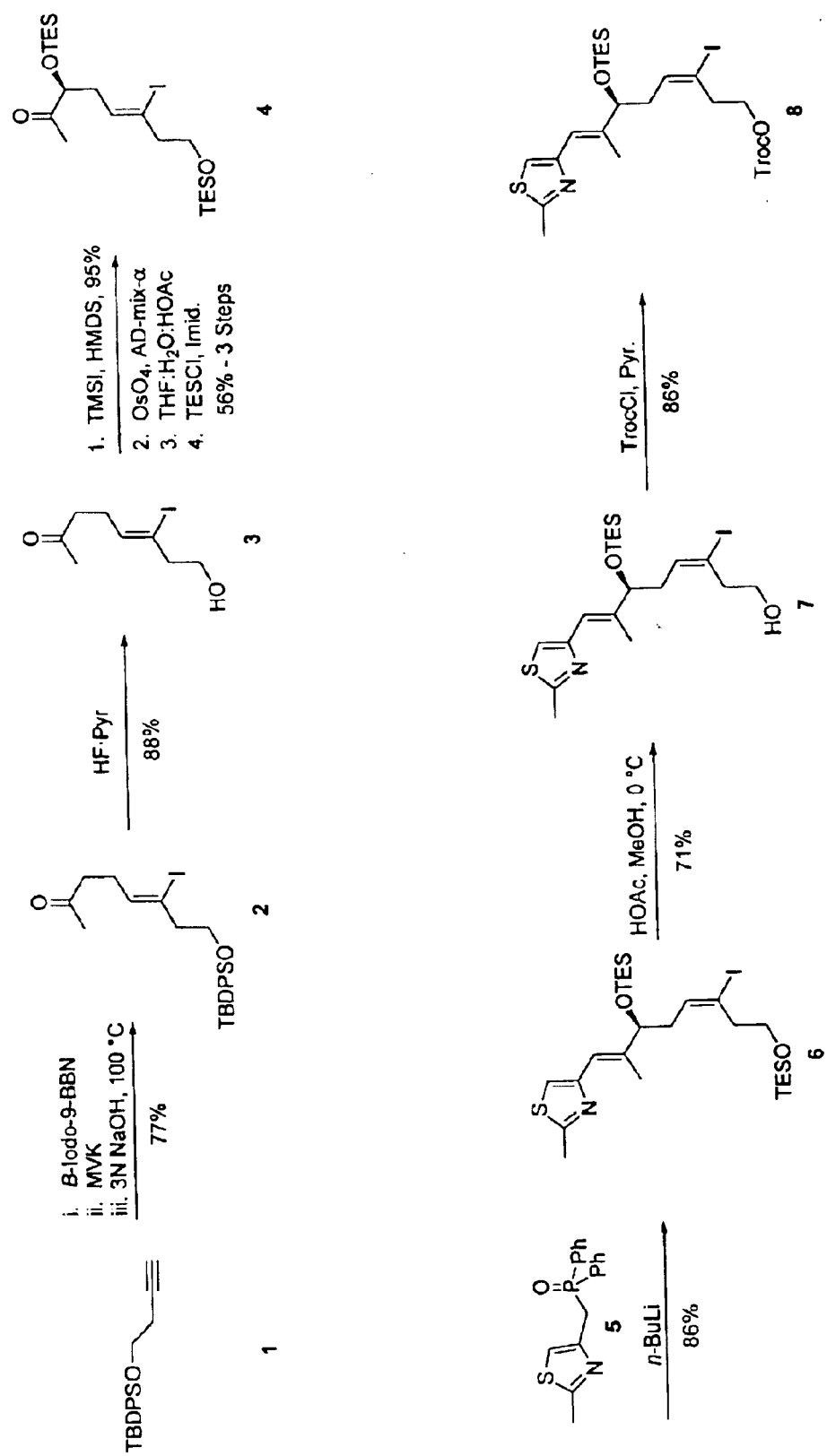
FIG. 46 depicts the synthesis of C12 ethyl dioxalane vinyl iodide.
Figure 47:
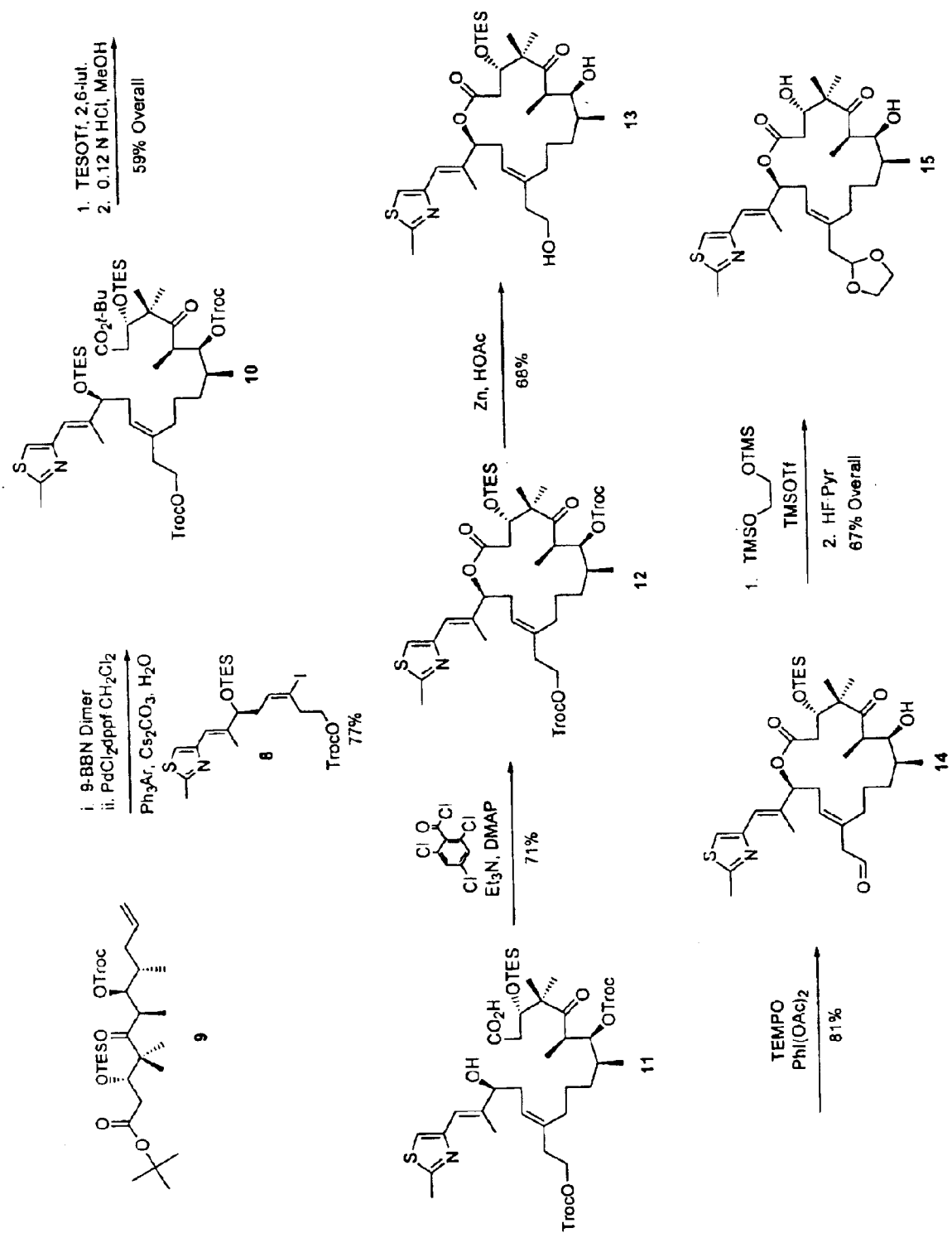
FIG. 47 depicts the synthesis of C12 cyclic acetal using novel methodologies as described herein.

Synthesis of Dioxalane Using Novel Synthetic Methodologies (FIGS. 46 and 47)

The synthesis of the C12 ethyl dioxalane dEpoB (C12-Diox-dEpoB) begins with the known TBDPS protected alkyne 1. Compound 1 undergoes an iodo-boration with B-Iodo-9-BBN. The resulting vinyl borane adds to methyl vinyl ketone in a 1,4 manner to provide ketone 2 in 78% yield. The silyl group is removed by treatment with HF-pyridine to afford primary alcohol 3. This proved to be necessary as the TBDPS ether is not compatible with the synthesis at a latter stage. At this point, the thermodynamic enol ether is generated in approximately a 9:1 ratio (thermo:kinetic) with TMSI and HMDS in 95% yield. The primary alcohol is simultaneously protected as the TMS ether during the reaction. Asymmetric installation of the hydroxyl group is accomplished by using the Sharpless dihydroxylation methodology to provide, following hydrolysis of the primary silyl group and protection of the resulting diol as the bis TES derivative, compound 4 in 56% overall yield. An efficient Homer olefination with phosphine oxide 5 and ketone 4 (86%) forms the final carbon-carbon bond in the vinyl iodide segment. Finally, the primary TES is removed under carefully controlled conditions using 2% acetic acid in methanol at 0° C. and the resulting alcohol is reprotected as the Troc carbonate to provide compound 8.

A crucial step in the synthesis involves the ligation of vinyl iodide 8 and polypropionate 9 to form the fully elaborated carbon skeleton. This is accomplished by using a Suzuki cross-coupling which provides compound 10 in 77% yield. The tert-Butyl ester is subsequently deprotected through treatment with TESOTf, and the resulting silyl ester and the C15 silyl ether are simultaneously hydrolyzed by treatment with dilute HCl in methanol. The resulting seco-acid undergoes a Yamaguichi cyclization to afford macro-lactone 12 in 71% yield. Both Troc carbonates are removed with zinc metal in acetic acid to provide diol 13 in 68% yield. Selective oxidation of the primary alcohol is accomplished with TEMPO/iodobenzene diacetate with no sign of C7 oxidation. The ethylene glycol acetal was synthesized by Noyori's procedure using bis(trimethylsilyl)ethylene glycol and catalytic TMSOTf. Finally, the crude product is subjected to desilylation utilizing HF-pyridine to provide the final product 15. This sequence has currently provided 50 mg of final product to support advanced in vivo biological testing.

What is claimed is:

1. A compound having the structure:

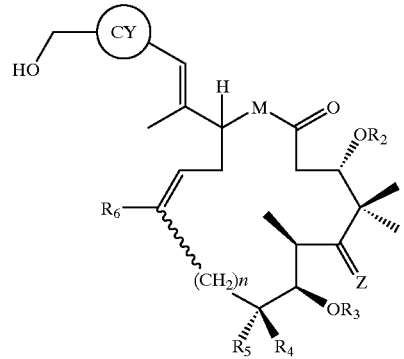

wherein M is O;

wherein CY is 4-thiazolyl, imidazolyl, or 4-oxazolyl;

wherein $R_2$ and $R_3$ are each independently hydrogen; substituted or unsubstituted aliphatic, heteroaliphatic, aryl, or heteroaryl; acyl; aroyl; benzoyl; or $Si(R_B)_3$, wherein each occurrence of $R_B$ is independently substituted or unsubstituted, cyclic or acyclic, linear or branched aliphatic, heteroaliphatic, aryl or heteroaryl;

wherein $R_4$ and $R_5$ are each independently hydrogen; or substituted or unsubstituted, linear or branched, cyclic or acyclic aliphatic, heteroaliphatic, aryl, or heteroaryl, optionally substituted by one or more of hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently hydrogen, phenyl, benzyl, linear or branched chain alkyl;

wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl;

wherein Z is O, $N(OR_E)$ or N—$NR_FR_G$; wherein $R_E$, $R_F$, and $R_G$ are each independently a substituted or unsubstituted, linear or branched, cyclic or acyclic aliphatic moiety; and wherein n is 0, 1, 2, or 3;

wherein said compound is prepared by a method comprising the steps of:

a) providing an alkyl sector having the structure:

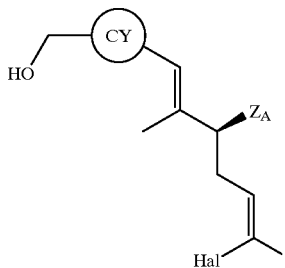

wherein $Z_A$ is OP or SP; wherein P is an oxygen or sulfur protecting group; wherein Hal is a halogen; wherein $R_6$ is independently hydrogen; $OR_A$; $SR_A$; $NR_AR_A$; $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; or linear or branched, substituted or unsubstituted, cyclic or acyclic, aliphatic, heteroaliphatic, aryl or heteroaryl, which further comprises the steps of:

i) providing a phosphine oxide having the structure:

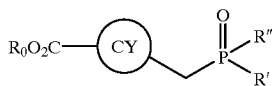

wherein $R_0$, R' and R" are independently $C_{1-8}$ linear or branched chain alkyl, or a substituted or unsubstituted phenyl, aryl, alkoxy or aryloxy;

ii) condensing the phosphine oxide with a ketone having the structure:

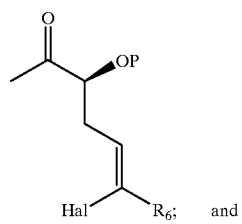

iii) reducing the ester formed instep ii) under suitable conditions to form the compound; and b) providing an acyl sector having the structure:

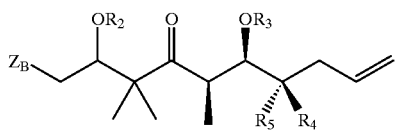

wherein $Z_B$ is $CO_2R_9$ or $COSR_9$, wherein $R_9$ is hydrogen or an oxygen or sulfur protecting group, wherein $R_2$ and $R_3$ are each independently hydrogen, substituted or unsubstituted aliphatic, heteroaliphatic, aryl, or heteroaryl; linear or branched, substituted or unsubstituted acyl, aroyl or benzoyl; or $Si(R_B)_3$, wherein each occurrence of $R_B$ is independently substituted or unsubstituted aliphatic, heteroaliphatic, aryl or heteroaryl; and wherein $R_4$ and $R_5$ are each independently hydrogen, linear or branched chain alkyl, optionally substituted by hydroxy, alkoxy, carboxy, carboxaldehyde, linear or branched alkyl or cyclic acetal, fluorine, $NR_CR_D$, N-hydroxyimino, or N-alkoxyimino, wherein $R_C$ and $R_D$ are each independently hydrogen, phenyl, benzyl, linear or branched chain alkyl; which further comprises:

i) protecting a ketoaldehyde having the structure:

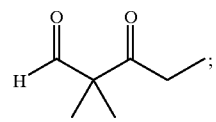

to generate a protected aldehyde and subsequently reacting said protected aldehyde with a compound having a structure:

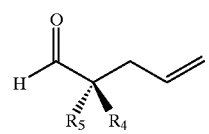

under suitable conditions to effect condensation to generate an aldol having the structure:

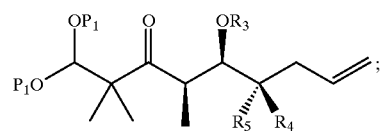

ii) hydrolyzing the protected acetal group to generate a ketoaldehyde having the structure:

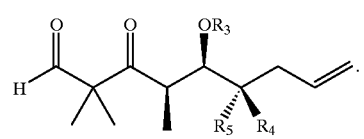

iii) reacting said ketoaldehyde under suitable conditions to effect a second aldol reaction, and optionally protecting the C3 alcohol to generate a compound having the structure:

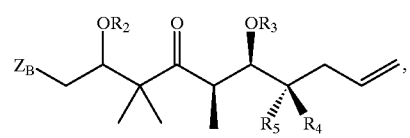

wherein $Z_B$, and $R_2$–$R_5$ are as defined above; and iv) reacting the acyl sector and the alkyl sector to generate a compound having the structure:

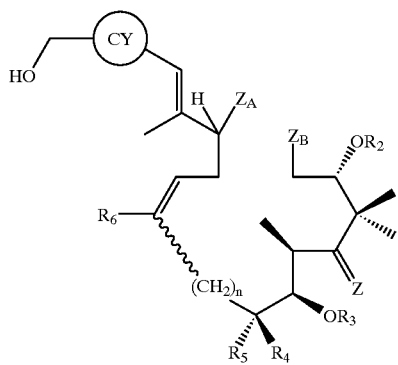

wherein $Z_A$, $Z_B$, CY, Z, and $R_2$–$R_6$ are as defined above; and c) subjecting the cyclization precursor to conditions to effect macrocyclization, and optionally subjecting to conditions to effect deprotection to generate the compound.

2. The compound of claim 1, wherein M is O, $R_2$ and $R_3$ are hydrogen, $R_4$ is methyl, $R_5$ is hydrogen, Z is O, CY is 4-thiazolyl, and $R_6$ is H, methyl, ethyl, n-propyl, n-butyl, n-hexyl,

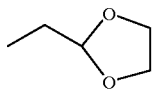

or $(CH_2)_p$—OH, wherein p is 1–6, and the compound has the structure:

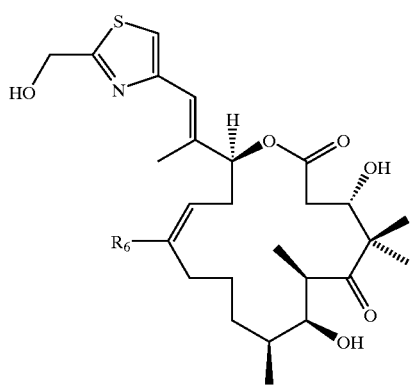

3. The compound of claim 1, wherein M is O, $R_2$ and $R_3$ are hydrogen, $R_4$ is methyl, $R_5$ is hydrogen, Z is O, $R_6$ is hydrogen, and CY is 4-thiazolyl and the compound has the structure:

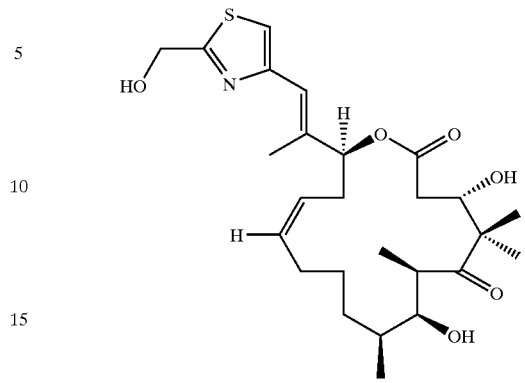

4. The compound of claim 1, wherein M is O, $R_2$ and $R_3$ are hydrogen, $R_4$ is methyl, $R_5$ is hydrogen, Z is O, $R_6$ is methyl, and CY is 4-thiazolyl, wherein the compound has the structure:

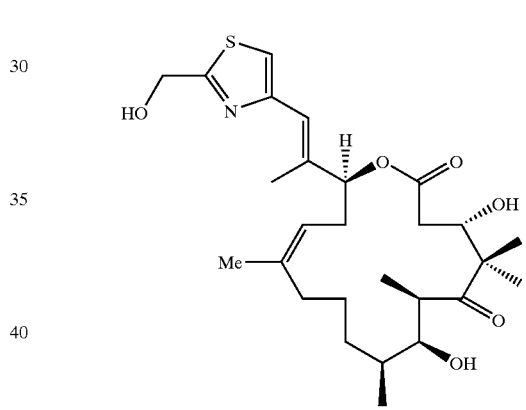

5. The compound of claim 1, wherein M is O, $R_2$ and $R_3$ are hydrogen, $R_4$ is methyl, $R_5$ is hydrogen, Z is O, $R_6$ is ethyl, and CY is 4-thiazolyl, wherein the compound has the structure:

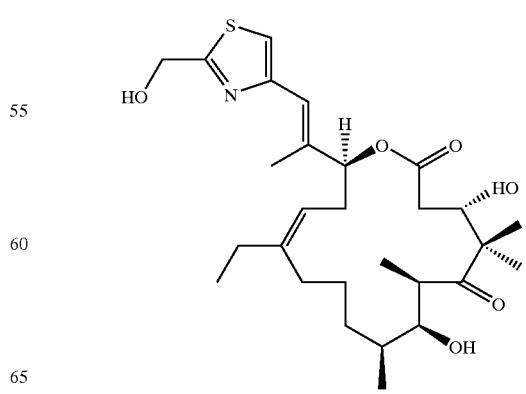

6. A compound having the structure:

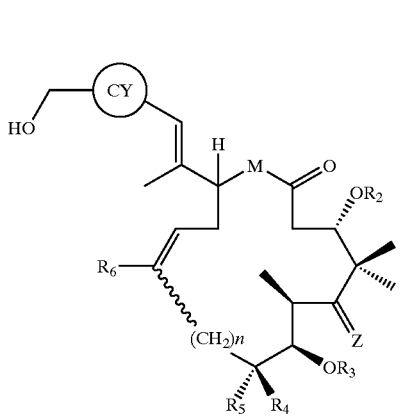

wherein M is O;

wherein CY is 4-thiazolyl, imidazolyl, or 4-oxazolyl;

wherein $R_2$ and $R_3$ are each independently hydrogen; substituted or unsubstituted aliphatic, heteroaliphatic, aryl, or heteroaryl; acyl; aroyl; benzoyl; or $Si(R_B)_3$, wherein each occurrence of $R_B$ is independently substituted or unsubstituted, cyclic or acyclic, linear or branched aliphatic, heteroaliphatic, aryl or heteroaryl;

wherein $R_4$ and $R_5$ are each independently hydrogen; or substituted or unsubstituted, linear or branched, cyclic or acyclic aliphatic, heteroaliphatic, aryl, or heteroaryl, optionally substituted by one or more of hydroxy, alkoxy, carboxy, carboxaldehyde, linear or branched alkyl or cyclic acetal, fluorine, $NR_CR_D$, N-hydroximino, or N-alkoxyimino, wherein $R_C$ and $R_D$ are each independently hydrogen, phenyl, benzyl, linear or branched chain alkyl;

wherein $R_6$ is independently hydrogen; $OR_A$; $SR_A$; $NR_AR_A$, $C(O)OR_A$; $C(O)R_A$; $CONHR_A$; $N_3$; $N_2R_A$; halogen; cyclic acetal; substituted or unsubstituted, cyclic or acyclic, linear or branched aliphatic, heteroaliphatic, aryl, or heteroaryl; wherein each occurrence of $R_A$ is independently hydrogen; linear or branched, substituted or unsubstituted, cyclic or acyclic, aliphatic, heteroaliphatic, aryl or heteroaryl;

wherein Z is O, $N(OR_E)$ or $N—NR_FR_G$; wherein $R_E$, $R_F$, and $R_G$ are each independently a substituted or unsubstituted, linear or branched, cyclic or acyclic aliphatic moiety; and wherein n is 0, 1, 2, or 3.

7. The compound of claim 6, wherein M is O, $R_2$ and $R_3$ are hydrogen, $R_4$ is methyl, $R_5$ is hydrogen, Z is O, CY is 4-thiazolyl, and $R_6$ is H, methyl, ethyl, n-propyl, n-butyl, n-hexyl,

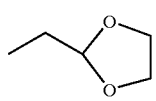

or $(CH_2)_p$—OH, wherein p is 1–6, and the compound has the structure:

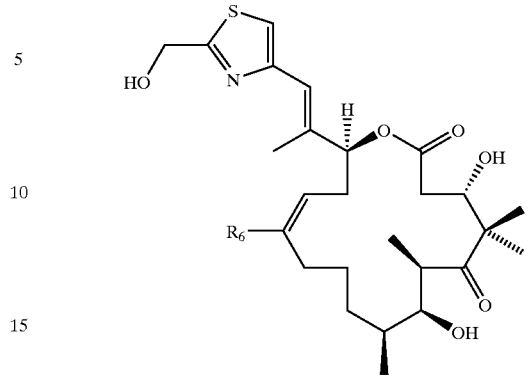

8. The compound of claim 6, wherein M is O, $R_2$ and $R_3$ are hydrogen, $R_4$ is methyl, $R_5$ is hydrogen, Z is O, $R_6$ is hydrogen, and CY is 4-thiazolyl and the compound has the structure:

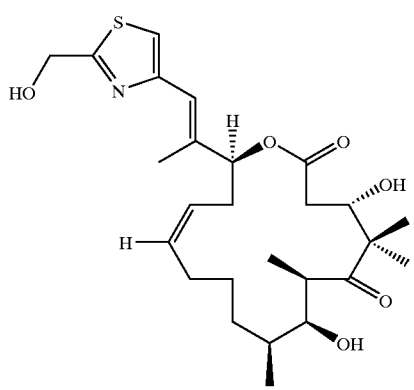

9. The compound of claim 6, wherein M is O, $R_2$ and $R_3$ are hydrogen, $R_4$ is methyl, $R_5$ is hydrogen, Z is O, $R_6$ is methyl, and CY is 4-thiazolyl, wherein the compound has the structure:

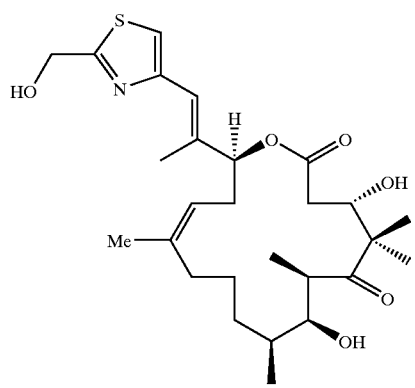

10. The compound of claim 6, wherein M is O, $R_2$ and $R_3$ are hydrogen, $R_4$ is methyl, $R_5$ is hydrogen, Z is O, $R_6$ is ethyl, and CY is 4-thiazolyl, wherein the compound has the structure:

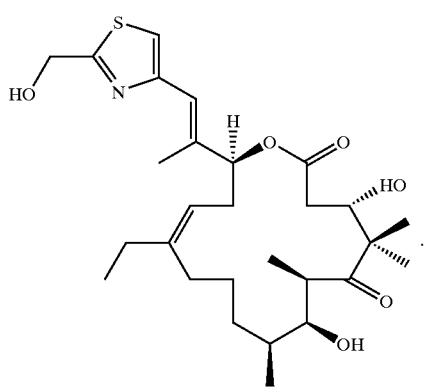

11. The compound of claim 6, wherein M is O, $R_2$ and $R_3$ are hydrogen, $R_4$ is methyl, $R_5$ is hydrogen, Z is O, CY is 4-oxazolyl, and $R_6$ is H, methyl, ethyl, n-propyl, n-butyl, n-hexyl,

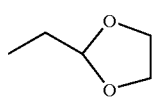

or $(CH_2)_p$—OH, wherein p is 1–6, and the compound has the structure:

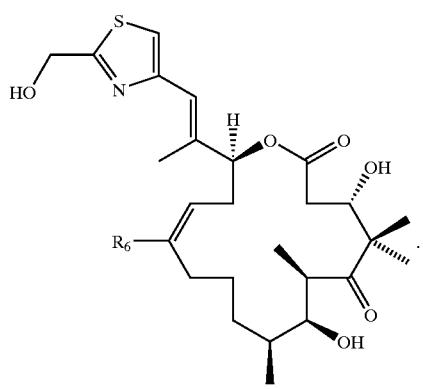

12. The compound of claim 6, wherein M is O, $R_2$ and $R_3$ are hydrogen, $R_4$ is methyl, $R_5$ is hydrogen, Z is O, $R_6$ is hydrogen, and CY is 4-oxazolyl and the compound has the structure:

13. The compound of claim 6, wherein M is O, $R_2$ and $R_3$ are hydrogen, $R_4$ is methyl, $R_5$ is hydrogen, Z is O, $R_6$ is methyl, and CY is 4-oxazolyl, wherein the compound has the structure:

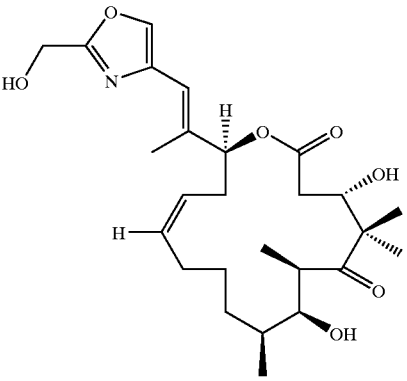

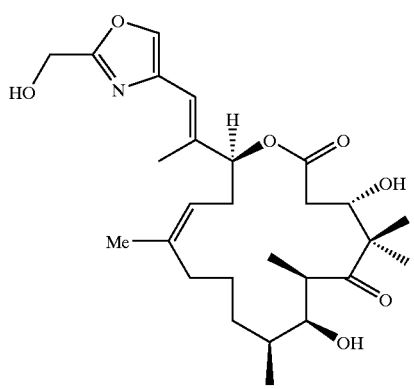

14. The compound of claim 6, wherein M is O, $R_2$ and $R_3$ are hydrogen, $R_4$ is methyl, $R_5$ is hydrogen, Z is O, $R_6$ is ethyl, and CY is 4-thiazolyl, wherein the compound has the structure:

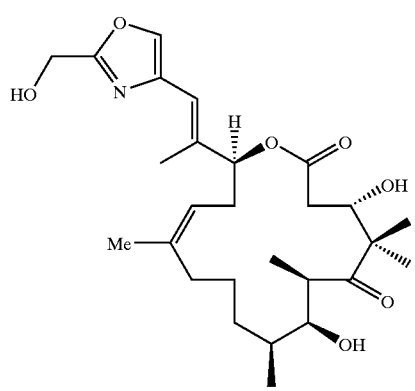

* * * * *

UNITED STATES PATENT AND TRADEMARK OFFICE
CERTIFICATE OF CORRECTION

PATENT NO. : 6,867,305 B2
DATED : March 15, 2005
INVENTOR(S) : Samuel J. Danishefsky et al.

It is certified that error appears in the above-identified patent and that said Letters Patent is hereby corrected as shown below:

Title page,
Item [75], Inventors, "Zhical Wu" should be changed to -- Zhicai Wu --
Item [63], Related U.S. Application Data, "[63] Continuation-in-part of application No. 09/257,072, filed on Feb. 24, 1999, now Pat. No. 6,204,388, which is a continuation-in-part of application No. 08/986,025, filed on Dec. 3, 1997, now patent No. 6,242,469.
[60] Provisional application No. 60/185,968, filed on Mar. 1, 2000, provisional application No. 60/250,447, filed on Nov. 30, 2000, provisional application No. 60/075,947, filed on Feb. 25, 1998, provisional application No. 60/092,319, filed on Jul. 9, 1998, provisional application No. 60/097,733, filed on Aug. 24, 1998, provisional application No. 60/032,282, filed on Dec. 3, 1996, provisional application No. 60/033,767, filed on Jan. 14, 1997, provisional application No. 60/047,566, filed on May 22, 1997, provisional application No.60/047,941, filed on May 29, 1997, and provisional application No. 60/055,533, filed on Aug. 13, 1997"
should be changed to -- [60] Provisional application No. 60/250,447, filed on Nov. 30, 2000 and provisional application No. 60/158,968, filed on Mar. 1, 2000 --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,867,305 B2
DATED : March 15, 2005
INVENTOR(S) : Samuel J. Danishefsky et al.

It is certified that error appears in the above-identified patent and that said Letters Patent is hereby corrected as shown below:

Title page,
Item [73], Assignee, "Sloan-Kettering Institute for Cancer Research, New York, NY (US)" should be changed to -- Sloan-Kettering Institute for Cancer Research, New York, NY (US) and The Trustees of Columbia University in the City of New York, New York (US) --.

Signed and Sealed this

Twenty-fifth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,867,305 B2
APPLICATION NO. : 09/796959
DATED : March 15, 2005
INVENTOR(S) : Danishefsky et al.

It is certified that error appears in the above-identified patent and that said Letters Patent is hereby corrected as shown below:

In column 1, beginning at line 23 and ending at line 33, under the subtitle "Government Support," please delete:

"This research was supported by Grants CA-28824, 25848, CA-08748, CA-39821, CA-GM-72231, GM-18248, CA-62948, F32CA81704, and AI0-9355 from the National Institutes of Health, and Grant CHE-9504805 from the National Science Foundation. Furthermore, this research was supported by Postdoctoral Fellowships for Chul Bom Lee (U.S. Army, Grant DAMD 17-98-1-8155), Shawn J. Stachel (NIH, Grant F32CA81704), and Mark D. Chappell. (NIH, Grant, F32GM199721). Accordingly, the government may have certain rights in this invention."

and insert:

--This invention was made with U.S. government support under grants CA-28824, 25848, CA-08748, CA-39821, CA-GM-72231, GM-18248, CA-62948, F32CA81704, F32GM199721, and AI0-9355 awarded by the National Institutes of Health, grant CHE-9504805 awarded by the National Science Foundation, and fellowship DAMD 17-98-1-8155 awarded by the United States Army. The U.S. government has certain rights in the invention.--

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 6,867,305 B2 | |
| APPLICATION NO. | : 09/796959 | |
| DATED | : March 15, 2005 | |
| INVENTOR(S) | : Samuel Danishefsky et al. | |

It is certified that error appears in the above-identified patent and that said Letters Patent is hereby corrected as shown below:

In the Specification

In column 1, beginning at line 14 and ending at line 21, please delete:

"This invention was made with government support under grants CA-28824, CA-39821, CA-GM 72231, CA-62948, and AI0-9355 from the National Institutes of Health, and grant CHE-9504805 from the National Science Foundation. Additionally, the present invention was supported in part by a fellowship from the United States Army to Dongfang Meng (DAMD 17-97-1-7146) and thus the government has certain rights in the invention."

and insert:

--This invention was made with government support under grant numbers: AI009355, CA028824, CA062948, CA081704, GM072231, GM199721 awarded by National Institutes of Health and DAMD17-98-1-8155 awarded by the Army Medical Research and Materiel Command. The government has certain rights in the invention.--

Signed and Sealed this
Twenty-third Day of February, 2016

Michelle K. Lee
*Director of the United States Patent and Trademark Office*